US010487365B2

(12) United States Patent
Zheng et al.

(10) Patent No.: US 10,487,365 B2
(45) Date of Patent: Nov. 26, 2019

(54) METHODS FOR DETECTING EXPRESSION OF LNC-FANCI-2 IN CERVICAL CELLS

(71) Applicant: The United States of America, as Represented by the Secretary,Department of Health and Human Services, Bethesda, MD (US)

(72) Inventors: Zhi-Ming Zheng, Rockville, MD (US); Junfen Xu, Frederick, MD (US); Jun Zhu, Potomac, MD (US); Yanqin Yang, Bethesda, MD (US); Xiaohong Wang, Germantown, MD (US)

(73) Assignee: THE UNITED STATES OF AMERICA, AS REPRESENTED BY THE SECRETARY, DEPARTMENT OF HEALTH AND HUMAN SERVICES, Bethesda, MD (US)

( * ) Notice: Subject to any disclaimer, the term of this patent is extended or adjusted under 35 U.S.C. 154(b) by 0 days.

(21) Appl. No.: 15/270,774

(22) Filed: Sep. 20, 2016

(65) Prior Publication Data

US 2018/0080084 A1 Mar. 22, 2018

(51) Int. Cl.

*C12Q 1/68* (2018.01)
*C12Q 1/6886* (2018.01)

(52) U.S. Cl.

CPC ...... *C12Q 1/6886* (2013.01); *C12Q 2600/112* (2013.01); *C12Q 2600/158* (2013.01)

(58) Field of Classification Search

None

See application file for complete search history.

(56) References Cited

U.S. PATENT DOCUMENTS 7,526,387 B2 4/2009 Baker et al.
7,659,062 B2 2/2010 Santin
7,927,795 B2 4/2011 Santin
7,939,261 B2 5/2011 Baker et al.
7,939,263 B2 5/2011 Clarke et al.
7,943,306 B2 5/2011 Chang et al.
8,110,358 B2 2/2012 Liew
8,669,058 B2 3/2014 Liew
8,741,574 B2 6/2014 Ried et al.
8,855,941 B2 10/2014 Noguchi et al.
2003/0225528 A1 12/2003 Baker et al.
2007/0141618 A1 6/2007 Dressman et al.
2008/0286781 A1* 11/2008 Monahan .............. C07K 14/47 435/6.14
2009/0136486 A1* 5/2009 Pyeon ................. C12Q 1/6886 424/130.1
2009/0215054 A1 8/2009 Carter et al.
2010/0316990 A1 12/2010 Dynan et al.
2011/0244459 A1 10/2011 Bertucci et al.
2012/0015827 A1 1/2012 Wirtz
2012/0129705 A1 5/2012 Iftner et al.
2013/0102488 A1 4/2013 Barrie et al.
2013/0280258 A1 10/2013 D'Andrea et al.
2014/0024539 A1 1/2014 Craig et al.
2014/0162254 A1 6/2014 Miller et al.
2014/0235479 A1 8/2014 Depinho et al.
2014/0342946 A1 11/2014 Kuriakose et al.
2015/0051103 A1 2/2015 Barrie et al.

OTHER PUBLICATIONS

Chen et al (Biomedicine & Pharmacotherapy. May 2015. 72: 83-90 (Year: 2015).*

Xu et al RNA. May 2015. The Twentieth Annual Meeting of the RNA Society, Abstract 178, available via URL <masociety.org/wp-content/uploads/2015/05/RNA-2015-Abstract-Book-print-150505.pdf> (Year: 2015).*

Fu et al Med Sci Monito. May 2015. 21: 1276-1287 (Year: 2015).*

Gibb et al Int J Gynecol Cancer. 2012. 22: 1557-1563 (Year: 2012).*

Camargo et al.; "GWAS Reveals New Recessive Loci Associated with Non-syndromic Facial Clefting"; Eur J Med Genet.; 55(10); pp. 510-514; (2012).

Expression of GLB1L2 in cancer—Summary—The Human Protein Atlas; printed May 6, 2015; 1 page; http://www.proteinatlas.org/ENSG00000149328-GLB1L2/cancer.

Flanagan et al.; "Genomics Screen in Transformed Stem Cell Reveals RNASEH2A, PPAP2C, and ADARB1 as Putative Anticancer Drug Targets"; Mol Cancer Ther; 8(1); pp. 249-260; (2009).

Itoh et al.; "Role of Growth Factor Receptor—Bound Protein 7 in Hepatocellular Carcinoma"; Mol Cancer Res; 5(7); pp. 667-673; (2007).

Nadler et al.; "Growth Factor Receptor-bound Protein-7 (Grb7) as a Prognostic Marker and Therapeutic Target in Breast Cancer"; Annals of Oncology; 21; pp. 466-473; (2010).

Takahashi et al.; Manuscript: Significance of Polypyrimidine Tract Binding Protein 1 Expression in Colorectal Cancer; Published OnlineFirst Apr. 22, 2015; DOI: 10.1158/1535-7163.MCT-14-0142; 50 pages (2015)_downloaded from mct.aacrjournals.org on Apr. 24, 2015.

Wang et al.; "Differential Functions of Growth Factor Receptor-Bound Protein 7 (GRB7) and Its Valiant GRB7v in Ovarian Carcinogenesis"; Clin Cancer Res; 16; pp. 2529-2539; (2010).

(Continued)

*Primary Examiner* — Carla J Myers

(74) *Attorney, Agent, or Firm* — Cantor Colburn LLP

(57) ABSTRACT

Described herein are biomarkers for HPV-associated pre-cancers and cancers such as cervical cancer and cervical intraepithelial neoplasia. The RNA binding protein (RBP) and long-noncoding RNA (lnc-RNA) biomarkers can be detected and used to diagnose HPV-associated pre-cancers and cancers. In addition, early diagnosis of HPV-associated pre-cancers and cancers can facilitate therapeutic intervention in patients, particularly in the pre-cancer stage which can delay or prevent progression to cancer.

3 Claims, 11 Drawing Sheets

(2 of 11 Drawing Sheet(s) Filed in Color)

Specification includes a Sequence Listing.

(56) References Cited

OTHER PUBLICATIONS

Williams et al.; "A Systems Genetics Approach Identifies CXCL14, ITGAX, and LPCAT2 as Novel Aggressive Prostate Cancer Susceptibility Genes"; PLoS Genet; 10(11): e1004809; 15 pages; (2014).

Yang et al.; "Identification of Genes with Correlated Patterns ofVariations in DNA Copy Number and Gene Expression Level in Gastric Cancer"; Genomics; 89; pp. 451-459; (2007).

Zhang et al.; "High Expression of Neuro-Oncological Ventral Antigen 1 Correlates with Poor Prognosis in Hepatocellular Carcinoma"; PLoS ONE; 9(3); c90955; 11 pages (2014).

* cited by examiner

95 RNA-binding proteins lnc-Fanconi Anemia, Complementation Group I
lnc-β-Galactosidase-1-Like Protein 2

SEQUENCE LISTING

```
<160> NUMBER OF SEQ ID NOS: 95

<210> SEQ ID NO 1
<211> LENGTH: 1267
<212> TYPE: DNA
<213> ORGANISM: Homo sapiens

<400> SEQUENCE: 1

cgagggctgc ttccggctgg tgcccccggg ggagacccaa cctggggcga cttcaggggt      60

gccacattcg ctaagtgctc ggagttaata gcacctcctc cgagcactcg ctcacggcgt     120

ccccttgcct ggaaagatac cgcggtccct ccagaggatt tgagggacag ggtcggaggg     180
```

```
ggctcttccg ccagcaccgg aggaagaaag aggaggggct ggctggtcac cagagggtgg    240

ggcggaccgc gtgcgctcgg cggctgcgga gagggggaga gcaggcagcg ggcggcgggg    300

agcagcatgg agccggcggc ggggagcagc atggagcctt cggctgactg gctggccacg    360

gccgcggccc ggggtcgggt agaggaggtg cgggcgctgc tggaggcggg ggcgctgccc    420

aacgcaccga atagttacgg tcggaggccg atccaggtca tgatgatggg cagcgcccga    480

gtggcggagc tgctgctgct ccacggcgcg gagcccaact gcgccgaccc cgccactctc    540

acccgacccg tgcacgacgc tgcccgggag ggcttcctgg acacgctggt ggtgctgcac    600

cgggccgggg cgcggctgga cgtgcgcgat gcctggggcc gtctgcccgt ggacctggct    660

gaggagctgg gccatcgcga tgtcgcacgg tacctgcgcg cggctgcggg gggcaccaga    720

ggcagtaacc atgcccgcat agatgccgcg gaaggtccct cagacatccc cgattgaaag    780

aaccagagag gctctgagaa acctcgggaa acttagatca tcagtcaccg aaggtcctac    840

agggccacaa ctgcccccgc cacaacccac cccgctttcg tagttttcat ttagaaaata    900

gagcttttaa aaatgtcctg ccttttaacg tagatatatg ccttccccca ctaccgtaaa    960

tgtccattta tatcattttt tatatattct tataaaaatg taaaaaagaa aaacaccgct   1020

tctgcctttt cactgtgttg gagttttctg gagtgagcac tcacgcccta agcgcacatt   1080

catgtgggca tttcttgcga gcctcgcagc ctccggaagc tgtcgacttc atgacaagca   1140

ttttgtgaac tagggaagct caggggggtt actggcttct cttgagtcac actgctagca   1200

aatggcagaa ccaaagctca aataaaaata aaataatttt cattcattca ctcaaaaaaa   1260

aaaaaaa                                                              1267
```

<210> SEQ ID NO 2
<211> LENGTH: 1464
<212> TYPE: DNA
<213> ORGANISM: Homo sapiens

<400> SEQUENCE: 2

```
cgagggctgc ttccggctgg tgcccccggg ggagacccaa cctggggcga cttcaggggt     60

gccacattcg ctaagtgctc ggagttaata gcacctcctc cgagcactcg ctcacggcgt    120

ccccttgcct ggaaagatac cgcggtccct ccagaggatt tgagggacag ggtcggaggg    180

ggctcttccg ccagcaccgg aggaagaaag aggaggggct ggctggtcac cagagggtgg    240

ggcggaccgc gtgcgctcgg cggctgcgga gagggggaga gcaggcagcg ggcggcgggg    300

agcagcatgg agccggcggc ggggagcagc atggagcctt cggctgactg gctggccacg    360

gccgcggccc ggggtcgggt agaggaggtg cgggcgctgc tggaggcggg ggcgctgccc    420

aacgcaccga atagttacgg tcggaggccg atccaggtca tgatgatggg cagcgcccga    480

gtggcggagc tgctgctgct ccacggcgcg gagcccaact gcgccgaccc cgccactctc    540

acccgacccg tgcacgacgc tgcccgggag ggcttcctgg acacgctggt ggtgctgcac    600

cgggccgggg cgcggctgga cgtgcgcgat gcctggggcc gtctgcccgt ggacctggct    660

gaggagctgg gccatcgcga tgtcgcacgg tacctgcgcg cggctgcggg gggcaccaga    720

ggcagtaacc atgcccgcat agatgccgcg gaaggtccct cagaaatgat cggaaaccat    780

ttgtgggttt gtagaagcag gcatgcgtag ggaagctacg ggattccgcc gaggagcgcc    840

agagcctgag gcgccctttg gttatcgcaa gctggctggc tcactccgca ccaggtgcaa    900

aagatgcctg ggatgcgggg aagggaaagg ccacatcttc acgccttcgc gcctggcatt    960

acatccccga ttgaaagaac cagagaggct ctgagaaacc tcgggaaact tagatcatca   1020
```

```
gtcaccgaag gtcctacagg gccacaactg cccccgccac aacccacccc gctttcgtag   1080

ttttcattta gaaaatagag cttttaaaaa tgtcctgcct tttaacgtag atatatgcct   1140

tcccccacta ccgtaaatgt ccatttatat catttttat atattcttat aaaaatgtaa   1200

aaaagaaaaa caccgcttct gccttttcac tgtgttggag ttttctggag tgagcactca   1260

cgccctaagc gcacattcat gtgggcattt cttgcgagcc tcgcagcctc cggaagctgt   1320

cgacttcatg acaagcattt tgtgaactag ggaagctcag gggggttact ggcttctctt   1380

gagtcacact gctagcaaat ggcagaacca aagctcaaat aaaaataaaa taattttcat   1440

tcattcactc aaaaaaaaaa aaaa                                          1464
```

<210> SEQ ID NO 3
<211> LENGTH: 1164
<212> TYPE: DNA
<213> ORGANISM: Homo sapiens

<400> SEQUENCE: 3

```
cgctcaggga aggcgggtgc gcgcctgcgg ggcggagatg ggcagggggc ggtgcgtggg     60

tcccagtctg cagttaaggg ggcaggagtg gcgctgctca cctctggtgc caaagggcgg    120

cgcagcggct gccgagctcg gccctggagg cggcgagaac atggtgcgca ggttcttggt    180

gaccctccgg attcggcgcg cgtgcggccc gccgcgagtg agggttttcg tggttcacat    240

cccgcggctc acgggggagt gggcagcgcc aggggcgccc gccgctgtgg ccctcgtgct    300

gatgctactg aggagccagc gtctagggca gcagccgctt cctagaagac caggtcatga    360

tgatgggcag cgcccgagtg gcggagctgc tgctgctcca cggcgcggag cccaactgcg    420

ccgaccccgc cactctcacc cgacccgtgc acgacgctgc ccgggagggc ttcctggaca    480

cgctggtggt gctgcaccgg gccggggcgc ggctggacgt gcgcgatgcc tggggccgtc    540

tgcccgtgga cctggctgag gagctgggcc atcgcgatgt cgcacggtac ctgcgcgcgg    600

ctgcgggggg caccagaggc agtaaccatg cccgcataga tgccgcggaa ggtccctcag    660

acatccccga ttgaaagaac cagagaggct ctgagaaacc tcgggaaact tagatcatca    720

gtcaccgaag gtcctacagg gccacaactg cccccgccac aacccacccc gctttcgtag    780

ttttcattta gaaaatagag cttttaaaaa tgtcctgcct tttaacgtag atatatgcct    840

tcccccacta ccgtaaatgt ccatttatat catttttat atattcttat aaaaatgtaa    900

aaaagaaaaa caccgcttct gccttttcac tgtgttggag ttttctggag tgagcactca    960

cgccctaagc gcacattcat gtgggcattt cttgcgagcc tcgcagcctc cggaagctgt   1020

cgacttcatg acaagcattt tgtgaactag ggaagctcag gggggttact ggcttctctt   1080

gagtcacact gctagcaaat ggcagaacca aagctcaaat aaaaataaaa taattttcat   1140

tcattcactc aaaaaaaaaa aaaa                                          1164
```

<210> SEQ ID NO 4
<211> LENGTH: 1235
<212> TYPE: DNA
<213> ORGANISM: Homo sapiens

<400> SEQUENCE: 4

```
atggagccgg cggcggggag cagcatggag ccttcggctg actggctggc cacggccgcg     60

gcccggggtc gggtagagga ggtgcgggcg ctgctggagg cgggggcgct gcccaacgca    120

ccgaatagtt acggtcggag gccgatccag gtgggtagag ggtctgcagc gggagcaggg    180
```

-continued

```
gatggcgggc gactctggag gacgaagttt gcaggggaat tggaatcagg tagcgcttcg    240
attctccgga aaaaggggag gcttcctggg gagttttcag aaggggtttg taatcacaga    300
cctcctcctg gcgacgccct gggggcttgg gaagccaagg aagaggaatg aggagccacg    360
cgcgtacaga tctctcgaat gctgagaaga tctgaagggg ggaacatatt tgtattagat    420
ggaagtcatg atgatgggca gcgcccgagt ggcggagctg ctgctgctcc acggcgcgga    480
gcccaactgc gccgaccccg ccactctcac ccgacccgtg cacgacgctg cccgggaggg    540
cttcctggac acgctggtgg tgctgcaccg ggccggggcg cggctggacg tgcgcgatgc    600
ctggggccgt ctgcccgtgg acctggctga ggagctgggc catcgcgatg tcgcacggta    660
cctgcgcgcg gctgcggggg gcaccagagg cagtaaccat gcccgcatag atgccgcgga    720
aggtccctca gacatccccg attgaaagaa ccagagaggc tctgagaaac ctcgggaaac    780
ttagatcatc agtcaccgaa ggtcctacag ggccacaact gcccccgcca caacccaccc    840
cgctttcgta gttttcattt agaaaataga gcttttaaaa atgtcctgcc ttttaacgta    900
gatatatgcc ttcccccact accgtaaatg tccatttata tcattttta tatattctta    960
taaaaatgta aaaaagaaaa acaccgcttc tgccttttca ctgtgttgga gttttctgga   1020
gtgagcactc acgccctaag cgcacattca tgtgggcatt tcttgcgagc ctcgcagcct   1080
ccggaagctg tcgacttcat gacaagcatt ttgtgaacta gggaagctca ggggggttac   1140
tggcttctct tgagtcacac tgctagcaaa tggcagaacc aaagctcaaa taaaaataaa   1200
ataattttca ttcattcact caaaaaaaaa aaaaa                              1235
```

<210> SEQ ID NO 5
<211> LENGTH: 3756
<212> TYPE: DNA
<213> ORGANISM: Homo sapiens

<400> SEQUENCE: 5

```
aacggcggga ccgcggcgcc tgggcgtcac tgaggcagta gccggccggg tgaggagggc     60
ggttgccggc gcggcgcggc gcggcgcggg tggggcgggg gttccgccgg cttccagtcc    120
cctttcccgc cgccgccgcc gccaccgcct ctccgcggag ctcgccccga gcgactcctc    180
cgcggcagtg ctgacggcca gcggcacgag ccgtagtagc tgcagcttcg agtcacagca    240
gcaggtaatt gctgccatgg aaacacaact gtctaatggg ccaacttgca ataacacagc    300
caatggtcca accaccataa acaacaactg ttcgtcacca gttgactctg ggaacacaga    360
agacagcaag accaacttaa tagtcaacta ccttcctcag aacatgacac aggaggaact    420
aaagagtctc tttgggagca ttggtgaaat agagtcctgt aagcttgtaa gagacaaaat    480
aacagggcag agcttgggat atggctttgt gaactacatt gaccccaagg atgcagagaa    540
agctatcaac accctgaatg gattgagact tcaaaccaaa acaataaaag tttcctatgc    600
tcgcccaagt tcagcttcta tcagagatgc aaatttatat gtcagcggac ttccaaaaac    660
aatgacccag aaggagttgg aacagctttt ttcacaatat ggacgcatta ttacttctcg    720
tattcttgtc gaccaggtca ctggcatatc aaggggtgta gggtttattc gatttgacaa    780
gcgaattgag gcagaagaag ctatcaaagg cctaaatggc cagaaacctc ccggtgccac    840
ggagccaatc actgtaaagt ttgctaataa cccaagccaa aaaaccaatc aggccatcct    900
ttcccagctg taccagtctc caaacagaag gtatccagga ccgctagctc agcaggcaca    960
gcgttttagg ttttctccaa tgaccattga cggaatgacc agtttggctg gaattaatat   1020
ccctgggcac cctggaacag ggtggtgtat atttgtgtac aacctggctc ctgacgcaga   1080
```

```
tgagagtatc ctgtggcaaa tgtttgggcc ttttggagct gtcaccaatg tgaaggtcat   1140
ccgtgacttt aacaccaata aatgcaaagg ttttggattt gtgactatga caaactatga   1200
tgaggctgcc atggcgatag ctagcctcaa tggataccgt ctgggagaca gagtactgca   1260
ggtctccttt aagacaaaca aaacgcacaa agcctaatga gctcttgtcc tcagtccatt   1320
tatatatgaa aactatacaa caaaggcaag ttaagagaaa ctttatacat tagtaaatgt   1380
ctttgtaagt cagtgttgag atggggataa aatgactact tagcatccta agaaatatgt   1440
gagatttttt attgctagta tttgaattaa aacttcttaa atatctttta tgtttgaata   1500
tggacaagag gtacagggtt tttacctgtc acattgcatt ctattgcctt ctttgaagaa   1560
ggtggacctt ttaaagtgtt tcagctaagg gaagacattt cttttctttt tacataactg   1620
ccttgaacct gtgagtaaat attgaggctt tgtgttgtaa ttcttcagtt ggttgtgtct   1680
tttttttccc cccttttttt ccttttctg attagctttg tgtttggttt acatttaaag    1740
cattgctgtt atgtctgttt aagaaaagta ttttgaagtt tacattttta tttatgaagt   1800
ttaaaacagt atttattttg taattatgat ttgggttggg gaaggggggg ctacattata   1860
aacgcttatt gtaagaatac tggagaactt ttcgtaaagc agtaccttgc caaagagata   1920
agagcctctt tgatgtgggt ttaaaaaaag catctatttt tataaaaaag aaaatttgga   1980
gaaacttttt actggtcctg gaacaaatat tttgacttga atactttgag aaatctcttc   2040
atatgacacc tagtgagctt ttaaaattta ccaggaaatt tgcagcggtt ggaaaattta   2100
gaaagattta tggtgtagaa aatacttttg agatctttgt atgaaaggag tagaatcaat   2160
ggggggaaac actgctggtt tcatttttgt aatcaccagt ggagcgtctg atcatcctgg   2220
ttattatgtg ataggtggct cacattgatt tgtgattttg aaacaaataa aaaaaattta   2280
caaaagaata tataagagca ggcaagaaat ttaaattacc gagagatggg ggaaaaaatc   2340
tgttcttcct aaagaaatcc cttcagatag agctcatggt gtttagtgat gtacttgcag   2400
tattgtttga agaattgttt tgtcttaagg aaaaaagacg ttgcacatga tttgtactgc   2460
agcaaatcag caaaagtgat ctgagttgga tatatttgaa ggtattttga aagttacgtt   2520
caaggctaac acctgagctt tgtgtaatgt aaataagacc ttgtgtttat gaacctttca   2580
gctaatttaa ttttttttcc cttacatgcc aagtgatgtt caggttttga atgtttttgt   2640
atcagttttt tcctttgtaa atggcattaa cattgttact tgaggtcttg cttaatcact   2700
tttgttgtcc tgaggacttg aatttacagt gcatcagatt tgttgcaaat tttgtctgta   2760
gatagtctag cttcagctgt ttatggtgat gctacatttt cgtttataaa tatgtttgtg   2820
gtataaaaaa atgagtataa ccataggttt tgaacaaatt tccttacatt tttcatacaa   2880
aaatcataaa tatctgtatg ctattgaaat ttaactttgt atgatgctta aaaaccacta   2940
tttggggaaa taataaaata agtctttacc atgtatgaaa gaaattttaa aaaatacaaa   3000
atattttctg attagcatct agcttataat aaattttcaa aaaagctgaa ggcaaaaatg   3060
ccttcatcag gatgcactga gaactatata gttacgtcct gctttttgta taaactgaga   3120
tgctcacatg cttcccctta gaacaggcaa tgtgctatgc ataacatagt tgtacattat   3180
ctttgcggtt gctttgagtt ttattttttta ttatttaaaa ttgtagttat aaaatttttc  3240
agtatagtac agtacatata ctgtgaggcg cgtgctaaag tgaataagcg agttttcatg   3300
ctgacccact caatgctatt cagaaatcaa ttggcttagc actttctcat atccttaggt   3360
gcatttagat tgccagagtt aaccttctgc gtttaaaaaa agaaaaacac taaaaaataa   3420
```

```
aatacatgta tatacttaaa aaaaaataat aaggtttccc tcaagggaaa acagcagcta   3480

catgcttctt tcctatacta ctgtagcaaa ccaaggcatt gatgagaggg catgcaaatt   3540

gtgcttcact ttacagtgtt ttatcagagc acttaataaa atgtaaggct ggtatttatt   3600

tgaagttgta cagtatgact taattcacat ctgttggaat agaaaatata ttctgttgag   3660

tatttaagag gctgtacatg ttttcttttg tgtttggatt ctttgtactt tttcatgttc   3720

agtacatcaa taaacaaagt tgaagggaaa aaaaaa                              3756


<210> SEQ ID NO 6
<211> LENGTH: 3769
<212> TYPE: DNA
<213> ORGANISM: Homo sapiens

<400> SEQUENCE: 6

agtccgaact ctgggcggga acactggtgg gggcggcgga ggttgtgccc gcgaagttcc     60

tagagctcag cccgttgcgg cgggagtaga gagaattggg cgcctcggga ggtggcaccg    120

cccctcccgt gggcacaagc aggttggggg cggcgggagc cgagcgggga cagtcgcgcc    180

tggcagcgtg cacgggcgtg gacgtgcccg ggtgcggccg cgtgtagcgc aagaaggaaa    240

ctgttgagac gcagcaggta attgctgcca tggaaacaca actgtctaat gggccaactt    300

gcaataacac agccaatggt ccaaccacca taaacaacaa ctgttcgtca ccagttgact    360

ctgggaacac agaagacagc aagaccaact taatagtcaa ctaccttcct cagaacatga    420

cacaggagga actaaagagt ctctttggga gcattggtga aatagagtcc tgtaagcttg    480

taagagacaa aataacaggg cagagcttgg gatatggctt tgtgaactac attgacccca    540

aggatgcaga gaaagctatc aacaccctga atggattgag acttcaaacc aaaacaataa    600

aagtttccta tgctcgccca agttcagctt ctatcagaga tgcaaattta tatgtcagcg    660

gacttccaaa aacaatgacc cagaaggagt tggaacagct tttttcacaa tatggacgca    720

ttattacttc tcgtattctt gtcgaccagg tcactggcat atcaaggggt gtagggttta    780

ttcgatttga caagcgaatt gaggcagaag aagctatcaa aggcctaaat ggccagaaac    840

ctcccggtgc cacggagcca atcactgtaa agtttgctaa taacccaagc caaaaaaacca    900

atcaggccat cctttcccag ctgtaccagt ctccaaacag aaggtatcca ggaccgctag    960

ctcagcaggc acagcgtttt aggttttctc caatgaccat tgacggaatg accagtttgg   1020

ctggaattaa tatccctggg caccctggaa cagggtggtg tatatttgtg tacaacctgg   1080

ctcctgacgc agatgagagt atcctgtggc aaatgtttgg gccttttgga gctgtcacca   1140

atgtgaaggt catccgtgac tttaacacca ataaatgcaa aggttttgga tttgtgacta   1200

tgacaaacta tgatgaggct gccatggcga tagctagcct caatggatac cgtctgggag   1260

acagagtact gcaggtctcc tttaagacaa acaaaacgca caaagcctaa tgagctcttg   1320

tcctcagtcc atttatatat gaaaactata caacaaaggc aagttaagag aaactttata   1380

cattagtaaa tgtctttgta agtcagtgtt gagatgggga taaaatgact acttagcatc   1440

ctaagaaata tgtgagattt tttattgcta gtatttgaat taaaacttct taaatatctt   1500

ttatgtttga atatggacaa gaggtacagg gtttttacct gtcacattgc attctattgc   1560

cttctttgaa gaaggtggac cttttaaagt gtttcagcta agggaagaca tttcttttct   1620

ttttacataa ctgccttgaa cctgtgagta aatattgagg ctttgtgttg taattcttca   1680

gttggttgtg tctttttttt ccccccttt tttcctttt ctgattagct ttgtgtttgg    1740

tttacattta aagcattgct gttatgtctg tttaagaaaa gtattttgaa gtttacattt   1800
```

```
ttatttatga agtttaaaac agtatttatt ttgtaattat gatttgggtt ggggaagggg   1860

gggctacatt ataaacgctt attgtaagaa tactggagaa cttttcgtaa agcagtacct   1920

tgccaaagag ataagagcct ctttgatgtg ggtttaaaaa aagcatctat tttataaaa   1980

aagaaaattt ggagaaactt tttactggtc ctggaacaaa tattttgact tgaatacttt   2040

gagaaatctc ttcatatgac acctagtgag cttttaaaat ttaccaggaa atttgcagcg   2100

gttggaaaat ttagaaagat ttatggtgta gaaaatactt ttgagatctt tgtatgaaag   2160

gagtagaatc aatgggggga aacactgctg gtttcatttt tgtaatcacc agtggagcgt   2220

ctgatcatcc tggttattat gtgataggtg gctcacattg atttgtgatt ttgaaacaaa   2280

taaaaaaaat ttacaaaaga atatataaga gcaggcaaga aatttaaatt accgagagat   2340

gggggaaaaa atctgttctt cctaaagaaa tcccttcaga tagagctcat ggtgtttagt   2400

gatgtacttg cagtattgtt tgaagaattg ttttgtctta aggaaaaaag acgttgcaca   2460

tgatttgtac tgcagcaaat cagcaaaagt gatctgagtt ggatatattt gaaggtattt   2520

tgaaagttac gttcaaggct aacacctgag ctttgtgtaa tgtaaataag accttgtgtt   2580

tatgaacctt tcagctaatt taatttttt tcccttacat gccaagtgat gttcaggttt   2640

tgaatgtttt tgtatcagtt ttttcctttg taaatggcat taacattgtt acttgaggtc   2700

ttgcttaatc acttttgttg tcctgaggac ttgaatttac agtgcatcag atttgttgca   2760

aattttgtct gtagatagtc tagcttcagc tgtttatggt gatgctacat tttcgtttat   2820

aaatatgttt gtggtataaa aaaatgagta taaccatagg ttttgaacaa atttccttac   2880

atttttcata caaaaatcat aaatatctgt atgctattga aatttaactt tgtatgatgc   2940

ttaaaaacca ctatttgggg aaataataaa ataagtcttt accatgtatg aaagaaattt   3000

taaaaaatac aaaatatttt ctgattagca tctagcttat aataaatttt caaaaaagct   3060

gaaggcaaaa atgccttcat caggatgcac tgagaactat atagttacgt cctgcttttt   3120

gtataaactg agatgctcac atgcttcccc ttagaacagg caatgtgcta tgcataacat   3180

agttgtacat tatctttgcg gttgctttga gttttatttt ttattattta aaattgtagt   3240

tataaaattt ttcagtatag tacagtacat atactgtgag gcgcgtgcta aagtgaataa   3300

gcgagttttc atgctgaccc actcaatgct attcagaaat caattggctt agcactttct   3360

catatcctta ggtgcattta gattgccaga gttaaccttc tgcgtttaaa aaaagaaaaa   3420

cactaaaaaa taaaatacat gtatatactt aaaaaaaaat aataaggttt ccctcaaggg   3480

aaaacagcag ctacatgctt ctttcctata ctactgtagc aaaccaaggc attgatgaga   3540

gggcatgcaa attgtgcttc actttacagt gttttatcag agcacttaat aaaatgtaag   3600

gctggtattt atttgaagtt gtacagtatg acttaattca catctgttgg aatagaaaat   3660

atattctgtt gagtatttaa gaggctgtac atgttttctt ttgtgtttgg attctttgta   3720

ctttttcatg ttcagtacat caataaacaa agttgaaggg aaaaaaaaa               3769
```

<210> SEQ ID NO 7
<211> LENGTH: 3814
<212> TYPE: DNA
<213> ORGANISM: Homo sapiens

<400> SEQUENCE: 7

```
caataggagg gtagtctctc cgtcttttta aactcttttt taagtttccc ctcccctttc     60

atattttttt tcgccatttc ttttagcatt ggactttggg gtcgaaagcg tttcttttta    120
```

-continued

```
tttgcttctt ttaagccgag cacagtttag gtttcgtgct gtcttaagag aactatccag    180
cagcttcttg ctcatcctta ttgggagaac tgcaccgtta ctttaaaaac acacatacac    240
aaaaacctta agggagaaag caggtaattg ctgccatgga aacacaactg tctaatgggc    300
caacttgcaa taacacagcc aatggtccaa ccaccataaa caacaactgt tcgtcaccag    360
ttgactctgg gaacacagaa gacagcaaga ccaacttaat agtcaactac cttcctcaga    420
acatgacaca ggaggaacta aagagtctct ttgggagcat tggtgaaata gagtcctgta    480
agcttgtaag agacaaaata acagggcaga gcttgggata tggctttgtg aactacattg    540
accccaagga tgcagagaaa gctatcaaca ccctgaatgg attgagactt caaaccaaaa    600
caataaaagt ttcctatgct cgcccaagtt cagcttctat cagagatgca aatttatatg    660
tcagcggact tccaaaaaca atgacccaga aggagttgga acagcttttt tcacaatatg    720
gacgcattat tacttctcgt attcttgtcg accaggtcac tggcatatca aggggtgtag    780
ggtttattcg atttgacaag cgaattgagg cagaagaagc tatcaaaggc ctaaatggcc    840
agaaacctcc cggtgccacg gagccaatca ctgtaaagtt tgctaataac ccaagccaaa    900
aaaccaatca ggccatcctt tcccagctgt accagtctcc aaacagaagg tatccaggac    960
cgctagctca gcaggcacag cgttttaggt tggacaatct gctcaatatg gcttatggag   1020
taaagaggtt ttctccaatg accattgacg gaatgaccag tttggctgga attaatatcc   1080
ctgggcaccc tggaacaggg tggtgtatat ttgtgtacaa cctggctcct gacgcagatg   1140
agagtatcct gtggcaaatg tttgggcctt ttggagctgt caccaatgtg aaggtcatcc   1200
gtgactttaa caccaataaa tgcaaaggtt ttggatttgt gactatgaca aactatgatg   1260
aggctgccat ggcgatagct agcctcaatg gataccgtct gggagacaga gtactgcagg   1320
tctcctttaa gacaaacaaa acgcacaaag cctaatgagc tcttgtcctc agtccattta   1380
tatatgaaaa ctatacaaca aaggcaagtt aagagaaact ttatacatta gtaaatgtct   1440
ttgtaagtca gtgttgagat ggggataaaa tgactactta gcatcctaag aaatatgtga   1500
gatttttat tgctagtatt tgaattaaaa cttcttaaat atcttttatg tttgaatatg   1560
gacaagaggt acagggtttt tacctgtcac attgcattct attgccttct ttgaagaagg   1620
tggacctttt aaagtgtttc agctaaggga agacatttct tttcttttta cataactgcc   1680
ttgaacctgt gagtaaatat tgaggctttg tgttgtaatt cttcagttgg ttgtgtcttt   1740
tttttccccc cttttttttcc tttttctgat tagctttgtg tttggtttac atttaaagca   1800
ttgctgttat gtctgtttaa gaaaagtatt ttgaagttta catttttatt tatgaagttt   1860
aaaacagtat ttattttgta attatgattt gggttgggga aggggggggct acattataaa   1920
cgcttattgt aagaatactg gagaactttt cgtaaagcag taccttgcca aagagataag   1980
agcctctttg atgtgggttt aaaaaaagca tctattttta taaaaaagaa aatttggaga   2040
aactttttac tggtcctgga acaaatattt tgacttgaat actttgagaa atctcttcat   2100
atgacaccta gtgagctttt aaaatttacc aggaaattg cagcggttgg aaaatttaga   2160
aagatttatg gtgtagaaaa tacttttgag atctttgtat gaaaggagta gaatcaatgg   2220
ggggaaacac tgctggtttc atttttgtaa tcaccagtgg agcgtctgat catcctggtt   2280
attatgtgat aggtggctca cattgatttg tgattttgaa acaaataaaa aaaatttaca   2340
aaagaatata taagagcagg caagaaattt aaattaccga gagatggggg aaaaaatctg   2400
ttcttcctaa agaaatccct tcagatagag ctcatggtgt ttagtgatgt acttgcagta   2460
ttgtttgaag aattgttttg tcttaaggaa aaaagacgtt gcacatgatt tgtactgcag   2520
```

```
caaatcagca aaagtgatct gagttggata tatttgaagg tattttgaaa gttacgttca   2580
aggctaacac ctgagctttg tgtaatgtaa ataagacctt gtgtttatga acctttcagc   2640
taatttaatt ttttttccct tacatgccaa gtgatgttca ggttttgaat gtttttgtat   2700
cagtttttc ctttgtaaat ggcattaaca ttgttacttg aggtcttgct taatcacttt   2760
tgttgtcctg aggacttgaa tttacagtgc atcagatttg ttgcaaattt tgtctgtaga   2820
tagtctagct tcagctgttt atggtgatgc tacattttcg tttataaata tgtttgtggt   2880
ataaaaaaat gagtataacc ataggttttg aacaaatttc cttacatttt tcatacaaaa   2940
atcataaata tctgtatgct attgaaattt aactttgtat gatgcttaaa aaccactatt   3000
tggggaaata ataaaataag tctttaccat gtatgaaaga aattttaaaa aatacaaaat   3060
attttctgat tagcatctag cttataataa attttcaaaa aagctgaagg caaaaatgcc   3120
ttcatcagga tgcactgaga actatatagt tacgtcctgc tttttgtata aactgagatg   3180
ctcacatgct tccccttaga acaggcaatg tgctatgcat aacatagttg tacattatct   3240
ttgcggttgc tttgagtttt atttttatt atttaaaatt gtagttataa aatttttcag   3300
tatagtacag tacatatact gtgaggcgcg tgctaaagtg aataagcgag ttttcatgct   3360
gacccactca atgctattca gaaatcaatt ggcttagcac tttctcatat ccttaggtgc   3420
atttagattg ccagagttaa ccttctgcgt ttaaaaaaag aaaaacacta aaaaataaaa   3480
tacatgtata tacttaaaaa aaaataataa ggtttccctc aagggaaaac agcagctaca   3540
tgcttctttc ctatactact gtagcaaacc aaggcattga tgagagggca tgcaaattgt   3600
gcttcacttt acagtgtttt atcagagcac ttaataaaat gtaaggctgg tatttatttg   3660
aagttgtaca gtatgactta attcacatct gttggaatag aaaatatatt ctgttgagta   3720
tttaagaggc tgtacatgtt ttcttttgtg tttggattct ttgtactttt tcatgttcag   3780
tacatcaata aacaaagttg aagggaaaaa aaaa                              3814
```

<210> SEQ ID NO 8
<211> LENGTH: 2130
<212> TYPE: DNA
<213> ORGANISM: Homo sapiens

<400> SEQUENCE: 8

```
agttaagggc ctggcgtctc cctccctgaa gacgtggtcc cagccgggtg tcctgacgct     60
cggggttcag gacaagggca cacaactggt tccgttaagc cctctctcg ctcagacgcc    120
atggagctgg atctgtctcc acctcatctt agcagctctc cggaagacct ttgcccagcc    180
cctgggaccc ctcctgggac tccccggccc cctgataccc ctctgcctga ggaggtaaag    240
aggtcccagc ctctcctcat cccaaccacc ggcaggaaac ttcgagagga ggagaggcgt    300
gccacctccc tcccctctat ccccaacccc ttccctgagc tctgcagtcc tccctcacag    360
agcccaattc tcgggggccc ctccagtgca agggggctgc tcccccgcga tgccagccgc    420
ccccatgtag taaaggtgta cagtgaggat ggggcctgca ggtctgtgga ggtggcagca    480
ggtgccacag ctcgccacgt gtgtgaaatg ctggtgcagc gagctcacgc cttgagcgac    540
gagacctggg ggctggtgga gtgccacccc cacctagcac tggagcgggg tttggaggac    600
cacgagtccg tggtggaagt gcaggctgcc tggcccgtgg gcggagatag ccgcttcgtc    660
ttccggaaaa acttcgccaa gtacgaactg ttcaagagct ccccacactc cctgttccca    720
gaaaaaatgg tctccagctg tctcgatgca cacactggta tatcccatga agacctcatc    780
```

```
cagaacttcc tgaatgctgg cagctttcct gagatccagg gctttctgca gctgcggggt    840
tcaggacgga agctttggaa acgctttttc tgcttcttgc gccgatctgg cctctattac    900
tccaccaagg gcacctctaa ggatccgagg cacctgcagt acgtggcaga tgtgaacgag    960
tccaacgtgt acgtggtgac gcagggccgc aagctctacg ggatgcccac tgacttcggt   1020
ttctgtgtca agcccaacaa gcttcgaaat ggccacaagg ggcttcggat cttctgcagt   1080
gaagatgagc agagccgcac ctgctggctg gctgccttcc gcctcttcaa gtacggggtg   1140
cagctgtaca agaattacca gcaggcacag tctcgccatc tgcatccatc ttgtttgggc   1200
tccccaccct tgagaagtgc ctcagataat accctggtgg ccatggactt ctctggccat   1260
gctgggcgtg tcattgagaa cccccgggag gctctgagtg tggccctgga ggaggcccag   1320
gcctggagga agaagacaaa ccaccgcctc agcctgccca tgccagcctc cggcacgagc   1380
ctcagtgcag ccatccaccg cacccaactc tggttccacg ggcgcatttc ccgtgaggag   1440
agccagcggc ttattggaca gcagggcttg gtagacggcc tgttcctggt ccgggagagt   1500
cagcggaacc cccagggctt tgtcctctct ttgtgccacc tgcagaaagt gaagcattat   1560
ctcatcctgc cgagcgagga ggagggccgc ctgtacttca gcatggatga tggccagacc   1620
cgcttcactg acctgctgca gctcgtggag ttccaccagc tgaaccgcgg catcctgccg   1680
tgcttgctgc gccattgctg cacgcgggtg gccctctgac caggccgtgg actggctcat   1740
gcctcagccc gccttcaggc tgcccgccgc ccctccaccc atccagtgga ctctggggcg   1800
cggccacagg ggacgggatg aggagcggga gggttccgcc actccagttt tctcctctgc   1860
ttctttgcct ccctcagata gaaaacagcc cccactccag tccactcctg acccctctcc   1920
tcaagggaag gccttgggtg gcccccctctc cttctcctag ctctggaggt gctgctctag   1980
ggcagggaat tatgggagaa gtgggggcag cccaggcggt ttcacgcccc acactttgta   2040
cagaccgaga ggccagttga tctgctctgt tttatactag tgacaataaa gattattttt   2100
tgatacaaaa aaaaaaaaaa aaaaaaaaaa                                     2130
```

```
<210> SEQ ID NO 9
<211> LENGTH: 2214
<212> TYPE: DNA
<213> ORGANISM: Homo sapiens

<400> SEQUENCE: 9

tgcgggctgc ggggagatgt ggggagggcc ccctccactt tggagggcag tgaaggagag     60
ggatcctcta aattgtcgag gcttcatctc tccagattgt atgcccttct cagcaacacc    120
gcctccggcc ctccgatggg aaagtggagg ccgggacaag ggcacacaac tggttccgtt    180
aagcccctct ctcgctcaga cgccatggag ctggatctgt ctccacctca tcttagcagc    240
tctccggaag acctttgccc agcccctggg acccctcctg ggactccccg gcccccctgat    300
acccctctgc ctgaggaggt aaagaggtcc cagcctctcc tcatcccaac caccggcagg    360
aaacttcgag aggaggagag gcgtgccacc tccctcccct ctatccccaa ccccttccct    420
gagctctgca gtcctccctc acagagccca attctcgggg gcccctccag tgcaaggggg    480
ctgctccccc gcgatgccag ccgcccccat gtagtaaagg tgtacagtga ggatggggcc    540
tgcaggtctg tggaggtggc agcaggtgcc acagctcgcc acgtgtgtga aatgctggtg    600
cagcgagctc acgccttgag cgacgagacc tgggggctgg tggagtgcca cccccaccta    660
gcactggagc ggggtttgga ggaccacgag tccgtggtgg aagtgcaggc tgcctggccc    720
gtgggcggag atagccgctt cgtcttccgg aaaaacttcg ccaagtacga actgttcaag    780
```

```
agctccccac actccctgtt cccagaaaaa atggtctcca gctgtctcga tgcacacact    840
ggtatatccc atgaagacct catccagaac ttcctgaatg ctggcagctt tcctgagatc    900
cagggctttc tgcagctgcg gggttcagga cggaagcttt ggaaacgctt tttctgcttc    960
ttgcgccgat ctggcctcta ttactccacc aagggcacct ctaaggatcc gaggcacctg   1020
cagtacgtgg cagatgtgaa cgagtccaac gtgtacgtgg tgacgcaggg ccgcaagctc   1080
tacgggatgc ccactgactt cggtttctgt gtcaagccca acaagcttcg aaatggccac   1140
aaggggcttc ggatcttctg cagtgaagat gagcagagcc gcacctgctg gctggctgcc   1200
ttccgcctct tcaagtacgg ggtgcagctg tacaagaatt accagcaggc acagtctcgc   1260
catctgcatc catcttgttt gggctcccca cccttgagaa gtgcctcaga taataccctg   1320
gtggccatgg acttctctgg ccatgctggg cgtgtcattg agaacccccg ggaggctctg   1380
agtgtggccc tggaggaggc ccaggcctgg aggaagaaga caaaccaccg cctcagcctg   1440
cccatgccag cctccggcac gagcctcagt gcagccatcc accgcaccca actctggttc   1500
cacgggcgca tttcccgtga ggagagccag cggcttattg gacagcaggg cttggtagac   1560
ggcctgttcc tggtccggga gagtcagcgg aacccccagg gctttgtcct ctctttgtgc   1620
cacctgcaga aagtgaagca ttatctcatc ctgccgagcg aggaggaggg ccgcctgtac   1680
ttcagcatgg atgatggcca gacccgcttc actgacctgc tgcagctcgt ggagttccac   1740
cagctgaacc gcggcatcct gccgtgcttg ctgcgccatt gctgcacgcg ggtggccctc   1800
tgaccaggcc gtggactggc tcatgcctca gcccgccttc aggctgcccg ccgcccctcc   1860
acccatccag tggactctgg ggcgcggcca caggggacgg gatgaggagc gggagggttc   1920
cgccactcca gttttctcct ctgcttcttt gcctccctca gatagaaaac agcccccact   1980
ccagtccact cctgacccct ctcctcaagg gaaggccttg ggtggccccc tctccttctc   2040
ctagctctgg aggtgctgct ctagggcagg gaattatggg agaagtgggg gcagcccagg   2100
cggtttcacg ccccacactt tgtacagacc gagaggccag ttgatctgct ctgttttata   2160
ctagtgacaa taaagattat tttttgatac aaaaaaaaaa aaaaaaaaaa aaaa         2214

<210> SEQ ID NO 10
<211> LENGTH: 2275
<212> TYPE: DNA
<213> ORGANISM: Homo sapiens

<400> SEQUENCE: 10

aggcaaaccc cagccttgga ctggccctct ctgatctctg aggccaggct ctaatgtgat     60
ttgaatctac ttctaacccc ttccaagcac tgccctcccg aattctctgc tcctctcccc    120
accccactgt tggtctgtga tttcgaggca ggcgtggccc cctgcagcct ggaatgaagt    180
cactggggct gtttggagac cggggctgtt tggaggacaa gggcacacaa ctggttccgt    240
taagcccctc tctcgctcag acgccatgga gctggatctg tctccacctc atcttagcag    300
ctctccggaa gacctttgcc cagcccctgg gacccctcct gggactcccc ggcccccctga    360
tacccctctg cctgaggagg taaagaggtc ccagcctctc ctcatcccaa ccaccggcag    420
gaaacttcga gaggaggaga ggcgtgccac ctccctcccc tctatcccca accccttccc    480
tgagctctgc agtcctccct cacagagccc aattctcggg ggcccctcca gtgcaagggg    540
gctgctcccc cgcgatgcca gccgccccca tgtagtaaag gtgtacagtg aggatggggc    600
ctgcaggtct gtggaggtgg cagcaggtgc cacagctcgc cacgtgtgtg aaatgctggt    660
```

```
gcagcgagct cacgccttga gcgacgagac ctgggggctg gtggagtgcc acccccacct    720

agcactggag cggggtttgg aggaccacga gtccgtggtg gaagtgcagg ctgcctggcc    780

cgtgggcgga gatagccgct tcgtcttccg gaaaaacttc gccaagtacg aactgttcaa    840

gagctcccca cactccctgt tcccagaaaa aatggtctcc agctgtctcg atgcacacac    900

tggtatatcc catgaagacc tcatccagaa cttcctgaat gctggcagct ttcctgagat    960

ccagggcttt ctgcagctgc ggggttcagg acggaagctt tggaaacgct ttttctgctt   1020

cttgcgccga tctggcctct attactccac caagggcacc tctaaggatc cgaggcacct   1080

gcagtacgtg gcagatgtga acgagtccaa cgtgtacgtg gtgacgcagg gccgcaagct   1140

ctacgggatg cccactgact tcggtttctg tgtcaagccc aacaagcttc gaaatggcca   1200

caaggggctt cggatcttct gcagtgaaga tgagcagagc cgcacctgct ggctggctgc   1260

cttccgcctc ttcaagtacg gggtgcagct gtacaagaat taccagcagg cacagtctcg   1320

ccatctgcat ccatcttgtt tgggctcccc acccttgaga agtgcctcag ataataccct   1380

ggtggccatg gacttctctg gccatgctgg gcgtgtcatt gagaaccccc gggaggctct   1440

gagtgtggcc ctggaggagg cccaggcctg gaggaagaag acaaaccacc gcctcagcct   1500

gcccatgcca gcctccggca cgagcctcag tgcagccatc caccgcaccc aactctggtt   1560

ccacgggcgc atttcccgtg aggagagcca gcggcttatt ggacagcagg gcttggtaga   1620

cggcctgttc ctggtccggg agagtcagcg gaacccccag ggctttgtcc tctctttgtg   1680

ccacctgcag aaagtgaagc attatctcat cctgccgagc gaggaggagg gccgcctgta   1740

cttcagcatg gatgatggcc agacccgctt cactgacctg ctgcagctcg tggagttcca   1800

ccagctgaac cgcggcatcc tgccgtgctt gctgcgccat tgctgcacgc gggtggccct   1860

ctgaccaggc cgtggactgg ctcatgcctc agcccgcctt caggctgccc gccgcccctc   1920

cacccatcca gtggactctg gggcgcggcc acaggggacg ggatgaggag cgggagggtt   1980

ccgccactcc agttttctcc tctgcttctt tgcctccctc agatagaaaa cagcccccac   2040

tccagtccac tcctgacccc tctcctcaag ggaaggcctt gggtggcccc ctctccttct   2100

cctagctctg gaggtgctgc tctagggcag ggaattatgg gagaagtggg ggcagcccag   2160

gcggtttcac gccccacact ttgtacagac cgagaggcca gttgatctgc tctgttttat   2220

actagtgaca ataaagatta tttttgata caaaaaaaaa aaaaaaaaaa aaaaa        2275
```

<210> SEQ ID NO 11
<211> LENGTH: 2285
<212> TYPE: DNA
<213> ORGANISM: Homo sapiens

<400> SEQUENCE: 11

```
acccgccccc atctgcccaa gataatttta gtttccttgg gcctggaatc tggacacaca     60

gggctccccc ccgcctctga cttctctgtc cgaagtcggg acaccctcct accacctgta    120

gagaagcggg agtggatctg aaataaaatc caggaatctg gggttcccta gacggagcca    180

gacttcggaa cgggtgtcct gctactcctg ctggggctcc tccaggacaa gggcacacaa    240

ctggttccgt taagcccctc tctcgctcag acgccatgga gctggatctg tctccacctc    300

atcttagcag ctctccggaa gacctttgcc cagcccctgg gaccccctcct gggactcccc    360

ggcccccctga taccctctg cctgaggagg taaagaggtc ccagcctctc ctcatcccaa    420

ccaccggcag gaaacttcga gaggaggaga ggcgtgccac ctccctcccc tctatcccca    480

acccccttccc tgagctctgc agtcctccct cacagagccc aattctcggg ggcccctcca    540
```

```
gtgcaagggg gctgctcccc cgcgatgcca gccgccccca tgtagtaaag gtgtacagtg    600
aggatggggc ctgcaggtct gtggaggtgg cagcaggtgc cacagctcgc cacgtgtgtg    660
aaatgctggt gcagcgagct cacgccttga gcgacgagac ctgggggctg gtggagtgcc    720
accccccacct agcactggag cggggtttgg aggaccacga gtccgtggtg gaagtgcagg    780
ctgcctggcc cgtgggcgga gatagccgct tcgtcttccg gaaaaacttc gccaagtacg    840
aactgttcaa gagctcccca cactccctgt tcccagaaaa aatggtctcc agctgtctcg    900
atgcacacac tggtatatcc catgaagacc tcatccagaa cttcctgaat gctggcagct    960
ttcctgagat ccagggcttt ctgcagctgc ggggttcagg acggaagctt tggaaacgct   1020
ttttctgctt cttgcgccga tctggcctct attactccac caagggcacc tctaaggatc   1080
cgaggcacct gcagtacgtg gcagatgtga acgagtccaa cgtgtacgtg gtgacgcagg   1140
gccgcaagct ctacgggatg cccactgact tcggtttctg tgtcaagccc aacaagcttc   1200
gaaatggcca caaggggctt cggatcttct gcagtgaaga tgagcagagc cgcacctgct   1260
ggctggctgc cttccgcctc ttcaagtacg gggtgcagct gtacaagaat taccagcagg   1320
cacagtctcg ccatctgcat ccatcttgtt tgggctcccc acccttgaga agtgcctcag   1380
ataataccct ggtggccatg gacttctctg gccatgctgg gcgtgtcatt gagaaccccc   1440
gggaggctct gagtgtggcc ctggaggagg cccaggcctg gaggaagaag acaaaccacc   1500
gcctcagcct gcccatgcca gcctccggca cgagcctcag tgcagccatc caccgcaccc   1560
aactctggtt ccacgggcgc atttcccgtg aggagagcca gcggcttatt ggacagcagg   1620
gcttggtaga cggcctgttc ctggtccggg agagtcagcg gaacccccag ggctttgtcc   1680
tctctttgtg ccacctgcag aaagtgaagc attatctcat cctgccgagc gaggaggagg   1740
gccgcctgta cttcagcatg gatgatggcc agacccgctt cactgacctg ctgcagctcg   1800
tggagttcca ccagctgaac cgcggcatcc tgccgtgctt gctgcgccat tgctgcacgc   1860
gggtggccct ctgaccaggc cgtggactgg ctcatgcctc agcccgcctt caggctgccc   1920
gccgcccctc cacccatcca gtggactctg gggcgcggcc acaggggacg ggatgaggag   1980
cgggagggtt ccgccactcc agttttctcc tctgcttctt tgcctccctc agatagaaaa   2040
cagcccccac tccagtccac tcctgacccc tctcctcaag ggaaggcctt gggtggcccc   2100
ctctccttct cctagctctg gaggtgctgc tctagggcag ggaattatgg gagaagtggg   2160
ggcagcccag gcggtttcac gccccacact ttgtacagac cgagaggcca gttgatctgc   2220
tctgttttat actagtgaca ataaagatta ttttttgata caaaaaaaaa aaaaaaaaaa   2280
aaaaa                                                               2285
```

<210> SEQ ID NO 12
<211> LENGTH: 914
<212> TYPE: DNA
<213> ORGANISM: Homo sapiens

<400> SEQUENCE: 12

```
gcatggggag gggcggccct caaacgggtc attgccatta atagagacct caaacaccgc     60
ctgctaaaaa tacccgactg gaggagcata aaagcgcagc cgagcccagc gccccgcact    120
tttctgagca gacgtccaga gcagagtcag ccagcatgac cgagcgccgc gtccccttct    180
cgctcctgcg gggccccagc tgggacccct tccgcgactg gtacccgcat agccgcctct    240
tcgaccaggc cttcgggctg ccccggctgc cggaggagtg gtcgcagtgg ttaggcggca    300
```

```
gcagctggcc aggctacgtg cgccccctgc cccccgccgc catcgagagc cccgcagtgg    360

ccgcgcccgc ctacagccgc gcgctcagcc ggcaactcag cagcggggtc tcggagatcc    420

ggcacactgc ggaccgctgg cgcgtgtccc tggatgtcaa ccacttcgcc ccggacgagc    480

tgacggtcaa gaccaaggat ggcgtggtgg agatcaccgg caagcacgag gagcggcagg    540

acgagcatgg ctacatctcc cggtgcttca cgcggaaata cacgctgccc cccggtgtgg    600

accccaccca agtttcctcc tccctgtccc ctgagggcac actgaccgtg gaggccccca    660

tgcccaagct agccacgcag tccaacgaga tcaccatccc agtcaccttc gagtcgcggg    720

cccagcttgg gggcccagaa gctgcaaaat ccgatgagac tgccgccaag taaagcctta    780

gcccggatgc ccacccctgc tgccgccact ggctgtgcct cccccgccac ctgtgtgttc    840

ttttgataca tttatcttct gtttttctca aataaagttc aaagcaacca cctgtcaaaa    900

aaaaaaaaaa aaaa                                                      914
```

<210> SEQ ID NO 13
<211> LENGTH: 3262
<212> TYPE: DNA
<213> ORGANISM: Homo sapiens

<400> SEQUENCE: 13

```
agagtgctcc gcggccgtgt ggagcgaggc cttgttcccg cgttgagccg ccgccgccgc     60

cgccgcctcc tcagcttcag cctccgcgcc aggcccggcc ccgccgcgcc atgtcggact    120

acagcacggg aggacccccg cccgggccgc cgccgcccgc cggcgggggc gggggagccg    180

gaggcgccgg gggaggccct ccgccgggcc cgccaggcgc gggggaccgg ggcggcggcg    240

gtcccggcgg cggcggcccg ggcgggggt cggccgggg ccccctctcag ccacccggcg    300

gaggcggccc gggaatccgc aaggacgctt tcgccgacgc cgtgcagcgg gcccgccaga    360

ttgcagccaa aattggaggc gatgctgcca cgacagtgaa taacagcact cctgattttg    420

gttttggggg ccaaaagaga cagttggaag atggagatca accggagagc aagaagctgg    480

cttcccaggg agactcaatc agttctcaac ttggacccat ccatcctccc ccaaggactt    540

caatgacaga agagtacagg gtcccagacg gcatggtggg cctgatcatt ggcagaggag    600

gtgaacaaat taacaaaatc caacaggatt caggctgcaa agtacagatt tctccagaca    660

gcggtggcct acccgagcgc agtgtgtcct tgacaggagc cccagaatct gtccagaaag    720

ccaagatgat gctggatgac attgtgtctc ggggtcgtgg gggcccccca ggacagttcc    780

acgacaacgc caacgggggc cagaacggca ccgtgcagga gatcatgatc cccgcgggca    840

aggccggcct ggtcattggc aagggcgggg agaccattaa gcagctgcag gaacgcgctg    900

gagtgaagat gatcttaatt caggacggat ctcagaatac gaatgtggac aaacctctcc    960

gcatcattgg ggatccttac aaagtgcagc aagcctgtga gatggtgatg gacatcctcc   1020

gggaacgtga ccaaggcggc tttggggacc ggaatgagta cggatctcgg attggcggag   1080

gcatcgatgt gccagtgccc aggcattctg ttggcgtggt cattggccgg agtggagaga   1140

tgatcaagaa gatccagaat gatgctggcg tgcggataca gttcaagcaa gatgacggga   1200

cagggcccga gaagattgct catataatgg ggcccccaga caggtgcgag cacgcagccc   1260

ggatcatcaa cgacctcctc cagagcctca ggagtggtcc cccaggtcct ccagggggtc   1320

caggcatgcc cccgggggc cgaggccgag gaagaggcca aggcaattgg ggtccccctg   1380

gcggggagat gaccttctcc atccccactc acaagtgtgg gctggtcatc ggccgaggtg   1440

gcgagaatgt gaaagccata aaccagcaga cgggagcctt cgtagagatc tcccggcagc   1500
```

```
tgccacccaa cggggacccc aacttcaagt tgttcatcat ccggggttca ccccagcaga   1560
ttgaccacgc caagcagctt atcgaggaaa agatcgaggg tcctctctgc ccagttggac   1620
caggcccagg tggcccaggc cctgctggcc caatggggcc cttcaatcct gggcccttca   1680
accaggggcc acccggggct cccccacatg ccggggggcc ccctcctcac cagtacccac   1740
cccagggctg gggcaatacc tacccccagt ggcagccgcc tgctcctcat gacccaagca   1800
aagcagctgc agcggccgcg gaccccaacg ccgcgtgggc cgcctactac tcacactact   1860
accagcagcc cccgggcccc gtccccggcc ccgcaccggc cctgcggccc ccaccggctc   1920
agggtgagcc ccctcagccc ccacccaccg gccagtcgga ctacactaag gcctgggaag   1980
agtattacaa aaagatcggc cagcagcccc agcagcccgg agcacccccca cagcaggact   2040
acacgaaggc ttgggaggag tactacaaga agcaagcgca agtggccacc ggagggggtc   2100
caggagctcc cccaggctcc cagccagact acagtgccgc ctgggcggaa tattacagac   2160
agcaggccgc ttactacgga cagaccccag gtcctggcgg cccccagccg ccgcccacgc   2220
agcagggaca gcagcaggct caatgaatcg aatgaatgtg aacttcttca tctgtgaaaa   2280
atcttttttt tttccatttt gttctgtttg ggggcttctg ttttgtttgg cgagagagcg   2340
atggctgccg tggggagtac tggggagccc tcgcggcaag cagggtgggg gggacttggg   2400
ggcatgccgg gccctcactc tctcgcctgt tctgtgtctc acatgctttt tctttcaaaa   2460
ttgggatcct tccatgttga gccagccaga gaagatagcg agatctaaat ctctgccaaa   2520
aaaaaaaaaa aacttaaaaa ttaaaaacac aaagagcaaa gcagaactta taaaattata   2580
tatatatata ttaaaaagtc tctattcttc accccccagc cttcctgaac ctgcctctct   2640
gaggataaag caattcattt tctcccaccc tcggccctct tgtttttaaa ataaactttt   2700
aaaaaggaaa aaaaaaagtc actcttgcta tttctttttt ttagttagag gtggaacatt   2760
ccttggacca ggtgttgtat tgcaggaccc cttcccccag cagccaagcc ccctcttctc   2820
tccctcccgc cctggctcag ctcccgcggc cccgcccgtc ccccctccca ggactggtct   2880
gttgtctttt catctgttca agaggagatt gaaactgaaa acaaaatgag aacaacaaaa   2940
aaaattgtat ggcagttttt actttttatc gctcgttttt aacttcacaa ataaatgata   3000
acaaaacctc cccgtctgcg ggtgctgtct gtctcccccc ctttccttcc ctccctgtag   3060
ttttgaagcg gatgtttgtt ctttatagat gttgtttaaa aagcctgata atggtgattg   3120
aaatttacaa actttgtgtt tttttttttt taagaaaaat ataaaatagt tttcttcagg   3180
ctcaatgtgc tttcctaacc gtgccccccc ccctttttttt tttttgttaa ataaagtgct   3240
ttttgtttaa aaaaaaaaaa aa                                          3262
```

```
<210> SEQ ID NO 14
<211> LENGTH: 3918
<212> TYPE: DNA
<213> ORGANISM: Homo sapiens

<400> SEQUENCE: 14

ctctcccttc tccactctct ccccctgtct cctttcttct tcttctttca ccctccgtct     60
ctcacacccc ctccattccc ctgtctcctt tctgacactg cactgcagct gctcctcagc    120
cctgccccct ccccagtgag aacaaaccag caacattgct tttttcccta aagagattta    180
tattgatccg attaaaaaaa aaaaacctta agaaacccca aacgcaaaaa aaaaaaaaaa    240
aaaaaaagaa aaaagaaaag aaaaagccaa aacaaaaggg agaaccttct cccggtagca    300
```

-continued

```
gcggcaggaa ctgcaaacat gatggcggca gctcccatcc agcagaacgg gacccacact    360
ggggttccca tagacctgga cccgccggac tcgcggaaaa ggccgctgga agccccccct    420
gaagccggca gcaccaagag gaccaatacg ggcgaagacg gccagtattt tctaaaggtt    480
ctcataccta gttatgctgc tggatctata attgggaagg gaggacagac aattgttcag    540
ttgcaaaaag aaactggagc caccatcaag ctgtctaagt ccaaagattt ttacccaggt    600
actactgagc gagtgtgctt gatccaggga acggttgaag cactgaatgc agttcatgga    660
ttcattgcag aaaaaattcg agaaatgccc caaaatgtgg ccaagacaga accagtcagc    720
attctacaac cccagaccac cgttaatcca gatcgcatca aacaaacatt gccatcttcc    780
ccaactacca ccaagtcctc tccatctgat cccatgacca cctccagagc taatcaggta    840
aagattatag ttcccaacag cacagcaggt ctgataatag ggaagggagg tgctactgtg    900
aaggctgtaa tggagcagtc agggggcttgg gtgcagcttt cccagaaacc tgatgggatc   960
aacttgcaag agagggttgt cactgtgagt ggagaacctg aacaaaaccg aaaagctgtt   1020
gaacttatca tccagaagat acaagaggat ccacaaagtg gcagctgtct caatatcagt   1080
tatgccaatg tgacaggtcc agtggcaaat tccaatccaa ccggatctcc ttatgcaaac   1140
actgctgaag tgttaccaac tgctgcagca gctgcagggc tattaggaca tgctaacctt   1200
gctggcgttg cagcctttcc agcagtttta tctggcttca caggcaatga cctggtggcc   1260
atcacctctg cacttaatac attagccagc tatggatata atctcaacac tttaggttta   1320
ggtctcagtc aagcagcagc aacaggggct ttggctgcag cagctgccag tgccaaccca   1380
gcagcagcag cagccaattt attggccacc tatgccagtg aagcctcagc cagtggcagc   1440
acagctggtg gtacggcggg gacatttgca ttaggtagcc tggctgctgc tactgctgca   1500
accaatggat attttggagc tgcttctccc ctagctgcca gtgccattct aggaacagaa   1560
aagtccacag atggatccaa ggatgtagtt gaaatagcag tgccagaaaa cttagttggt   1620
gcaatacttg gcaaaggagg gaaaacatta gtggaatacc aggagttgac tggtgcaagg   1680
atacagatct ccaaaaaagg agaattcgta cctggcacaa ggaatcggaa ggtaaccatt   1740
actggaacac cagctgcaac acaggctgct caatatttaa ttacacaaag gatcacatat   1800
gagcaaggag ttcgggctgc caatcctcag aaagtgggtt gagtgcccca gttacacatc   1860
agattgtttt aacccctcct ttaccccatt ttcaagaagg atgtactgta ctttgcagaa   1920
gtgaagtttt tctgttatta atatataatt atgcaaatga atgcgactat gttgacaatg   1980
tgtatatgta aataatatgt gttttaccag atgtttcata gaaagaattt tttcttgatc   2040
tgttttgttc tctatacttt gcttgtgtat atttgtcaga ggtgtttcta gtgtaagatt   2100
taagcctgcc attttaccag cattattgta gtttaatgat tgaatgtaga cagggatatg   2160
cgtatagttt tcagtattag ttctagataa cactaaatta actactgtta ggttgagtat   2220
ggtggggtca gtgacctaaa atggagtgag gccaaagcac tgtcctgtaa gtcttacttc   2280
ctgcttaggg cacagtgaag taggaaacaa tattttgaaa ataagtttta aatttaaaat   2340
gatcaaaaag caatatagtt gcataaaagc actgtaaaat atttaaaagg ttaaaactgt   2400
ggaaaattat attggtaagt ttacagatca ataaaagcac ctgttctcca tctgaactag   2460
acaatggaaa taatgctgca tgctggccat ggcccattct tcatcatttg taagttcaac   2520
aaaagttctc acatggagtc ccacctcttc agaggtttgt acatttgttt ttaagcactg   2580
aattcactac tgatcccatc gcctggccag tagaacagtc attactccat taacatcctc   2640
actgtttaga cacataactg tggtacagtg tattggaaat tttataaaca aaagtgaaag   2700
```

```
tgccaacaaa ttattgatag ctgataatgt ttcattatct gcaactgctt gataagtatg   2760

ttgcatttta agagcttata attgtgtata atttgttaac actagaaacc tattagtatt   2820

gtgaatgtag attttactgt gaagctatct gtgatttagc tgtttgctcc catgatggag   2880

tctttgcagc atggcgctag cagccaatgc agtttctaat actcggtaat ttgcatgttt   2940

tgtggagcat ttttatgtca ccaaccagac agtatttcct gcatgcttat ttagaagagg   3000

cagcttatct tgagaggtag tgttatctac ctttgtcagg ctttttgaca ggtcatttca   3060

gagtaagcct ttgttcccaa gacccaacaa ctgtcaccct cttctgtacc tctcctgagt   3120

gccaactgtc caggccattt gacacaccat ctgttaacct ctgagtttgc ccactcaagg   3180

ccactcatag gggcatccat ccccaagcac ctcctcatgc tgtgcatgca gtcttaaatt   3240

caatggacaa aaataaaatg ctggctacct ctggatcatc tggctgagca actgaattac   3300

aaaagagaat tacttccatc tcaacttcaa cccattgatt acgtccatcc tagcaagcta   3360

aatggcatcc cagctgctcc tttctgtgca accaattaaa gaacaatgag tgtgatgctc   3420

catgtctgaa tttcgtccag cctctctctg aactgtgatc tttgtcctca tgaactttcc   3480

cttttgttca ttgaactata tggactcttc atttcatatt gatttactgt gcaatttact   3540

tttggacatt gagaacttga aattatttcc tgatcccttc cccttccact attaataatt   3600

catttctgtc aaactgtaag agtagactca tttttttttt tttagttttt aacattggac   3660

tgttatttca tttagagttc tctatctcta aatatttatt tagagaatga ttttaaaagg   3720

gaatgatatg cttgtttaaa tgaaagagaa aagctgtagt aaactgtgtt aattggtaat   3780

gactatttat cgtcgatact ctgtagctgt gtaagttttg acaaatagtg tatctcgtgg   3840

aatcagtggt tagcattgcc gctattatat ttactcattt tatcattata aatgtgctta   3900

gttcatcatg tagcatca                                                 3918
```

<210> SEQ ID NO 15
<211> LENGTH: 3846
<212> TYPE: DNA
<213> ORGANISM: Homo sapiens

<400> SEQUENCE: 15

```
ctctcccttc tccactctct ccccctgtct cctttcttct tcttctttca ccctccgtct     60

ctcacacccc ctccattccc ctgtctcctt tctgacactg cactgcagct gctcctcagc    120

cctgccccct ccccagtgag aacaaaccag caacattgct ttttttccta aagagattta    180

tattgatccg attaaaaaaa aaaaaccttta agaaacccca aacgcaaaaa aaaaaaaaaa    240

aaaaaaagaa aaaagaaaag aaaaagccaa aacaaaaggg agaaccttct cccggtagca    300

gcggcaggaa ctgcaaacat gatggcggca gctcccatcc agcagaacgg gacccacact    360

ggggttccca tagacctgga cccgccggac tcgcggaaaa ggccgctgga agcccccccct    420

gaagccggca gcaccaagag gaccaatacg ggcgaagacg gccagtattt tctaaaggtt    480

ctcataccta gttatgctgc tggatctata attgggaagg gaggacagac aattgttcag    540

ttgcaaaaag aaactggagc caccatcaag ctgtctaagt ccaaagattt ttacccaggt    600

actactgagc gagtgtgctt gatccaggga acggttgaag cactgaatgc agttcatgga    660

ttcattgcag aaaaaattcg agaaatgccc caaaatgtgg ccaagacaga accagtcagc    720

attctacaac cccagaccac cgttaatcca gatcgcatca aacaagtaaa gattatagtt    780

cccaacagca cagcaggtct gataataggg aagggaggtg ctactgtgaa ggctgtaatg    840
```

```
gagcagtcag gggcttgggt gcagctttcc cagaaacctg atgggatcaa cttgcaagag    900
agggttgtca ctgtgagtgg agaacctgaa caaaaccgaa aagctgttga acttatcatc    960
cagaagatac aagaggatcc acaaagtggc agctgtctca atatcagtta tgccaatgtg   1020
acaggtccag tggcaaattc caatccaacc ggatctcctt atgcaaacac tgctgaagtg   1080
ttaccaactg ctgcagcagc tgcagggcta ttaggacatg ctaaccttgc tggcgttgca   1140
gcctttccag cagttttatc tggcttcaca ggcaatgacc tggtggccat cacctctgca   1200
cttaatacat tagccagcta tggatataat ctcaacactt taggtttagg tctcagtcaa   1260
gcagcagcaa caggggcttt ggctgcagca gctgccagtg ccaacccagc agcagcagca   1320
gccaatttat tggccaccta tgccagtgaa gcctcagcca gtggcagcac agctggtggt   1380
acggcgggga catttgcatt aggtagcctg gctgctgcta ctgctgcaac caatggatat   1440
tttggagctg cttctcccct agctgccagt gccattctag gaacagaaaa gtccacagat   1500
ggatccaagg atgtagttga aatagcagtg ccagaaaact tagttggtgc aatacttggc   1560
aaaggaggga aaacattagt ggaataccag gagttgactg gtgcaaggat acagatctcc   1620
aaaaaaggag aattcgtacc tggcacaagg aatcggaagg taaccattac tggaacacca   1680
gctgcaacac aggctgctca atatttaatt acacaaagga tcacatatga gcaaggagtt   1740
cgggctgcca atcctcagaa agtgggttga gtgccccagt tacacatcag attgttttaa   1800
cccctccttt accccatttt caagaaggat gtactgtact ttgcagaagt gaagtttttc   1860
tgttattaat atataattat gcaaatgaat gcgactatgt tgacaatgtg tatatgtaaa   1920
taatatgtgt tttaccagat gtttcataga aagaattttt tcttgatctg ttttgttctc   1980
tatactttgc ttgtgtatat ttgtcagagg tgtttctagt gtaagattta agcctgccat   2040
tttaccagca ttattgtagt ttaatgattg aatgtagaca gggatatgcg tatagttttc   2100
agtattagtt ctagataaca ctaaattaac tactgttagg ttgagtatgg tggggtcagt   2160
gacctaaaat ggagtgaggc caaagcactg tcctgtaagt cttacttcct gcttagggca   2220
cagtgaagta ggaaacaata ttttgaaaat aagttttaaa tttaaaatga tcaaaaagca   2280
atatagttgc ataaaagcac tgtaaaatat ttaaaaggtt aaaactgtgg aaaattatat   2340
tggtaagttt acagatcaat aaaagcacct gttctccatc tgaactagac aatggaaata   2400
atgctgcatg ctggccatgg cccattcttc atcatttgta agttcaacaa aagttctcac   2460
atggagtccc acctcttcag aggtttgtac atttgttttt aagcactgaa ttcactactg   2520
atcccatcgc ctggccagta gaacagtcat tactccatta acatcctcac tgtttagaca   2580
cataactgtg gtacagtgta ttggaaattt tataaacaaa agtgaaagtg ccaacaaatt   2640
attgatagct gataatgttt cattatctgc aactgcttga taagtatgtt gcattttaag   2700
agcttataat tgtgtataat ttgttaacac tagaaaccta ttagtattgt gaatgtagat   2760
tttactgtga agctatctgt gatttagctg tttgctccca tgatggagtc tttgcagcat   2820
ggcgctagca gccaatgcag tttctaatac tcggtaattt gcatgttttg tggagcattt   2880
ttatgtcacc aaccagacag tatttcctgc atgcttattt agaagaggca gcttatcttg   2940
agaggtagtg ttatctacct ttgtcaggct ttttgacagg tcatttcaga gtaagccttt   3000
gttcccaaga cccaacaact gtcaccctct tctgtacctc tcctgagtgc caactgtcca   3060
ggccatttga cacaccatct gttaacctct gagtttgccc actcaaggcc actcataggg   3120
gcatccatcc ccaagcacct cctcatgctg tgcatgcagt cttaaattca atggacaaaa   3180
ataaaatgct ggctacctct ggatcatctg gctgagcaac tgaattacaa aagagaatta   3240
```

```
cttccatctc aacttcaacc cattgattac gtccatccta gcaagctaaa tggcatccca   3300

gctgctcctt tctgtgcaac caattaaaga acaatgagtg tgatgctcca tgtctgaatt   3360

tcgtccagcc tctctctgaa ctgtgatctt tgtcctcatg aactttccct tttgttcatt   3420

gaactatatg gactcttcat ttcatattga tttactgtgc aatttacttt tggacattga   3480

gaacttgaaa ttatttcctg atcccttccc cttccactat taataattca tttctgtcaa   3540

actgtaagag tagactcatt ttttttttt tagtttttaa cattggactg ttatttcatt   3600

tagagttctc tatctctaaa tatttattta gagaatgatt ttaaaaggga atgatatgct   3660

tgtttaaatg aaagagaaaa gctgtagtaa actgtgttaa ttggtaatga ctatttatcg   3720

tcgatactct gtagctgtgt aagttttgac aaatagtgta tctcgtggaa tcagtggtta   3780

gcattgccgc tattatattt actcatttta tcattataaa tgtgcttagt tcatcatgta   3840

gcatca                                                              3846
```

<210> SEQ ID NO 16
<211> LENGTH: 3340
<212> TYPE: DNA
<213> ORGANISM: Homo sapiens

<400> SEQUENCE: 16

```
tgcgggcgtc tccgccattt tgtgagtcta taactcggag ccgttgggtc ggttcctgct     60

attccggcgc ctccactccg tcccccgcgg gtctgctctg tgtgccatgg acggcattgt    120

cccagatata gccgttggta caaagcgggg atctgacgag cttttctcta cttgtgtcac    180

taacggaccg tttatcatga gcagcaactc ggcttctgca gcaaacggaa atgacagcaa    240

gaagttcaaa ggtgacagcc gaagtgcagg cgtcccctct agagtgatcc acatccggaa    300

gctccccatc gacgtcacgg agggggaagt catctccctg ggctgccct ttgggaaggt     360

caccaacctc ctgatgctga aggggaaaaa ccaggccttc atcgagatga acacggagga    420

ggctgccaac accatggtga actactacac ctcggtgacc cctgtgctgc gcggccagcc    480

catctacatc cagttctcca accacaagga gctgaagacc gacagctctc ccaaccaggc    540

gcgggcccag gcggccctgc aggcggtgaa ctcggtccag tcggggaacc tggccttggc    600

tgcctcggcg gcggccgtgg acgcagggat ggcgatggcc gggcagagcc ccgtgctcag    660

gatcatcgtg gagaacctct tctaccctgt gaccctggat gtgctgcacc agattttctc    720

caagttcggc acagtgttga agatcatcac cttcaccaag aacaaccagt tccaggccct    780

gctgcagtat gcggaccccg tgagcgccca gcacgccaag ctgtcgctgg acgggcagaa    840

catctacaac gcctgctgca cgctgcgcat cgacttttcc aagctcacca gcctcaacgt    900

caagtacaac aatgacaaga gccgtgacta cacacgccca gacctgcctt ccggggacag    960

ccagccctcg ctggaccaga ccatggccgc ggccttcggt gcacctggta taatctcagc   1020

ctctccgtat gcaggagctg gtttccctcc cacctttgcc attcctcaag ctgcaggcct   1080

ttccgttccg aacgtccacg gcgccctggc ccccctggcc atcccctcgg cggcggcggc   1140

agctgcggcg gcaggtcgga tcgccatccc gggcctggcg ggggcaggaa attctgtatt   1200

gctggtcagc aacctcaacc cagagagagt cacaccccaa agcctcttta ttcttttcgg   1260

cgtctacggt gacgtgcagc gcgtgaagat cctgttcaat aagaaggaga acgccctagt   1320

gcagatggcg gacggcaacc aggcccagct ggccatgagc cacctgaacg ggcacaagct   1380

gcacgggaag cccatccgca tcacgctctc gaagcaccag aacgtgcagc tgccccgcga   1440
```

gggccaggag gaccagggcc tgaccaagga ctacggcaac tcacccctgc accgcttcaa 1500
gaagccgggc tccaagaact tccagaacat attcccgccc tcggccacgc tgcacctctc 1560
caacatcccg ccctcagtct ccgaggagga tctcaaggtc ctgttttcca gcaatggggg 1620
cgtcgtcaaa ggattcaagt tcttccagaa ggaccgcaag atggcactga tccagatggg 1680
ctccgtggag gaggcggtcc aggccctcat tgacctgcac aaccacgacc tcggggagaa 1740
ccaccacctg cgggtctcct tctccaagtc caccatctag ggcacaggc ccccacggcc 1800 gggcccccctg gcgacaactt ccatcattcc agagaaaagc cactttaaaa acagctgaag 1860
tgaccttagc agaccagaga ttttattttt ttaaagagaa atcagtttac ctgtttttaa 1920
aaaaattaaa tctagttcac cttgctcacc ctgcggtgac agggacagct caggctcttg 1980
gtgactgtgg cagcgggagt tcccggccct ccacacccgg ggccagaccc tcggggccat 2040
gccttggtgg ggcctgtgtc gggcgtgggg cctgcaggtg ggcgccccga ccacgacttg 2100
gcttccttgt gccttaaaaa acctgccttc ctgcagccac acacccaccc ggggtgtcct 2160
ggggacccaa ggggtggggg ggtcacacca gagagaggca gggggcctgg ccggctcctg 2220
caggatcatg cagctggggc gcggcggccg cggctgcgac accccaaccc cagccctcta 2280
atcaagtcac gtgattctcc cttcaccccg cccccagggc cttcccttct gcccccaggc 2340
gggctccccg ctgctccagc tgcggagctg gtcgacataa tctctgtatt atatactttg 2400
cagttgcaga cgtctgtgcc tagcaatatt tccagttgac caaatattct aatctttttt 2460
catttatatg caaaagaaat agttttaagt aactttttat agcaagatga tacaatggta 2520
tgagtgtaat ctaaacttcc ttgtggtatt accttgtatg ctgttacttt tattttattc 2580
cttgtaatta agtcacaggc aggacccagt ttccagagag caggcggggc cgcccagtgg 2640
gtcaggcaca gggagccccg gtcctatctt agagcccctg agcttcaggg aaggggcggg 2700
cgtgtcgccg cctctggcat cgcctccggt tgccttacac cacgccttca cctgcagtcg 2760
cctagaaaac ttgctctcaa acttcagggt tttttcttcc ttcaaatttt ggaccaaagt 2820
ctcatttctg tgttttgcct gcctctgatg ctgggacccg gaaggcgggc gctcctcctg 2880
tcttctctgt gctctttcta ccgcccccgc gtcctgtccc gggggctctc ctaggatccc 2940
ctttccgtaa aagcgtgtaa caagggtgta aatatttata attttttata cctgttgtga 3000
gacccgaggg gcggcggcgc ggttttttat ggtgacacaa atgtatattt tgctaacagc 3060
aattccaggc tcagtattgt gaccgcggag ccacagggga ccccacgcac attccgttgc 3120
cttacccgat ggcttgtgac gcggagagaa ccgattaaaa ccgtttgaga aactcctccc 3180
ttgtctagcc ctgtgttcgc tgtggacgct gtagaggcag gttggccagt ctgtacctgg 3240
acttcgaata aatcttctgt atcctcgctc cgttccgcct taaaaaaaaa aaaaaaaaaa 3300
aaaaaaaaaa aaaaaaaaaa aaaaaaaaaa aaaaaaaaaa 3340

<210> SEQ ID NO 17
<211> LENGTH: 3319
<212> TYPE: DNA
<213> ORGANISM: Homo sapiens

<400> SEQUENCE: 17
tgcgggcgtc tccgccattt tgtgagtcta taactcggag ccgttgggtc ggttcctgct 60
attccggcgc ctccactccg tcccccgcgg gtctgctctg tgtgccatgg acggcattgt 120
cccagatata gccgttggta caaagcgggg atctgacgag cttttctcta cttgtgtcac 180
taacggaccg tttatcatga gcagcaactc ggcttctgca gcaaacggaa atgacagcaa 240
gaagttcaaa ggtgacagcc gaagtgcagg cgtcccctct agagtgatcc acatccggaa 300
gctccccatc gacgtcacgg agggggaagt catctccctg ggctgccct ttgggaaggt 360 caccaacctc ctgatgctga aggggaaaaa ccaggccttc atcgagatga acacggagga 420
ggctgccaac accatggtga actactacac ctcggtgacc cctgtgctgc gcggccagcc 480
catctacatc cagttctcca accacaagga gctgaagacc gacagctctc ccaaccaggc 540
gcgggcccag gcggccctgc aggcggtgaa ctcggtccag tcggggaacc tggccttggc 600
tgcctcggcg gcggccgtgg acgcagggat ggcgatggcc gggcagagcc ccgtgctcag 660
gatcatcgtg gagaacctct tctaccctgt gaccctggat gtgctgcacc agatttctc 720 caagttcggc acagtgttga agatcatcac cttcaccaag aacaaccagt tccaggccct 780
gctgcagtat gcggaccccg tgagcgccca gcacgccaag ctgtcgctgg acgggcagaa 840
catctacaac gcctgctgca cgctgcgcat cgacttttcc aagctcacca gcctcaacgt 900
caagtacaac aatgacaaga gccgtgacta cacacgccca gacctgcctt ccggggacag 960
ccagccctcg ctggaccaga ccatggccgc ggccttcgcc tctccgtatg caggagctgg 1020
tttccctccc acctttgcca ttcctcaagc tgcaggcctt tccgttccga acgtccacgg 1080
cgccctggcc cccctggcca tcccctcggc ggcggcggca gctgcggcgg caggtcggat 1140
cgccatcccg ggcctggcgg gggcaggaaa ttctgtattg ctggtcagca acctcaaccc 1200
agagagagtc acaccccaaa gcctctttat tcttttcggc gtctacggtg acgtgcagcg 1260
cgtgaagatc ctgttcaata agaaggagaa cgccctagtg cagatggcgg acggcaacca 1320
ggcccagctg gccatgagcc acctgaacgg gcacaagctg cacgggaagc ccatccgcat 1380
cacgctctcg aagcaccaga acgtgcagct gccccgcgag ggccaggagg accagggcct 1440
gaccaaggac tacggcaact cacccctgca ccgcttcaag aagccgggct ccaagaactt 1500
ccagaacata ttcccgccct cggccacgct gcacctctcc aacatcccgc cctcagtctc 1560
cgaggaggat ctcaaggtcc tgttttccag caatgggggc gtcgtcaaag gattcaagtt 1620
cttccagaag gaccgcaaga tggcactgat ccagatgggc tccgtggagg aggcggtcca 1680
ggccctcatt gacctgcaca accacgacct cggggagaac caccacctgc gggtctcctt 1740
ctccaagtcc accatctagg ggcacaggcc cccacggccg ggccccctgg cgacaacttc 1800
catcattcca gagaaaagcc actttaaaaa cagctgaagt gaccttagca gaccagagat 1860
tttatttttt taaagagaaa tcagtttacc tgtttttaaa aaaattaaat ctagttcacc 1920
ttgctcaccc tgcggtgaca gggacagctc aggctcttgg tgactgtggc agcgggagtt 1980
cccggccctc cacacccggg gccagaccct cggggccatg ccttggtggg gcctgtgtcg 2040
ggcgtggggc ctgcaggtgg gcgccccgac cacgacttgg cttccttgtg ccttaaaaaa 2100
cctgccttcc tgcagccaca cacccacccg gggtgtcctg ggacccaag gggtgggggg 2160 gtcacaccag agagaggcag gggcctggc cggctcctgc aggatcatgc agctggggcg 2220
cggcggccgc ggctgcgaca ccccaacccc agccctctaa tcaagtcacg tgattctccc 2280
ttcaccccgc ccccagggcc ttcccttctg cccccaggcg ggctccccgc tgctccagct 2340
gcggagctgg tcgacataat ctctgtatta tatactttgc agttgcagac gtctgtgcct 2400
agcaatattt ccagttgacc aaatattcta atcttttttc atttatatgc aaaagaaata 2460
gttttaagta actttttata gcaagatgat acaatggtat gagtgtaatc taaacttcct 2520
tgtggtatta ccttgtatgc tgttactttt attttattcc ttgtaattaa gtcacaggca 2580

```
ggacccagtt tccagagagc aggcggggcc gcccagtggg tcaggcacag ggagccccgg   2640

tcctatctta gagcccctga gcttcaggga aggggcgggc gtgtcgccgc ctctggcatc   2700

gcctccggtt gccttacacc acgccttcac ctgcagtcgc ctagaaaact tgctctcaaa   2760

cttcagggtt ttttcttcct tcaaattttg gaccaaagtc tcatttctgt gttttgcctg   2820

cctctgatgc tgggacccgg aaggcgggcg ctcctcctgt cttctctgtg ctctttctac   2880

cgcccccgcg tcctgtcccg gggctctcc taggatcccc tttccgtaaa agcgtgtaac   2940

aagggtgtaa atatttataa ttttttatac ctgttgtgag acccgagggg cggcggcgcg   3000

gtttttatg gtgacacaaa tgtatatttt gctaacagca attccaggct cagtattgtg   3060

accgcggagc cacaggggac cccacgcaca ttccgttgcc ttacccgatg gcttgtgacg   3120

cggagagaac cgattaaaac cgtttgagaa actcctccct tgtctagccc tgtgttcgct   3180

gtggacgctg tagaggcagg ttggccagtc tgtacctgga cttcgaataa atcttctgta   3240

tcctcgctcc gttccgcctt aaaaaaaaaa aaaaaaaaaa aaaaaaaaaa aaaaaaaaaa   3300

aaaaaaaaaa aaaaaaaaa                                                3319


<210> SEQ ID NO 18
<211> LENGTH: 3262
<212> TYPE: DNA
<213> ORGANISM: Homo sapiens

<400> SEQUENCE: 18

tgcgggcgtc tccgccattt tgtgagtcta taactcggag ccgttgggtc ggttcctgct     60

attccggcgc ctccactccg tccccccgcgg gtctgctctg tgtgccatgg acggcattgt    120

cccagatata gccgttggta caaagcgggg atctgacgag cttttctcta cttgtgtcac    180

taacggaccg tttatcatga gcagcaactc ggcttctgca gcaaacggaa atgacagcaa    240

gaagttcaaa ggtgacagcc gaagtgcagg cgtcccctct agagtgatcc acatccggaa    300

gctccccatc gacgtcacgg agggggaagt catctccctg ggctgccct ttgggaaggt    360

caccaacctc ctgatgctga aggggaaaaa ccaggccttc atcgagatga acacggagga    420

ggctgccaac accatggtga actactacac ctcggtgacc cctgtgctgc gcggccagcc    480

catctacatc cagttctcca accacaagga gctgaagacc gacagctctc ccaaccaggc    540

gcgggcccag gcggccctgc aggcggtgaa ctcggtccag tcggggaacc tggccttggc    600

tgcctcggcg gcggccgtgg acgcagggat ggcgatggcc gggcagagcc ccgtgctcag    660

gatcatcgtg gagaacctct tctaccctgt gaccctggat gtgctgcacc agattttctc    720

caagttcggc acagtgttga agatcatcac cttcaccaag aacaaccagt tccaggccct    780

gctgcagtat gcggaccccg tgagcgccca gcacgccaag ctgtcgctgg acgggcagaa    840

catctacaac gcctgctgca cgctgcgcat cgacttttcc aagctcacca gcctcaacgt    900

caagtacaac aatgacaaga gccgtgacta cacacgccca gacctgcctt ccggggacag    960

ccagccctcg ctggaccaga ccatggccgc ggccttcggc ctttccgttc cgaacgtcca   1020

cggcgccctg gccccccctgg ccatcccctc ggcggcggcg gcagctgcgg cggcaggtcg   1080

gatcgccatc ccgggcctgg cgggggcagg aaattctgta ttgctggtca gcaacctcaa   1140

cccagagaga gtcacacccc aaagcctctt tattcttttc ggcgtctacg gtgacgtgca   1200

gcgcgtgaag atcctgttca ataagaagga gaacgcccta gtgcagatgg cggacggcaa   1260

ccaggcccag ctggccatga gccacctgaa cgggcacaag ctgcacggga agcccatccg   1320

catcacgctc tcgaagcacc agaacgtgca gctgccccgc gagggccagg aggaccaggg   1380
```

```
cctgaccaag gactacggca actcacccct gcaccgcttc aagaagccgg gctccaagaa   1440
cttccagaac atattcccgc cctcggccac gctgcacctc tccaacatcc cgccctcagt   1500
ctccgaggag gatctcaagg tcctgttttc cagcaatggg ggcgtcgtca aaggattcaa   1560
gttcttccag aaggaccgca agatggcact gatccagatg ggctccgtgg aggaggcggt   1620
ccaggccctc attgacctgc acaaccacga cctcggggag aaccaccacc tgcgggtctc   1680
cttctccaag tccaccatct aggggcacag gcccccacgg ccgggccccc tggcgacaac   1740
ttccatcatt ccagagaaaa gccactttaa aaacagctga agtgacctta gcagaccaga   1800
gattttattt ttttaaagag aaatcagttt acctgttttt aaaaaaatta aatctagttc   1860
accttgctca ccctgcggtg acagggacag ctcaggctct tggtgactgt ggcagcggga   1920
gttcccggcc ctccacaccc ggggccagac cctcggggcc atgccttggt ggggcctgtg   1980
tcgggcgtgg ggcctgcagg tgggcgcccc gaccacgact tggcttcctt gtgccttaaa   2040
aaacctgcct tcctgcagcc acacacccac ccggggtgtc ctggggaccc aaggggtggg   2100
ggggtcacac cagagagagg caggggggcct ggccggctcc tgcaggatca tgcagctggg   2160
gcgcggcggc cgcggctgcg acaccccaac cccagccctc taatcaagtc acgtgattct   2220
cccttcaccc cgcccccagg gccttccctt ctgcccccag gcgggctccc cgctgctcca   2280
gctgcggagc tggtcgacat aatctctgta ttatatactt tgcagttgca gacgtctgtg   2340
cctagcaata tttccagttg accaaatatt ctaatctttt ttcatttata tgcaaaagaa   2400
atagttttaa gtaacttttt atagcaagat gatacaatgg tatgagtgta atctaaactt   2460
ccttgtggta ttaccttgta tgctgttact tttattttat tccttgtaat taagtcacag   2520
gcaggaccca gtttccagag agcaggcggg gccgcccagt gggtcaggca cagggagccc   2580
cggtcctatc ttagagcccc tgagcttcag ggaaggggcg ggcgtgtcgc cgcctctggc   2640
atcgcctccg gttgccttac accacgcctt cacctgcagt cgcctagaaa acttgctctc   2700
aaacttcagg gtttttttctt ccttcaaatt ttggaccaaa gtctcatttc tgtgttttgc   2760
ctgcctctga tgctgggacc cggaaggcgg gcgctcctcc tgtcttctct gtgctctttc   2820
taccgccccc gcgtcctgtc ccgggggctc tcctaggatc ccctttccgt aaaagcgtgt   2880
aacaagggtg taaatattta taattttttta tacctgttgt gagacccgag gggcggcggc   2940
gcggtttttt atggtgacac aaatgtatat tttgctaaca gcaattccag gctcagtatt   3000
gtgaccgcgg agccacaggg gaccccacgc acattccgtt gccttacccg atggcttgtg   3060
acgcggagag aaccgattaa aaccgtttga gaaactcctc ccttgtctag ccctgtgttc   3120
gctgtggacg ctgtagaggc aggttggcca gtctgtacct ggacttcgaa taaatcttct   3180
gtatcctcgc tccgttccgc cttaaaaaaa aaaaaaaaaa aaaaaaaaaa aaaaaaaaaa   3240
aaaaaaaaaa aaaaaaaaaa aa                                            3262
```

<210> SEQ ID NO 19
<211> LENGTH: 1148
<212> TYPE: DNA
<213> ORGANISM: Homo sapiens

<400> SEQUENCE: 19

```
gcgccgagac ccgctcctgc agtattagtt cttgcagctg gtggtggcgg ctgaggcggc     60
atggatctca gcgagctgga gagagacaat acaggccgct gtcgcctgag ttcgcctgtg    120
cccgcggtgt gccgcaagga gccttgcgtc ctgggcgtcg atgaggcggg caggggcccc    180
```

gtgctgggcc ccatggtcta cgccatctgt tattgtcccc tgcctcgcct ggcagatctg 240
gaggcgctga aagtggcaga ctcaaagacc ctattggaga gcgagcggga aaggctgttt 300
gcgaaaatgg aggacacgga ctttgtcggc tgggcgctgg atgtgctgtc tccaaacctc 360
atctctacca gcatgcttgg gcgggtcaaa tacaacctga actccctgtc acatgataca 420
gccactgggc ttatacagta tgcattggac cagggcgtga acgtcaccca ggtattcgtg 480
gacaccgtag ggatgccaga gacataccag gcgcggctgc agcaaagttt tcccgggatt 540
gaggtgacgg tcaaggccaa agcagatgcc ctctacccgg tggttagtgc tgccagcatc 600
tgtgccaagg tggcccggga ccaggccgtg aagaaatggc agttcgtgga gaaactgcag 660
gacttggata ctgattatgg ctcaggctac cccaatgatc ccaagacaaa agcgtggttg 720
aaggagcacg tggagcctgt gttcggcttc cccagtttg tccggttcag ctggcgcacg 780
gcccagacca tcctggagaa agaggcggaa gatgttatat gggaggactc agcatccgag 840
aatcaggagg gactcaggaa gatcacatcc tacttcctca atgaagggtc ccaagcccgt 900
ccccgttctt cccaccgata tttcctggaa cgcggcctgg agtcagcaac cagcctctag 960
cagctgcctc tacgcgctct acctgcttcc ccaacccaga cattaaaatt gtttaaggag 1020
aaccacacgt aggggatgta cttttgggac agaagcaagg tgggagtgtg ctctgcagcc 1080
gggtccagct acttcctttt ggaaccttaa atagaatggg tgttggttga ttaattttat 1140
ttaaaaaa 1148

<210> SEQ ID NO 20
<211> LENGTH: 1613
<212> TYPE: DNA
<213> ORGANISM: Homo sapiens

<400> SEQUENCE: 20
ggagaaacac acacgggcgg gcggagggga cccggggcga gtcatcaagg gcgcgtggtt 60
cggcgtgcca ggcgcgctgc tctgcctgct ctcttggctt ctgtctccct tcgaccgatc 120
gccccctatc ctgaagcttt ccaatgtcat cttggagccc caaagtttcc tggggcctcc 180
gcgttgtgcg tcccagaacc ccttgcctgc ccctgaggga aacgcggagc cataggcagc 240
gggacgtcgg gagccagccc aggggaggcc agattcagca tttggacagc ggctctgggg 300
cgcagtcggc ccagcgagtt tgccggtgaa cagcctcggg cacatggcgg gtaggagggc 360
cgcagggctg ctctgggtct tgaagaagca ggacccagcc tagagggcat ccccagctcc 420
gaatgggaca cgttttcccg agataaaaga tcccttctga gctcacacgg gagccccggg 480
accatccaat ccagcgtgga tatccccagc ctaaccaaca cctgtgctgg ggggaaagat 540
aagacgcccc ctttcagcca ggaggtggac gaccctcatg ccctcagctc tccattcttc 600
ccaaagcagc tcggatccct aagtctggag ctgccagcga ggcttccaac ccgctgcttg 660
ccatcacctc ccaggtcgtt ggtggctccg attactcccc tgctggtgcc tccctccttg 720
gcgcgcttcc cacctgcgat cggcgccctc ttcgcagtca cgaactcgcc agcagctagc 780
agcactgact agtaggaggg cccgccggag gagagccgcg cggcccacag aagcggaacg 840
cgcgtcgaga gcgccctgtc cgctcgcccc agacagatgc ccggttattc attaccgcga 900
ggcctagagg aaagagtggc tgccgtcttc ctgcccacag cccgccggac cctccgtcgc 960
ggctgcccgg tccccggagc cgcagccgcc gagcccggct gtgcgtgtcg tggctgctgg 1020
ggagaaagag gcttccggac atgctctgga gtcagaagac agcgaaaaga gaagcagaag 1080
ccccggtggc aagagtctga aggaaggatg actgtagcct gtggattgta ctgcagtagg 1140

```
aaactgtcct agcaaggctc cactttgccc cagcttcaag ctggaaagga ggagaacatg   1200

aaacattgct tgaagacaat ggccgagaca gcaggtccca ccctgcacag ccaccagcat   1260

ctctcccctc agccctgtct cctcttctgc agttgggatc tgcacattta agcctgaaat   1320

tgtcctgtga agtgaagtat gatcggacag cctcttttca gcttttatga caatggagac   1380

agaggaattg tggctcttgc caaggtcaca ggattggaat acagagccaa gccaccccag   1440

gacatgcaag agcctcagaa gggaaaaaag cccagcagga agggagaaca agtagcctct   1500

gtcctgaagt tgtaacagcc aggggccagg atggaggagg aggaccccat aatctgccca   1560

tctgggactt ggcaggggac ctgggaaaat gtaccccaac ccatccctta agg          1613

<210> SEQ ID NO 21
<211> LENGTH: 606
<212> TYPE: RNA
<213> ORGANISM: Homo sapiens

<400> SEQUENCE: 21

ccugcuggug ccucccuccu uggcgcgcuu cccaccugcg aucggcgccc ucuucgcagu     60

cacgaacucg ccagcagcua gcagcacuga cuaguaggag ggcccgccgg aggagaggac    120

augcucugga gucagaagac agcgaaaaga gaagcagaag ccccggugc aagagucuga     180

agcuggaaag gaggagaaca ugaaacauug cuugaagaca auggccgaga cagcagguccc   240

cacccugcac agccaccagc aucucucccc ucagcccugu cuccucuucu gcaguuggga    300

ucugcacauu uaagccugaa auuguccugu gaagugaagu augaucggac agccucuuuu    360

cagcuuuuau gacaauggag acagaggaau uguggcucuu gccaagguca caggauugga    420

auacagagcc aagccacccc aggacaugca agagccucag aagggaaaaa agcccagcag    480

gaagggagaa caaguagccu cuguccugaa guuguaacag ccaggggcca ggauggagga    540

ggaggacccc auaaucugcc caucugggac uuggcagggg accugggaaa auguacccca    600

acccau                                                               606

<210> SEQ ID NO 22
<211> LENGTH: 551
<212> TYPE: DNA
<213> ORGANISM: Homo sapiens

<400> SEQUENCE: 22

cttcgcagtc acgaactcgc cagcagctag cagcactgac tagtaggagg gcccgccgga     60

ggagaggaag ccccagagag attggtgagg gtgatttccc aggaagacgc agtgtgctct    120

gacttctgtg acagtgagca acgggaccag tggatgtcca gatgctggca atgagacatg    180

ctctggagtc agaagacagc gaaaagagaa gcagaagccc cggtggcaag agtctgaagg    240

aaggatgact gtagcctgtg gattgtactg cagtaggaaa ctgtcctagc aaggctccac    300

tttgccccag cttcaagctg gaaaggagga gaacatgaaa cattgcttga agacaatggc    360

cgagacagca ggtcccaccc tgcacagcca ccagcatctc tcccctcagc cctgtctcct    420

cttctgcagt tgggatctgc acatttaagc ctgaaattgt cctgtgaagt gaagtatgat    480

cggacagcct cttttcagct tttatgacaa tggagacaga ggaattgtgg ctcttgccaa    540

ggtcacagga t                                                         551

<210> SEQ ID NO 23
<211> LENGTH: 1877
<212> TYPE: DNA
```

<213> ORGANISM: Homo sapiens

<400> SEQUENCE: 23

```
tcgccagcag ctagcagcac tgactagtag gagggcccgc cggaggagag ccgcgcggcc      60
cacagaagcg gaacgcgcgt cgagagcgcc ctgtccgctc gccccagaca gatgcccggt     120
tattcattac cgcgaggcct agaggaaaga gtggctgccg tcttcctgcc cacagcccgc     180
cggaccctcc gtcgcggctg cccggtcccc ggagccgcag ccgccgagcc cggctgtgcg     240
tgtcgtggct gctggggaga aagaggcttc cggaagcccc agagagattg gtgagggtga     300
tttcccagga agacgcagtg tgctctgact tctgtgacag tgagcaacgg gaccagtgga     360
tgtccagatg ctggcaatga gacatgctct ggagtcagaa gacagcgaaa agagaagcag     420
aagccccggt ggcaagagtc tgaagcagga aggatgactg tagcctgtgg attgtactgc     480
agtaggaaac tgtcctagca aggctccact ttgccccagc ttcaagctgg aaaggaggag     540
aacatgaaac attgcttgaa gacaatggcc gagacagcag gtcccaccct gcacagccac     600
cagcatctct cccctcagcc ctgtctcctc ttctgcagtt gggatctgca catttaagcc     660
tgaaattgtc ctgtgaagtg aagtatgatc ggacagcctc ttttcagctt ttatgacaat     720
ggagacagag gaattgtggc tcttgccaag gtcacaggat tggaatacag agccaagcca     780
ccccaggaca tgcaagagcc tcagaaggga aaaaagccca gcaggaaggg agaacaagta     840
gcctctgtcc tgaagttgta acagccaggg gccaggatgg aggaggagga ccccataatc     900
tgcccatctg ggacttggca ggggacctgg gaaaatgtac cccaacccat cccttaaggg     960
cctttgtctt tggcccattg gcctagcatc tacttcttca ccgtgtctgt tcttgtcaca    1020
cctagtcagg tctgtttggg tctgaggtgc atggaacatt ctgggtaggc ctccagcaaa    1080
cggaagctct tcaccgtgtt tccagcctgg gaccaagggc agcatactgg caaagttgcc    1140
aaagcaaggg actccagcct cttaggagtt aatgactccc tctccccagc tgtcctcccc    1200
ttggtgctcc tcttcctccc tcctcctgct cacagcaggc agggcctaga cccgggagcc    1260
atgctgctgt gctgttgcca ggggagcacg gaggcagatc tgagctatgc agggaaaagg    1320
cccagcctgt caaagtgtct gagatgaacc gccgccgtcc ctgtgcagct gggctcagac    1380
gtgtctcagc tcttgttctg tgcctgagaa tggcgaaacc cagtgaggtt caagggcaaa    1440
ctcgctattc attagtcagg ggttcttgac gtcccgtctc tcccagggat gagttccccc    1500
ctcctctttc tccccctcct atgacacatt cctgggtgcc tttggtgagg actgcacacc    1560
ctcctcctgc ctagccccct ctccaaaggc ccctgaataa actcccccca aggagaccag    1620
gcagggcaga gacaatggct gcaggaaatc attcaggcgg gacatgctgg cctgccctcc    1680
acccagtccc cctgtgggcc ccactccctt ctgattcagg gcacccttgg gcccccagcc    1740
tatacaggcc tggacaggaa gaaaccactg ggaaccaccc taaggacaac atgctagtcc    1800
agtgccattc ttcgctggct ctgtgggtgc ctttgtggcc tgtaccgact ggctggctaa    1860
ttttgtggtt tctgtac                                                   1877
```

<210> SEQ ID NO 24
<211> LENGTH: 561
<212> TYPE: DNA
<213> ORGANISM: Homo sapiens

<400> SEQUENCE: 24

```
agcactgact agtaggaggg cccgccggag gagaggacat gctctggagt cagaagacag      60
cgaaaagaga agcagaagcc ccggtggcaa gagtctgaag caggaaggat gactgtagcc     120
```

```
tgtggattgt actgcagtag gaaactgtcc tagcaaggct ccactttgcc ccagcttcaa    180

gctggaaagg aggagaacat gaaacattgc ttgaagacaa tggccgagac agcaggtccc    240

accctgcaca gccaccagca tctctcccct cagccctgtc tcctcttctg cagttgggat    300

ctgcacattt aagcctgaaa ttgtcctgtg aagtgaagta tgatcggaca gcctcttttc    360

agcttttatg acaatggaga cagaggaatt gtggctcttg ccaaggtcac aggattggaa    420

tacagagcca agccacccca ggacatgcaa gagcctcaga agggaaaaaa gcccagcagg    480

aagggagaac aagtagcctc tgtcctgaag ttgtaacagc caggggccag gatggaggag    540

gaggacccca taatctgccc a                                              561
```

<210> SEQ ID NO 25
<211> LENGTH: 786
<212> TYPE: DNA
<213> ORGANISM: Homo sapiens

<400> SEQUENCE: 25

```
ctgggagtgg cgcggctgct tcccgcccgc gcaggatcag gccggccccc gcgggcctgg     60

agctggatcc agagctaggg aaactggaaa aacaggcaca aactcggaag ccgcggtacg    120

gcaagagcct aagcaaagaa tcctttccaa gattcacacc tcgtctacac cagggcaccg    180

cctgggccta cggccttccg aacccgaagc gcccgcagcc cagagctggc atcaggccat    240

caggccggga aggtcgtcgc aggccccaga gtgcgggcgc ggggggcgcg cgcccacagg    300

acgcccgggg ttgggtaggc aggagagaag ggcgccagca ggcccgcggc tgtttcccct    360

cggtccgcac agcgggcccg ggaggccatt ttgagagcgc gaagaggggc ggcaagatgg    420

ctgcgtgggc acccggaagg tcgccgcgcc aagggcccgc tgagcccctc ctcccattcg    480

tccagccgcg cggcccacag aagcggaacg cgcgtcgaga gcgccctgtc cgctcgcccc    540

agacagatgc ccggttattc attaccgcga ggcctagagg aaagagtggc tgccgtcttc    600

ctgcccacag cccgccggac cctccgtcgc ggctgcccgg tccccggagc cgcagccgcc    660

gagcccggct gtgcgtgtcg tggctgctgg ggagaaagag gcttccggac atgctctgga    720

gtcagaagac agcgaaaaga gaagcagaag ccccggtggc aagagtctga agcaggaagg    780

atgact                                                               786
```

<210> SEQ ID NO 26
<211> LENGTH: 569
<212> TYPE: DNA
<213> ORGANISM: Homo sapiens

<400> SEQUENCE: 26

```
ttaccgcgag gcctagagga aagagtggct gccgtcttcc tgcccacagc ccgccggacc     60

ctccgtcgcg gctgcccggt ccccggagcc gcagccgccg agcccggctg tgcgtgtcgt    120

ggctgctggg gagaaagagg cttccggaca tgctctggag tcagaagaca gcgaaaagag    180

aagcagaagc cccggtggca agagtctgaa gggagaaaat aacccagttt gggaaggaca    240

tttaaaaggg gaaaatatta ggaaggatga ctgtagcctg tggattgtac tgcagtagga    300

aactgtccta gcaaggctcc actttgcccc agcttcaagc tggaaaggag gagaacatga    360

aacattgctt gaagacaatg gccgagacag caggtcccac cctgcacagc caccagcatc    420

tctcccctca gccctgtctc ctcttctgca gttgggatct gcacatttaa gcctgaaatt    480

gtcctgtgaa gtgaagtatg atcggacagc ctcttttcag cttttatgac aatggagaca    540
```

gaggaattgt ggctcttgcc aaggtcaca 569

<210> SEQ ID NO 27
<211> LENGTH: 3779
<212> TYPE: DNA
<213> ORGANISM: Homo sapiens

<400> SEQUENCE: 27
gtgtcgtggc tgctggggag aaagaggctt ccggacatgc tctggagtca gaagacagcg 60
aaaagagaag cagaagcccc ggtggcaaga gtctgaagca ggaaggatga ctgtagcctg 120
tggattgtac tgcagtagga aactgtccta gcaaggctcc actttgcccc agcttcaagc 180
tggaaaggag gagaacatga aacattgctt gaagacaatg gccgagacag caggtcccac 240
cctgcacagc caccagcatc tctcccctca gccctgtctc ctcttctgca gttgggatct 300
gcacatttaa gcctgaaatt gtcctgtgaa gtgaagtatg atcggacagc ctcttttcag 360
cttttatgac aatggagaca gaggaattgt ggctcttgcc aaggtcacag gattggaata 420
cagagccaag ccaccccagg acatgcaaga gcctcagaag ggaaaaaagc ccagcaggaa 480
gggagaacaa gtagcctctg tcctgaagtt gtaacagcca ggggccagga tggaggagga 540
ggaccccata atctgcccat ctgggacttg gcaggggacc tgggaaaatg taccccaacc 600
catcccttaa gggcctttgt ctttggccca ttggcctagc atctacttct tcaccgtgtc 660
tgttcttgtc acacctagtc aggtctgttt gggtctgagg tgcatggaac attctgggta 720
ggcctccagc aaacggaagc tcttcaccgt gtttccagcc tgggaccaag ggcagcatac 780
tggcaaagtt gccaaagcaa gggactccag cctcttagga gttaatgact ccctctcccc 840
agctgtcctc cccttggtgc tcctcttcct ccctcctcct gctcacagca ggcagggcct 900
agacccggga gccatgctgc tgtgctgttg ccaggggagc acggaggcag atctgagcta 960
tgcagggaaa aggcccagcc tgtcaaagtg tctgagatga accgccgccg tccctgtgca 1020
gctgggctca gacgtgtctc agctcttgtt ctgtgcctga gaatggcgaa acccagtgag 1080
gttcaagggc aaactcgcta ttcattagtc aggggttctt gacgtcccgt ctctcccagg 1140
gatgagttcc cccctcctct ttctcccccct cctatgacac attcctgggt gcctttggtg 1200
aggactgcac accctcctcc tgcctagccc cctctccaaa ggcccctgaa taaactcccc 1260
ccaaggagac caggcagggc agagacaatg gctgcaggaa atcattcagg cgggacatgc 1320
tggcctgccc tccacccagt ccccctgtgg gccccactcc cttctgattc agggcaccct 1380
tgggccccca gcctatacag gcctggacag gaagaaacca ctgggaacca ccctaaggac 1440
aacatgctag tccagtgcca ttcttcgctg gctctgtggg tgcctttgtg gcctgtaccg 1500
actggctggc taattttgtg gtttctgtac catcacatgc ctattttaag acactctcca 1560
gcactgtcgg ttagggagtg taaattttgc aatattttct gaaatgtggc aatatcaaaa 1620
tgtaaaaggc acacatactt ggtcacaaac aaatggcact atttactctg tgggcatatt 1680
tgtaaaagtt gccaaagaat tatatacaag gatgttcatc agagcatttc ttttgaagag 1740
taaagaaatg gacatgaacc tgtggtccgt tcatacggtg gaatacctat gcagctgtaa 1800
aaatcagtgt ggtagatctc cgtatatgag ttgatgtgga aggttggcca gttcacatga 1860
taaggtgaat agaataagtt acagaacagg ctgtagagta tgatcttatt tgtagatgtt 1920
taaaactgag tcataagtat gcttatatac agatcgtttc tggaagtatg tactggaagt 1980
ctacctctgg ggagtgggga tgggggagtg cactcttcta tactgttata ttttcttttc 2040
atgctcctaa ggtactttta ttggaagatg taaagcggtt caatgtaata ggcttaactt 2100
ctgtcaacta agttggcgtg ggtgctttaa gagggtggta gtgatgttgc tggagaaagt 2160
atcccacagt cactggtggc ttcagccacg ggccattttg gggcctaata atcacatatc 2220
atcatggttg ctagtgttaa tcgaaaacct actaagtgcc aggcttactg tctctgggtc 2280
ttgcttacgt ggatgtcatt tttccagttg caccaaatcg aaagaggtta attggtttgt 2340
tggagttcct ttgtaggtga agggcagagc caggagcttg gctagggaca ggggaggtga 2400
gtgggggatg gtggataggt cttggctccc agtttccttc tgggcagaca ttgcccctct 2460
gccctgagga cctgcttgtt tgggggaaga ggcctttaga ggcaccaggg tcatgccagg 2520
tgttggacat ggtgaactgg gaagtgctcc catctggcca cagcgcagaa gtatcaccgt 2580
gctgggggat ggggaacagg gctgtgaatg ggcctatttg cataagcagc atgtgtctgg 2640
agagaaagac atcacagagc agaagagtgc gggtgcccag gagtgcactt gccaccccta 2700
cttcatccct gaaagagtaa atggcctgga aggtgtctct gagaggtaat gccgcacacc 2760
accctccctg ggggcagggt caggctacac ctgccttagg tcgggggctg cagcagcctg 2820
agagctctca gtagggcctc agtagcctgg gagggagcag gggcaggggg cagggaaaga 2880
ggcgtaatgg ggctgtccag aggggcctgg gaaacctggt ccctgaggcc tgggcacagc 2940
tacaatcact tcaaattggc tgtggggcca gtggactggg aaggaaaaaa gcaataagag 3000
tgaccaagtg cagaaggctg tcaggtccca ggtcacatgc cttagtgcag tgactcctca 3060
tcattttatg gggtgtgggt gtcgttggta cacccatttt acagatgagg acaccgaggc 3120
ccagaaaagt taagttacat gtcctaagtc acacagcttg taagtgccag aactgagatc 3180
aaaaccaagt ctctttgact ttaaagtctg tactctgacc ccaaagagat cctgtttggc 3240
cacttatagg aggtccctaa agctgcagac tccccttgcc ggcacccaca tatagagaca 3300
ttaacccttc ccctgcaggg tcacctcaaa tagtctttta gctgggcttc tcctgcaatt 3360
ccacctaatg ccatcccctg ggttttgccc aaacctgaac tgggcagtgg ggtgagagga 3420
ggggtttaca gggttacaga gcctcataca gataggagcc catggctgct ggtcatctgc 3480
attcctgcag gattggctgt tccttggggt ccttggcagg aaaatgagga ttgctccgag 3540
gcctgctcca gtacttccca gaggctggcc tggtgtgggg ctctgggaag gctgaggctg 3600
gagaagcgta agtaggaggg cagagatggc actcaggtag cttgaatcac caggacccttt 3660 ccaagcccca caggttctga gggagtacta gggccagctc tgggagaggt ctcttcctat 3720
gctgtgaacc ccctgccttt cttgcagcct acaacgaata aattttcttt gcaaaggct 3779

<210> SEQ ID NO 28
<211> LENGTH: 3670
<212> TYPE: DNA
<213> ORGANISM: Homo sapiens

<400> SEQUENCE: 28
cttccggaca tgctctggag tcagaagaca gcgaaaagag aagcagaagc cccggtggca 60
agagtctgaa gctggaaagg aggagaacat gaaacattgc ttgaagacaa tggccgagac 120
agcaggtccc accctgcaca gccaccagca tctctcccct cagccctgtc tcctcttctg 180
cagttgggat ctgcacattt aagcctgaaa ttgtcctgtg aagtgaagta tgatcggaca 240
gcctcttttc agcttttatg acaatggaga cagaggaatt gtggctcttg ccaaggtcac 300
aggattggaa tacagagcca agccacccca ggacatgcaa gagcctcaga agggaaaaaa 360
gcccagcagg aagggagaac aagtagcctc tgtcctgaag ttgtaacagc caggggccag 420

```
gatggaggag gaggacccca taatctgccc atctgggact tggcagggga cctgggaaaa    480
tgtaccccaa cccatccctt aagggccttt gtctttggcc cattggccta gcatctactt    540
cttcaccgtg tctgttcttg tcacacctag tcaggtctgt ttgggtctga ggtgcatgga    600
acattctggg taggcctcca gcaaacggaa gctcttcacc gtgtttccag cctgggacca    660
agggcagcat actggcaaag ttgccaaagc aagggactcc agcctcttag gagttaatga    720
ctccctctcc ccagctgtcc tccccttggt gctcctcttc ctccctcctc ctgctcacag    780
caggcagggc ctagacccgg gagccatgct gctgtgctgt tgccagggga gcacggaggc    840
agatctgagc tatgcaggga aaaggcccag cctgtcaaag tgtctgagat gaaccgccgc    900
cgtccctgtg cagctgggct cagacgtgtc tcagctcttg ttctgtgcct gagaatggcg    960
aaacccagtg aggttcaagg gcaaactcgc tattcattag tcaggggttc ttgacgtccc   1020
gtctctccca gggatgagtt ccccccctcct ctttctcccc ctcctatgac acattcctgg   1080
gtgcctttgg tgaggactgc acaccctcct cctgcctagc cccctctcca aaggcccctg   1140
aataaactcc ccccaaggag accaggcagg gcagagacaa tggctgcagg aaatcattca   1200
ggcgggacat gctggcctgc cctccaccca gtccccctgt gggccccact cccttctgat   1260
tcagggcacc cttgggcccc cagcctatac aggcctggac aggaagaaac cactgggaac   1320
caccctaagg acaacatgct agtccagtgc cattcttcgc tggctctgtg ggtgcctttg   1380
tggcctgtac cgactggctg gctaattttg tggtttctgt accatcacat gcctatttta   1440
agacactctc cagcactgtc ggttagggag tgtaaatttt gcaatatttt ctgaaatgtg   1500
gcaatatcaa aatgtaaaag gcacacatac ttggtcacaa acaaatggca ctatttactc   1560
tgtgggcata tttgtaaaag ttgccaaaga attatataca aggatgttca tcagagcatt   1620
tcttttgaag agtaaagaaa tggacatgaa cctgtggtcc gttcatacgg tggaatacct   1680
atgcagctgt aaaaatcagt gtggtagatc tccgtatatg agttgatgtg gaaggttggc   1740
cagttcacat gataaggtga atagaataag ttacagaaca ggctgtagag tatgatctta   1800
tttgtagatg tttaaaactg agtcataagt atgcttatat acagatcgtt tctggaagta   1860
tgtactggaa gtctacctct ggggagtggg gatgggggag tgcactcttc tatactgtta   1920
tattttcttt tcatgctcct aaggtacttt tattggaaga tgtaaagcgg ttcaatgtaa   1980
taggcttaac ttctgtcaac taagttggcg tgggtgcttt aagagggtgg tagtgatgtt   2040
gctggagaaa gtatcccaca gtcactggtg gcttcagcca cgggccattt tggggcctaa   2100
taatcacata tcatcatggt tgctagtgtt aatcgaaaac ctactaagtg ccaggcttac   2160
tgtctctggg tcttgcttac gtggatgtca tttttccagt tgcaccaaat cgaaagaggt   2220
taattggttt gttggagttc ctttgtaggt gaagggcaga gccaggagct tggctaggga   2280
caggggaggt gagtggggga tggtggatag gtcttggctc ccagtttcct tctgggcaga   2340
cattgcccct ctgccctgag gacctgcttg tttgggggaa gaggccttta gaggcaccag   2400
ggtcatgcca ggtgttggac atggtgaact gggaagtgct cccatctggc cacagcgcag   2460
aagtatcacc gtgctggggg atggggaaca gggctgtgaa tgggcctatt tgcataagca   2520
gcatgtgtct ggagagaaag acatcacaga gcagaagagt gcgggtgccc aggagtgcac   2580
ttgccacccc tacttcatcc ctgaaagagt aaatggcctg gaaggtgtct ctgagaggta   2640
atgccgcaca ccaccctccc tgggggcagg gtcaggctac acctgcctta ggtcgggggc   2700
tgcagcagcc tgagagctct cagtagggcc tcagtagcct gggagggagc aggggcaggg   2760
ggcagggaaa gaggcgtaat ggggctgtcc agaggggcct gggaaacctg gtccctgagg   2820
```

```
cctgggcaca gctacaatca cttcaaattg gctgtggggc cagtggactg ggaaggaaaa   2880

aagcaataag agtgaccaag tgcagaaggc tgtcaggtcc caggtcacat gccttagtgc   2940

agtgactcct catcatttta tggggtgtgg gtgtcgttgg tacacccatt ttacagatga   3000

ggacaccgag gcccagaaaa gttaagttac atgtcctaag tcacacagct tgtaagtgcc   3060

agaactgaga tcaaaaccaa gtctctttga ctttaaagtc tgtactctga ccccaaagag   3120

atcctgtttg gccacttata ggaggtccct aaagctgcag actccccttg ccggcaccca   3180

catatagaga cattaaccct tcccctgcag ggtcacctca aatagtcttt tagctgggct   3240

tctcctgcaa ttccacctaa tgccatcccc tgggttttgc ccaaacctga actgggcagt   3300

ggggtgagag gaggggttta cagggttaca gagcctcata cagataggag cccatggctg   3360

ctggtcatct gcattcctgc aggattggct gttccttggg gtccttggca ggaaaatgag   3420

gattgctccg aggcctgctc cagtacttcc cagaggctgg cctggtgtgg ggctctggga   3480

aggctgaggc tggagaagcg taagtaggag ggcagagatg gcactcaggt agcttgaatc   3540

accaggaccc ttccaagccc cacaggttct gagggagtac tagggccagc tctgggagag   3600

gtctcttcct atgctgtgaa ccccctgcct ttcttgcagc ctacaacgaa taaattttct   3660

ttgcaaaggc                                                          3670
```

```
<210> SEQ ID NO 29
<211> LENGTH: 3784
<212> TYPE: DNA
<213> ORGANISM: Homo sapiens

<400> SEQUENCE: 29
```

```
gctaacagct tcaggagaat tcagcctcac cttgacagga catgctctgg agtcagaaga     60

cagcgaaaag agaagcagaa gccccggtgg caagagtctg aagcaggaag gatgactgta    120

gcctgtggat tgtactgcag taggaaactg tcctagcaag gctccacttt gccccagctt    180

caagctggaa aggaggagaa catgaaacat tgcttgaaga caatggccga gacagcaggt    240

cccaccctgc acagccacca gcatctctcc cctcagccct gtctcctctt ctgcagttgg    300

gatctgcaca tttaagcctg aaattgtcct gtgaagtgaa gtatgatcgg acagcctctt    360

ttcagctttt atgacaatgg agacagagga attgtggctc ttgccaaggt cacaggattg    420

gaatacagag ccaagccacc ccaggacatg caagagcctc agaagggaaa aaagcccagc    480

aggaagggag aacaagtagc ctctgtcctg aagttgtaac agccaggggc caggatggag    540

gaggaggacc ccataatctg cccatctggg acttggcagg ggacctggga aaatgtaccc    600

caacccatcc cttaagggcc tttgtctttg gcccattggc ctagcatcta cttcttcacc    660

gtgtctgttc ttgtcacacc tagtcaggtc tgtttgggtc tgaggtgcat ggaacattct    720

gggtaggcct ccagcaaacg gaagctcttc accgtgtttc cagcctggga ccaagggcag    780

catactggca aagttgccaa agcaagggac tccagcctct taggagttaa tgactccctc    840

tccccagctg tcctcccctt ggtgctcctc ttcctccctc ctcctgctca cagcaggcag    900

ggcctagacc cgggagccat gctgctgtgc tgttgccagg ggagcacgga ggcagatctg    960

agctatgcag ggaaaaggcc cagcctgtca aagtgtctga gatgaaccgc cgccgtccct   1020

gtgcagctgg gctcagacgt gtctcagctc ttgttctgtg cctgagaatg gcgaaaccca   1080

gtgaggttca agggcaaact cgctattcat tagtcagggg ttcttgacgt cccgtctctc   1140

ccagggatga gttccccccct cctctttctc cccctcctat gacacattcc tgggtgcctt   1200
```

```
tggtgaggac tgcacaccct cctcctgcct agccccctct ccaaaggccc ctgaataaac   1260
tccccccaag gagaccaggc agggcagaga caatggctgc aggaaatcat tcaggcggga   1320
catgctggcc tgccctccac ccagtccccc tgtgggcccc actcccttct gattcagggc   1380
acccttgggc cccagcccta tacaggcctg gacaggaaga aaccactggg aaccacccta   1440
aggacaacat gctagtccag tgccattctt cgctggctct gtgggtgcct ttgtggcctg   1500
taccgactgg ctggctaatt ttgtggtttc tgtaccatca catgcctatt ttaagacact   1560
ctccagcact gtcggttagg gagtgtaaat tttgcaatat tttctgaaat gtggcaatat   1620
caaaatgtaa aaggcacaca tacttggtca caaacaaatg gcactattta ctctgtgggc   1680
atatttgtaa aagttgccaa agaattatat acaaggatgt tcatcagagc atttcttttg   1740
aagagtaaag aaatggacat gaacctgtgg tccgttcata cggtggaata cctatgcagc   1800
tgtaaaaatc agtgtggtag atctccgtat atgagttgat gtggaaggtt ggccagttca   1860
catgataagg tgaatagaat aagttacaga acaggctgta gagtatgatc ttatttgtag   1920
atgtttaaaa ctgagtcata agtatgctta tatacagatc gtttctggaa gtatgtactg   1980
gaagtctacc tctggggagt ggggatgggg gagtgcactc ttctatactg ttatattttc   2040
ttttcatgct cctaaggtac ttttattgga agatgtaaag cggttcaatg taataggctt   2100
aacttctgtc aactaagttg gcgtgggtgc tttaagaggg tggtagtgat gttgctggag   2160
aaagtatccc acagtcactg gtggcttcag ccacgggcca ttttggggcc taataatcac   2220
atatcatcat ggttgctagt gttaatcgaa aacctactaa gtgccaggct tactgtctct   2280
gggtcttgct tacgtggatg tcatttttcc agttgcacca aatcgaaaga ggttaattgg   2340
tttgttggag ttcctttgta ggtgaagggc agagccagga gcttggctag ggacagggga   2400
ggtgagtggg ggatggtgga taggtcttgg ctcccagttt ccttctgggc agacattgcc   2460
cctctgccct gaggacctgc ttgtttgggg gaagaggcct ttagaggcac caggtcatg   2520
ccaggtgttg gacatggtga actgggaagt gctcccatct ggccacagcg cagaagtatc   2580
accgtgctgg gggatgggga acagggctgt gaatgggcct atttgcataa gcagcatgtg   2640
tctggagaga aagacatcac agagcagaag agtgcgggtg cccaggagtg cacttgccac   2700
ccctacttca tccctgaaag agtaaatggc ctggaaggtg tctctgagag gtaatgccgc   2760
acaccaccct ccctgggggc agggtcaggc tacacctgcc ttaggtcggg ggctgcagca   2820
gcctgagagc tctcagtagg gcctcagtag cctgggaggg agcaggggca gggggcaggg   2880
aaagaggcgt aatggggctg tccagagggg cctgggaaac ctggtccctg aggcctgggc   2940
acagctacaa tcacttcaaa ttggctgtgg ggccagtgga ctgggaagga aaaaagcaat   3000
aagagtgacc aagtgcagaa ggctgtcagg tcccaggtca catgccttag tgcagtgact   3060
cctcatcatt ttatggggtg tgggtgtcgt tggtacaccc attttacaga tgaggacacc   3120
gaggcccaga aaagttaagt tacatgtcct aagtcacaca gcttgtaagt gccagaactg   3180
agatcaaaac caagtctctt tgactttaaa gtctgtactc tgaccccaaa gagatcctgt   3240
ttggccactt ataggaggtc cctaaagctg cagactcccc ttgccggcac ccacatatag   3300
agacattaac ccttcccctg cagggtcacc tcaaatagtc ttttagctgg gcttctcctg   3360
caattccacc taatgccatc ccctgggttt tgcccaaacc tgaactgggc agtggggtga   3420
gaggaggggt ttacagggtt acagagcctc atacagatag gagcccatgg ctgctggtca   3480
tctgcattcc tgcaggattg gctgttcctt ggggtccttg gcaggaaaat gaggattgct   3540
ccgaggcctg ctccagtact tcccagaggc tggcctggtg tggggctctg ggaaggctga   3600
```

```
ggctggagaa gcgtaagtag gagggcagag atggcactca ggtagcttga atcaccagga   3660

cccttccaag ccccacaggt tctgagggag tactagggcc agctctggga gaggtctctt   3720

cctatgctgt gaaccccctg cctttcttgc agcctacaac gaataaattt tctttgcaaa   3780

ggct                                                                3784
```

```
<210> SEQ ID NO 30
<211> LENGTH: 779
<212> TYPE: DNA
<213> ORGANISM: Homo sapiens

<400> SEQUENCE: 30

gcacgacttg ttcttgcctt ctaaagcaga gaggagcttt tgtgggtagt tcctacaggg     60

atacatggta gaaaattcac caaacccagt gctggagtgt ttctcttcct cagaagaaat    120

cagatgctgt tcagagcacg aaggctagaa ttttaccctg gttctcatgc taccttgcac    180

ccaggttgga tcctgagtac agtttttggc aggaagcccc agagagattg gtgagggtga    240

tttcccagga agacgcagtg tgctctgact tctgtgacag tgagcaacgg gaccagtgga    300

tgtccagatg ctggcaatga gacatgctct ggagtcagaa gacagcgaaa agagaagcag    360

aagccccggt ggcaagagtc tgaaggaagg atgactgtag cctgtggatt gtactgcagt    420

aggaaactgt cctagcaagg ctccactttg ccccagcttc aaggtatatc gtctcaaaat    480

gcaggggact tcagatgagt tttgagcacc ctttctttta ttataaaaaa aattccagac    540

agttcagcca atactgacta agggctgaga ccagttccat gcttttctgt ctccagagga    600

atttgcttcc atctggatgc ctgaaacgct ggaaaggagg agaacatgaa acattgcttg    660

aagacaatgg ccgagacagc aggtcccacc ctgcacagcc accagcatct ctcccctcag    720

ccctgtctcc tcttctgcag ttgggatctg cacatttaag cctgaaattg tcctgtgaa     779
```

```
<210> SEQ ID NO 31
<211> LENGTH: 1611
<212> TYPE: DNA
<213> ORGANISM: Homo sapiens

<400> SEQUENCE: 31

ggagaaacac acacgggcgg gcggagggga cccggggcga gtcatcaagg gcgcgtggtt     60

cggcgtgcca ggcgcgctgc tctgcctgct ctcttggctt ctgtctccct tcgaccgatc    120

gccccctatc ctgaagcttt ccaatgtcat cttggagccc caaagtttcc tggggcctcc    180

gcgttgtgcg tcccagaacc ccttgcctgc ccctgaggga aacgcggagc cataggcagc    240

gggacgtcgg gagccagccc aggggaggcc agattcagca tttggacagc ggctctgggg    300

cgcagtcggc ccagcgagtt tgccggtgaa cagcctcggg cacatggcgg gtaggagggc    360

cgcagggctg ctctgggtct tgaagaagca ggacccagcc tagagggcat ccccagctcc    420

gaatgggaca cgttttcccg agataaaaga tcccttctga gctcacacgg gagccccggg    480

accatccaat ccagcgtgga tatccccagc ctaaccaaca cctgtgctgg ggggaaagat    540

aagacgcccc ctttcagcca ggaggtggac gaccctcatg ccctcagctc tccattcttc    600

ccaaagcagc tcggatccct aagtctggag ctgccagcga ggcttccaac ccgctgcttg    660

ccatcacctc ccaggtcgtt ggtggctccg attactcccc tgctggtgcc tccctccttg    720

gcgcgcttcc cacctgcgat cggcgccctc ttcgcagtca cgaactcgcc agcagctagc    780

agcactgact agtaggaggg cccgccggag gagagccgcg cggcccacag aagcggaacg    840
```

```
cgcgtcgaga gcgccctgtc cgctcgcccc agacagatgc ccggttattc attaccgcga    900

ggcctagagg aaagagtggc tgccgtcttc ctgcccacag cccgccggac cctccgtcgc    960

ggctgcccgg tccccggagc cgcagccgcc gagcccggct gtgcgtgtcg tggctgctgg   1020

ggagaaagag gcttccggac atgctctgga gtcagaagac agcgaaaaga gaagcagaag   1080

ccccggtggc aagagtctga aggaaggatg actgtagcct gtggattgta ctgcagtagg   1140

aaactgtcct agcaaggctc cactttgccc cagcttcaag ctggaaagga ggagaacatg   1200

aaacattgct tgaagacaat ggccgagaca gcaggtccca ccctgcacag ccaccagcat   1260

ctctcccctc agccctgtct cctcttctgc agttgggatc tgcacattta agcctgaaat   1320

tgtcctgtga agtgaagtat gatcggacag cctcttttca gcttttatga caatggagac   1380

agaggaattg tggctcttgc caaggtcaca ggattggaat acagagccaa gccaccccag   1440

gacatgcaag agcctcagaa gggaaaaaag cccagcagga agggagaaca agtagcctct   1500

gtcctgaagt tgtaacagcc aggggccagg atggaggagg aggaccccat aatctgccca   1560

tctgggactt ggcaggggac ctgggaaaat gtaccccaac ccatccctta a            1611
```

<210> SEQ ID NO 32
<211> LENGTH: 2718
<212> TYPE: DNA
<213> ORGANISM: Homo sapiens

<400> SEQUENCE: 32

```
atcaagcgat cctcccacct gggcctccca aagtgttgag attacagcat gagccaccac     60

acccagacta aaaggcagtt tgattttaca aatcaaaata gcagtaatct atggagattt    120

acttgtgaga ttggtaggaa acatcttaaa tgtaatcaaa caataactta catcttgatg    180

aattcacgtg taggtttctc ttcctcagaa gaaatcagat gctgttcaga gcacgaaggc    240

tagaatttta ccctggttct catgctacct tgcacccagg ttggatcctg agtacagttt    300

ttggcaggtg ggcctgcata taagttagca atgggggata cccagctgcc tctcttcata    360

cagctgaggt tttggggagt cattcttata gcccctgggt tgggcctagt cctgcaaatg    420

aattcaccag ccctaaagcc caaattgcag cctctgtcat tcaccttcca ggagtggaaa    480

gggcagtaag tttcatctta ttattattgc tattttggtg gttttgttga ggttggtgtg    540

tgtatgttag taagataaag ctctcagaaa ttacatagca tttgtcaagg atataagagg    600

gactgtgcca catctggctg tatagaaggt ggttccatat ctttaaatag agccccaggt    660

ccttagccac cagaaaggtt ttcaggggaa gtgtgcaccc tcagcagctg ctgctggtgg    720

gcaggatggg cacgcatgga acaggctttc ctctgtggcc aggtgagaag caggtggtga    780

gacacagagc agtgctgggc tctgcttctg aagcctccaa cctttccttc cctaggaagc    840

cccagagaga ttggtgaggg tgatttccca ggaagacgca gtgtgctctg acttctgtga    900

cagtgagcaa cgggaccagt ggatgtccag atgctggcaa tgagtaggcc ttccctacgc    960

tgggtggcgt ccacaccctc cggcttccat tgcctgggtc tcctggaggt ggtttgctgg   1020

atgaataccg catgcacaga ggctggcctt gggtttgaat atggcagcca gtggacagca   1080

tgtgcttcag ttatgagact gcccaggaga tgcttcttcc aaggcagagc acgtgcagag   1140

tccagtgctg gagaggccgg gtgcgcagtt gacccatttc cagttctgtt ttccctctca   1200

tgttcctctg tccccatcta ggacatgctc tggagtcaga agacagcgaa aagagaagca   1260

gaagccccgg tggcaagagt ctgaagcagg aaggatgact gtagcctgtg gattgtactg   1320

cagtaggaaa ctgtcctagc aaggctccac tttgccccag cttcaagctg gaaaggagga   1380
```

gaacatgaaa cattgcttga agacaatggc cgagacagca ggtcccaccc tgcacagcca 1440
ccagcatctc tcccctcagc cctgtctcct cttctgcagt tgggatctgc acatttaagc 1500
ctgaaattgt cctgtgaagt gaagtatgat cggacagcct cttttcagct tttatgacaa 1560
tggagacaga ggaattgtgg ctcttgccaa ggtcacagga ttggaataca gagccaagcc 1620
accccaggac atgcaagagc ctcagaaggg aaaaaagccc agcaggaagg gagaacaagt 1680
agcctctgtc ctgaagttgt aacagccagg ggccaggatg gaggaggagg accccataat 1740
ctgcccatct gggacttggc aggggacctg ggaaaatgta ccccaaccca tcccttaagg 1800
gcctttgtct ttggcccatt ggcctagcat ctacttcttc accgtgtctg ttcttgtcac 1860
acctagtcag gtctgtttgg gtctgaggtg catggaacat tctgggtagg cctccagcaa 1920
acggaagctc ttcaccgtgt ttccagcctg ggaccaaggg cagcatactg gcaaagttgc 1980
caaagcaagg gactccagcc tcttaggagt taatgactcc ctctccccag ctgtcctccc 2040
cttggtgctc ctcttcctcc ctcctcctgc tcacagcagg cagggcctag acccgggagc 2100
catgctgctg tgctgttgcc aggggagcac ggaggcagat ctgagctatg cagggaaaag 2160
gcccagcctg tcaaagtgtc tgagatgaac cgccgccgtc cctgtgcagc tgggctcaga 2220
cgtgtctcag ctcttgttct gtgcctgaga atggcgaaac ccagtgaggt tcaagggcaa 2280
actcgctatt cattagtcag ggttcttgga cgtcccgtct ctcccaggga tgagttcccc 2340
cctcctcttt ctccccctcc tatgacacat tcctgggtgc ctttggtgag gactgcacac 2400
cctcctcctg cctagccccc tctccaaagg cccctgaata aactcccccc aaggagacca 2460
ggcagggcag agacaatggc tgcaggaaat cattcaggcg ggacatgctg gcctgccctc 2520
cacccagtcc ccctgtgggc cccactccct tctgattcag ggcacccttg ggcccccagc 2580
ctatacaggc ctggacagga agaaaccact gggaaccacc ctaaggacaa catgctagtc 2640
cagtgccatt cttcgctggc tctgtgggtg cctttgtggc ctgtaccgac tggctggcta 2700
attttgtggt ttctgtac 2718

<210> SEQ ID NO 33
<211> LENGTH: 3723
<212> TYPE: DNA
<213> ORGANISM: Homo sapiens

<400> SEQUENCE: 33
gagagattgg tgagggtgat ttcccaggaa gacgcagtgt gctctgactt ctgtgacaga 60
catgctctgg agtcagaaga cagcgaaaag agaagcagaa gccccggtgg caagagtctg 120
aagctggaaa ggaggagaac atgaaacatt gcttgaagac aatggccgag acagcaggtc 180
ccaccctgca cagccaccag catctctccc ctcagccctg tctcctcttc tgcagttggg 240
atctgcacat ttaagcctga aattgtcctg tgaagtgaag tatgatcgga cagcctcttt 300
tcagctttta tgacaatgga gacagaggaa ttgtggctct tgccaaggtc acaggattgg 360
aatacagagc caagccaccc caggacatgc aagagcctca gaagggaaaa aagcccagca 420
ggaagggaga acaagtagcc tctgtcctga agttgtaaca gccaggggcc aggatggagg 480
aggaggaccc cataatctgc ccatctggga cttggcaggg gacctgggaa aatgtacccc 540
aacccatccc ttaagggcct ttgtctttgg cccattggcc tagcatctac ttcttcaccg 600
tgtctgttct tgtcacacct agtcaggtct gtttgggtct gaggtgcatg gaacattctg 660
ggtaggcctc cagcaaacgg aagctcttca ccgtgtttcc agcctgggac caagggcagc 720

```
atactggcaa agttgccaaa gcaagggact ccagcctctt aggagttaat gactccctct    780
ccccagctgt cctccccttg gtgctcctct tcctccctcc tcctgctcac agcaggcagg    840
gcctagaccc gggagccatg ctgctgtgct gttgccaggg gagcacggag gcagatctga    900
gctatgcagg gaaaaggccc agcctgtcaa agtgtctgag atgaaccgcc gccgtccctg    960
tgcagctggg ctcagacgtg tctcagctct tgttctgtgc ctgagaatgg cgaaacccag   1020
tgaggttcaa gggcaaactc gctattcatt agtcaggggt tcttgacgtc ccgtctctcc   1080
cagggatgag ttccccccctc ctctttctcc ccctcctatg acacattcct gggtgccttt   1140
ggtgaggact gcacaccctc ctcctgccta gccccctctc caaaggcccc tgaataaact   1200
ccccccaagg agaccaggca gggcagagac aatggctgca ggaaatcatt caggcgggac   1260
atgctggcct gccctccacc cagtccccct gtgggcccca ctcccttctg attcagggca   1320
cccttgggcc cccagcctat acaggcctgg acaggaagaa accactggga accaccctaa   1380
ggacaacatg ctagtccagt gccattcttc gctggctctg tgggtgcctt tgtggcctgt   1440
accgactggc tggctaattt tgtggtttct gtaccatcac atgcctattt taagacactc   1500
tccagcactg tcggttaggg agtgtaaatt ttgcaatatt ttctgaaatg tggcaatatc   1560
aaaatgtaaa aggcacacat acttggtcac aaacaaatgg cactatttac tctgtgggca   1620
tatttgtaaa agttgccaaa gaattatata caaggatgtt catcagagca tttcttttga   1680
agagtaaaga aatggacatg aacctgtggt ccgttcatac ggtggaatac ctatgcagct   1740
gtaaaaatca gtgtggtaga tctccgtata tgagttgatg tggaaggttg gccagttcac   1800
atgataaggt gaatagaata agttacagaa caggctgtag agtatgatct tatttgtaga   1860
tgtttaaaac tgagtcataa gtatgcttat atacagatcg tttctggaag tatgtactgg   1920
aagtctacct ctggggagtg gggatggggg agtgcactct tctatactgt tatattttct   1980
tttcatgctc ctaaggtact tttattggaa gatgtaaagc ggttcaatgt aataggctta   2040
acttctgtca actaagttgg cgtgggtgct ttaagagggt ggtagtgatg ttgctggaga   2100
aagtatccca cagtcactgg tggcttcagc cacgggccat tttggggcct aataatcaca   2160
tatcatcatg gttgctagtg ttaatcgaaa acctactaag tgccaggctt actgtctctg   2220
ggtcttgctt acgtggatgt catttttcca gttgcaccaa atcgaaagag gttaattggt   2280
ttgttggagt tcctttgtag gtgaagggca gagccaggag cttggctagg gacaggggag   2340
gtgagtgggg gatggtggat aggtcttggc tcccagtttc cttctgggca gacattgccc   2400
ctctgccctg aggacctgct tgtttggggg aagaggcctt tagaggcacc agggtcatgc   2460
caggtgttgg acatggtgaa ctgggaagtg ctcccatctg gccacagcgc agaagtatca   2520
ccgtgctggg ggatggggaa cagggctgtg aatgggccta tttgcataag cagcatgtgt   2580
ctggagagaa agacatcaca gagcagaaga gtgcgggtgc ccaggagtgc acttgccacc   2640
cctacttcat ccctgaaaga gtaaatggcc tggaaggtgt ctctgagagg taatgccgca   2700
caccaccctc cctgggggca gggtcaggct acacctgcct taggtcgggg gctgcagcag   2760
cctgagagct ctcagtaggg cctcagtagc ctgggaggga gcaggggcag ggggcaggga   2820
aagaggcgta atggggctgt ccagaggggc ctgggaaacc tggtccctga ggcctgggca   2880
cagctacaat cacttcaaat tggctgtggg gccagtggac tgggaaggaa aaaagcaata   2940
agagtgacca agtgcagaag gctgtcaggt cccaggtcac atgccttagt gcagtgactc   3000
ctcatcattt tatggggtgt gggtgtcgtt ggtacaccca ttttacagat gaggacaccg   3060
aggcccagaa aagttaagtt acatgtccta agtcacacag cttgtaagtg ccagaactga   3120
```

gatcaaaacc aagtctcttt gactttaaag tctgtactct gaccccaaag agatcctgtt 3180
tggccactta taggaggtcc ctaaagctgc agactcccct tgccggcacc cacatataga 3240
gacattaacc cttcccctgc agggtcacct caaatagtct tttagctggg cttctcctgc 3300
aattccacct aatgccatcc cctgggtttt gcccaaacct gaactgggca gtggggtgag 3360
aggaggggtt tacagggtta cagagcctca tacagatagg agcccatggc tgctggtcat 3420
ctgcattcct gcaggattgg ctgttccttg gggtccttgg caggaaaatg aggattgctc 3480
cgaggcctgc tccagtactt cccagaggct ggcctggtgt ggggctctgg gaaggctgag 3540
gctggagaag cgtaagtagg agggcagaga tggcactcag gtagcttgaa tcaccaggac 3600
ccttccaagc cccacaggtt ctgagggagt actagggcca gctctgggag aggtctcttc 3660
ctatgctgtg aaccccctgc ctttcttgca gcctacaacg aataaatttt ctttgcaaag 3720
gct 3723

<210> SEQ ID NO 34
<211> LENGTH: 4778
<212> TYPE: RNA
<213> ORGANISM: Homo sapiens

<400> SEQUENCE: 34
ggagaaacac acacgggcgg gcggagggga cccggggcga gucaucaagg gcgcgugguu 60
cggcgugcca ggcgcgcugc ucugccugcu cucuuggcuu cugucucccu ucgaccgauc 120
gcccccuauc cugaagcuuu ccaaugucau cuuggagccc caaaguuucc uggggccucc 180
gcguugugcg ucccagaacc ccuugccugc cccugaggga aacgcggagc cauaggcagc 240
gggacgucgg gagccagccc aggggaggcc agauucagca uuuggacagc ggcucugggg 300
cgcagucggc ccagcgaguu ugccggugaa cagccucggg cacauggcgg guaggagggc 360
cgcagggcug cucugggucu ugaagaagca ggacccagcc uagagggcau ccccagcucc 420
gaaugggaca cguuuucccg agauaaaaga ucccuucuga gcucacacgg gagccccggg 480
accauccaau ccagcgugga uaucccccagc cuaaccaaca ccugugcugg ggggaaagau 540
aagacgcccc cuuucagcca ggagguggac gacccucaug cccucagcuc uccauucuuc 600
ccaaagcagc ucggaucccu aagucuggag cugccagcga ggcuuccaac ccgcugcuug 660
ccaucaccuc ccaggucguu gguggcuccg auuacucccc ugcuggugcc ucccuccuug 720
gcgcgcuucc caccugcgau cggcgcccuc uucgcaguca cgaacucgcc agcagcuagc 780
agcacugacu aguaggaggg cccgccggag gagagccgcg cggcccacag aagcggaacg 840
cgcgucgaga gcgcccuguc cgcucgcccc agacagaugc ccgguuauuc auuaccgcga 900
ggccuagagg aaagaguggc ugccgucuuc cugcccacag cccgccggac ccuccgucgc 960
ggcugcccgg uccccggagc cgcagccgcc gagcccggcu gugcgugucg uggcugcugg 1020
ggagaaagag gcuuccggac augcucugga gucagaagac agcgaaaaga gaagcagaag 1080 ccccggguggc aagagucuga aggaaggaug acuguagccu guggauugua cugcaguagg 1140
aaacuguccu agcaaggcuc cacuuugccc cagcuucaag cuggaaagga ggagaacaug 1200
aaacauugcu ugaagacaau ggccgagaca gcagguccca cccugcacag ccaccagcau 1260
cucuccccuc agcccugucu ccucuucugc aguugggauc ugcacauuua agccugaaau 1320
uguccuguga agugaaguau gaucggacag ccucuuuuca gcuuuuauga caauggagac 1380
agaggaauug uggcucuugc caaggucaca ggauuggaau acagagccaa gccaccccag 1440

-continued

```
gacaugcaag agccucagaa gggaaaaaag cccagcagga agggagaaca aguagccucu   1500
guccugaagu uguaacagcc aggggccagg auggaggagg aggaccccau aaucugccca   1560
ucugggacuu ggcaggggac cugggaaaau guaccccaac ccaucccuua agggccuuug   1620
ucuuuggccc auuggccuag caucuacuuc uucaccgugu cuguucuugu cacaccuagu   1680
caggucuguu ugggucugag gugcauggaa cauucugggu aggccuccag caaacggaag   1740
cucuucaccg uguuuccagc cugggaccaa gggcagcaua cuggcaaagu ugccaaagca   1800
agggacucca gccucuuagg aguuaaugac ucccucuccc cagcuguccu ccccuuggug   1860
cuccucuucc ucccucuccc ugcucacagc aggcagggcc uagacccggg agccaugcug   1920
cugugcuguu gccaggggag cacggaggca gaucugagcu augcagggaa aaggcccagc   1980
cugucaaagu gucugagaug aaccgccgcc gucccugugc agcugggcuc agacgugucu   2040
cagcucuugu ucugugccug agaauggcga aacccaguga gguucaaggg caaacucgcu   2100
auucauuagu caggggguucu ugacgucccg ucucucccag ggaugaguuc cccccuccuc   2160
uuucuccccc uccuaugaca cauuccuggg ugccuuuggu gaggacugca cacccuccuc   2220
cugccuagcc cccucuccaa aggccccuga auaaacuccc cccaaggaga ccaggcaggg   2280
cagagacaau ggcugcagga aaucauucag gcgggacaug cuggccugcc cuccacccag   2340
ucccccugug ggccccacuc ccuucugauu cagggcaccc uugggccccc agccuauaca   2400
ggccuggaca ggaagaaacc acugggaacc acccuaagga caacaugcua guccagugcc   2460
auucuucgcu ggcucugugg gugccuuugu ggccuguacc gacuggcugg cuaauuuugu   2520
gguuucugua ccaucacaug ccuauuuuaa gacacucucc agcacugucg guuagggagu   2580
guaaauuuug caauauuuuc ugaaaugugg caauaucaaa auguaaaagg cacacauacu   2640
uggucacaaa caaauggcac uauuuacucu gugggcauau uuguaaaagu ugccaaagaa   2700
uuauauacaa ggauguucau cagagcauuu cuuuugaaga guaaagaaau ggacaugaac   2760
cuguggucceg uucauacggu ggaauaccua ugcagcugua aaaaucagug ugguagaucu   2820
ccguauauga guugaugugg aagguuggcc aguucacaug auaaggugaa uagaauaagu   2880
uacagaacag gcuguagagu augaucuuau uuguagaugu uuaaaacuga gucauaagua   2940
ugcuuauaua cagaucguuu cuggaaguau guacuggaag ucuaccucug gggaguggggg   3000
augggggagu gcacucuucu auacuguuau auuuucuuuu caugcuccua agguacuuuu   3060
auuggaagau guaaagcggu ucaauguaau aggcuuaacu ucugucaacu aaguuggcgu   3120
gggugcuuua agaggguggu agugauguug cuggagaaag uaucccacag ucacuggugg   3180
cuucagccac gggccauuuu ggggccuaau aaucacauau caucaugguu gcuaguguua   3240
aucgaaaacc uacuaagugc caggcuuacu gucucugggu cuugcuuacg uggaugucau   3300
uuuuccaguu gcaccaaauc gaaagagguu aauugguuug uuggaguucc uuuguaggug   3360
aagggcagag ccaggagcuu ggcuagggac aggggaggug aguggggggau gguggauagg   3420
ucuuggcucc caguuuccuu cugggcagac auugccccuc ugcccugagg accugcuugu   3480
uuggggggaag aggccuuuag aggcaccagg gucaugccag guguuggaca uggugaacug   3540
ggaagugcuc ccaucuggcc acagcgcaga aguaucaccg ugcuggggga uggggaacag   3600
ggcugugaau gggccuauuu gcauaagcag caugugucug gagagaaaga caucacagag   3660
cagaagagug cgggugccca ggagugcacu ugccaccccu acuucauccc ugaaagagua   3720
aauggccugg aaggugucuc ugagagguaa ugccgcacac cacccucccu gggggcaggg   3780
ucaggcuaca ccugccuuag gucgggggcu gcagcagccu gagagcucuc aguagggccu   3840
```

caguagccug ggagggagca ggggcagggg gcagggaaag aggcguaaug gggcugucca 3900
gaggggccug ggaaaccugg ucccugaggc cugggcacag cuacaaucac uucaaauugg 3960 cugugggggcc aguggacugg gaaggaaaaa agcaauaaga gugaccaagu gcagaaggcu 4020 gucaggucccc aggucacaug ccuuagugca gugacuccuc aucauuuuau ggggugugggg 4080 ugucguuggu acacccauuu uacagaugag gacaccgagg cccagaaaag uuaaguuaca 4140
uguccuaagu cacacagcuu guaagugcca gaacugagau caaaaccaag ucucuuugac 4200
uuuaaagucu guacucugac cccaaagaga uccuguuugg ccacuuauag gaggucccua 4260
aagcugcaga cuccccuugc cggcacccac auauagagac auuaacccuu ccccugcagg 4320
gucaccucaa auagucuuuu agcugggcuu cuccugcaau uccaccuaau gccaucccccu 4380 ggguuuugcc caaaccugaa cugggcagug gggugagagg aggggguuuac aggguuacag 4440 agccucauac agauaggagc ccauggcugc uggucaucug cauuccugca ggauuggcug 4500
uuccuugggg uccuuggcag gaaaaugagg auugcuccga ggccugcucc aguacuuccc 4560
agaggcuggc cuggugugggg gcucugggaa ggcugaggcu ggagaagcgu aaguaggagg 4620
gcagagaugg cacucaggua gcuugaauca ccaggacccu uccaagcccc acagguucug 4680
agggaguacu agggccagcu cugggagagg ucucuuccua ugcugugaac ccccugccuu 4740
ucuugcagcc uacaacgaau aaauuuucuu ugcaaagg 4778

<210> SEQ ID NO 35
<211> LENGTH: 4113
<212> TYPE: RNA
<213> ORGANISM: Homo sapiens

<400> SEQUENCE: 35
gauucucaca acuucugcgu gcgagcgccc gccccaccga ccgccccggc ccggcccgca 60
agagccagag gagccgagag gagcccagcg ccggcccagc ggacuccagc ucgacggagc 120
ggccgcgccc cgaccaguua cuccccugcu ggugccuccc uccuuggcgc gcuucccacc 180
ugcgaucggc gcccucuucg cagucacgaa cucgccagca gcuagcagca cugacuagua 240
ggagggcccg ccggaggaga ggaagcccca gagagauugg ugagggugau uucccaggaa 300
gacgcagugu gcucugacuu cugugacagu gagcaacggg accaguggau guccagaugc 360
uggcaaugag acaugcucug gagucagaag acagcgaaaa gagaagcaga agccccggug 420
gcaagagucu gaagcaggaa ggaugacugu agccugugga uuguacugca guaggaaacu 480
guccuagcaa ggcuccacuu ugccccagcu ucaagcugga aaggaggaga acaugaaaca 540
uugcuugaag acaauggccg agacagcagg ucccacccug cacagccacc agcaucucuc 600
cccucagccc ugucuccucu ucugcaguug ggaucugcac auuuaagccu gaaauugucc 660
ugugaaguga aguaugaucg gacagccucu uuucagcuuu uaugacaaug gagacagagg 720
aauuguggcu cuugccaagg ucacaggauu ggaauacaga gccaagccac cccaggacau 780
gcaagagccu cagaagggaa aaaagcccag caggaaggga gaacaaguag ccucuguccu 840
gaaguuguaa cagccagggg ccaggaugga ggaggaggac cccauaaucu gcccaucugg 900
gacuuggcag gggaccuggg aaaauguacc ccaacccauc ccuuaagggc cuuugucuuu 960
ggcccauugg ccuagcaucu acuucuucac cgugucuguu cuugucacac cuagucaggu 1020
cuguuugggu cugaggugca uggaacauuc uggguaggcc uccagcaaac ggaagcucuu 1080
caccguguuu ccagccuggg accaagggca gcauacuggc aaaguugcca aagcaaggga 1140

-continued

```
cuccagccuc uuaggaguua augacucccu cuccccagcu guccuccccu uggugcuccu   1200
cuuccucccu ccuccugcuc acagcaggca gggccuagac ccgggagcca ugcugcugug   1260
cuguugccag gggagcacgg aggcagaucu gagcuaugca gggaaaaggc ccagccuguc   1320
aaagugucug agaugaaccg ccgccguccc ugugcagcug ggcucagacg ugucucagcu   1380
cuuguucugu gccugagaau ggcgaaaccc agugagguuc aagggcaaac ucgcuauuca   1440
uuagucaggg guucuugacg ucccgucucu cccagggaug aguucccccc uccucuuucu   1500
cccccuccua ugacacauuc cugggugccu uuggugagga cugcacaccc uccuccugcc   1560
uagcccccuc uccaaaggcc ccugaauaaa cuccccccaa ggagaccagg cagggcagag   1620
acaauggcug caggaaauca uucaggcggg acaugcuggc cugcccucca cccagucccc   1680
cugugggccc cacucccuuc ugauucaggg cacccuuggg cccccagccu auacaggccu   1740
ggacaggaag aaaccacugg gaaccacccu aaggacaaca ugcuagucca gugccauucu   1800
ucgcuggcuc ugugggugcc uuuguggccu guaccgacug gcuggcuaau uuugugguuu   1860
cuguaccauc acaugccuau uuuaagacac ucuccagcac ugucgguuag ggaguguaaa   1920
uuuugcaaua uuuucugaaa uguggcaaua ucaaaaugua aaaggcacac auacuugguc   1980
acaaacaaau ggcacuauuu acucugugg cauauuugua aaaguugcca aagaauuaua   2040
uacaaggaug uucaucagag cauuucuuuu gaagaguaaa gaaauggaca ugaaccugug   2100
guccguucau acgguggaau accuaugcag cuguaaaaau caguguggua gaucuccgua   2160
uaugaguuga uguggaaggu uggccaguuc acaugauaag gugaauagaa uaaguuacag   2220
aacaggcugu agaguaugau cuuauuugua gauguuuaaa acugagucau aaguaugcuu   2280
auauacagau cguuucugga aguauguacu ggaagucuac cucuggggag uggggauggg   2340
ggagugcacu cuucuauacu guuauauuuu cuuuucaugc uccuaaggua cuuuuauugg   2400
aagauguaaa gcgguucaau guaauaggcu uaacuucugu caacuaaguu ggcgugggug   2460
cuuuaagagg gugguaguga uguugcugga gaaaguaucc cacagucacu gguggcuuca   2520
gccacgggcc auuuuggggc cuaauaauca cauaucauca ugguugcuag uguuaaucga   2580
aaaccuacua agugccaggc uuacugucuc ugggucuugc uuacguggau gucauuuuuc   2640
caguugcacc aaaucgaaag agguuaauug guuuguugga guuccuuugu aggugaaggg   2700
cagagccagg agcuuggcua gggacagggg aggugagugg gggauggugg auaggucuug   2760
gcucccaguu uccuucuggg cagacauugc cccucugccc ugaggaccug cuuguuuggg   2820
ggaagaggcc uuuagaggca ccagggucau gccaggugu uggacauggug aacugggaag   2880
ugcucccauc uggccacagc gcagaaguau caccgugcug ggggaugggg aacagggcug   2940
ugaaugggcc uauuugcaua agcagcaugu gucuggagag aaagacauca cagagcagaa   3000
gagugcgggu gcccaggagu gcacuugcca ccccuacuuc aucccugaaa gaguaaaugg   3060
ccuggaaggu gucucugaga gguaaugccg cacaccaccc ucccuggggg cagggucagg   3120
cuacaccugc cuuaggucgg gggcugcagc agccugagag cucucaguag ggccucagua   3180
gccugggagg gagcaggggc agggggcagg gaaagaggcg uaauggggcu guccagaggg   3240
gccugggaaa ccugguccu gaggccuggg cacagcuaca aucacuucaa auuggcugug   3300
gggccagugg acugggaagg aaaaaagcaa uaagagugac caagugcaga aggcugucag   3360
gucccagguc acaugccuua gugcagugac uccucaucau uuuaugggu gugggugucg   3420
uugguacacc cauuuuacag augaggacac cgaggcccag aaaaguuaag uuacaugucc   3480
uaagucacac agcuuguaag ugccagaacu gagaucaaaa ccaagucucu uugacuuuaa   3540
```

```
agucuguacu cugaccccaa agagauccug uuuggccacu uauaggaggu cccuaaagcu   3600

gcagacuccc cuugccggca cccacauaua gagacauuaa cccuuccccu gcagggucac   3660

cucaaauagu cuuuuagcug ggcuucuccu gcaauuccac cuaaugccau ccccuggguu   3720

uugcccaaac cugaacuggg caguggggug agaggagggg uuuacagggu uacagagccu   3780

cauacagaua ggagcccaug gcugcugguc aucugcauuc cugcaggauu ggcuguuccu   3840

ugggguccuu ggcaggaaaa ugaggauugc uccgaggccu gcuccaguac uucccagagg   3900

cuggccuggu guggggcucu gggaaggcug aggcuggaga agcguaagua ggagggcaga   3960

gauggcacuc agguagcuug aaucaccagg acccuuccaa gccccacagg uucugaggga   4020

guacuagggc cagcucuggg agaggucucu uccuaugcug ugaacccccu gccuuucuug   4080

cagccuacaa cgaauaaauu uucuuugcaa agg                                4113
```

<210> SEQ ID NO 36
<211> LENGTH: 3936
<212> TYPE: RNA
<213> ORGANISM: Homo sapiens

<400> SEQUENCE: 36

```
ggagccgaga ggagcccagc gccggcccag cggacuccag cucgacggag cggccgcgcc     60

ccgaccaguu acuccccugc uggugccucc cuccuuggcg cgcuucccac cugcgaucgg    120

cgcccucuuc gcagucacga acucgccagc agcuagcagc acugacuagu aggagggccc    180

gccggaggag aggacaugcu cuggagucag aagacagcga aaagagaagc agaagccccg    240

guggcaagag ucugaaggaa ggaugacugu agccugugga uuguacugca guaggaaacu    300

guccuagcaa ggcuccacuu ugccccagcu ucaagcugga aaggaggaga acaugaaaca    360

uugcuugaag acaauggccg agacagcagg ucccacccug cacagccacc agcaucucuc    420

cccucagccc ugucuccucu ucugcaguug ggaucugcac auuuaagccu gaaauugucc    480

ugugaaguga aguaugaucg gacagccucu uuucagcuuu uaugacaaug gagacagagg    540

aauuguggcu cuugccaagg ucacaggauu ggaauacaga gccaagccac cccaggacau    600

gcaagagccu cagaagggaa aaaagcccag caggaaggga gaacaaguag ccucuguccu    660

gaaguuguaa cagccagggg ccaggaugga ggaggaggac cccauaaucu gcccaucugg    720

gacuuggcag gggaccuggg aaaauguacc ccaacccauc ccuuaagggc cuuugucuuu    780

ggcccauugg ccuagcaucu acuucuucac cgugucuguu cuugucacac cuagucaggu    840

cuguuugggu cugaggugca uggaacauuc uggguaggcc uccagcaaac ggaagcucuu    900

caccguguuu ccagccuggg accaagggca gcauacuggc aaaguugcca aagcaaggga    960

cuccagccuc uuaggaguua augacucccu cuccccagcu guccuccccu uggugcuccu   1020

cuuccucccu ccuccugcuc acagcaggca gggccuagac ccgggagcca ugcugcugug   1080

cuguugccag gggagcacgg aggcagaucu gagcuaugca gggaaaaggc ccagccuguc   1140

aaagugucug agaugaaccg ccgccguccc ugugcagcug ggcucagacg ugucucagcu   1200

cuuguucugu gccugagaau ggcgaaaccc agugagguuc aagggcaaac ucgcuauuca   1260

uuagucaggg guucuugacg ucccgucucu cccagggaug aguucccccc uccucuuucu   1320

cccccuccua ugacacauuc cugggugccu uuggugagga cugcacaccc uccuccugcc   1380

uagcccccuc uccaaaggcc ccugaauaaa cucccccaa ggagaccagg cagggcagag    1440

acaauggcug caggaaauca uucaggcggg acaugcuggc cugcccucca cccagucccc   1500
```

```
cugugggccc cacucccuuc ugauucaggg cacccuuggg cccccagccu auacaggccu   1560

ggacaggaag aaaccacugg gaaccacccu aaggacaaca ugcuagucca gugccauucu   1620

ucgcuggcuc ugugggugcc uuuguggccu guaccgacug gcuggcuaau uuugugguuu   1680

cuguaccauc acaugccuau uuuaagacac ucuccagcac ugucgguuag ggaguguaaa   1740

uuuugcaaua uuuucugaaa uguggcaaua ucaaaaugua aaaggcacac auacuugguc   1800

acaaacaaau ggcacuauuu acucuguggg cauauuugua aaaguugcca aagaauuaua   1860

uacaaggaug uucaucagag cauuucuuuu gaagaguaaa gaaauggaca ugaaccugug   1920

guccguucau acgguggaau accuaugcag cuguaaaaau caguguggua gaucuccgua   1980

uaugaguuga uguggaaggu uggccaguuc acaugauaag gugaauagaa uaaguuacag   2040

aacaggcugu agaguaugau cuuauuugua gauguuuaaa acugagucau aaguaugcuu   2100

auauacagau cguuucugga aguauguacu ggaagucuac cucuggggag uggggauggg   2160

ggagugcacu cuucuauacu guuauauuuu cuuuucaugc uccuaaggua cuuuuauugg   2220

aagauguaaa gcgguucaau guaauaggcu uaacuucugu caacuaaguu ggcgugggug   2280

cuuuaagagg gugguaguga uguugcugga gaaaguaucc cacagucacu gguggcuuca   2340

gccacgggcc auuuuggggc cuaauaauca cauaucauca ugguugcuag uguuaaucga   2400

aaaccuacua agugccaggc uuacugucuc ugggucuugc uuacguggau gucauuuuuc   2460

caguugcacc aaaucgaaag agguuaauug guuuguugga guuccuuugu aggugaaggg   2520

cagagccagg agcuuggcua gggacagggg aggugagugg gggauggugg auaggucuug   2580

gcucccaguu uccuucuggg cagacauugc cccucugccc ugaggaccug cuuguuuggg   2640

ggaagaggcc uuuagaggca ccagggucau gccagguguu ggacauggug aacugggaag   2700

ugcucccauc uggccacagc gcagaaguau caccgugcug ggggaugggg aacagggcug   2760

ugaaugggcc uauuugcaua agcagcaugu gucuggagag aaagacauca cagagcagaa   2820

gagugcgggu gcccaggagu gcacuugcca ccccuacuuc aucccugaaa gaguaaaugg   2880

ccuggaaggu gucucugaga gguaaugccg cacaccaccc ucccuggggg cagggucagg   2940

cuacaccugc cuuaggucgg gggcugcagc agccugagag cucucaguag ggccucagua   3000

gccugggagg gagcaggggc agggggcagg gaaagaggcg uaauggggcu guccagaggg   3060

gccugggaaa ccuggucccu gaggccuggg cacagcuaca aucacuucaa auuggcugug   3120

gggccagugg acugggaagg aaaaaagcaa uaagagugac caagugcaga aggcugucag   3180

gucccagguc acaugccuua gugcagugac uccucaucau uuuauggggu gugggugucg   3240

uugguacacc cauuuuacag augaggacac cgaggcccag aaaaguuaag uuacaugucc   3300

uaagucacac agcuuguaag ugccagaacu gagaucaaaa ccaagucucu uugacuuuaa   3360

agucuguacu cugaccccaa agagauccug uuuggccacu uauaggaggu cccuaaagcu   3420

gcagacuccc cuugccggca cccacauaua gagacauuaa cccuuccccu gcagggucac   3480

cucaaauagu cuuuuagcug ggcuucuccu gcaauuccac cuaaugccau ccccuggguu   3540

uugcccaaac cugaacuggg caguggggug agaggagggg uuuacagggu uacagagccu   3600

cauacagaua ggagcccaug gcugcugguc aucugcauuc cugcaggauu ggcuguuccu   3660

uggggguccuu ggcaggaaaa ugaggauugc uccgaggccu gcuccaguac uucccagagg   3720

cuggccuggu gugggggcucu gggaaggcug aggcuggaga agcguaagua ggagggcaga   3780

gauggcacuc agguagcuug aaucaccagg acccuuccaa gccccacagg uucugaggga   3840

guacuagggc cagcucuggg agaggucucu uccuaugcug ugaaccccccu gccuuucuug   3900
```

cagccuacaa cgaauaaauu uucuuugcaa aggcuu 3936

<210> SEQ ID NO 37
<211> LENGTH: 4026
<212> TYPE: RNA
<213> ORGANISM: Homo sapiens

<400> SEQUENCE: 37
gggggucccg gccccacaca gugcuagggu cccucucgag uuucucaucu gccuucaggu 60
cacuuuccac ccugaugccu uggcuugucc ugaagcucag ggccccugua gcuugggaaa 120
ccucccaagc uccccagcga guggcuguag accaaggaag ggacccugcc cggcuucagg 180
gaagaaagga agaaaguuac uccccugcug gugccucccu ccuuggcgcg cuucccaccu 240
gcgaucggcg cccucuucgc agucacgaac ucgccagcag cuagcagcac ugacuaguag 300
gagggcccgc cggaggagag gacaugcucu ggagucagaa gacagcgaaa agagaagcag 360
aagccccggu ggcaagaguc ugaaggaagg augacuguag ccuguggauu guacugcagu 420
aggaaacugu ccuagcaagg cuccacuuug ccccagcuuc aagcuggaaa ggaggagaac 480
augaaacauu gcuugaagac aauggccgag acagcagguc ccacccugca cagccaccag 540
caucucuccc cucagcccug ucuccucuuc ugcaguuggg aucugcacau uuaagccuga 600
aauuguccug ugaagugaag uaugaucgga cagccucuuu ucagcuuuua ugacaaugga 660
gacagaggaa uuguggcucu ugccaagguc acaggauugg aauacagagc caagccaccc 720
caggacaugc aagagccuca gaagggaaaa aagcccagca ggaagggaga acaaguagcc 780
ucuguccuga aguuguaaca gccaggggcc aggauggagg aggaggaccc cauaaucugc 840
ccaucuggga cuuggcaggg gaccugggaa aauguacccc aacccauccc uuaagggccu 900
uugucuuugg cccauuggcc uagcaucuac uucuucaccg ugucuguucu ugucacaccu 960
agucaggucu guuugggucu gaggugcaug gaacauucug gguaggccuc cagcaaacgg 1020
aagcucuuca ccguguuucc agccugggac caagggcagc auacuggcaa aguugccaaa 1080
gcaagggacu ccagccucuu aggaguuaau gacucccucu ccccagcugu ccucccccuug 1140 gugcuccucu uccucccucc uccugcucac agcaggcagg gccuagaccc gggagccaug 1200
cugcugugcu guugccaggg gagcacggag gcagaucuga gcuaugcagg gaaaaggccc 1260
agccugucaa agugucugag augaaccgcc gccgucccug ugcagcuggg cucagacgug 1320
ucucagcucu uguucugugc cugagaaugg cgaaacccag ugagguucaa gggcaaacuc 1380
gcuauucauu agucaggggu ucuugacguc ccgucucucc cagggaugag uuccccccuc 1440
cucuuucucc cccuccuaug acacauuccu gggugccuuu ggugaggacu gcacacccuc 1500
cuccugccua gcccccucuc caaaggcccc ugaauaaacu ccccccaagg agaccaggca 1560
gggcagagac aauggcugca ggaaaucauu caggcgggac augcuggccu gcccuccacc 1620 caguccccccu gugggcccca cucccuucug auucagggca cccuugggcc cccagccuau 1680
acaggccugg acaggaagaa accacuggga accacccuaa ggacaacaug cuaguccagu 1740
gccauucuuc gcuggcucug ugggugccuu uguggccugu accgacuggc uggcuaauuu 1800
ugugguuucu guaccaucac augccuauuu uaagacacuc uccagcacug ucgguuaggg 1860
aguguaaauu uugcaauauu uucugaaaug uggcaauauc aaaauguaaa aggcacacau 1920
acuuggucac aaacaaaugg cacuauuuac ucugugggca uauuuguaaa aguugccaaa 1980
gaauuauaua caaggauguu caucagagca uuucuuuuga agaguaaaga aauggacaug 2040 aaccugugu ccguucauac gguggaauac cuaugcagcu guaaaaauca guguugguaga 2100 ucuccguaua ugaguugaug uggaagguug gccaguucac augauaaggu gaauagaaua 2160
aguuacagaa caggcuguag aguaugaucu uauuuguaga uguuuaaaac ugagucauaa 2220
guaugcuuau auacagaucg uuucuggaag uauguacugg aagucuaccu cuggggagug 2280 gggaugggg agugcacucu ucuauacugu uauauuuucu uuucaugcuc cuaagguacu 2340
uuuauuggaa gauguaaagc gguucaaugu aauaggcuua acuucuguca acuaaguugg 2400
cgugggugcu uuaagagggu gguagugaug uugcuggaga aaguauccca cagucacugg 2460
uggcuucagc cacgggccau uuuggggccu aauaaucaca uaucaucaug guugcuagug 2520
uuaaucgaaa accuacuaag ugccaggcuu acugucucug ggucuugcuu acguggaugu 2580
cauuuuucca guugcaccaa aucgaaagag guuaauuggu uuguuggagu ucccuuguag 2640
gugaagggca gagccaggag cuuggcuagg gacaggggag gugagugggg gaugguggau 2700
aggucuuggc ucccaguuuc cuucugggca gacauugccc cucugcccug aggaccugcu 2760
uguuuggggg aagaggccuu uagaggcacc agggucaugc cagguguugg acauggugaa 2820
cugggaagug cucccaucug gccacagcgc agaaguauca ccgugcuggg ggaugggggaa 2880 cagggcugug aaugggccua uuugcauaag cagcaugugu cuggagagaa agacaucaca 2940
gagcagaaga gugcgggugc ccaggagugc acuugccacc ccuacuucau cccugaaaga 3000
guaaauggcc uggaaggugu cucugagagg uaaugccgca caccacccuc ccuggggggca 3060 gggucaggcu acaccugccu uaggucgggg gcugcagcag ccugagagcu cucaguaggg 3120
ccucaguagc cugggaggga gcaggggcag gggcaggga aagaggcgua augggggcugu 3180 ccagaggggc cugggaaacc uggucccuga ggccugggca cagcuacaau cacuucaaau 3240
uggcuguggg gccaguggac ugggaaggaa aaaagcaaua agagugacca agugcagaag 3300
gcugucaggu cccaggucac augccuuagu gcagugacuc cucaucauuu uauggggugu 3360
gggugucguu gguacaccca uuuuacagau gaggacaccg aggcccagaa aaguuaaguu 3420
acauguccua agucacacag cuuguaagug ccagaacuga gaucaaaacc aagucucuuu 3480
gacuuuaaag ucuguacucu gaccccaaag agauccuguu uggccacuua uaggaggucc 3540
cuaaagcugc agacuccccu ugccggcacc cacauauaga gacauuaacc cuuccccugc 3600
agggucaccu caaauagucu uuuagcuggg cuucuccugc aauuccaccu aaugccaucc 3660
ccuggguuuu gcccaaaccu gaacugggca guggggugag aggaggggguu uacaggguua 3720 cagagccuca uacagauagg agcccauggc ugcuggucau cugcauuccu gcaggauugg 3780
cuguuccuug gguccuugg caggaaaaug aggauugcuc cgaggccugc uccaguacuu 3840
cccagaggcu ggccuggugu ggggcucugg gaaggcugag gcuggagaag cguaaguagg 3900
agggcagaga uggcacucag guagcuugaa ucaccaggac ccuuccaagc cccacagguu 3960
cugagggagu acuagggcca gcucugggag aggucucuuc cuaugcugug aacccccugc 4020
cuuucu 4026

<210> SEQ ID NO 38
<211> LENGTH: 4334
<212> TYPE: RNA
<213> ORGANISM: Homo sapiens

<400> SEQUENCE: 38
ugaggcgcca ccggugccca gcaaccuccc caggcugugg uugugaccug aggacgcgug 60
uguccccgcc cucaggccac cgcuacgcga cccugagugc accuucaaga aggccgggca 120

```
cguuucuggg cgggcguggg gggugccuga uaucuccgcu cuauuuuaca guuacucccc    180

ugcugguguc ucccuccuug gcgcgcuucc caccugcgau cggcgcccuc uucgcaguca    240

cgaacucgcc agcagcuagc agcacugacu aguaggaggg cccgccggag gagaggaagc    300

cccagagaga uuggugaggg ugauuuccca ggaagacgca gugugcucug acuucuguga    360

cagugagcaa cgggaccagu ggauguccag augcuggcaa ugaguaggcc uucccuacgc    420

uggguggcgu ccacacccuc cggcuuccau ugccugggu uccuggaggu gguuugcugg    480

augaauaccg caugcacaga ggcuggccuu ggguuugaau auggcagcca guggacagca    540

ugugcuucag uuaugagacu gcccaggaga ugcuucuucc aaggcagagc acgugcagag    600

uccagugcug gagaggccgg gugcgcaguu gacccauuuc caguucuguu uucccucuca    660

uguuccucug uccccaucua ggacaugcuc uggagucaga agacagcgaa aagagaagca    720

gaagccccgg uggcaagagu cugaagcugg aaaggaggag aacaugaaac auugcuugaa    780

gacaauggcc gagacagcag gucccacccu gcacagccac cagcaucucu ccccucagcc    840

cugucuccuc uucugcaguu gggaucugca cauuuaagcc ugaaauuguc cugugaagug    900

aaguaugauc ggacagccuc uuuucagcuu uuaugacaau ggagacagag gaauuguggc    960

ucuugccaag gucacaggau uggaauacag agccaagcca ccccaggaca ugcaagagcc   1020

ucagaaggga aaaaagccca gcaggaaggg agaacaagua gccucugucc ugaaguugua   1080

acagccaggg gccaggaugg aggaggagga ccccauaauc ugcccaucug ggacuuggca   1140

ggggaccugg gaaaauguac cccaacccau cccuuaaggg ccuuugucuu uggcccauug   1200

gccuagcauc uacuucuuca ccgugucugu ucuugucaca ccuagucagg ucuguuuggg   1260

ucugaggugc auggaacauu cuggguaggc cuccagcaaa cggaagcucu ucaccguguu   1320

uccagccugg gaccaagggc agcauacugg caaaguugcc aaagcaaggg acuccagccu   1380

cuuaggaguu aaugacuccc ucuccccagc uguccucccc uuggugcucc ucuuccuccc   1440

uccuccugcu cacagcaggc agggccuaga cccgggagcc augcugcugu gcuguugcca   1500

ggggagcacg gaggcagauc ugagcuaugc agggaaaagg cccagccugu caaagugucu   1560

gagaugaacc gccgccgucc cugugcagcu gggcucagac gugucucagc ucuuguucug   1620

ugccugagaa uggcgaaacc cagugagguu caagggcaaa cucgcuauuc auuagucagg   1680

gguucuugac gucccgucuc ucccagggau gaguuccccc cuccucuuuc ucccccuccu   1740

augacacauu ccugggugcc uuuggugagg acugcacacc cuccuccugc cuagcccccu   1800

cuccaaaggc cccugaauaa acuccccccca aggagaccag gcagggcaga gacaauggcu   1860

gcaggaaauc auucaggcgg gacaugcugg ccugcccucc acccaguccc ccugugggcc   1920

ccacucccuu cugauucagg gcacccuugg gcccccagcc uauacaggcc uggacaggaa   1980

gaaaccacug ggaaccaccc uaaggacaac augcuagucc agugccauuc uucgcuggcu   2040

cugugggugc cuuuguggcc uguaccgacu ggcuggcuaa uuuuguggu ucuguaccau    2100

cacaugccua uuuuaagaca cucuccagca cugucgguua gggaguguaa auuuugcaau   2160

auuuucugaa auguggcaau aucaaaaugu aaaaggcaca cauacuuggu cacaaacaaa   2220

uggcacuauu uacucugugg gcauauuugu aaaaguugcc aaagaauuau auacaaggau   2280

guucaucaga gcauuucuuu ugaagaguaa agaaauggac augaaccugu gguccguuca   2340

uacgguggaa uaccuaugca gcuguaaaaa ucagugugu agaucuccgu auaugaguug    2400

auguggaagg uuggccaguu cacaugauaa ggugaauaga auaaguuaca gaacaggcug   2460
```

```
uagaguauga ucuuauuugu agauguuuaa aacugaguca uaaguaugcu uauauacaga   2520

ucguuucugg aaguauguac uggaagucua ccucugggga guggggaugg gggagugcac   2580

ucuucuauac uguuauauuu ucuuuucaug cuccuaaggu acuuuuauug gaagauguaa   2640

agcgguucaa uguaauaggc uuaacuucug ucaacuaagu uggcgugggu gcuuuaagag   2700

ggugguagug auguugcugg agaaaguauc ccacagucac ugguggcuuc agccacgggc   2760

cauuuugggg ccuaauaauc acauaucauc augguugcua guguuaaucg aaaaccuacu   2820

aagugccagg cuuacugucu cugggucuug cuuacgugga ugucauuuuu ccaguugcac   2880

caaaucgaaa gagguuaauu gguuuguugg aguuccuuug uaggugaagg gcagagccag   2940

gagcuuggcu agggacaggg gaggugagug ggggauggug gauaggucuu ggcucccagu   3000

uuccuucugg gcagacauug ccccucugcc cugaggaccu gcuuguuugg gggaagaggc   3060

cuuuagaggc accaggguca ugccaggugu uggacauggu gaacugggaa gugcucccau   3120

cuggccacag cgcagaagua ucaccgugcu gggggauggg gaacagggcu gugaaugggc   3180

cuauuugcau aagcagcaug ugucuggaga gaaagacauc acagagcaga agagugcggg   3240

ugcccaggag ugcacuugcc accccuacuu caucccugaa agaguaaaug gccuggaagg   3300

ugucucugag agguaaugcc gcacaccacc cucccugggg gcagggucag gcuacaccug   3360

ccuuaggucg ggggcugcag cagccugaga gcucucagua gggccucagu agccugggag   3420

ggagcagggg cagggggcag ggaaagaggc guaauggggc uguccagagg ggccugggaa   3480

accugguccc ugaggccugg gcacagcuac aaucacuuca aauuggcugu ggggccagug   3540

gacugggaag gaaaaaagca auaagaguga ccaagugcag aaggcuguca ggucccaggu   3600

cacaugccuu agugcaguga cuccucauca uuuuaugggg ugugggugu c guugguacac   3660

ccauuuuaca gaugaggaca ccgaggccca gaaaaguuaa guuacauguc cuaagucaca   3720

cagcuuguaa gugccagaac ugagaucaaa accaagucuc uuugacuuua aagucuguac   3780

ucugacccca aagagauccu guuuggccac uuauaggagg ucccuaaagc ugcagacucc   3840

ccuugccggc acccacauau agagacauua acccuucccc ugcaggguca ccucaaauag   3900

ucuuuuagcu gggcuucucc ugcaauucca ccuaaugcca uccccugggu uuugcccaaa   3960

ccugaacugg gcaguggggu gagaggaggg guuuacaggg uuacagagcc ucauacagau   4020

aggagcccau ggcugcuggu caucugcauu ccugcaggau uggcuguucc uuggggaccu   4080

uggcaggaaa augaggauug cuccgaggcc ugcuccagua cuucccagag gcuggccugg   4140

ugugggcuc ugggaaggcu gaggcuggag aagcguaagu aggagggcag agauggcacu    4200

cagguagcuu gaaucaccag gacccuucca agccccacag guucugaggg aguacuaggg   4260

ccagcucugg gagaggucuc uuccuaugcu gugaaccccc ugccuuucuu gcagccuaca   4320

acgaauaaau uuuc                                                     4334
```

<210> SEQ ID NO 39
<211> LENGTH: 3868
<212> TYPE: RNA
<213> ORGANISM: Homo sapiens

<400> SEQUENCE: 39

```
uuacucccu gcuggugccu cccuccuugg cgcgcuuccc accugcgauc ggcgcccucu      60

ucgcagucac gaacucgcca gcagcuagca gcacugacua guaggagggc ccgccggagg    120

agaggacaug cucuggaguc agaagacagc gaaaagagaa gcagaagccc cgguggcaag    180

agucugaagc aggaaggaug acuguagccu guggauugua cugcaguagg aaacuguccu    240
```

```
agcaaggcuc cacuuugccc cagcuucaag cuggaaagga ggagaacaug aaacauugcu    300
ugaagacaau ggccgagaca gcaggucccca cccugcacag ccaccagcau cucuccccuc   360
agcccugucu ccucuucugc aguugggauc ugcacauuua agccugaaau uguccuguga    420
agugaaguau gaucggacag ccucuuuuca gcuuuuauga caauggagac agaggaauug    480
uggcucuugc caaggucaca ggauuggaau acagagccaa gccaccccag gacaugcaag    540
agccucagaa gggaaaaaag cccagcagga agggagaaca aguagccucu guccugaagu    600
uguaacagcc aggggccagg auggaggagg aggaccccau aaucugccca ucugggacuu    660
ggcaggggac cugggaaaau guaccccaac ccaucccuua agggccuuug ucuuuggccc    720
auuggccuag caucuacuuc uucaccgugu cuguucuugu cacaccuagu caggucuguu    780
ugggucugag gugcauggaa cauucugggu aggccuccag caaacggaag cucuucaccg    840
uguuuccagc cugggaccaa gggcagcaua cuggcaaagu ugccaaagca agggacucca    900
gccucuuagg aguuaaugac ucccucuccc cagcuguccu ccccuuggug cuccucuucc    960
ucccuccucc ugcucacagc aggcagggcc uagacccggg agccaugcug cugugcuguu   1020
gccaggggag cacggaggca gaucugagcu augcagggaa aaggcccagc cugucaaagu   1080
gucugagaug aaccgccgcc gucccugugc agcugggcuc agacgugucu cagcucuugu   1140
ucugugccug agaauggcga aacccaguga gguucaaggg caaacucgcu auucauuagu   1200
caggguucu ugacgucccg ucucucccag ggaugaguuc cccccuccuc uuucuccccc    1260
uccuaugaca cauuccuggg ugccuuuggu gaggacugca cacccuccuc cugccuagcc   1320
cccucuccaa aggccccuga auaaacuccc cccaaggaga ccaggcaggg cagagacaau   1380
ggcugcagga aaucauucag gcgggacaug cuggccugcc cuccacccag ucccccugug   1440
ggccccacuc ccuucugauu cagggcaccc uugggccccc agccuauaca ggccuggaca   1500
ggaagaaacc acugggaacc acccuaagga caacaugcua guccagugcc auucuucgcu   1560
ggcucugugg gugccuuugu ggccuguacc gacuggcugg cuaauuuugu gguuucugua   1620
ccaucacaug ccuauuuuaa gacacucucc agcacugucg guuagggagu guaaauuuug   1680
caauauuuuc ugaaaugugg caauaucaaa auguaaaagg cacacauacu uggucacaaa   1740
caaauggcac uauuuacucu gugggcauau uuguaaaagu ugccaaagaa uuauauacaa   1800
ggauguucau cagagcauuu cuuuugaaga guaaagaaau ggacaugaac cuguggucug   1860
uucauacggu ggaauaccua ugcagcugua aaaaucagug ugguagaucu ccguauauga   1920
guugaugugg aagguuggcc aguucacaug auaaggugaa uagaauaagu uacagaacag   1980
gcuguagagu augaucuuau uuguagaugu uuaaaacuga gucauaagua ugcuuauaua   2040
cagaucguuu cuggaaguau guacuggaag ucuaccucug gggagugggg augggggagu   2100
gcacucuucu auacuguuau auuucuuuu caugcuccua agguacuuuu auuggaagau    2160
guaaagcggu ucaauguaau aggcuuaacu ucugucaacu aaguuggcgu gggugcuuua   2220
agaggguggu agugauguug cuggagaaag uaucccacag ucacuggugg cuucagccac   2280
gggccauuuu ggggccuaau aaucacauau caucaugguu gcuaguguua aucgaaaacc   2340
uacuaagugc caggcuuacu gucucugggu cuugcuuacg uggaugucau uuuuccaguu   2400
gcaccaaauc gaaagagguu aauugguuug uuggaguucc uuuguaggug aagggcagag   2460
ccaggagcuu ggcuagggac aggggaggug agugggggau gguggauagg ucuuggcucc   2520
caguuuccuu cugggcagac auugccccuc ugcccugagg accugcuugu uuggggggaag   2580
```

aggccuuuag aggcaccagg gucaugccag guguuggaca uggugaacug ggaagugcuc 2640
ccaucuggcc acagcgcaga aguaucaccg ugcuggggga uggggaacag ggcugugaau 2700
gggccuauuu gcauaagcag cauguguacug gagagaaaga caucacagag cagaagagug 2760
cgggugccca ggagugcacu ugccaccccu acuucauccc ugaaagagua aauggccugg 2820
aaggugucuc ugagagguaa ugccgcacac cacccucccu gggggcaggg ucaggcuaca 2880
ccugccuuag gucgggggcu gcagcagccu gagagcucuc aguagggccu caguagccug 2940
ggagggagca ggggcagggg gcagggaaag aggcguaaug ggcugucca gaggggccug 3000 ggaaaccugg ucccugaggc cugggcacag cuacaaucac uucaaauugg cuguggggcc 3060
aguggacugg gaaggaaaaa agcaauaaga gugaccaagu gcagaaggcu gucaggaccc 3120
aggucacaug ccuuagugca gugacuccuc aucauuuuau ggggugaggg ugucguuggu 3180
acacccauuu uacagaugag gacaccgagg cccagaaaag uuaaguuaca uguccuaagu 3240
cacacagcuu guaagugcca gaacugagau caaaaccaag ucucuuugac uuuaaagucu 3300
guacucugac cccaaagaga uccuguuugg ccacuuauag gaggucccua aagcugcaga 3360
cuccccuugc cggcacccac auauagagac auuaacccuu ccccugcagg gucaccucaa 3420
auagucuuuu agcugggcuu cuccugcaau uccaccuaau gccaucccu ggguuuugcc 3480 caaaccugaa cugggcagug gggugagagg aggggguuuac aggguuacag agccucauac 3540
agauaggagc ccauggcugc uggucaucug cauuccugca ggauuggcug uuccuugggg 3600
uccuuggcag gaaaaugagg auugcuccga ggccugcucc aguacuuccc agaggcuggc 3660 cuggugugggg gcucugggaa ggcugaggcu ggagaagcgu aaguaggagg gcagagaugg 3720
cacucaggua gcuugaauca ccaggacccu uccaagcccc acagguucug agggaguacu 3780
agggccagcu cugggagagg ucucuuccua ugcugugaac cccugccuu ucuugcagcc 3840 uacaacgaau aaauuuucuu ugcaaagg 3868

<210> SEQ ID NO 40
<211> LENGTH: 3978
<212> TYPE: RNA
<213> ORGANISM: Homo sapiens

<400> SEQUENCE: 40
ggucgccgcg ccaagggccc gcugagcccc uccucccauu cguccagccg cgcggcccac 60
agaagcggaa cgcgcgucga gagcgcccug uccgcucgcc ccagacagau gcccgguuau 120
ucauuaccgc gaggccuaga ggaaagagug gcugccgucu uccugcccac agcccgccgg 180
acccuccguc gcggcugccc ggucccccgga gccgcagccg ccgagcccgg cugugcgugu 240
cguggcugcu ggggagaaag aggcuuccgg acaugcucug gagucagaag acagcgaaaa 300
gagaagcaga agccccggug gcaagagucu gaagcaggaa ggaugacugu agccugugga 360
uuguacugca guaggaaacu guccuagcaa ggcuccacuu ugccccagcu ucaagcugga 420
aaggaggaga acaugaaaca uugcuugaag acaauggccg agacagcagg ucccacccug 480
cacagccacc agcaucucuc cccucagccc ugucuccucu ucugcaguug ggaucugcac 540
auuuaagccu gaaauugucc ugugaaguga aguaugaucg gacagccucu uuucagcuuu 600
uaugacaaug gagacagagg aauuguggcu cuugccaagg ucacaggauu ggaauacaga 660
gccaagccac cccaggacau gcaagagccu cagaagggaa aaaagcccag caggaaggga 720
gaacaaguag ccucuguccu gaaguuguaa cagccagggg ccaggaugga ggaggaggac 780
cccauaaucu gcccaucugg gacuuggcag gggaccuggg aaaauguacc ccaacccauc 840

```
ccuuaagggc cuuugucuuu ggcccauugg ccuagcaucu acuucuucac cgugucuguu    900
cuugucacac cuagucaggu cuguuugggu cugaggugca uggaacauuc ugguuaggcc    960
uccagcaaac ggaagcucuu caccguguuu ccagccuggg accaagggca gcauacuggc   1020
aaaguugcca aagcaaggga cuccagccuc uuaggaguua augacucccu cuccccagcu   1080
guccuccccu uggugcuccu cuuccucccu ccuccugcuc acagcaggca gggccuagac   1140
ccgggagcca ugcugcugug cuguugccag gggagcacgg aggcagaucu gagcuaugca   1200
gggaaaaggc ccagccuguc aaagugucug agaugaaccg ccgccguccc ugugcagcug   1260
ggcucagacg ugucucagcu cuuguucugu gccugagaau ggcgaaaccc agugagguuc   1320
aagggcaaac ucgcuauuca uuagucaggg guucuugacg ucccgucucu cccagggaug   1380
aguuccccc uccucuuucu cccccuccua ugacacauuc cugggugccu uuggugagga   1440
cugcacaccc uccuccugcc uagcccccuc uccaaaggcc ccugaauaaa cucccccaa   1500
ggagaccagg cagggcagag acaauggcug caggaaauca uucaggcggg acaugcuggc   1560
cugcccucca cccagucccc cugugggccc cacucccuuc ugauucaggg cacccuuggg   1620
cccccagccu auacaggccu ggacaggaag aaaccacugg gaaccacccu aaggacaaca   1680
ugcuagucca gugccauucu ucgcuggcuc ugugggugcc uuuguggccu guaccgacug   1740
gcuggcuaau uuugugguuu cuguaccauc acaugccuau uuuaagacac ucuccagcac   1800
ugucgguuag ggaguguaaa uuuugcaaua uuuucugaaa uguggcaaua ucaaaaugua   1860
aaaggcacac auacuugguc acaaacaaau ggcacuauuu acucuguggg cauauuugua   1920
aaaguugcca aagaauuaua uacaaggaug uucaucagag cauuucuuuu gaagaguaaa   1980
gaaauggaca ugaaccugug guccguucau acgguggaau accuaugcag cuguaaaaau   2040
cagugugggua gaucuccgua uaugaguuga uguggaaggu uggccaguuc acaugauaag   2100
gugaauagaa uaaguuacag aacaggcugu agaguaugau cuuauuugua gauguuuaaa   2160
acugagucau aaguaugcuu auauacagau cguuucugga aguauguacu ggaagucuac   2220
cucuggggag uggggauggg ggagugcacu cuucuauacu guuauauuuu cuuuucaugc   2280
uccuaaggua cuuuuauugg aagauguaaa gcgguucaau guaauaggcu uaacuucugu   2340
caacuaaguu ggcgugggug cuuuaagagg gugguaguga uguugcugga gaaaguaucc   2400
cacagucacu gguggcuuca gccacgggcc auuuuggggc cuaauaauca cauaucauca   2460
ugguugcuag uguuaaucga aaaccuacua agugccaggc uuacugucuc ugggucuugc   2520
uuacguggau gucauuuuuc caguugcacc aaaucgaaag agguuaauug guuuguugga   2580
guuccuuugu aggugaaggg cagagccagg agcuuggcua gggacagggg aggugagugg   2640
gggauggugg auaggucuug gcucccaguu uccuucuggg cagacauugc cccucugccc   2700
ugaggaccug cuuguuuggg ggaagaggcc uuuagaggca ccagggucau gccagguguu   2760
ggacauggug aacugggaag ugcucccauc uggccacagc gcagaaguau caccgugcug   2820
ggggaugggg aacagggcug ugaaugggcc uauuugcaua agcagcaugu gucuggagag   2880
aaagacauca cagagcagaa gagugcgggu gcccaggagu gcacuugcca ccccuacuuc   2940
aucccugaaa gaguaaaugg ccuggaaggu gucucugaga gguaaugccg cacaccaccc   3000
ucccuggggg cagggucagg cuacaccugc cuuaggucgg gggcugcagc agccugagag   3060
cucucaguag ggccucagua gccugggagg gagcaggggc agggggcagg gaaagaggcg   3120
uaaugggggcu guccagaggg gccugggaaa ccugguccu gaggccuggg cacagcuaca   3180
```

```
aucacuucaa auuggcugug gggccagugg acugggaagg aaaaaagcaa uaagagugac   3240
caagugcaga aggcugucag gucccagguc acaugccuua gugcagugac uccucaucau   3300
uuuaugggggu gugggugucg uugguacacc cauuuuacag augaggacac cgaggcccag   3360
aaaaguuaag uuacaugucc uaagucacac agcuuguaag ugccagaacu gagaucaaaa   3420
ccaagucucu uugacuuuaa agucuguacu cugaccccaa agagauccug uuuggccacu   3480
uauaggaggu cccuaaagcu gcagacuccc cuugccggca cccacauaua gagacauuaa   3540
cccuuccccu gcagggucac cucaaauagu cuuuuagcug ggcuucuccu gcaauuccac   3600
cuaaugccau ccccuggguu uugcccaaac cugaacuggg caguggggug agaggagggg   3660
uuuacagggu uacagagccu cauacagaua ggagcccaug gcugcugguc aucugcauuc   3720
cugcaggauu ggcuguuccu uggggguccuu ggcaggaaaa ugaggauugc uccgaggccu   3780
gcuccaguac uucccagagg cuggccuggu guggggcucu gggaaggcug aggcuggaga   3840
agcguaagua ggagggcaga gauggcacuc agguagcuug aaucaccagg acccuuccaa   3900
gccccacagg uucugaggga guacuagggc cagcucuggg agaggucucu uccuaugcug   3960
ugaacccccu gccuuucu                                                   3978
```

<210> SEQ ID NO 41
<211> LENGTH: 3837
<212> TYPE: RNA
<213> ORGANISM: Homo sapiens

<400> SEQUENCE: 41

```
ccaggcgugu gcauuuauau gcagagugac caagaaacuu caguaauacu aguuuguguc     60
uuuggagucc cacuuuuugc cagggcuagu gcuaacagcu ucaggagaau ucagccucac    120
cuugacagga caugcucugg agucagaaga cagcgaaaag agaagcagaa gccccggugg    180
caagagucug aagcaggaag gaugacugua gccuguggau uguacugcag uaggaaacug    240
uccuagcaag gcuccacuuu gccccagcuu caagcuggaa aggaggagaa caugaaacau    300
ugcuugaaga caauggccga gacagcaggu cccacccugc acagccacca gcaucucucc    360
ccucagcccu gucuccucuu cugcaguugg gaucugcaca uuuaagccug aaauuguccu    420
gugaagugaa guaugaucgg acagccucuu uucagcuuuu augacaaugg agacagagga    480
auuguggcuc uugccaaggu cacaggauug gaauacagag ccaagccacc ccaggacaug    540
caagagccuc agaagggaaa aaagcccagc aggaagggag aacaaguagc cucuguccug    600
aaguuguaac agccaggggc caggauggag gaggaggacc ccauaaucug cccaucuggg    660
acuuggcagg ggaccuggga aaauguaccc caacccaucc cuuaagggcc uuugucuuug    720
gcccauuggc cuagcaucua cuucuucacc gugucuguuc uugucacacc uagucagguc    780
uguuugggguc ugaggugcau ggaacauucu ggguaggccu ccagcaaacg gaagcucuuc    840
accguguuuc cagccuggga ccaagggcag cauacuggca aaguugccaa agcaagggac    900
uccagccucu uaggaguuaa ugacucccuc uccccagcug uccuccccuu ggugcuccuc    960
uuccucccuc cuccugcuca cagcaggcag ggccuagacc cgggagccau gcugcugugc   1020
uguugccagg ggagcacgga ggcagaucug agcuaugcag ggaaaaggcc cagccuguca   1080
aagugucuga gaugaaccgc cgccgucccu gugcagcugg gcucagacgu gucucagcuc   1140
uuguucugug ccugagaaug gcgaaaccca gugagguuca agggcaaacu cgcuauucau   1200
uagucagggg uucuugacgu cccgucucuc ccagggauga guucccccu ccucuuucuc   1260
ccccuccuau gacacauucc ugggugccuu uggugaggac ugcacacccu ccuccugccu   1320
```

-continued

```
agccccccucu ccaaaggccc cugaauaaac uccccccaag gagaccaggc agggcagaga   1380
caauggcugc aggaaaucau ucaggcggga caugcuggcc ugcccuccac ccaguccccc   1440
ugugggcccc acucccuucu gauucagggc acccuugggc ccccagccua uacaggccug   1500
gacaggaaga aaccacuggg aaccacccua aggacaacau gcuaguccag ugccauucuu   1560
cgcuggcucu gugggugccu uuguggccug uaccgacugg cuggcuaauu uugugguuuc   1620
uguaccauca caugccuauu uuaagacacu cuccagcacu gucgguuagg gaguguaaau   1680
uuugcaauau uuucugaaau guggcaauau caaaauguaa aaggcacaca uacuugguca   1740
caaacaaaug gcacuauuua cucugugggc auauuuguaa aaguugccaa agaauuauau   1800
acaaggaugu ucaucagagc auuucuuuug aagaguaaag aaauggacau gaaccugugg   1860
uccguucaua cgguggaaua ccuaugcagc uguaaaaauc agugugguag aucuccguau   1920
augaguugau guggaagguu ggccaguuca caugauaagg ugaauagaau aaguuacaga   1980
acaggcugua gaguaugauc uuauuuguag auguuuaaaa cugagucaua aguaugcuua   2040
uauacagauc guuucuggaa guauguacug gaagucuacc ucuggggagu ggggaugggg   2100
gagugcacuc uucuauacug uuauauuuuc uuuucaugcu ccuaagguac uuuuauugga   2160
agauguaaag cgguucaaug uaauaggcuu aacuucuguc aacuaaguug gcgugggugc   2220
uuuaagaggg ugguagugau guugcuggag aaaguauccc acagucacug guggcuucag   2280
ccacgggcca uuuuggggcc uaauaaucac auaucaucau gguugcuagu guuaaucgaa   2340
aaccuacuaa gugccaggcu uacugucucu gggucuugcu uacguggaug ucauuuuucc   2400
aguugcacca aaucgaaaga gguuaauugg uuuguuggag uuccuuugua ggugaagggc   2460
agagccagga gcuuggcuag ggacagggga ggugaguggg ggauggugga uaggucuugg   2520
cucccaguuu ccuucugggc agacauugcc ccucugcccu gaggaccugc uuguuugggg   2580
gaagaggccu uuagaggcac cagggucaug ccagguguug gacaugguga acugggaagu   2640
gcucccaucu ggccacagcg cagaaguauc accgugcugg gggaugggga acagggcugu   2700
gaaugggccu auuugcauaa gcagcaugug ucuggagaga aagacaucac agagcagaag   2760
agugcgggug cccaggagug cacuugccac ccccuacuuca ucccugaaag aguaaauggc   2820
cuggaaggug ucucugagag guaaugccgc acaccacccu cccugggggc agggucaggc   2880
uacaccugcc uuaggucggg ggcugcagca gccugagagc ucucaguagg gccucaguag   2940
ccugggaggg agcaggggca gggggcaggg aaagaggcgu aauggggcug uccagagggg   3000
ccugggaaac cugguccccug aggccugggc acagcuacaa ucacuucaaa uuggcugugg   3060
ggccagugga cugggaagga aaaaagcaau aagagugacc aagugcagaa ggcugucagg   3120
ucccagguca caugccuuag ugcagugacu ccucaucauu uuauggggug ugggugucgu   3180
ugguacaccc auuuuacaga ugaggacacc gaggcccaga aaaguuaagu uacauguccu   3240
aagucacaca gcuuguaagu gccagaacug agaucaaaac caagucucuu ugacuuuaaa   3300
gucuguacuc ugaccccaaa gagauccugu uuggccacuu auaggagguc ccuaaagcug   3360
cagacucccc uugccggcac ccacauauag agacauuaac ccuuccccug cagggucacc   3420
ucaaauaguc uuuuagcugg gcuucuccug caauuccacc uaaugccauc cccuggguuu   3480
ugcccaaacc ugaacugggc aguggggguga gaggaggggu uuacaggguu acagagccuc   3540
auacagauag gagcccaugg cugcugguca ucugcauucc ugcaggauug gcuguuccuu   3600
gggguccuug gcaggaaaau gaggauugcu ccgaggccug cuccaguacu ucccagaggc   3660
```

uggccuggug uggggcucug ggaaggcuga ggcuggagaa gcguaaguag gagggcagag 3720
auggcacuca gguagcuuga aucaccagga cccuuccaag ccccacaggu ucugagggag 3780
uacuagggcc agcucuggga gaggucucuu ccuaugcugu gaaccccug ccuuucu 3837

<210> SEQ ID NO 42
<211> LENGTH: 571
<212> TYPE: DNA
<213> ORGANISM: Homo sapiens

<400> SEQUENCE: 42
gtgcccgccc gagaaggcgg cgctgggagc cgctcagagc ccagagaagc ggcgcgcggc 60
caggagcccc cgctccgcca ctgccgtgcc tgcctcccgc agctgtctgc catgcgctcg 120
ccggggcagg ggcgcccgga gggcggctag agctgggcct gagcccggga acgcgcctga 180
tcaggggtgg cggagccgcg gtccccacag ccgccccacc cgcgccgctg cctcgctggg 240
gcccgggccc ccttcccggt ccttactccc ctgctggtgc ctccctcctt ggcgcgcttc 300
ccacctgcga tcggcgccct cttcgcagtc acgaactcgc cagcagctag cagcactgac 360
tagtaggagg gcccgccgga ggagagccgc gcggcccaca gaagcggaac gcgcgtcgag 420
agcgccctgt ccgctcgccc cagacagatg cccggttatt cattaccgcg aggcctagag 480
gaaagagtgg ctgccgtctt cctgcccaca gcccgccgga ccctccgtcg cggctgcccg 540
gtccccggag ccgcagccgc cgagcccggc t 571

<210> SEQ ID NO 43
<211> LENGTH: 4915
<212> TYPE: DNA
<213> ORGANISM: Homo sapiens

<400> SEQUENCE: 43
ccaccacacc cagactaaaa ggcagtttga ttttacaaat caaaatagca gtaatctatg 60
gagatttact tgtgagattg gtaggaaaca tcttaaatgt aatcaaacaa taacttacat 120
cttgatgaat tcacgtgtag gtttctcttc ctcagaagaa atcagatgct gttcagagca 180
cgaaggctag aattttaccc tggttctcat gctaccttgc acccaggttg gatcctgagt 240
acagtttttg gcaggtgggc ctgcatataa gttagcaatg gggataccc agctgcctct 300 cttcatacag ctgaggtttt ggggagtcat tcttatagcc cctgggttgg gcctagtcct 360
gcaaatgaat tcaccagccc taaagcccaa attgcagcct ctgtcattca ccttccagga 420
gtggaaaggg cagtaagttt catcttatta ttattgctat tttggtggtt ttgttgaggt 480
tggtgtgtgt atgttagtaa gataaagctc tcagaaatta catagcattt gtcaaggata 540
taagagggac tgtgccacat ctggctgtat agaaggtggt tccatatctt taaatagagc 600
cccaggtcct tagccaccag aaaggttttc aggggaagtg tgcaccctca gcagctgctg 660
ctggtgggca ggatgggcac gcatggaaca ggctttcctc tgtggccagg tgagaagcag 720
gtggtgagac acagagcagt gctgggctct gcttctgaag cctccaacct ttccttccct 780
aggaagcccc agagagattg gtgagggtga tttcccagga agacgcagtg tgctctgact 840
tctgtgacag tgagcaacgg gaccagtgga tgtccagatg ctggcaatga gtaggccttc 900
cctacgctgg gtggcgtcca caccctccgg cttccattgc ctgggtctcc tggaggtggt 960
ttgctggatg aataccgcat gcacagaggc tggccttggg tttgaatatg gcagccagtg 1020
gacagcatgt gcttcagtta tgagactgcc caggagatgc ttcttccaag gcagagcacg 1080
tgcagagtcc agtgctggag aggccgggtg cgcagttgac ccatttccag ttctgttttc 1140

```
cctctcatgt tcctctgtcc ccatctagga catgctctgg agtcagaaga cagcgaaaag   1200
agaagcagaa gccccggtgg caagagtctg aagcaggaag gatgactgta gcctgtggat   1260
tgtactgcag taggaaactg tcctagcaag gctccacttt gccccagctt caagctggaa   1320
aggaggagaa catgaaacat tgcttgaaga caatggccga gacagcaggt cccaccctgc   1380
acagccacca gcatctctcc cctcagccct gtctcctctt ctgcagttgg gatctgcaca   1440
tttaagcctg aaattgtcct gtgaagtgaa gtatgatcgg acagcctctt ttcagctttt   1500
atgacaatgg agacagagga attgtggctc ttgccaaggt cacaggattg gaatacagag   1560
ccaagccacc ccaggacatg caagagcctc agaagggaaa aaagcccagc aggaagggag   1620
aacaagtagc ctctgtcctg aagttgtaac agccaggggc caggatggag gaggaggacc   1680
ccataatctg cccatctggg acttggcagg ggacctggga aaatgtaccc caacccatcc   1740
cttaagggcc tttgtctttg gcccattggc ctagcatcta cttcttcacc gtgtctgttc   1800
ttgtcacacc tagtcaggtc tgtttgggtc tgaggtgcat ggaacattct gggtaggcct   1860
ccagcaaacg gaagctcttc accgtgtttc cagcctggga ccaagggcag catactggca   1920
aagttgccaa agcaagggac tccagcctct taggagttaa tgactccctc tccccagctg   1980
tcctcccctt ggtgctcctc ttcctccctc ctcctgctca cagcaggcag ggcctagacc   2040
cgggagccat gctgctgtgc tgttgccagg ggagcacgga ggcagatctg agctatgcag   2100
ggaaaaggcc cagcctgtca aagtgtctga gatgaaccgc cgccgtccct gtgcagctgg   2160
gctcagacgt gtctcagctc ttgttctgtg cctgagaatg gcgaaaccca gtgaggttca   2220
agggcaaact cgctattcat tagtcagggg ttcttgacgt cccgtctctc ccagggatga   2280
gttcccccct cctctttctc cccctcctat gacacattcc tgggtgcctt tggtgaggac   2340
tgcacaccct cctcctgcct agccccctct ccaaaggccc ctgaataaac tccccccaag   2400
gagaccaggc agggcagaga caatggctgc aggaaatcat tcaggcggga catgctggcc   2460
tgccctccac ccagtccccc tgtgggcccc actcccttct gattcagggc acccttgggc   2520
ccccagccta tacaggcctg gacaggaaga aaccactggg aaccacccta aggacaacat   2580
gctagtccag tgccattctt cgctggctct gtgggtgcct ttgtggcctg taccgactgg   2640
ctggctaatt ttgtggtttc tgtaccatca catgcctatt ttaagacact ctccagcact   2700
gtcggttagg gagtgtaaat tttgcaatat tttctgaaat gtggcaatat caaaatgtaa   2760
aaggcacaca tacttggtca caaacaaatg gcactattta ctctgtgggc atatttgtaa   2820
aagttgccaa agaattatat acaaggatgt tcatcagagc atttcttttg aagagtaaag   2880
aaatggacat gaacctgtgg tccgttcata cggtggaata cctatgcagc tgtaaaaatc   2940
agtgtggtag atctccgtat atgagttgat gtggaaggtt ggccagttca catgataagg   3000
tgaatagaat aagttacaga acaggctgta gagtatgatc ttatttgtag atgtttaaaa   3060
ctgagtcata agtatgctta tatacagatc gtttctggaa gtatgtactg gaagtctacc   3120
tctggggagt ggggatgggg gagtgcactc ttctatactg ttatattttc ttttcatgct   3180
cctaaggtac ttttattgga agatgtaaag cggttcaatg taataggctt aacttctgtc   3240
aactaagttg gcgtgggtgc tttaagaggg tggtagtgat gttgctggag aaagtatccc   3300
acagtcactg gtggcttcag ccacgggcca ttttggggcc taataatcac atatcatcat   3360
ggttgctagt gttaatcgaa aacctactaa gtgccaggct tactgtctct gggtcttgct   3420
tacgtggatg tcatttttcc agttgcacca aatcgaaaga ggttaattgg tttgttggag   3480
```

```
ttcctttgta ggtgaagggc agagccagga gcttggctag ggacagggga ggtgagtggg   3540

ggatggtgga taggtcttgg ctcccagttt ccttctgggc agacattgcc cctctgccct   3600

gaggacctgc ttgtttgggg gaagaggcct ttagaggcac cagggtcatg ccaggtgttg   3660

gacatggtga actgggaagt gctcccatct ggccacagcg cagaagtatc accgtgctgg   3720

gggatgggga acagggctgt gaatgggcct atttgcataa gcagcatgtg tctggagaga   3780

aagacatcac agagcagaag agtgcgggtg cccaggagtg cacttgccac ccctacttca   3840

tccctgaaag agtaaatggc ctggaaggtg tctctgagag gtaatgccgc acaccacccct   3900

ccctgggggc agggtcaggc tacacctgcc ttaggtcggg ggctgcagca gcctgagagc   3960

tctcagtagg gcctcagtag cctgggaggg agcaggggca gggggcaggg aaagaggcgt   4020

aatggggctg tccagagggg cctgggaaac ctggtccctg aggcctgggc acagctacaa   4080

tcacttcaaa ttggctgtgg ggccagtgga ctgggaagga aaaaagcaat aagagtgacc   4140

aagtgcagaa ggctgtcagg tcccaggtca catgccttag tgcagtgact cctcatcatt   4200

ttatggggtg tgggtgtcgt tggtacaccc attttacaga tgaggacacc gaggcccaga   4260

aaagttaagt tacatgtcct aagtcacaca gcttgtaagt gccagaactg agatcaaaac   4320

caagtctctt tgactttaaa gtctgtactc tgaccccaaa gagatcctgt ttggccactt   4380

ataggaggtc cctaaagctg cagactcccc ttgccggcac ccacatatag agacattaac   4440

ccttcccctg cagggtcacc tcaaatagtc ttttagctgg gcttctcctg caattccacc   4500

taatgccatc ccctgggttt tgcccaaacc tgaactgggc agtggggtga gaggaggggt   4560

ttacagggtt acagagcctc atacagatag gagcccatgg ctgctggtca tctgcattcc   4620

tgcaggattg gctgttcctt ggggtccttg gcaggaaaat gaggattgct ccgaggcctg   4680

ctccagtact tcccagaggc tggcctggtg tggggctctg ggaaggctga ggctggagaa   4740

gcgtaagtag gagggcagag atggcactca ggtagcttga atcaccagga cccttccaag   4800

ccccacaggt tctgagggag tactagggcc agctctggga gaggtctctt cctatgctgt   4860

gaaccccctg cctttcttgc agcctacaac gaataaattt tctttgcaaa ggctt        4915
```

<210> SEQ ID NO 44
<211> LENGTH: 4687
<212> TYPE: DNA
<213> ORGANISM: Homo sapiens

<400> SEQUENCE: 44

```
uuccucagaa gaaaucagau gcuguucaga gcacgaaggc uagaauuuua cccugguucu     60

caugcuaccu ugcacccagg uuggauccug aguacaguuu uuggcaggug ggccugcaua    120

uaaguuagca augggggaua cccagcugcc ucucuucaua cagcugaggu uuuggggagu    180

cauucuuaua gccccugggu ugggccuagu ccugcaaaug aauucaccag cccuaaagcc    240

caaauugcag ccucugucau ucaccuucca ggaguggaaa gggcaguaag uuucaucuua    300

uuauuauugc uauuuuggug guuuuguuga gguuggugug uguauguuag uaagauaaag    360

cucucagaaa uuacauagca uuugucaagg auauaagagg gacugugcca caucuggcug    420

uauagaaggu gguuccauau cuuuaaauag agccccaggu ccuuagccac cagaaagguu    480

uucaggggaa gugugcaccc ucagcagcug cugcuggugg gcaggauggg cacgcaugga    540

acaggcuuuc cucuguggcc aggugagaag caggugguga gacacagagc agugcugggc    600

ucugcuucug aagccuccaa ccuuuccuuc ccuaggaagc cccagagaga uuggugaggg    660

ugauuuccca ggaagacgca gugugcucug acuucuguga cagugagcaa cgggaccagu    720
```

```
ggauguccag augcuggcaa ugaguaggcc uucccuacgc ugggguggcgu ccacacccuc    780
cggcuuccau ugccugggguc uccuggaggu gguuugcugg augaauaccg caugcacaga    840
ggcuggccuu ggguuugaau auggcagcca guggacagca ugugcuucag uuaugagacu    900
gcccaggaga ugcuucuucc aaggcagagc acgugcagag uccagugcug gagaggccgg    960
gugcgcaguu gacccauuuc caguucuguu uucccucuca uguuccucug uccccaucua   1020
ggacaugcuc uggagucaga agacagcgaa aagagaagca gaagccccgg uggcaagagu   1080
cugaagcugg aaaggaggag aacaugaaac auugcuugaa gacaauggcc gagacagcag   1140
gucccacccu gcacagccac cagcaucucu ccccucagcc cugucuccuc uucugcaguu   1200
gggaucugca cauuuaagcc ugaaauuguc cugugaagug aaguaugauc ggacagccuc   1260
uuuucagcuu uuaugacaau ggagacagag gaauuguggc ucuugccaag gucacaggau   1320
uggaauacag agccaagcca ccccaggaca ugcaagagcc ucagaaggga aaaaagccca   1380
gcaggaaggg agaacaagua gccucugucc ugaaguugua acagccaggg gccaggaugg   1440
aggaggagga ccccauaauc ugcccaucug ggacuuggca ggggaccugg gaaaauguac   1500
cccaacccau cccuuaaggg ccuuugucuu uggcccauug gccuagcauc uacuucuuca   1560
ccgugucugu ucuugucaca ccuagucagg ucuguuuggg ucugaggugc auggaacauu   1620
cuggguaggc cuccagcaaa cggaagcucu ucaccguguu uccagccugg gaccaagggc   1680
agcauacugg caaaguugcc aaagcaaggg acuccagccu cuuaggaguu aaugacuccc   1740
ucuccccagc uguccucccc uuggugcucc ucuuccuccc uccuccugcu cacagcaggc   1800
agggccuaga cccgggagcc augcugcugu gcuguugcca ggggagcacg gaggcagauc   1860
ugagcuaugc agggaaaagg cccagccugu caaagugucu gagaugaacc gccgccgucc   1920
cugugcagcu gggcucagac gugucucagc ucuuguucug ugccugagaa uggcgaaacc   1980
cagugagguu caagggcaaa cucgcuauuc auuagucagg gguucuugac gucccgucuc   2040
ucccagggau gaguuccccc cuccucuuuc ucccccuccu augacacauu ccugggugcc   2100
uuuggugagg acugcacacc cuccuccugc cuagccccccu cuccaaaggc cccugaauaa   2160
acucccccca aggagaccag gcagggcaga gacaauggcu gcaggaaauc auucaggcgg   2220
gacaugcugg ccugcccucc acccaguccc ccugugggcc ccacucccuu cugauucagg   2280
gcacccuugg gcccccagcc uauacaggcc uggacaggaa gaaaccacug ggaaccaccc   2340
uaaggacaac augcuagucc agugccauuc uucgcuggcu cugugggugc cuuuguggcc   2400
uguaccgacu ggcuggcuaa uuuugugguu ucuguaccau cacaugccua uuuuaagaca   2460
cucuccagca cugucgguua gggaguguaa auuuugcaau auuuucugaa auguggcaau   2520
aucaaaaugu aaaaggcaca cauacuuggu cacaaacaaa uggcacuauu uacucugugg   2580
gcauauuugu aaaaguugcc aaagaauuau auacaaggau guucaucaga gcauuucuuu   2640
ugaagaguaa agaaauggac augaaccugu gguccguuca uacgguggaa uaccuaugca   2700
gcuguaaaaa ucaguguggu agaucuccgu auaugaguug auguggaagg uuggccaguu   2760
cacaugauaa ggugaauaga auaaguuaca gaacaggcug uagaguauga ucuuauuugu   2820
agauguuuaa aacugaguca uaaguaugcu uauauacaga ucguuucugg aaguauguac   2880
uggaagucua ccucuggggga gugggggaugg gggagugcac ucuucuauac uguuauauuu   2940
ucuuuucaug cuccuaaggu acuuuuauug gaagauguaa agcgguucaa uguaauaggc   3000
uuaacuucug ucaacuaagu uggcguggggu gcuuuaagag ggugguagug auguugcugg   3060
```

```
agaaaguauc ccacagucac ugguggcuuc agccacgggc cauuuugggg ccuaauaaauc   3120
acauaucauc augguugcua guguuaaucg aaaaccuacu aagugccagg cuuacugucu   3180
cugggucuug cuuacgugga ugucauuuuu ccaguugcac caaaucgaaa gagguuaauu   3240
gguuuguugg aguuccuuug uaggugaagg gcagagccag gagcuuggcu agggacaggg   3300
gaggugagug ggggauggug gauaggucuu ggcucccagu uuccuucugg gcagacauug   3360
ccccucugcc cugaggaccu gcuuguuugg gggaagaggc cuuuagaggc accaggguca   3420
ugccaggugu uggacauggu gaacugggaa gugcucccau cuggccacag cgcagaagua   3480
ucaccgugcu gggggauggg gaacagggcu gugaaugggc cuauuugcau aagcagcaug   3540
ugucuggaga gaaagacauc acagagcaga agagugcggg ugcccaggag ugcacuugcc   3600
accccuacuu caucccugaa agaguaaaug gccuggaagg ugucucugag agguaaugcc   3660
gcacaccacc cucccugggg gcagggucag gcuacaccug ccuuaggucg ggggcugcag   3720
cagccugaga gcucucagua gggccucagu agccugggag ggagcagggg caggggcag   3780
ggaaagaggc guaaugggc uguccagagg ggccugggaa accugguccc ugaggccugg   3840
gcacagcuac aaucacuuca aauuggcugu ggggccagug gacugggaag gaaaaaagca   3900
auaagaguga ccaagugcag aaggcuguca gguccccaggu cacaugccuu agugcaguga   3960
cuccucauca uuuuaugggg ugugggugu guugguacac ccauuuuaca gaugaggaca   4020
ccgaggccca gaaaaguuaa guuacauguc cuaagucaca cagcuuguaa gugccagaac   4080
ugagaucaaa accaagucuc uuugacuuua aagucuguac ucugacccca aagagauccu   4140
guuuggccac uuauaggagg ucccuaaagc ugcagacucc ccuugccggc acccacauau   4200
agagacauua acccuucccc ugcaggguca ccucaaauag ucuuuuagcu gggcuucucc   4260
ugcaauucca ccuaaugcca uccccugggu uuugcccaaa ccugaacugg gcaguggggu   4320
gagaggaggg guuuacaggg uuacagagcc ucauacagau aggagcccau ggcugcuggu   4380
caucugcauu ccugcaggau uggcuguucc uuggggguccu uggcaggaaa augaggauug   4440
cuccgaggcc ugcuccagua cuucccagag gcuggccugg ugugggggcuc ugggaaggcu   4500
gaggcuggag aagcguaagu aggagggcag agauggcacu cagguagcuu gaaucaccag   4560
gacccuucca agccccacag guucugaggg aguacuaggg ccagcucugg gagaggucuc   4620
uuccuaugcu gugaaccccc ugccuuucuu gcagccuaca acgaauaaau uuucuuugca   4680
aaggcuu                                                              4687
```

<210> SEQ ID NO 45
<211> LENGTH: 706
<212> TYPE: DNA
<213> ORGANISM: Homo sapiens

<400> SEQUENCE: 45

```
cucagaaauu acauagcauu ugucaaggau auaagaggga cugugccaca ucuggcugua     60
uagaaggugg uuccauaucu uuaaauagag ccccaggucc uuagccacca gaaagguuuu    120
caggggaagu gugcacccuc agcagcugcu gcuggugggc aggaugggca cgcauggaac    180
aggcuuuccu cuguggccag gugagaagca gguggugaga cacagagcag ugcugggcuc    240
ugcuucugaa gccuccaacc uuuccuuccc uaggaagccc cagagagauu ggugagggug    300
auuucccagg aagacgcagu gugcucugac uucugugaca gugagcaacg ggaccagugg    360
auguccagau gcuggcaaug agacaugcuc uggagucaga agacagcgaa aagagaagca    420
gaagccccgg uggcaagagu cugaaggugg guuccuuccu gacaugggca uugggcugcg    480
```

```
caugugugu cgcaguucuu uccagcugcu guucugaccu cuuugugcag uguauuuaug    540

uggcuguaga uggaugucc aagguagauu uagguuuugg aauacuguuu uuuuuuucua    600

cuucagggag aaaauaaccc aguuugggaa ggacauuuaa aaggggaaaa uauuagguau    660

gauggcacac cugcaguccc agcuauucgg gaggcuaagg cuggag                  706


<210> SEQ ID NO 46
<211> LENGTH: 3922
<212> TYPE: DNA
<213> ORGANISM: Homo sapiens

<400> SEQUENCE: 46

cacgcaugga acaggcuuuc cucuguggcc aggugagaag caggugguga gacacagagc     60

agugcugggc ucugcuucug aagccuccaa ccuuuccuuc ccuaggaagc cccagagaga    120

uuggugaggg ugauuuccca ggaagacgca gugugcucug acuucuguga cagugagcaa    180

cgggaccagu ggauguccag augcuggcaa ugagacaugc ucuggaguca gaagacagcg    240

aaaagagaag cagaagcccc gguggcaaga gucugaagca ggaaggauga cuguagccug    300

uggauuguac ugcaguagga aacuguccua gcaaggcucc acuuugcccc agcuucaagc    360

uggaaaggag gagaacauga aacauugcuu gaagacaaug gccgagacag cagguccac    420

ccugcacagc caccagcauc ucuccccuca gcccugucuc cucuucugca guugggaucu    480

gcacauuuaa gccugaaauu guccugugaa gugaaguaug aucggacagc cucuuuucag    540

cuuuuaugac aauggagaca gaggaauugu ggcucuugcc aaggucacag gauuggaaua    600

cagagccaag ccaccccagg acaugcaaga gccucagaag ggaaaaaagc ccagcaggaa    660

gggagaacaa guagccucug uccugaaguu guaacagcca ggggccagga uggaggagga    720

ggaccccaua aucugcccau cugggacuug gcaggggacc ugggaaaaug uaccccaacc    780

caucccuuaa gggccuuugu cuuuggccca uuggccuagc aucuacuucu ucaccguguc    840

uguucuuguc acaccuaguc aggucuguuu gggucugagg ugcauggaac auucugggua    900

ggccuccagc aaacggaagc ucuucaccgu guuuccagcc ugggaccaag ggcagcauac    960

uggcaaaguu gccaaagcaa gggacuccag ccucuuagga guuaaugacu cccucucccc   1020

agcuguccuc cccuuggugc uccucuuccu cccuccuccu gcucacagca ggcagggccu   1080

agacccggga gccaugcugc ugugcuguug ccaggggagc acggaggcag aucugagcua   1140

ugcagggaaa aggcccagcc ugucaaagug ucugagauga accgccgccg ucccugugca   1200

gcugggcuca gacgugucuc agcucuuguu cugugccuga gaauggcgaa acccagugag   1260

guucaagggc aaacucgcua uucauuaguc aggguucuu gacgucccgu cucucccagg   1320

gaugaguucc ccccuccucu uucuccccu ccuaugacac auuccugggu gccuuuggug   1380

aggacugcac acccuccucc ugccuagccc ccucuccaaa ggccccugaa uaaacucccc   1440

ccaaggagac caggcagggc agagacaaug gcugcaggaa aucauucagg cgggacaugc   1500

uggccugccc uccacccagu cccccugugg gccccacucc cuucugauuc agggcacccu   1560

ugggccccca gccuauacag gccuggacag gaagaaacca cugggaacca cccuaaggac   1620

aacaugcuag uccagugcca uucuucgcug gcucuguggg ugccuuugug gccuguaccg   1680

acuggcuggc uaauuuugug guuucuguac caucacaugc cuauuuuaag acacucucca   1740

gcacugucgg uuagggagug uaaauuuugc aauauuuucu gaaauguggc aauaucaaaa   1800

uguaaaaggc acacauacuu ggucacaaac aaauggcacu auuuacucug ugggcauauu   1860
```

```
uguaaaaguu gccaaagaau uauauacaag gauguucauc agagcauuuc uuuugaagag   1920
uaaagaaaug gacaugaacc uguggucegu ucauacggug gaauaccuau gcagcuguaa   1980
aaaucagugu gguagaucuc cguauaugag uugaugugga agguuggcca guucacauga   2040
uaaggugaau agaauaaguu acagaacagg cuguagagua ugaucuuauu uguagauguu   2100
uaaaacugag ucauaaguau gcuuauauac agaucguuuc uggaaguaug uacuggaagu   2160
cuaccucugg ggaguggga ugggggagug cacucuucua uacuguuaua uuuucuuuuc   2220
augcuccuaa gguacuuuua uuggaagaug uaaagcgguu caauguaaua ggcuuaacuu   2280
cugucaacua aguuggcgug ggugcuuuaa gaggguggua gugauguugc uggagaaagu   2340
aucccacagu cacugguggc uucagccacg ggccauuuug gggccuaaua aucacauauc   2400
aucaugguug cuaguguuaa ucgaaaaccu acuaagugcc aggcuuacug ucucuggguc   2460
uugcuuacgu ggaugucauu uuuccaguug caccaaaucg aaagagguua auugguuugu   2520
uggaguuccu uuguagguga agggcagagc caggagcuug gcuagggaca ggggagguga   2580
gugggggaug guggauaggu cuuggcuccc aguuuccuuc ugggcagaca uugccccucu   2640
gcccugagga ccugcuuguu ugggggaaga ggccuuuaga ggcaccaggg ucaugccagg   2700
uguuggacau ggugaacugg gaagugcucc caucuggcca cagcgcagaa guaucaccgu   2760
gcugggggau ggggaacagg gcugugaaug ggccuauuug cauaagcagc augugucugg   2820
agagaaagac aucacagagc agaagagugc gggugcccag gagugcacuu gccaccccua   2880
cuucaucccu gaaagaguaa auggccugga aggugucucu gagagguaau gccgcacacc   2940
acccucccug ggggcagggu caggcuacac cugccuuagg ucgggggcug cagcagccug   3000
agagcucuca guagggccuc aguagccugg gagggagcag gggcaggggg cagggaaaga   3060
ggcguaaugg ggcuguccag aggggccugg gaaaccuggu cccugaggcc ugggcacagc   3120
uacaaucacu ucaaauuggc ugugggggcca guggacuggg aaggaaaaaa gcaauaagag   3180
ugaccaagug cagaaggcug ucaggucccca ggucacaugc cuuagugcag ugacuccuca   3240
ucauuuuaug ggguguggu gucguuggua cacccauuuu acagaugagg acaccgaggc   3300
ccagaaaagu uaaguuacau guccuaaguc acacagcuug uaagugccag aacugagauc   3360
aaaaccaagu cucuuugacu uuaaagucug uacucugacc ccaaagagau ccuguuuggc   3420
cacuuauagg agguccuaa agcugcagac uccccuugcc ggcacccaca uauagagaca   3480
uuaacccuuc cccugcaggg ucaccucaaa uagucuuuua gcugggcuuc uccugcaauu   3540
ccaccuaaug ccauccccug gguuuugccc aaaccugaac ugggcagugg ggugagagga   3600
gggguuuaca ggguuacaga gccucauaca gauaggagcc cauggcugcu ggucaucugc   3660
auuccugcag gauuggcugu uccuuggggu ccuuggcagg aaaaugagga uugcuccgag   3720
gccugcucca guacuuccca gaggcuggcc ugguguggggg cucugggaag gcugaggcug   3780
gagaagcgua aguaggaggg cagagauggc acucagguag cuugaaucac caggacccuu   3840
ccaagcccca cagguucuga gggaguacua gggccagcuc ugggagaggu cucuuccuau   3900
gcugugaacc cccugccuuu cu                                            3922
```

<210> SEQ ID NO 47
<211> LENGTH: 3690
<212> TYPE: DNA
<213> ORGANISM: Homo sapiens

<400> SEQUENCE: 47

```
uuuaacagca ggaaggauga cuguagccug uggauuguac ugcaguagga aacuguccua     60
```

```
gcaaggcucc acuuugcccc agcuucaagc uggaaaggag gagaacauga aacauugcuu    120
gaagacaaug gccgagacag caggucccac ccugcacagc caccagcauc ucuccccuca    180
gcccugucuc cucuucugca guugggaucu gcacauuuaa gccugaaauu guccugugaa    240
gugaaguaug aucggacagc cucuuuucag cuuuuaugac aauggagaca gaggaauugu    300
ggcucuugcc aaggucacag gauuggaaua cagagccaag ccaccccagg acaugcaaga    360
gccucagaag ggaaaaaagc ccagcaggaa gggagaacaa guagccucug uccugaaguu    420
guaacagcca ggggccagga uggaggagga ggaccccaua aucugcccau cugggacuug    480
gcaggggacc ugggaaaaug uaccccaacc caucccuuaa gggccuuugu cuuuggccca    540
uuggccuagc aucuacuucu ucaccguguc uguucuuguc acaccuaguc aggucuguuu    600
gggucugagg ugcauggaac auucugggua ggccuccagc aaacggaagc ucuucaccgu    660
guuuccagcc ugggaccaag ggcagcauac uggcaaaguu gccaaagcaa gggacuccag    720
ccucuuagga guuaaugacu cccucucccc agcuguccuc cccuuggugc uccucuuccu    780
cccuccuccu gcucacagca ggcagggccu agacccggga gccaugcugc ugugcuguug    840
ccaggggagc acggaggcag aucugagcua ugcagggaaa aggcccagcc ugucaaagug    900
ucugagauga accgccgccg ucccugugca gcugggcuca gacgugucuc agcucuuguu    960
cugugccuga gaauggcgaa acccagugag guucaagggc aaacucgcua uucauuaguc   1020
agggguucuu gacgucccgu cucucccagg gaugaguucc ccccuccucu uucucccccu   1080
ccuaugacac auuccugggu gccuuuggug aggacugcac acccuccucc ugccuagccc   1140
ccucuccaaa ggccccugaa uaaacucccc ccaaggagac caggcagggc agagacaaug   1200
gcugcaggaa aucauucagg cgggacaugc uggccugccc uccacccagu cccccugugg   1260
gccccacucc cuucugauuc agggcacccu ugggccccca gccuauacag gccuggacag   1320
gaagaaacca cugggaacca cccuaaggac aacaugcuag uccagugcca uucuucgcug   1380
gcucuguggg ugccuuugug gccuguaccg acuggcuggc uaauuuugug guuucuguac   1440
caucacaugc cuauuuuaag acacucucca gcacugucgg uuagggagug uaaauuuugc   1500
aauauuuucu gaaauguggc aauaucaaaa uguaaaaggc acacauacuu ggucacaaac   1560
aaauggcacu auuuacucug ugggcauauu uguaaaaguu gccaaagaau uauauacaag   1620
gauguucauc agagcauuuc uuuugaagag uaaagaaaug gacaugaacc uguggucegu   1680
ucauacggug gaauaccuau gcagcuguaa aaaucagugu gguagaucuc cguauaugag   1740
uugaugugga agguuggcca guucacauga uaaggugaau agaauaaguu acagaacagg   1800
cuguagagua ugaucuuauu uguagauguu uaaaacugag ucauaaguau gcuuauauac   1860
agaucguuuc uggaaguaug uacuggaagu cuaccucugg ggaguggggga ugggggagug   1920
cacucuucua uacuguuaua uuuucuuuuc augcuccuaa gguacuuuua uuggaagaug   1980
uaaagcgguu caauguaaua ggcuuaacuu cugucaacua aguuggcgug ggugcuuuaa   2040
gaggguggua gugauguugc uggagaaagu aucccacagu cacuggugge uucagccacg   2100
ggccauuuug gggccuaaua aucacauauc aucaugguug cuaguguuaa ucgaaaaccu   2160
acuaagugcc aggcuuacug ucucuggguc uugcuuacgu ggaugucauu uuuccaguug   2220
caccaaaucg aaagagguua auugguuugu uggaguuccu uuguagguga agggcagagc   2280
caggagcuug gcuagggaca ggggagguga gugggggaug guggauaggu cuuggcuccc   2340
aguuuccuuc ugggcagaca uugccccucu gcccugagga ccugcuuguu ugggggaaga   2400
```

```
ggccuuuaga ggcaccaggg ucaugccagg uguuggacau ggugaacugg gaagugcucc   2460
caucuggcca cagcgcagaa guaucaccgu gcugggggau ggggaacagg gcugugaaug   2520
ggccuauuug cauaagcagc augugucugg agagaaagac aucacagagc agaagagugc   2580
gggugcccag gagugcacuu gccaccccua cuucaucccu gaaagaguaa auggccugga   2640
aggugucucu gagagguaau gccgcacacc acccucccug gggcagggu caggcuacac    2700
cugccuuagg ucgggggcug cagcagccug agagcucuca guagggccuc aguagccugg   2760
gagggagcag gggcaggggg cagggaaaga ggcguaaugg ggcuguccag aggggccugg   2820
gaaaccuggu cccugaggcc ugggcacagc uacaaucacu ucaaauuggc uguggggcca   2880
guggacuggg aaggaaaaaa gcaauaagag ugaccaagug cagaaggcug ucaggUccca   2940
ggucacaugc cuuagugcag ugacuccuca ucauuuuaug gggugugggu gucguuggua   3000
cacccauuuu acagaugagg acaccgaggc ccagaaaagu uaaguuacau guccuaaguc   3060
acacagcuug uaagugccag aacugagauc aaaaccaagu cucuuugacu uuaaagucug   3120
uacucugacc ccaaagagau ccuguuuggc cacuuauagg agguccuaa agcugcagac    3180
uccccuugcc ggcacccaca uauagagaca uuaacccuuc cccugcaggg ucaccucaaa   3240
uagucuuuua gcugggcuuc uccugcaauu ccaccuaaug ccaucccug gguuuugccc    3300
aaaccugaac ugggcagugg ggugagagga gggguuuaca ggguuacaga gccucauaca   3360
gauaggagcc cauggcugcu ggucaucugc auuccugcag gauuggcugu uccuuggggu   3420
ccuuggcagg aaaaugagga uugcuccgag gccugcucca guacuuccca gaggcuggcc   3480
uggugugggg cucugggaag gcugaggcug gagaagcgua aguaggaggg cagagauggc   3540
acucagguag cuugaaucac caggacccuu ccaagcccca cagguucuga gggaguacua   3600
gggccagcuc ugggagaggu cucuuccuau gcugugaacc cccugccuuu cuugcagccu   3660
acaacgaaua aauuuucuuu gcaaaggcuu                                   3690
```

<210> SEQ ID NO 48
<211> LENGTH: 4093
<212> TYPE: DNA
<213> ORGANISM: Homo sapiens

<400> SEQUENCE: 48

```
cuuuuagcca ccccagugcu gggcagccag ggugugggcu uuugacugaa ugcacuugcc     60
cuccugcauu cauuacacca uugucagugu gugugucugg ggcugccucu gggugugcau    120
gguuuuuuuu gugucugcgu gucaguguca ggcuaugugu gucuguuucu gucggccugu    180
cuaggcgcgc ucagugcaac aaggagcugg gggagguggc gguaaagagg aagggcauuu    240
caaagcccag cuguccuccu cagggaccuc aggagaugcg ugugugugug ugugugugug    300
ugugugugug ugugugugua uuuuuuucca ugcugcucau ugugugggc ugcaugcgag     360
ugucugacca ggugugguga gagcagccgc ugggcugggu gagccccauc ugccgugagc    420
ucccagacuu gccuucuagc ccucugccgc cauccauggg gagccucucc cuucgcagcu    480
caccgucucu ucucuaauuu auuagcugga aaggaggaga acaugaaaca uugcuugaag    540
acaauggccg agacagcagg ucccacccug cacagccacc agcaucucuc cccucagccc    600
ugucuccucu ucugcaguug ggaucugcac auuuaagccu gaaauugucc ugugaaguga    660
aguaugaucg gacagccucu uuucagcuuu uaugacaaug gagacagagg aauuguggcu    720
cuugccaagg ucacaggauu ggaauacaga gccaagccac cccaggacau gcaagagccu    780
cagaagggaa aaaagcccag caggaaggga gaacaaguag ccucuguccu gaaguuguaa    840
```

-continued cagccagggg ccaggaugga ggaggaggac cccauaaucu gcccaucugg gacuuggcag 900
gggaccuggg aaaauguacc ccaacccauc ccuuaagggc cuuugucuuu ggcccauugg 960
ccuagcaucu acuucuucac cgugucuguu cuugucacac cuagucaggu cuguuugggu 1020
cugaggugca uggaacauuc uggguaggcc uccagcaaac ggaagcucuu caccguguuu 1080
ccagccuggg accaagggca gcauacuggc aaaguugcca aagcaaggga cuccagccuc 1140
uuaggaguua augacucccu cuccccagcu guccuccccu uggugcuccu cuuccucccu 1200
ccuccugcuc acagcaggca gggccuagac ccgggagcca ugcugcugug cuguugccag 1260
gggagcacgg aggcagaucu gagcuaugca gggaaaaggc ccagccuguc aaagugucug 1320
agaugaaccg ccgccguccc ugugcagcug ggcucagacg ugucucagcu cuuguucugu 1380
gccugagaau ggcgaaaccc agugagguuc aagggcaaac ucgcuauuca uuagucaggg 1440
guucuugacg ucccgucucu cccagggaug aguucccccc uccucuuucu cccccuccua 1500
ugacacauuc cugggugccu uuggugagga cugcacaccc uccuccugcc uagccccuc 1560 uccaaaggcc ccugaauaaa cuccccccaa ggagaccagg cagggcagag acaauggcug 1620
caggaaauca uucaggcggg acaugcuggc cugcccucca cccagucccc cugugggccc 1680
cacucccuuc ugauucaggg cacccuuggg cccccagccu auacaggccu ggacaggaag 1740
aaaccacugg gaaccacccu aaggacaaca ugcuagucca gugccauucu ucgcuggcuc 1800
ugugggugcc uuuguggccu guaccgacug gcuggcuaau uuugugguuu cuguaccauc 1860
acaugccuau uuuaagacac ucuccagcac ugucgguuag ggaguguaaa uuuugcaaua 1920
uuuucugaaa uguggcaaua ucaaaaugua aaaggcacac auacuugguc acaaacaaau 1980
ggcacuauuu acucuguggg cauauuugua aaaguugcca aagaauuaua uacaaggaug 2040
uucaucagag cauuucuuuu gaagaguaaa gaaauggaca ugaaccugug guccguucau 2100
acgguggaau accuaugcag cuguaaaaau caguguggua gaucuccgua uaugaguuga 2160
uguggaaggu uggccaguuc acaugauaag gugaauagaa uaaguuacag aacaggcugu 2220
agaguaugau cuuauuugua gauguuuaaa acugagucau aaguaugcuu auauacagau 2280
cguuucugga aguauguacu ggaagucuac cucuggggag uggggauggg ggagugcacu 2340
cuucuauacu guuauauuuu cuuuucaugc uccuaaggua cuuuuauugg aagauguaaa 2400
gcgguucaau guaauaggcu uaacuucugu caacuaaguu ggcgugggug cuuuaagagg 2460
gugguaguga uguugcugga gaaaguaucc cacagucacu gguggcuuca gccacgggcc 2520
auuuuggggc cuaauaauca cauaucauca ugguugcuag uguuaaucga aaaccuacua 2580
agugccaggc uuacugucuc ugggucuugc uuacguggau gucauuuuuc caguugcacc 2640
aaaucgaaag agguuaauug guuuguugga guuccuuugu aggugaaggg cagagccagg 2700
agcuuggcua gggacagggg aggugagugg gggauggugg auaggucuug gcucccaguu 2760
uccuucuggg cagacauugc cccucugccc ugaggaccug cuuguuuggg ggaagaggcc 2820
uuuagaggca ccagggucau gccagguguu ggacauggug aacugggaag ugcucccauc 2880
uggccacagc gcagaaguau caccgugcug ggggaugggg aacagggcug ugaaugggcc 2940
uauuugcaua agcagcaugu gucuggagag aaagacauca cagagcagaa gagugcgggu 3000
gcccaggagu gcacuugcca ccccuacuuc aucccugaaa gaguaaaugg ccuggaaggu 3060
gucucugaga gguaaugccg cacaccaccc ucccuggggg cagggucagg cuacaccugc 3120
cuuaggucgg gggcugcagc agccugagag cucucaguag ggccucagua gccugggagg 3180

```
gagcaggggc agggggcagg gaaagaggcg uaaugggcu guccagaggg gccugggaaa   3240

ccugguccu gaggccuggg cacagcuaca aucacuucaa auuggcugug gggccagugg   3300

acugggaagg aaaaaagcaa uaagagugac caagugcaga aggcugucag gucccagguc   3360

acaugccuua gugcagugac uccucaucau uuuaugggu gugggugucg uugguacacc   3420

cauuuuacag augaggacac cgaggcccag aaaaguuaag uuacauguc uaagucacac   3480

agcuuguaag ugccagaacu gagaucaaaa ccaagucucu uugacuuuaa agucuguacu   3540

cugaccccaa agagauccug uuuggccacu uauaggaggu cccuaaagcu gcagacuccc   3600

cuugccggca cccacauaua gagacauuaa cccuuccccu gcagggucac cucaaauagu   3660

cuuuuagcug ggcuucuccu gcaauuccac cuaaugccau ccccuggguu uugcccaaac   3720

cugaacuggg caguggggug agaggagggg uuuacagggu uacagagccu cauacagaua   3780

ggagcccaug gcugcugguc aucugcauuc cugcaggauu ggcuguuccu uggggguccuu   3840

ggcaggaaaa ugaggauugc uccgaggccu gcuccaguac uucccagagg cuggccuggu   3900

guggggcucu gggaaggcug aggcuggaga agcguaagua ggagggcaga gauggcacuc   3960

agguagcuug aaucaccagg acccuuccaa gccccacagg uucugaggga guacuagggc   4020

cagcucuggg agaggucucu uccuaugcug ugaacccccu gccuuucuug cagccuacaa   4080

cgaauaaauu uuc                                                      4093
```

<210> SEQ ID NO 49
<211> LENGTH: 957
<212> TYPE: DNA
<213> ORGANISM: Homo sapiens

<400> SEQUENCE: 49

```
aaggcggcgc tgggagccgc tcagagccca gagaagcggc gcgcggccag gagcccccgc     60

tccgccactg ccgtgcctgc ctcccgcagc tgtctgccat gcgctcgccg gggcaggggc    120

gcccggaggg cggctagagc tgggcctgag cccgggaacg cgcctgatca ggggtggcgg    180

agccgcggtc cccacagccg ccccacccgc gccgctgcct cgctggggcc cgggcccccct   240

tcccgttact cccctgctgg tgcctccctc cttggcgcgc ttcccacctg cgatcggcgc    300

cctcttcgca gtcacgaact cgccagcagc tagcagcact gactagtagg agggcccgcc    360

ggaggagagg acatgctctg gagtcagaag acagcgaaaa gagaagcaga agccccggtg    420

gcaagagtct gaagcaggaa ggatgactgt agcctgtgga ttgtactgca gtaggaaact    480

gtcctagcaa ggctccactt tgccccagct tcaagctgga aaggaggaga acatgaaaca    540

ttgcttgaag acaatggccg agacagcagg tcccaccctg cacagccacc agcatctctc    600

ccctcagccc tgtctcctct tctgcagttg ggatctgcac atttaagcct gaaattgtcc    660

tgtgaagtga agtatgatcg gacagcctct tttcagcttt tatgacaatg gagacagagg    720

aattgtggct cttgccaagg tcacaggatt ggaatacaga gccaagccac cccaggacat    780

gcaagagcct cagaagggaa aaaagcccag caggaaggga gaacaagtag cctctgtcct    840

gaagttgtaa cagccagggg ccaggatgga ggaggaggac cccataatct gcccatctgg    900

gacttggcag gggacctggg aaaatgtacc ccaacccatc ccttaagggc ctttgtc       957
```

<210> SEQ ID NO 50
<211> LENGTH: 2124
<212> TYPE: DNA
<213> ORGANISM: Homo sapiens

<400> SEQUENCE: 50

```
gattctcaca acttctgcgt gcgagcgccc gccccaccga ccgccccggc ccggcccgca     60

agagccagag gagccgagag gagcccagcg ccggcccagc ggactccagc tcgacggagc    120

ggccgcgccc cgaccagtta ctcccctgct ggtgcctccc tccttggcgc gcttcccacc    180

tgcgatcggc gccctcttcg cagtcacgaa ctcgccagca gctagcagca ctgactagta    240

ggagggcccg ccggaggaga ggaagcccca gagagattgg tgagggtgat ttcccaggaa    300

gacgcagtgt gctctgactt ctgtgacagt gagcaacggg accagtggat gtccagatgc    360

tggcaatgag acatgctctg gagtcagaag acagcgaaaa gagaagcaga agccccggtg    420

gcaagagtct gaagcaggaa ggatgactgt agcctgtgga ttgtactgca gtaggaaact    480

gtcctagcaa ggctccactt tgccccagct tcaagctgga aaggaggaga acatgaaaca    540

ttgcttgaag acaatggccg agacagcagg tcccaccctg cacagccacc agcatctctc    600

ccctcagccc tgtctcctct tctgcagttg ggatctgcac atttaagcct gaaattgtcc    660

tgtgaagtga agtatgatcg gacagcctct tttcagcttt tatgacaatg gagacagagg    720

aattgtggct cttgccaagg tcacaggatt ggaatacaga gccaagccac cccaggacat    780

gcaagagcct cagaagggaa aaaagcccag caggaaggga gaacaagtag cctctgtcct    840

gaagttgtaa cagccagggg ccaggatgga ggaggaggac cccataatct gcccatctgg    900

gacttggcag gggacctggg aaaatgtacc ccaacccatc ccttaagggc ctttgtcttt    960

ggcccattgg cctagcatct acttcttcac cgtgtctgtt cttgtcacac ctagtcaggt   1020

ctgtttgggt ctgaggtgca tggaacattc tgggtaggcc tccagcaaac ggaagctctt   1080

caccgtgttt ccagcctggg accaagggca gcatactggc aaagttgcca aagcaaggga   1140

ctccagcctc ttaggagtta atgactccct ctccccagct gtcctcccct tggtgctcct   1200

cttcctccct cctcctgctc acagcaggca gggcctagac ccgggagcca tgctgctgtg   1260

ctgttgccag gggagcacgg aggcagatct gagctatgca gggaaaaggc ccagcctgtc   1320

aaagtgtctg agatgaaccg ccgccgtccc tgtgcagctg ggctcagacg tgtctcagct   1380

cttgttctgt gcctgagaat ggcgaaaccc agtgaggttc aagggcaaac tcgctattca   1440

ttagtcaggg gttcttgacg tcccgtctct cccagggatg agttcccccc tcctctttct   1500

ccccctccta tgacacattc ctgggtgcct ttggtgagga ctgcacaccc tcctcctgcc   1560

tagccccctc tccaaaggcc cctgaataaa ctccccccaa ggagaccagg cagggcagag   1620

acaatggctg caggaaatca ttcaggcggg acatgctggc ctgcccttca cctcaaatag   1680

tcttttagct gggcttctcc tgcaattcca cctaatgcca tcccctgggt tttgcccaaa   1740

cctgaactgg gcagtggggt gagaggaggg gtttacaggg ttacagagcc tcatacagat   1800

aggagcccat ggctgctggt catctgcatt cctgcaggat tggctgttcc ttggggtcct   1860

tggcaggaaa atgaggattg ctccgaggcc tgctccagta cttcccagag gctggcctgg   1920

tgtggggctc tgggaaggct gaggctggag aagcgtaagt aggagggcag agatggcact   1980

caggtagctt gaatcaccag gacccttcca agccccacag gttctgaggg agtactaggg   2040

ccagctctgg gagaggtctc ttcctatgct gtgaaccccc tgcctttctt gcagcctaca   2100

acgaataaat ttctttgca aagg                                           2124
```

<210> SEQ ID NO 51
<211> LENGTH: 576
<212> TYPE: DNA
<213> ORGANISM: Homo sapiens

<400> SEQUENCE: 51
agtgcgtggg ggtcccggcc ccacacagtg ctagggtccc tctcgagttt ctcatctgcc 60
ttcaggtcac tttccaccct gatgccttgg cttgtcctga agctcagggc ccctgtagct 120
tgggaaacct cccaagctcc ccagcgagtg gctgtagacc aaggaaggga ccctgcccgg 180
cttcagggaa gaaaggaaga aagttactcc cctgctggtg cctccctcct tggcgcgctt 240
cccacctgcg atcggcgccc tcttcgcagt cacgaactcg ccagcagcta gcagcactga 300
ctagtaggag ggcccgccgg aggagagccg cgcggcccac agaagcggaa cgcgcgtcga 360
gagcgccctg tccgctcgcc ccagacagat gcccggttat tcattaccgc gaggcctaga 420
ggaaagagtg gctgccgtct tcctgcccac agcccgccgg accctccgtc gcggctgccc 480
ggtccccgga gccgcagccg ccgagcccgg ctgtgcgtgt cgtggctgct ggggagaaag 540
aggcttccgg acatgctctg gagtcagaag acagcg 576

<210> SEQ ID NO 52
<211> LENGTH: 6547
<212> TYPE: DNA
<213> ORGANISM: Homo sapiens

<400> SEQUENCE: 52
gagcaatgtc ctgggaggcc tggctgagct tgtgtccagg agcactggac ttgtgttaaa 60
cactgtcccc ttggatgggc ccagaagtca aacctgtcca ttagattttt ttttttttc 120 ctttgggaga gctggtatgg gctggttgtc ctccaggaga gccctgttct cacccgaggt 180
ctgttaatga gctggggaca ggtgagcctc acacgttcca acttggctgc cttcagcggc 240
atccaggagc agtggtgagc tattaatgga aggtgccggc tttgtgctaa ttagaacttc 300
ctttcagctt ccatctgtgc agacactgga gcccctcact ggtcagcctc gccgtcccaa 360 ccccccctcag tttgcaacct agtttttgtc ccccccaccc cccatgaatt agggggtgct 420
atgagtggag ctgctttcct ctagctctgg tcaaatcccg gctctttgtg tattgcagaa 480
ctgtactggg tggtatttct cagggcttct ctctcttgtt ggggtggaga tggacctgga 540
agatggagtt ggaaagggat ttgggcacca tggccaccct cctgggtagg ctggacttac 600
atcatcgacc tgagtttgtt ttgtgaaaga cctctctcct ctgccctctg gagactgtga 660
cttcagaccc ttgtcctctc cattacccca gtcctgatgt ctcccaagtc tgatggtacc 720
cacccatgtc aactacagct gccatctttg ccatctcagg cagcctacag gtgggggctg 780
tgtccttgac cctcttctga aaaagaaaaa cctatttttt tccttcactt ttgcttttta 840
tttctttcac ctcaggccca atggatatat atatatatat atatatatat acatatatat 900
atatacatat atacatatat atatatatat atatatatat attttaatgg aggttgtctc 960
ttacagaggt ttcattgaaa aagaagaaac aatgtcccat taacgtcatt taaagaaaaa 1020
gcacctctca gaatggaggt tgggaaagct agggtttctt gcctgaatat cagttgggat 1080
gaaatccctt gtaaggaact caagagagga gcgtttcctc agaatgcttt ctttagctcc 1140
tgagtctcct taggtctcca ctggggttgt gtgtaaaaat accaagccct ccctgacaat 1200
gcatctcatt ctcttctgct tgaattatcc tgataatgag agatcaccca cttctttgac 1260
agtgtagact aggattttaa aaattgggag tgaattattg gacagtgtgg cacttcacca 1320
gcttccctca aggttctgga tctatgctaa agaggggtgg aaatgcttct ggggtgtcca 1380
gaagggctgc agaaattcct cgtcactggt catggggaga gcaggactgg cttgcctctg 1440
tggcctcttc tgcctctgga ggtgacaatt cctgatttga ggcactaggg tggaagactc 1500

```
aggactatcc aggaccaggt taataaaccg gcagtccaga ttgcagaagg gcagcagctg   1560
ggggctgggg acatgcccat gcctgtggga cagagttctt ttgcatgctt tggcctttac   1620
gactctgtat ccttgacaag tcacaggcat ctctgggtga aatggggaca atagtaccca   1680
tacctccaag ggttatgtga gaattaagta aaatatgcaa ataaagtgcc tggcatacag   1740
taggcactga gcaaacggta gctctttttt ccaggctggg gcaagggatg catataaatg   1800
tctggatctg aagtttgaaa ttccacctgc tggagacagt gaacacccca gtagataccc   1860
caaatcacac agaaggacgg atgaccagct gccttcttcc cccagggcat gccatacaca   1920
ctgggcctga agtgggagaa tcgggacccc aaaaaaacgg cttgtggagc ggggttgcac   1980
atgggtgtaa agttcccagc ttggctgcct ggggaggggg agcatgtaaa tgtctttaga   2040
gatttgaagg gaccaggatc tggactgatt tgcgttgccc agggggctgg ggctgggagc   2100
caagggggtg ctgccgggag gcccaggtta gcttggggta tggcatttct aacagttggc   2160
gcctgcggaa aatggcctgg ggttccagct ctggaaggtt ccgaatctca gtattcacga   2220
gcggcgctgt ccggagcagc cagggttgtc ccttggtggt ctcgggcagg ttctccgcga   2280
tgcgcttgct gggtcgcagg tgagaacctc acggttctcc atttccggag atccagctct   2340
gagcaggcag agggtcgctc ccgtcgcctg cccctgcggt agccaagcgg gtggctggaa   2400
gcgtggctag ctggcaggta aggagctcca ggtgagacgg aacacgaccc ccaacccccct   2460
tagccggtgc cccacccgat ttctctcctg cgtcctggga gggcatggtt gaggcgccac   2520
cggtgcccag caacctcccc aggctgtggt tgtgacctga ggacgcgtgt gtccccgccc   2580
tcaggccacc gctacgcgac cctgagtgca ccttcaagaa ggccgggcac gtttctgggc   2640
gggcgtgggg ggtgcctgat atctccgctc tattttacag ttactcccct gctggtgcct   2700
ccctccttgg cgcgcttccc acctgcgatc ggcgccctct tcgcagtcac gaactcgcca   2760
gcagctagca gcactgacta gtaggagggc ccgccggagg agaggacatg ctctggagtc   2820
agaagacagc gaaaagagaa gcagaagccc cggtggcaag agtctgaagg aaggatgact   2880
gtagcctgtg gattgtactg cagtaggaaa ctgtcctagc aaggctccac tttgccccag   2940
cttcaagctg gaaaggagga gaacatgaaa cattgcttga agacaatggc cgagacagca   3000
ggtcccaccc tgcacagcca ccagcatctc tcccctcagc cctgtctcct cttctgcagt   3060
tgggatctgc acatttaagc ctgaaattgt cctgtgaagt gaagtatgat cggacagcct   3120
cttttcagct tttatgacaa tggagacaga ggaattgtgg ctcttgccaa ggtcacagga   3180
ttggaataca gagccaagcc accccaggac atgcaagagc ctcagaaggg aaaaaagccc   3240
agcaggaagg gagaacaagt agcctctgtc ctgaagttgt aacagccagg ggccaggatg   3300
gaggaggagg accccataat ctgcccatct gggacttggc aggggacctg ggaaaatgta   3360
ccccaaccca tcccttaagg gcctttgtct ttggcccatt ggcctagcat ctacttcttc   3420
accgtgtctg ttcttgtcac acctagtcag gtctgtttgg gtctgaggtg catggaacat   3480
tctgggtagg cctccagcaa acggaagctc ttcaccgtgt ttccagcctg ggaccaaggg   3540
cagcatactg gcaaagttgc caaagcaagg gactccagcc tcttaggagt taatgactcc   3600
ctctccccag ctgtcctccc cttggtgctc ctcttcctcc ctcctcctgc tcacagcagg   3660
cagggcctag acccgggagc catgctgctg tgctgttgcc aggggagcac ggaggcagat   3720
ctgagctatg cagggaaaag gcccagcctg tcaaagtgtc tgagatgaac cgccgccgtc   3780
cctgtgcagc tgggctcaga cgtgtctcag ctcttgttct gtgcctgaga atggcgaaac   3840
```

```
ccagtgaggt tcaagggcaa actcgctatt cattagtcag gggttcttga cgtcccgtct   3900
ctcccaggga tgagttcccc cctcctcttt ctccccctcc tatgacacat tcctgggtgc   3960
ctttggtgag gactgcacac cctcctcctg cctagccccc tctccaaagg cccctgaata   4020
aactcccccc aaggagacca ggcagggcag agacaatggc tgcaggaaat cattcaggcg   4080
ggacatgctg gcctgccctc cacccagtcc ccctgtgggc cccactccct tctgattcag   4140
ggcacccttg ggcccccagc ctatacaggc ctggacagga agaaaccact gggaaccacc   4200
ctaaggacaa catgctagtc cagtgccatt cttcgctggc tctgtgggtg cctttgtggc   4260
ctgtaccgac tggctggcta attttgtggt ttctgtacca tcacatgcct attttaagac   4320
actctccagc actgtcggtt agggagtgta aattttgcaa tattttctga aatgtggcaa   4380
tatcaaaatg taaaaggcac acatacttgg tcacaaacaa atggcactat ttactctgtg   4440
ggcatatttg taaaagttgc caaagaatta tatacaagga tgttcatcag agcatttctt   4500
ttgaagagta aagaaatgga catgaacctg tggtccgttc atacggtgga atacctatgc   4560
agctgtaaaa atcagtgtgg tagatctccg tatatgagtt gatgtggaag gttggccagt   4620
tcacatgata aggtgaatag aataagttac agaacaggct gtagagtatg atcttatttg   4680
tagatgttta aaactgagtc ataagtatgc ttatatacag atcgtttctg gaagtatgta   4740
ctggaagtct acctctgggg agtggggatg gggagtgca ctcttctata ctgttatatt    4800
ttcttttcat gctcctaagg tacttttatt ggaagatgta aagcggttca atgtaatagg   4860
cttaacttct gtcaactaag ttggcgtggg tgctttaaga gggtggtagt gatgttgctg   4920
gagaaagtat cccacagtca ctggtggctt cagccacggg ccattttggg gcctaataat   4980
cacatatcat catggttgct agtgttaatc gaaaacctac taagtgccag gcttactgtc   5040
tctgggtctt gcttacgtgg atgtcatttt tccagttgca ccaaatcgaa agaggttaat   5100
tggtttgttg gagttccttt gtaggtgaag ggcagagcca ggagcttggc tagggacagg   5160
ggaggtgagt gggggatggt ggataggtct tggctcccag tttccttctg ggcagacatt   5220
gcccctctgc cctgaggacc tgcttgtttg ggggaagagg cctttagagg caccagggtc   5280
atgccaggtg ttggacatgg tgaactggga agtgctccca tctggccaca gcgcagaagt   5340
atcaccgtgc tgggggatgg ggaacagggc tgtgaatggg cctatttgca taagcagcat   5400
gtgtctggag agaaagacat cacagagcag aagagtgcgg gtgcccagga gtgcacttgc   5460
cacccctact tcatccctga aagagtaaat ggcctggaag gtgtctctga gaggtaatgc   5520
cgcacaccac cctccctggg ggcagggtca ggctacacct gccttaggtc gggggctgca   5580
gcagcctgag agctctcagt agggcctcag tagcctggga gggagcaggg gcagggggca   5640
gggaaagagg cgtaatgggg ctgtccagag gggcctggga aacctggtcc ctgaggcctg   5700
ggcacagcta caatcacttc aaattggctg tggggccagt ggactgggaa ggaaaaaagc   5760
aataagagtg accaagtgca gaaggctgtc aggtcccagg tcacatgcct tagtgcagtg   5820
actcctcatc attttatggg gtgtgggtgt cgttggtaca cccattttac agatgaggac   5880
accgaggccc agaaaagtta agttacatgt cctaagtcac acagcttgta agtgccagaa   5940
ctgagatcaa aaccaagtct ctttgacttt aaagtctgta ctctgacccc aaagagatcc   6000
tgtttggcca cttataggag gtccctaaag ctgcagactc cccttgccgg cacccacata   6060
tagagacatt aacccttccc ctgcagggtc acctcaaata gtcttttagc tgggcttctc   6120
ctgcaattcc acctaatgcc atcccctggg ttttgcccaa acctgaactg ggcagtgggg   6180
tgagaggagg ggtttacagg gttacagagc ctcatacaga taggagccca tggctgctgg   6240
```

```
tcatctgcat tcctgcagga ttggctgttc cttggggtcc ttggcaggaa aatgaggatt   6300

gctccgaggc ctgctccagt acttcccaga ggctggcctg gtgtggggct ctgggaaggc   6360

tgaggctgga gaagcgtaag taggagggca gagatggcac tcaggtagct tgaatcacca   6420

ggacccttcc aagccccaca ggttctgagg gagtactagg gccagctctg ggagaggtct   6480

cttcctatgc tgtgaacccc ctgcctttct tgcagcctac aacgaataaa ttttctttgc   6540

aaaggct                                                             6547
```

```
<210> SEQ ID NO 53
<211> LENGTH: 3814
<212> TYPE: DNA
<213> ORGANISM: Homo sapiens

<400> SEQUENCE: 53

cacgtttctg ggcgggcgtg gggggtgcct gatatctccg ctctatttta cagttactcc     60

cctgctggtg cctccctcct tggcgcgctt cccacctgcg atcggcgccc tcttcgcagt    120

cacgaactcg ccagcagcta gcagcactga ctagtaggag ggcccgccgg aggagaggac    180

atgctctgga gtcagaagac agcgaaaaga gaagcagaag ccccggtggc aagagtctga    240

agctggaaag gaggagaaca tgaaacattg cttgaagaca atggccgaga cagcaggtcc    300

caccctgcac agccaccagc atctctcccc tcagccctgt ctcctcttct gcagttggga    360

tctgcacatt taagcctgaa attgtcctgt gaagtgaagt atgatcggac agcctctttt    420

cagcttttat gacaatggag acagaggaat tgtggctctt gccaaggtca caggattgga    480

atacagagcc aagccacccc aggacatgca agagcctcag aagggaaaaa agcccagcag    540

gaagggagaa caagtagcct ctgtcctgaa gttgtaacag ccaggggcca ggatggagga    600

ggaggacccc ataatctgcc catctgggac ttggcagggg acctgggaaa atgtacccca    660

acccatccct taagggcctt tgtctttggc ccattggcct agcatctact tcttcaccgt    720

gtctgttctt gtcacaccta gtcaggtctg tttgggtctg aggtgcatgg aacattctgg    780

gtaggcctcc agcaaacgga agctcttcac cgtgtttcca gcctgggacc aagggcagca    840

tactggcaaa gttgccaaag caagggactc cagcctctta ggagttaatg actccctctc    900

cccagctgtc ctccccttgg tgctcctctt cctccctcct cctgctcaca gcaggcaggg    960

cctagacccg ggagccatgc tgctgtgctg ttgccagggg agcacggagg cagatctgag   1020

ctatgcaggg aaaaggccca gcctgtcaaa gtgtctgaga tgaaccgccg ccgtccctgt   1080

gcagctgggc tcagacgtgt ctcagctctt gttctgtgcc tgagaatggc gaaacccagt   1140

gaggttcaag ggcaaactcg ctattcatta gtcaggggtt cttgacgtcc cgtctctccc   1200

agggatgagt tccccctcc tctttctccc cctcctatga cacattcctg ggtgcctttg   1260

gtgaggactg cacaccctcc tcctgcctag ccccctctcc aaaggcccct gaataaactc   1320

cccccaagga gaccaggcag ggcagagaca atggctgcag gaaatcattc aggcgggaca   1380

tgctggcctg ccctccaccc agtccccctg tgggccccac tcccttctga ttcagggcac   1440

ccttgggccc ccagcctata caggcctgga caggaagaaa ccactgggaa ccaccctaag   1500

gacaacatgc tagtccagtg ccattcttcg ctggctctgt gggtgccttt gtggcctgta   1560

ccgactggct ggctaatttt gtggtttctg taccatcaca tgcctatttt aagacactct   1620

ccagcactgt cggttaggga gtgtaaattt tgcaatattt tctgaaatgt ggcaatatca   1680

aaatgtaaaa ggcacacata cttggtcaca aacaaatggc actatttact ctgtgggcat   1740
```

```
atttgtaaaa gttgccaaag aattatatac aaggatgttc atcagagcat ttcttttgaa   1800
gagtaaagaa atggacatga acctgtggtc cgttcatacg gtggaatacc tatgcagctg   1860
taaaaatcag tgtggtagat ctccgtatat gagttgatgt ggaaggttgg ccagttcaca   1920
tgataaggtg aatagaataa gttacagaac aggctgtaga gtatgatctt atttgtagat   1980
gtttaaaact gagtcataag tatgcttata tacagatcgt ttctggaagt atgtactgga   2040
agtctacctc tggggagtgg ggatgggga gtgcactctt ctatactgtt atattttctt    2100
ttcatgctcc taaggtactt ttattggaag atgtaaagcg gttcaatgta ataggcttaa   2160
cttctgtcaa ctaagttggc gtgggtgctt taagagggtg gtagtgatgt tgctggagaa   2220
agtatcccac agtcactggt ggcttcagcc acgggccatt ttggggccta ataatcacat   2280
atcatcatgg ttgctagtgt taatcgaaaa cctactaagt gccaggctta ctgtctctgg   2340
gtcttgctta cgtggatgtc atttttccag ttgcaccaaa tcgaaagagg ttaattggtt   2400
tgttggagtt cctttgtagg tgaagggcag agccaggagc ttggctaggg acaggggagg   2460
tgagtggggg atggtggata ggtcttggct cccagtttcc ttctgggcag acattgcccc   2520
tctgccctga ggacctgctt gtttggggga agaggccttt agaggcacca gggtcatgcc   2580
aggtgttgga catggtgaac tgggaagtgc tcccatctgg ccacagcgca gaagtatcac   2640
cgtgctgggg gatggggaac agggctgtga atgggcctat ttgcataagc agcatgtgtc   2700
tggagagaaa gacatcacag agcagaagag tgcgggtgcc caggagtgca cttgccaccc   2760
ctacttcatc cctgaaagag taaatggcct ggaaggtgtc tctgagaggt aatgccgcac   2820
accaccctcc ctgggggcag ggtcaggcta cacctgcctt aggtcggggg ctgcagcagc   2880
ctgagagctc tcagtagggc ctcagtagcc tgggagggag caggggcagg gggcagggaa   2940
agaggcgtaa tggggctgtc cagaggggcc tgggaaacct ggtccctgag gcctgggcac   3000
agctacaatc acttcaaatt ggctgtgggg ccagtggact gggaaggaaa aaagcaataa   3060
gagtgaccaa gtgcagaagg ctgtcaggtc ccaggtcaca tgccttagtg cagtgactcc   3120
tcatcatttt atggggtgtg ggtgtcgttg gtacacccat tttacagatg aggacaccga   3180
ggcccagaaa agttaagtta catgtcctaa gtcacacagc ttgtaagtgc cagaactgag   3240
atcaaaacca agtctctttg actttaaagt ctgtactctg accccaaaga gatcctgttt   3300
ggccacttat aggaggtccc taaagctgca gactcccctt gccggcaccc acatatagag   3360
acattaaccc ttcccctgca gggtcacctc aaatagtctt ttagctgggc ttctcctgca   3420
attccaccta atgccatccc ctgggttttg cccaaacctg aactgggcag tggggtgaga   3480
ggaggggttt acagggttac agagcctcat acagatagga gcccatggct gctggtcatc   3540
tgcattcctg caggattggc tgttccttgg ggtccttggc aggaaaatga ggattgctcc   3600
gaggcctgct ccagtacttc ccagaggctg gcctggtgtg gggctctggg aaggctgagg   3660
ctggagaagc gtaagtagga gggcagagat ggcactcagg tagcttgaat caccaggacc   3720
cttccaagcc ccacaggttc tgagggagta ctagggccag ctctgggaga ggtctcttcc   3780
tatgctgtga accccctgcc tttcttgcag ccta                               3814
```

<210> SEQ ID NO 54
<211> LENGTH: 4198
<212> TYPE: DNA
<213> ORGANISM: Homo sapiens

<400> SEQUENCE: 54

```
ttactcccct gctggtgcct ccctccttgg cgcgcttccc acctgcgatc ggcgccctct     60
```

```
tcgcagtcac gaactcgcca gcagctagca gcactgacta gtaggagggc ccgccggagg    120
agagccgcgc ggcccacaga agcggaacgc gcgtcgagag cgccctgtcc gctcgcccca    180
gacagatgcc cggttattca ttaccgcgag gcctagagga aagagtggct gccgtcttcc    240
tgcccacagc ccgccggacc ctccgtcgcg gctgcccggt ccccggagcc gcagccgccg    300
agcccggctg tgcgtgtcgt ggctgctggg gagaaagagg cttccggaag ccccagagag    360
attggtgagg gtgatttccc aggaagacgc agtgtgctct gacttctgtg acagtgagca    420
acgggaccag tggatgtcca gatgctggca atgagacatg ctctggagtc agaagacagc    480
gaaaagagaa gcagaagccc cggtggcaag agtctgaagc aggaaggatg actgtagcct    540
gtggattgta ctgcagtagg aaactgtcct agcaaggctc cactttgccc cagcttcaag    600
ctggaaagga ggagaacatg aaacattgct tgaagacaat ggccgagaca gcaggtccca    660
ccctgcacag ccaccagcat ctctcccctc agccctgtct cctcttctgc agttgggatc    720
tgcacattta agcctgaaat tgtcctgtga agtgaagtat gatcggacag cctcttttca    780
gcttttatga caatggagac agaggaattg tggctcttgc caaggtcaca ggattggaat    840
acagagccaa gccaccccag gacatgcaag agcctcagaa gggaaaaaag cccagcagga    900
agggagaaca agtagcctct gtcctgaagt tgtaacagcc aggggccagg atggaggagg    960
aggaccccat aatctgccca tctgggactt ggcaggggac ctgggaaaat gtaccccaac   1020
ccatccctta agggcctttg tctttggccc attggcctag catctacttc ttcaccgtgt   1080
ctgttcttgt cacacctagt caggtctgtt tgggtctgag gtgcatggaa cattctgggt   1140
aggcctccag caaacggaag ctcttcaccg tgtttccagc ctgggaccaa gggcagcata   1200
ctggcaaagt tgccaaagca agggactcca gcctcttagg agttaatgac tccctctccc   1260
cagctgtcct cccottggtg ctcctcttcc tccctcctcc tgctcacagc aggcagggcc   1320
tagacccggg agccatgctg ctgtgctgtt gccaggggag cacggaggca gatctgagct   1380
atgcagggaa aaggcccagc ctgtcaaagt gtctgagatg aaccgccgcc gtccctgtgc   1440
agctgggctc agacgtgtct cagctcttgt tctgtgcctg agaatggcga aacccagtga   1500
ggttcaaggg caaactcgct attcattagt caggggttct tgacgtcccg tctctcccag   1560
ggatgagttc ccccctcctc tttctccccc tcctatgaca cattcctggg tgcctttggt   1620
gaggactgca caccctcctc ctgcctagcc ccctctccaa aggcccctga ataaactccc   1680
cccaaggaga ccaggcaggg cagagacaat ggctgcagga aatcattcag gcgggacatg   1740
ctggcctgcc ctccacccag tcccccctgtg ggccccactc ccttctgatt cagggcaccc   1800
ttgggccccc agcctataca ggcctggaca ggaagaaacc actgggaacc accctaagga   1860
caacatgcta gtccagtgcc attcttcgct ggctctgtgg gtgcctttgt ggcctgtacc   1920
gactggctgg ctaattttgt ggtttctgta ccatcacatg cctattttaa gacactctcc   1980
agcactgtcg gttagggagt gtaaattttg caatattttc tgaaatgtgg caatatcaaa   2040
atgtaaaagg cacacatact tggtcacaaa caaatggcac tatttactct gtgggcatat   2100
ttgtaaaagt tgccaaagaa ttatatacaa ggatgttcat cagagcattt cttttgaaga   2160
gtaaagaaat ggacatgaac ctgtggtccg ttcatacggt ggaataccta tgcagctgta   2220
aaaatcagtg tggtagatct ccgtatatga gttgatgtgg aaggttggcc agttcacatg   2280
ataaggtgaa tagaataagt tacagaacag gctgtagagt atgatcttat ttgtagatgt   2340
ttaaaactga gtcataagta tgcttatata cagatcgttt ctggaagtat gtactggaag   2400
```

```
tctacctctg gggagtgggg atgggggagt gcactcttct atactgttat attttctttt   2460
catgctccta aggtactttt attggaagat gtaaagcggt tcaatgtaat aggcttaact   2520
tctgtcaact aagttggcgt gggtgcttta agagggtggt agtgatgttg ctggagaaag   2580
tatcccacag tcactggtgg cttcagccac gggccatttt ggggcctaat aatcacatat   2640
catcatggtt gctagtgtta atcgaaaacc tactaagtgc caggcttact gtctctgggt   2700
cttgcttacg tggatgtcat ttttccagtt gcaccaaatc gaaagaggtt aattggtttg   2760
ttggagttcc tttgtaggtg aagggcagag ccaggagctt ggctagggac aggggaggtg   2820
agtgggggat ggtggatagg tcttggctcc cagtttcctt ctgggcagac attgcccctc   2880
tgccctgagg acctgcttgt ttgggggaag aggcctttag aggcaccagg gtcatgccag   2940
gtgttggaca tggtgaactg ggaagtgctc ccatctggcc acagcgcaga agtatcaccg   3000
tgctgggga tggggaacag ggctgtgaat gggcctattt gcataagcag catgtgtctg   3060
gagagaaaga catcacagag cagaagagtg cgggtgccca ggagtgcact tgccacccct   3120
acttcatccc tgaaagagta aatggcctgg aaggtgtctc tgagaggtaa tgccgcacac   3180
caccctccct gggggcaggg tcaggctaca cctgccttag gtcgggggct gcagcagcct   3240
gagagctctc agtagggcct cagtagcctg ggagggagca ggggcagggg gcagggaaag   3300
aggcgtaatg gggctgtcca gaggggcctg ggaaacctgg tccctgaggc ctgggcacag   3360
ctacaatcac ttcaaattgg ctgtggggcc agtggactgg gaaggaaaaa agcaataaga   3420
gtgaccaagt gcagaaggct gtcaggtccc aggtcacatg ccttagtgca gtgactcctc   3480
atcattttat ggggtgtggg tgtcgttggt acacccattt tacagatgag gacaccgagg   3540
cccagaaaag ttaagttaca tgtcctaagt cacacagctt gtaagtgcca gaactgagat   3600
caaaaccaag tctctttgac tttaaagtct gtactctgac cccaaagaga tcctgtttgg   3660
ccacttatag gaggtcccta aagctgcaga ctccccttgc cggcacccac atatagagac   3720
attaaccctt cccctgcagg gtcacctcaa atagtctttt agctgggctt ctcctgcaat   3780
tccacctaat gccatcccct gggttttgcc caaacctgaa ctgggcagtg gggtgagagg   3840
aggggtttac agggttacag agcctcatac agataggagc ccatggctgc tggtcatctg   3900
cattcctgca ggattggctg ttccttgggg tccttggcag gaaaatgagg attgctccga   3960
ggcctgctcc agtacttccc agaggctggc ctggtgtggg gctctgggaa ggctgaggct   4020
ggagaagcgt aagtaggagg gcagagatgg cactcaggta gcttgaatca ccaggaccct   4080
tccaagcccc acaggttctg agggagtact agggccagct ctgggagagg tctcttccta   4140
tgctgtgaac cccctgcctt tcttgcagcc tacaacgaat aaattttctt tgcaaagg     4198
```

<210> SEQ ID NO 55
<211> LENGTH: 1402
<212> TYPE: DNA
<213> ORGANISM: Homo sapiens

<400> SEQUENCE: 55

```
ctgtctcaag cctccaatca acagatcaga cagcttgtac tcacaggcca aggacacgtg     60
gaaagaggct caattttcta gatgggtggc aacagccatg atcttctgtc ctctgggtcc    120
ccacaagcct ggatgaactc aagatctgac tcagtggcac agtgaggaga cctttgaggc    180
ctcagtgacc atccttggac ttcacctctc acggctttca ggcagagagg ccctcccatg    240
cccacaacag gctgagccca gccttcctcg gggtttgctt ccaggcctga cttttactcc    300
cctttctaag tgaggcagcc atgactggcc acttcatgtg ctcctggaga agggcttgca    360
```

ccagccgttt tcaggaaagt caagcagctg ttgactcctg agtctgggtg aatttgtgtg 420
aagagcataa ggcgctgttt cttaaccaaa acgcttcctc ttgcagtgca gatgggatgt 480
gcttctccac aggaggcccc acggcttccc cacccctcag aggagcgccg tgcgtgcgtc 540
tgtgtggagg attggcagct cctgcagtcg gcccttggtc ctatttggcg acgcctctgc 600
cttcccctta attatacagt catgagccgc cctggaatca cggcagctcc ggatggatcc 660
tggatgccag aatgcagcct cagcacgggg ctgcaggaca ggagtgagcg aggggctgca 720
gagccggcgg ccgcggtggg caccatggag ggggctgccc tgggcagcac gggcatgagt 780
ctcaaggccc aggtttgagt aacaggtgtt gagagcttac ttacttttcc tgagacacag 840
tttcctcatc tcgagagcac ggaaaatcat tctaacttca gaggattgtt gtgaaagtta 900
aatgagatta aagaggtaaa gcccatgacg tgcttagctc gtgcttggct cttggtcaat 960
gccagttagc gctgcatttt ctcccctctc cctccctcct tctctctttc ttttcttcta 1020
ttctccattc ctgttttctc ccccacccca ctccccaaag ctctgcgttg agaaccagat 1080
gctgtctggt gggttagggc cagaggagga aaagctgccc gccgtgggct gcacccatac 1140
cctcttcatt ccaatgacat gaggggaggg gaaaggacag aggtagactg tcctccccta 1200
cctcctccta atacaaatgg aattcctgga actggaaaac aaagaatacc cccataaaaa 1260
taagacagta cttctggtgc ggtgtaataa aggggaaagt aaccctcaat gtcaggaaac 1320
tccgcacctc ccagctcata tttgtgtgga ggaaaagtta aatattaatt tggactcaac 1380
tgaatgtgga cacaaacaat gg 1402

<210> SEQ ID NO 56
<211> LENGTH: 295
<212> TYPE: DNA
<213> ORGANISM: Homo sapiens

<400> SEQUENCE: 56
tctctcatct gtgttttcag ggcatggact ggaactccca atacccctga catgggctga 60
gtcaacgtgg tcatgaacat gtgacaggag gcagcagaag ttgcagagaa gagtgaggca 120
cgtttgaaaa aggctgaaaa atgtttctgt ccaggcaagg gtgtgtgctg aatgactcaa 180
ggattttttg gtgcattgaa tgaacagcgg gacattggac acctgctgat ccatcacccc 240
gggcccgggc aggcccgtgg atgaagagag atggagaaga ccaggcatga gactg 295

<210> SEQ ID NO 57
<211> LENGTH: 374
<212> TYPE: DNA
<213> ORGANISM: Homo sapiens

<400> SEQUENCE: 57
gcagcagaag ttgcagagaa gagtgaggca cgtttgaaaa aggctgaaaa atgtttctgt 60
ccaggcaagg gtgtgtgctg aatgactcaa ggattttttg gtgcattgaa tgaacagcgg 120
gacattggac acctgctgat ccatcacccc gggcccgggc aggcccgtgg atgaagagag 180
atggagaaga ccaggcatga gactgtggag aagccacacc accagaaacc cctgccccat 240
gcgccgtcca gcccacacct gtggatgcac gggggattgc aggcagggct cccaccgtgg 300
actcaggaac aggcagggaa gctgctgcct caccaggcga aggggccagg agggggaggc 360
ggagaggccc gtct 374

<210> SEQ ID NO 58

<211> LENGTH: 2737
<212> TYPE: DNA
<213> ORGANISM: Homo sapiens

<400> SEQUENCE: 58
gcctccaatc aacagatcag acagcttgta ctcacaggcc aaggacacgt ggaaagaggc 60
tcaattttct agatgggtgg caacagccat gatcttctgt cctctgggtc cccacaagcc 120
tggatgaact caagatctga ctcagtggca cagtgaggag acctttgagg cctcagtgac 180
catccttgga cttcacctct cacggctttc aggcagagag gccctcccat gcccacaaca 240
ggctgagccc agccttcctc ggggtttgct tccaggcctg acttttactc ccctttctaa 300
gtgtgcagat gggatgtgct tctccacagg aggccccacg gcttccccac ccctcagagg 360
agcgccgtgc gtgcgtctgt gtggaggatt ggcagctcct gcagtcggcc cttggtccta 420
tttggcgacg cctctgcctt cccccttaatt atacagtcat gagccgccct ggaatcacgg 480
cagctccgga tggatcctgg atgccagaat gcagcctcag cacggggctg caggacagga 540
gtgagcgagg ggctgcagag ccggcggccg cggtgggcac catggagggg gctgccctgg 600
gcagcacggg catgagtctc aaggcccagg tttgagtaac aggtgttgag agcttactta 660
cttttcctga gacacagttt cctcatctcg agagcacgga aaatcattct aacttcagag 720
gattgttgtg aaagttaaat gagattaaag aggtaaagcc catgacgtgc ttagctcgtg 780
cttggctctt ggtcaatgcc agttagcgct gcattttctc ccctctccct ccctccttct 840
ctctttcttt tcttctattc tccattcctg ttttctcccc caccccactc cccaaagctc 900
tgcgttgaga accagatgct gtctggtggg ttagggccag aggaggaaaa gctgcccgcc 960
gtgggctgca cccataccct cttcattcca atgacatgag gggaggggaa aggacagagg 1020
tagactgtcc tcccctacct cctcctaata caaatggaat tcctggaact ggaaaacaaa 1080
gaataccccc ataaaaataa gacagtactt ctggtgcggt gtaataaagg ggaaagtaac 1140
cctcaatgtc aggaaactcc gcacctccca gctcatattt gtgtggagga aaagttaaat 1200
attaatttgg actcaactga atgtggacac aaacaatggt caccaagtcc cggaacaggt 1260
tgtgtgagcc tcttcagggg ttcatccagc gctgttttgg agaaatctct atttcaattt 1320
attcctatac gttagttact gaaaaacaac agacaatcgc aaaagcaagt tgcccgtttt 1380
gtgttccttg agcccaatca tgaagtgccg tcgtgactgg gcctcatgac aaacaacttg 1440
taacaagtaa caacagagct caggtcccag accgcactga agctctgtga gacctctcct 1500
catctgtgca tgaacgagtg tctgactctg gagcccagcc tgctgcttcc cagtctggtg 1560
gtgaatcctc cgtagtctga tggaggtttg ctcttgttgc ccaggctgga gtgcaatggc 1620
acaatctcgg ctcactgcag cccctgcctc ccaggctcaa gcaattctta cgcctcagcc 1680
tcctgagtag atggaactac agggcatgga ctggaactcc caatacccct gacatgggct 1740
gagtcaacgt ggtcatgaac atgtgacagg aggcagcaga agttgcagag aagagtgagg 1800
cacgtttgaa aaaggctgaa aaatgtttct gtccaggcaa gggtgtgtgc tgaatgactc 1860
aaggattttt tgggcaacac aaaccaacac gagccgtgtg aggatcaggt gacagctgcc 1920
caaaagctga cacaaggaac aagcctggag gagtgaggat gggtgctgtg aaggaggttg 1980
tgcagctggg cccgcagtcg gacctggtga gatcagagga gggggtgcca ccagtctgtg 2040
gacgaagatg agaagctgga atagagcaga aaacaggagg ctgccactct ccatctttcc 2100
caaagtcact ccaggagcaa gggtgtcatt tactgaaatg acagactctc catttcacat 2160
ttttccccca agtgcagagt gcagggaagc agatgggcta aatttttaga gtcagggtta 2220

```
ttaatgtata ctttacatag taaactttcc ccttttaagt gtgcaggcct gaggtttgcc   2280

aaatatgtgt aggcatttaa tcaccaccac gatcaagatg tagaatattc ccactatcaa   2340

aaagtttgct gtgtcccttg atggtcatgc cccattccac agccccagcc ccagcccctg   2400

gagattgctg tctgctttat gttccagtgg ttttatcttt tccagactgt atggatgtga   2460

atggaatcag atgtgattcc aaggtgtttt atcttttcca gatgtgaatg gaatcagatg   2520

tacgaaatcc tatggtaggg ggtcttctga gtctagctcc ttttgtttag cgtgatgcat   2580

ttgaaattaa tccatgtctc aggcatcagg agttcatttc tttttctgct gagtagtatt   2640

tcattgtatg gatgtactgc aatttgccta tccattcacc tgttgatgta catttgagat   2700

ttttggcaat tatgaataaa gctgctataa acagaca                            2737
```

```
<210> SEQ ID NO 59
<211> LENGTH: 15706
<212> TYPE: DNA
<213> ORGANISM: Homo sapiens

<400> SEQUENCE: 59

cagatgctaa aattgacacc aaaagcgtag gtgatgagct tgaatcaggt aagaattata     60

ttctacttcc agctaaagaa gaggatatag aagatcaata gcttaaacaa aacagaaggt    120

cttctcatgg actaaaacag tgacagtgag tgcaactcta cctatcatgt tcatattcta    180

ggtagaaact ggggaaaaga gaaaaggcgg gaaaaaggcg tttctctaca aagatcacac    240

ataatcttct gtctgcatct cattggtcgg catttagtca catggccata actaccagca    300

agggaagctg ggaaatgtag tttttcaatg gcacattgct acccttaata aaataaggat    360

atgctaccaa caaagaatga atatgggaaa ggcccctagc aatgtctgct gcatctgcca    420

ctgtggtttt ctctgatttc cacagacatt gctcttccac atagagcgca ttctgattcc    480

caagccacca ctcccaaatc acacccagtt tctgcatcta gcttgtgtgt gggcagtctg    540

ctccatcagt cccagatgtg gcttctcatg gctggtgacc tatgaactaa aagacaggcc    600

attttttcc caacctaccc taccttttct ccttgagagg aaagataaaa taaccacaat    660

ttaaaaatgt caatcttcca ttcagaaaag ggaggaaaga gaaacacaga gatcactggt    720

ttacagtgat ggacccaccc tgctaggcag gagtgaaaag gcctctccgt ccggcagtgg    780

actgggttcc ttggctggcc catgtggtcc ccacccactg tctccaggag catcgccttg    840

aactgtgtct tcatggcttt tggctccgcc ttcagaaggg tcctccctgt caatcatcct    900

ccattgccac ctctgatgtg ggcactaggg agctggtcct tcccagagga tgcatgattt    960

tgacaccgtg cagtgtggga tgttggacca gggaatccag catattttcg ggcttttgta   1020

gtctcagact gggcctgaga tttctttaga aatatattaa cggttccttc aacactccaa   1080

tgggcatata gcctatttac ttctgatcat tgtaatgtgc aaataaccac agccccattt   1140

ctttgtgtcc agatgcagtt tttaggcttg aatattcatc tgttttactc actggcctct   1200

gtcactgagt ctgtcccctt agctattaaa ttaatggtga ctatgataac acttttcacc   1260

cgatccttgc tagtgcattg acttgcgttg tctgcatcga gttcttaaaa gatgcttggt   1320

aaagtcttgg gtcacagttt taacttctgc tggggttcct gctccacagc cctcatttag   1380

aactgtttca ctttggctat tgtttagctt tgggccatat ttggctgttt tttagctttg   1440

taaaaatgct catttaacgg acacaaggcc tgggttagaa aatgtagtat ttccttcccc   1500

ctctgtttgc gtaggagcta gcgctagtgg aagcccatct ctcccttgca ggattttgtg   1560
```

```
gaaagtgacg aaaataactc aaaccacatc agtgttctgc ttgatttcca ccattcttgg   1620
atgctataac ttcagaaagc acatgatcta acttcccaag ggacagcagg gcctcgacca   1680
aatgccgttg tgctgagggc tgccggccgc cccgctaggc tgctgcaccc tccccgcgct   1740
gccccacacc ttgcacagag ctcaggcagc attctagcac catcagacaa attcttcatg   1800
agtcagaaat cgcacctgtc tcttaatagc gatctggcct caggtggctg aaacacacag   1860
ggttgaaatg ctgcggtgcc tgcgctcatt gtgcggtgaa gccatagagt ccgcgctgaa   1920
acccggggcg cccgcctcct gtccgcgcag gcgctgcacg ctgtcgccgg ggcagcttca   1980
ctcagcttca gcctctccat ctgcagagga ggagtaatcc cgtgctgcct catggggccg   2040
tttcaagaag gaaatgagat gtggtataaa gtgttagagg agtatttagt gttattatta   2100
atgtgttttc tcatctggga acatgatttg cattttaagc agaacttcaa catttggact   2160
caaaggagtg atgtggatgg ggagaatttc aggcatcgtg caggctggca ttagaaatgc   2220
tcaccggaaa tggagcacag gcagcaactt cagcccctag aattcttcct cctatgtcac   2280
ttccgtccct caaacccttt ctgcagcccc tgtcctctct cctgcaatgg cagtgagcag   2340
gtggtctcct ggtgtctctg gaaaattccc atatggagtc ctggttgaga tgagccagaa   2400
ggctaggaag gagcctacag tcccggtctc agcgcccagg aggtttttct aatggagttg   2460
gcatgcagaa gctggggcat accctgggag cagccctgtg gctggatgag ggatggacag   2520
cagcactggg cgggtggagc cgggtgcgag gtccccacag cctgcctccc agtcccactg   2580
gccagcccgg ggagggtgct gaagacaggc ttcctctctg gtcaagctct ggctagcttg   2640
gcaagtgcag gcaggaccct ggacctgcca tatggtgcac attttgagga catcattagc   2700
aggtttggaa ggttgtgatt ctggttgtgg gagagaagga acctgggagt tgagcaggtg   2760
gtgggtggag ctatgcatgc aactgagtgt gaggagtgct ttggccatgc tagggtctcc   2820
tctgggctgg aagccttgtc ttcaagaggg ttggggtagg aggcttttta ttatagtggg   2880
aagcctcaag cctggacctg ggaaaacact ttctgggtat gaggaattaa aataaacctt   2940
gaagcactat ttaggaagaa catagtatca cttcatagat attttccccc ctaaatggtt   3000
acaaagtaaa atggcagagg tacaaagagg aaaatgaaaa ccacccaatc ccttccctga   3060
gcgatggccc tgttatcctt gggctctgtg gccatctgac ctctctctgg ggacagaagt   3120
acatgaggag aggggccact tcataagacg gagatgctct cttcctgttc cctgcctctg   3180
catcgtgctg gggatgtctg tcctcatcaa ctaagagacc catgtagacc gcagctctga   3240
gatcttctat ttttgtaaac agaacagttt gtagggagat gtgagatgtt aggtggtgct   3300
ggagagcctg ggctttgtct gtttggacaa ggctccatca aggcatcctt tgtccgacgg   3360
tgaggcatct tgagggctct ggacccagag ctggtcctgc aagagtcctg tctgagagcc   3420
caggccccac tccactagga gggacaggag ggaacagagc agagctgagt cccttcacct   3480
acccaaaccc atacatgttt ctagagcaga gtaactgctt gtgaaacaga ccatcagagc   3540
acagggcagc accgagctgc gttctgcagg gctcggtcta ggtgatctgg agggcttggg   3600
gagctggctt ctcccctcat ccagcatgta gctacccaca gccacctgca tttcacaggg   3660
ccagtgccta gggacattgg gccagaagcc agaatttctt ttttcttttt ttttttcccc   3720
tctagcattc actactagcg caagctagtg catcccaaag ttttggccct gcgtggataa   3780
tcaatccaca atttatcttc cgtctgttgc caaagtaatt tagctaaaat gcagatctca   3840
actggtcact tccctgcgta aaagcttcaa tagctttcta tcgcctacag gcaaaagtcc   3900
ctcttctgaa aagcggcttg caaagcccta gtagctggct ccatgccccc cagcaatacg   3960
```

```
tggcctcctc agacgcatct tctagcaaag gagagctgct cagtgacatc cacaaaccga   4020
gctgcttctc acctacctgt tttccttctc tttgggatgc cccccgccct caccttctgc   4080
ttctggctaa ctcctaggca tccttgaagg cttggctcag tatcctctcc tccaggaagc   4140
tgtccctcac cttctctcct ttccctccat cccagtcacc atgcaccaca cccatatccc   4200
cattgcatcc tgcagctacc ttgtgcctgc acacgttggg ctgggcatgc atctccttct   4260
ctctcaagac ctggatccct tcactttgtg tctctggacc ccccagtgtg ctgataatgg   4320
ggttggaacc catcatattt ctcttgaacg agttaatgat gggactgcta tttctctaac   4380
tgttgccttg gaggccctgt cacgtgctca tggaagagag ccaggggggt ggaggtgatt   4440
cttgttaccc agaggacgtg ggtctggat acacgtttct gccatctgcc atctgccagc   4500
ttctttctgg ttggtagctt tggagcctgg tgcagctggg gccagtcccg agcctggact   4560
ctgctgggca gtggcaagag cactgtctgg agctctcctg aggagcccac agatccaact   4620
ccctaggcca aggctgcagc ctggggcaga gatgcagagg cctggaggag cctagggcac   4680
gcggcctgcg ggctggctgg ggttcagagt tcgtatgtgt gtggagtgac tgggcaggtg   4740
ttcagaaatg aaggctggca ctgccaggta aggcccttcc ctccctgatg tgagagccct   4800
ggagccaccg cagaggccca gtcagatctc tgttctaatt ctggcctggt gtggaggatg   4860
aggagagacg gcccagaaag gaaggcagac tgtgcagacc ccatgtcttc tggcccgcga   4920
ggccctcctc ctgtgcctgc ttatcttaaa gaatccggga taagaggtga cttgggcctt   4980
ggccgggagg cccctcctca gcttcagaca aggagggagc tctgggcatg aggacattga   5040
gcaagaggcg atggcagtgc ccacaactta ccctcagctc ggctctgttg ggtccgagaa   5100
gttgcatgga aagggctcct tgggggccag ttgtcagtaa gctgcagaag cctggagccg   5160
gccaggaaat aaccacgtgt aggagccttc tcagctgaga ggaaggagga ctcacgcgcg   5220
gcgagcacat gcttggagcc aggcacaggt ttgaactaag ctatttcatc tcgattctta   5280
tgacaagctc cacgtagttt gctcctattt tacagatgtg gaagctgagg ctcagagagg   5340
ttaagcgact tgtcccaaat cgcattgtca atcagtgaag gggctgggat ttgagctagt   5400
cacctgcctc taggttcagt gtgctttcta ctctgctccc ctccatgcct gcccgaccct   5460
ttgctgatga cacattcctg agacctcaaa ggagtcctac tttgaatcat gaatggcctc   5520
gcgtttcccc agagggcatg acgcaagctt cgccacctca ctcccaccct caccactggc   5580
tggttgctct taggaagatg ctgtttacag gatcacgcag tggttcaggc caccacgatg   5640
ccacttcccc tgctcttaac cccccaccaa actgcaggtg gcttccctgg gagactcggg   5700
gcaacaccct ctcgtcctgt atgaagcttg tacctttctc cacccaagtg agtgacagct   5760
ggcgggagtt ttgcactgtg gaacagggta cacaaagaca ctggagtgag aaggcagggg   5820
catggccagt ctatgtctag gaggtggtgg ctccaccttc cttgtggact cagctttgga   5880
gtcatgcagg ctgctctctg ggcactcctg tgagccattt cttctgctga tagggaggaa   5940
cgtcccactg ccccaagatg ggttctgtgc agagtctccc cagggtcaag acaggagcta   6000
gaatgtatgt catagaagga tgatctaaat ggtgacttct ggctggtgag gagaggctat   6060
ggcacctcca cggctggtgg cctcttgctg aagtaagcat ggtcagcatc ccccctgcac   6120
cctgtggagg tggcttaatg cattcccttg actgcaaagg actccttgcc aaagagacct   6180
tcttccccat gaggctgagg cctcctagga ccctcagtgc tcaggaaatt ataaccagcc   6240
acccccatct ccattcattg gagaaggagt gacggccgcc tcagtgccat taactctgtg   6300
```

```
ctgtgattaa atggatccca aggagactcc tgctcaggga cacccccctgt aggactgatg   6360
ccagggctag gcttgccgca cagtgctcta ttcctttggt tatgcacctt ccttggcaga   6420
atccacgctt accaagagga gtcactctga gctgcttgct gccagtcaca tgcttagcag   6480
tagaagatat cttgtgcttg tcaggtgact gtgagtgaga gggaaggggg cccagcgtga   6540
agccaggtgg gacggcttct gcggggcaag acaccccact ggaggaggca ggggcgcgct   6600
gtgcaggcct cagcaccagc tctggctgct gtggtgggat ctcagatcag tcactttgcc   6660
tttttggcct cagttttctc atctgtacat catggatttg ggattaaagg atttctgaag   6720
attttactca ttctgagatt atggtccctg gaaaccttta gggaaaaggg agcttcttct   6780
cttcattatt ttaacatact tgatctttta tgttctttgg tagggagaga tgataggtag   6840
ttagagaaga agcagctcag tgaaaaagct gaaagccttg tggaaaaata agttaaattg   6900
acccactgtg actccaggga cctggggaga ctttgatgtc cgtgtttttg attacacatc   6960
tcttctctca gagtgaagat gcgcagttct aaggaattat gcccaatggc agaattggca   7020
agggacaggg aactgtccag cagagaagct gctgaaaccc ttcagggaac attccattcc   7080
gccagggccc ggctctcacg ctctgctctg cagcgcatcc ggtgccaagg aggggagtag   7140
cgaacgttga ccttgtccct aaggagctta cacgcaggga ggtcagcaca gacactggaa   7200
tatctaggac tctgctatcg aaaaacacaa ttgctggcac atgggttcag aagacagaga   7260
aggaaaagag ctgtaaagag ttgggtgggc tgaggtttga aatgggcttt aattatgact   7320
ggacacaatt tggtgacaaa tgggtgaaat ttcaagcaga agaggtagca tgagcaaaaa   7380
ggggtgtgca gtctttgtga agagaagggg gagggagtgg caagggaata ggacagagag   7440
gaggaggagg gagaggaagc cagagataag gagccagggg gggaagaaaa gggcagaaac   7500
gaatgtgaag gagattctga agacaagcca ctgtggtggt ccaggtggtt ccatggtgcc   7560
gcgccaagcc aggggcttgg aatttagtct gggaggatgg tgctgagtat ggatgaggaa   7620
ggagaggaat ggagagggga gaaacgggaa ggtacttcac actgattaag caagctcctc   7680
acagggctat gacttctccc ttctcagaag gaggtgccct gtggcatgcc tctaggccca   7740
gagttaaaga gctggagcca ttaggagcag caaggggctg cctccccact tgtctggtta   7800
cttctggtta cttctccctc agggtaagtc ctcatgaggg atcatctctg cccatggagc   7860
tgcttccgct gcccttaggc tggtgtaaga ggaaggctgt gtaccagagg tagatcttgc   7920
tcctagtcca ccagcaaaac acatccagtt atttctatgc ctcagtctcc cttccccaca   7980
ctgatctctt tattccccta ctacctagaa atggaaggga gacaatgagg tgggaaatag   8040
agtttttcga aaggtgtttt ttggataaga caaaggcctc tcagagcaga gctggccatt   8100
ggaatggttt ccttttgtta tttaataccg gggctttcac acaggagttt agcccagctt   8160
ttaagtcttc agtatcaaat agtagttggt gtcacatccc tgctgaaata cagccatgaa   8220
aatgtttctt agtgatagat ttaggttgta ctccttaaga aaagcccaaa tgtcaagaat   8280
tgcttcccac tggtacactt tattggggag aagggcatct caaatagaag gatggttggt   8340
ctgtctagaa atggtaagaa tactacaggt taaaggcagt ggtggtctgg actaaatgac   8400
ccctgaaact cggattttat ggtgttttca atctctggct gagtacaggt tcctccctct   8460
ccctttgtgc ctccttgggg acctgggcta ttttctcctc cgtgaaagag aatggataca   8520
tccattatga aaaccaattg atataatttg agcctgcatg caggtaaaaa ctatattaag   8580
aaggtttata aaatctaacc ttctggctta acaagctgat tctcaaagtg gcctctcaga   8640
ccctggctga gggatggtgg tcaggggttg cagagggacc cgcacagctg ctgaggaggc   8700
```

```
tgtgggacag gaggcgctat cactgtctac ctcttccatc catgcacctg tgtgcaggtg   8760
tgagaagggc accgtgctgc aaagaagggt cctttccacc ctctgcgggt tgctgccggc   8820
tccccgatgc ctgcctctga ggcctgagcc tggggctggg gagtgtgctg gcctcacctc   8880
tggaggatac tgcctcagtg ttacagcctg accccccacc ttgtcatcac tgcctactac   8940
agaccagagg ggacggccac agagactctg caaccatggg ctctgccctt cttccttctg   9000
cctgtgtatc tgtgaaaaac ttttttttt ttaaatggag aaagctacct tgacttctca    9060
gagagttgaa tggggtcagg ggatagaatc tatattttt agttatgggc acttacccat    9120
attcaaaaag atttgaggag gctggcagaa tggagctggg agaagaaaac cctcccctgg   9180
gaggaagctg tcctgtgcat gttggccagg ctgcctcttt gattagggac aatggaaacc   9240
ggcctgaggg cacgggtgaa agcagttgag tgtagaggag gctctgcagc agaagccaga   9300
ggacacagga gccagtgaag acacacaata agtcagaaag gagggatctt tgcagcccca   9360
aaagtagaaa ttcttaccat ctactgcaaa gagcaaaagt tgaaaattgg tctgatttct   9420
atctaaatgt gcttacatat tcgtgttctg ttaaatactt ctgtaacctg tgtgtctcac   9480
ataaatgcag ctttctttag ttttggaaat aaatcacatg aatcctgaat agtagtcttt   9540
aataatttgc ttagttgtag ggcagtgttg tgttttcaga aggcaagtgt atttgctaga   9600
agagtgagct gggaggtgtg aaccacatcg tcacatctgc tgtaagccta gccgttcata   9660
atacggagtt acagttagga cacgtcgccc tgaagagcta ccatcgaatg tgtgctcatc   9720
aaatgcctgg cagcgtcctc ggtgcttcac ctgccatagc cgacagtggc tgacctccca   9780
tgcctgttgc cttttctttc tgttggatca gggatacact gccatgtgtg ttaagaaaag   9840
ctggccttac ctacagggct ggccagtccc ggtcacgttt ctagtaagcc attgccttac   9900
ataagggtaa cggcatggga cgctatctta gccaatgtga taaaagtgga catgaggtga   9960
gaggcttcag agagaggttt taaaaaagag acaaaagcag gacgttgcct ctcttcctcc  10020
tctccacgtg tcctacccgg atgtgaagcc aaaacagatg caggcttagt gcaaccatgg  10080
ggaacccagc ataagcacag attcaacagc agaagagtgg cagagggaga aggtgaaagg  10140
aacctaggtt ttcctgtcct tgttgagtca ttcagttaaa aatccctgga attttcctct  10200
ctccggcagt gtgttttgtg ggataatgag ttgccttatt ggggttggct tgctagtcgg  10260
gatgtttcgc tcccatcaac atccatacgc ttgctctgtg aaccaatgac ctgatgaggt  10320
agtattagca ccaccatcat tatgctgagg atgagattta tggcacagtg gttcagtagc  10380
ttgcccaagg ccatgcggct ggtaggttct ggaggagggc tcagggcacc ccctgagcta  10440
cccctgctgg ccattgcacc accccataaa gctgctggca gtcacttctc tgaggggtta  10500
gcatgtaaga aatgtcctcc tgaatgctgg ccagacaaat ggaaatctgc cagggttggg  10560
tacccccatg acagcagcca gcctgccctc ttagtccctg acagctgcag tgacagcatc  10620
tgtgattgca aagcgtgaca atttatatct ctcatttcat cacaccatct atcagcagac  10680
agtcaggctt taaaaatcaa tcccacactg actcagtccc cagcagagat ggcctctgac  10740
aacagtatcc acactgcagg ctggacaagg gccctattaa ttttgagact cagccaaatt  10800
tccttctgac cctaagctgg tgaatccctg ctcctttgct ttggttgggg ttggtgtgag  10860
ctaaggctgt gatcccattt gctcctatgg cctccaggtg gcctgggcct ccatgaatgg  10920
gccacatggt catactgaat gcttgattac actcagacct agcagtcgtc tgggcgcagc  10980
tggtttatgg atcactttgt cacaatgttc catccttcca ggtccccatc cccgcggtgg  11040
```

```
gaaaacattg ctttaggcag tgctagagga cttcagcagg cattggcagc ttctggattc  11100
aggattagaa caaagaagga ggagtcacag caaagatagg aacagaaggc agagagaaca  11160
gacagatggg ggtgtttgag aaggagggcc tttgagacct cagggagtgg gagacactgg  11220
ctcgagaata ataataatgg caatttctct catctgtgtt ttcagggcat ggactggaac  11280
tcccaatacc cctgacatgg gctgagtcaa cgtggtcatg aacatgtgac aggaggcagc  11340
agaagttgca gagaagagtg aggcacgttt gaaaaaggct gaaaaatgtt tctgtccagg  11400
caagggtgtg tgctgaatga ctcaaggatt ttttggagag aattggagtg tctcaccaga  11460
ggagaccacg tctgaagggc tttgcatccc tccttggaca tgtctaatac ctaacactca  11520
gaaagcatcc agtaaatatt cgtggaaaga aaggagtgga gaaggggaga aaggggaaag  11580
ggagtaggcg agagagaaga aagactctgc ttcttgccca gggcctggca tggggcggag  11640
gcaaagcagt ggggtcctca gctatgtccc actgtgagtg cacagcgagt cctgaccttc  11700
agagggtgca gcccgagggg ccctggcctg tctgaagggt gcgccagccg agtggcctgc  11760
tctgaccacc aggctcaccc atgactacct gggtggctac agccagttcc tgacaatgag  11820
tacagcactc agttatcggg gcccttccac ccacacgctg tccacttcct ggggtactgc  11880
tgtgggcatg tgagtgcttg ctccccgggg cactgctgtg ggcatgcgag tgcttgctcc  11940
ccggggcact gctgtccact tcctggggta ctgctgtggg catgcgagtg cttgctcccc  12000
ggggcactgc tgtggacatg tgatagcttg ctccccagct ccactagtga cactggcggc  12060
ccctcgctgg ggccttcccc gcctgctccg ctccattacc gctgccgggc tcctcacgtc  12120
tctccttgct gcttcctgca ctggggtgag gagagtgggg ctggtcccct tgagaccgga  12180
gaagctccag gcttttaagg aaaactgcca gggacgaaga gaagatatca cttccccacg  12240
tggttggctt ccagattcag aaggaatgtc tgtccttgtg gattccgtac cagatgaccc  12300
cagatgctgc ctcagtacta ggtccctgtg gctctggagc ctttgctggg tctgggcagt  12360
gtctcttcct ctccagttca tccttgggtc tcttcaccct tgccaggggc aggcttcctg  12420
gtgagaggtc gacctcctgc atgaaggctc tcaagaggcc agttcaaagc caagctccgg  12480
gtctgtgcct gtggggctgc tcctcgatca ggagatggtc actcccctcc tggtctgtat  12540
ctgtgggatt ctcctccatc aggagatggt ctctcccctc ctggtctata cccgtgggat  12600
tctcctccat caggagatgg tcactcccca tcctggtcta tacccgtggg attctcctcc  12660
attagatggt cactcccctc ctggtctatt cccgtggggc tgctcctcca tcaggaggtg  12720
gtcactcccc ctcctggtct atacccgtgg ggctgctcct ccatcaggag atagtcactc  12780
cccctcctgg tctatacccg tgggattctc ctccatctgg agatggtcac tcccctcctg  12840
gtctataccc atgggattct cctccatctg gagatggtca ctcccctcct ggtctatacc  12900
catgggattc tcctccatct ggagatagtc actcccctcc tggtctatac ccgtggggtt  12960
ctcctcaatc aggaggtggt cactcccctc ctggtctata cccgtgggat tctcctccat  13020
caggagatgg tcactctccc tcctggtcta tacccgtggg gctgctcctc catcaggaga  13080
tggtcactcc cctcctggtc tatacctgtg ggattctcct ccctcagaag atggtcactc  13140
cccctcctgg tctataccca tgggattctc ctccctcaga agatggtcac tccccctcct  13200
ggtctatacc cgtggggctg ctcctccatc aggagatggt cactctccct ctcggttgct  13260
cagtccaaaa acaacctctc tggaaaactg cgtggaattt ttttttaaag aattgaaact  13320
agaactagca tttgatccag ccatctgcct actgggaata cacccaaaga aaaataaatc  13380
attatatcag aaagatagaa tatgcatgtg gatgttcatt gcagcaccat ttactatagc  13440
```

```
aaagatgggc agttgagcta agtgtccaac agtggtagac tggataaaga gaatgtgtta  13500
cacacacagc atggaatatt actcaggcat agcaaagaat gaaatcatgc cttttgcagc  13560
aacatggttg gaggtggagg tcaggagtta gagaccagcc tggccaacat ggtgaaatcg  13620
tgtctctact aaaaatacaa aaattagccg ggcatggggg tgcacacctg tagtcccagc  13680
tactctggag gctgaggcag gagaatcgct tgaacccagg aggtggagat ggcagtgagc  13740
tgagatcaca ccactgcact ccagcctggg caacagagtg aaatcctgtc tcaaaaacaa  13800
aaataaaaac aaaaaaagca tacaaaccac aggagctcct cttggtcccc ctttgtcttt  13860
cattccacct ccagaaatcc cagcagaatc accttcaaaa actcctagaa tccaattttt  13920
cccctccatt gctactgccc tgatctgagc ctccataacc cttacccaaa tgcttcctaa  13980
acgtatcctg gctggtgctg ctgaattcca tgtctttcca gctgcccttt aaaatacggt  14040
aggaggcaag tcttttctca aaaccctcca gtggcttctc tctcagagtt aagatcctgc  14100
agtggccttc ctggcctcag gtagtgtctg ctgtcctgta ccctcggcca ctatactcca  14160
gccacatggc tttgtgtttc ccttggacat atccagcatg tttctgcccc acggttttgg  14220
cacttgctgt cctttctgcc tggagctcct tctcctccct ctgcactgaa gaccctccct  14280
tcctttcagg atggcagaga cattatgctg tcataaccac accccatatt caccccttaca  14340
cgatgtgtcc ctctctggcc agctaggggc tcagctccat gagccccttg tcctggcaac  14400
aaagctggct ggggcggcca cctgaagtat gtctcatgga gctgactcaa tgagagacac  14460
agttcattcc atgcacagtc cacgccacag taagtcacgt ggccagcgct gacttcccct  14520
gcacaggaag aacctgcacc caccacccgc ggagaaggat ctagagctgg gatgactgag  14580
caggatgcta acaacctcaa agttcttctt agacctcatg tcttgaacag ccctaggcaa  14640
catagcaaca cacgccatga caaccccaca agaaggcaac ccgtcctctg acagcttctg  14700
gtgacaaagc caccccgctt gtgacaacct caggtcacac agcagctcct cccctgacaa  14760
cctaaggtca cacaacaact tctcctttta aagtctcagg tgacacagca gactctcccc  14820
tgacaaactc aggtcacaca gtaacccttc agctgacctc aggtgacaca gccacccctc  14880
ccctgacaac ctcaggtcac acagccaccc ctcccctgac aacctcaggt cacacagcca  14940
cccctcccct gacaacctca ggtcacacag ctacccttca actgacaacc tcaggtcaca  15000
cagccacccc tcccctgaca acctcaggtc acacagccac ccctcccctg acaacctcag  15060
gtcacacagc cacccctctc ctgacaactt caggtcacac agccacccct cccctgacaa  15120
cctcaggtca cacagccacc cctctcctga caacttcagg tcacacagcc acccctcccc  15180
tgacaacctc aggccacaca gccacccctc acctgacaat ctcaggtgac acagccaccc  15240
ctcccctcac aacctcaggt cacacagcca cccctcctca gacaacttct gacatagcaa  15300
ctccttgcct gacaacccta ggtaacatag caaccctccc ttgacaaccc atgtgacatg  15360
gcaatgcttc tcctgacagc cacatgtcag caacctctgc ctgacaaccc aggtgacata  15420
acagcacccc ccgacaaccg catgttacct tgccaccctc ccataccgac tgtatgtggg  15480
tatcccctcc taccccgcct tgggagcccc atgtgaggta gccagccttt ccctggccct  15540
gggccctcca tttctgcttg ctgtctcctc tgttcctccc aagaactcac tgctctaccg  15600
tgtaatctct tgtttctctg ctgtcttagt ccgcttgggc tgccggagga gcacaccttg  15660
ggcagggagg cttagatgca cctgtgcatg gttctggagg cccagg                15706
```

<210> SEQ ID NO 60

<211> LENGTH: 744
<212> TYPE: DNA
<213> ORGANISM: Homo sapiens

<400> SEQUENCE: 60

```
aagcgtaggt gatgagcttg aatcagggca tggactggaa ctcccaatac ccctgacatg      60

ggctgagtca acgtggtcat gaacatgtga caggaggcag cagaagttgc agagaagagt     120

gaggcacgtt tgaaaaaggc tgaaaaatgt ttctgtccag gcaagggtgt gtgctgaatg     180

actcaaggat tttttggtgc attgaatgaa cagcgggaca ttggacacct gctgatccat     240

caccccgggc ccgggcaggc ccgtggatga agagagatgg agaagaccag gcatgagact     300

gtggagaagc cacaccacca gaaacccctg ccccatgcgc cgtccagccc acacctgtgg     360

atgcacgggg gattgcaggc agggctccca ccgtggactc aggaacaggc agggaagctg     420

ctgcctcacc aggcgaaggg gccaggaggg ggaggcggag aggcccgtct agcccctgcg     480

gctgtcaccg tggtgcctcc tcactggcca gtgcggtcgc gcctcagctt cgttaatagg     540

ggagggggcc taagagtttt cacgtccagg ctcgggcagt ggggaggcag gcaggagtgg     600

ccgctggttt ttcagacctc ccagggaggc cgaggaaatg gcccgtcctg gagtgggcgt     660

ggttctgtct tcagatggat gctggagggt tgggctgcgt gggaccctgg gccctgctgc     720

ttcccggagg atgcgctgtc cggg                                            744
```

<210> SEQ ID NO 61
<211> LENGTH: 1129
<212> TYPE: DNA
<213> ORGANISM: Homo sapiens

<400> SEQUENCE: 61

```
aagcgtaggt gatgagcttg aatcaggtaa gaattatatt ctacttccag ctaaagaaga      60

ggatatagaa gatcaatagc ttaaacaaaa cagaagggca tggactggaa ctcccaatac     120

ccctgacatg ggctgagtca acgtggtcat gaacatgtga caggaggcag cagaagttgc     180

agagaagagt gaggcacgtt tgaaaaaggc tgaaaaatgt ttctgtccag gcaagggtgt     240

gtgctgaatg actcaaggat tttttgggca acacaaacca acacgagccg tgtgaggatc     300

aggtgacagc tgcccaaaag ctgacacaag gaacaagcct ggaggagtga ggatgggtgc     360

tgtgaaggag gttgtgcagc tgggcccgca gtcggacctg gtgagatcag aggagggggt     420

gccaccagtc tgtggacgaa gatgagaagc tggaatagag cagaaaacag gaggctgcca     480

ctctccatct ttcccaaagt cactccagga gcaagggtgt catttactga aatgacagac     540

tctccatttc acatttttcc cccaagtgca gagtgcaggg aagcagatgg gctaaatttt     600

tagagtcagg gttattaatg tatactttac atagtaaact ttccccttt aagtgtgcag      660

gcctgaggtt tgccaaatat gtgtaggcat ttaatcacca ccacgatcaa gatgtagaat     720

attcccacta tcaaaaagtt tgctgtgtcc cttgatggtc atgccccatt ccacagcccc     780

agccccagcc cctggagatt gctgtctgct ttatgttcca gtggttttat cttttccaga     840

ctgtatggat gtgaatggaa tcagatgtga ttccaaggtg ttttatcttt tccagatgtg     900

aatggaatca gatgtacgaa atcctatggt agggggtctt ctgagtctag ctccttttgt     960

ttagcgtgat gcatttgaaa ttaatccatg tctcaggcat caggagttca tttcttttc     1020

tgctgagtag tatttcattg tatggatgta ctgcaatttg cctatccatt cacctgttga    1080

tgtacatttg agatttttgg caattatgaa taaagctgct ataaacaga                1129
```

<210> SEQ ID NO 62
<211> LENGTH: 1843
<212> TYPE: DNA
<213> ORGANISM: Homo sapiens

<400> SEQUENCE: 62

```
atttagctaa aatgcagatc tcaactggtc acttccctgc gtaaaagctt caatagcttt     60

ctatcgccta caggcaaaag tccctcttct gaaaagcggc ttgcaaagcc ctagtagctg    120

gctccatgcc ccccagcaat acgtggcctc ctcagacgca tcttctagca aaggagagct    180

gctcagtgac atccacaaac cgagctgctt ctcacctacc tgttttcctt ctctttggga    240

tgccccccgc cctcaccttc tgcttctggc taactcctag gcatccttga aggcttggct    300

cagtatcctc tcctccagga agctgtccct caccttctct cctttccctc catcccagtc    360

accatgcacc acacccatat ccccattgca tcctgcagct accttgtgcc tgcacacgtt    420

gggctgggca tgcatctcct tctctctcaa gacctggatc ccttcacttt gtgtctctgg    480

acccccccagt gtgctgataa tggggttgga acccatcata tttctcttga acgagttaat    540

gatgggactg ctatttctct aactgttgcc ttggaggccc tgtcacgtgc tcatggaaga    600

gagccagggg ggtggaggtg attcttgtta cccagaggac gtggggtctg gatacacgtt    660

tctgccatct gccatctgcc agcttctttc tggttggtag ctttggagcc tggtgcagct    720

ggggccagtc ccgagcctgg actctgctgg gcagtggcaa gagcactgtc tggagctctc    780

ctgaggagcc cacagatcca actccctagg ccaaggctgc agcctggggc agagatgcag    840

aggcctggag gagcctaggg cacgcggcct gcgggctggc tggggttcag agttcgtatg    900

tgtgtggagt gactgggcag gtgttcagaa atgaaggctg gcactgccag gtaaggccct    960

tccctccctg atgtgagagc cctggagcca ccgcagaggc ccagtcagat ctctgttcta   1020

attctggcct ggtgtggagg atgaggagag acggcccaga aaggaaggca gactgtgcag   1080

accccatgtc ttctggcccg cgaggccctc ctcctgtgcc tgcttatctt aaagaatccg   1140

ggataagagg tgacttgggc cttggccggg aggcccctcc tcagcttcag acaaggaggg   1200

agctctgggc atgaggacat tgagcaagag gcgatggcag tgcccacaac ttaccctcag   1260

ctcggctctg ttgggtccga gaagttgcat ggaaagggct ccttgggggc cagttgtcag   1320

taagctgcag aagcctggag ccggccagga aataaccacg tgtaggagcc ttctcagctg   1380

agaggaagga ggactcacgc gcggcgagca catgcttgga gccaggcaca gggcatggac   1440

tggaactccc aataccccctg acatgggctg agtcaacgtg gtcatgaaca tgtgacagga   1500

ggcagcagaa gttgcagaga agagtgaggc acgtttgaaa aaggctgaaa aatgtttctg   1560

tccaggcaag ggtgtgtgct gaatgactca aggatttttt ggtgcattga atgaacagcg   1620

ggacattgga cacctgctga tccatcaccc cgggcccggg caggcccgtg gatgaagaga   1680

gatggagaag accaggcatg agactgtgga gaagccacac caccagaaac ccctgcccca   1740

tgcgccgtcc agcccacacc tgtggatgca cgggggattg caggcagggc tcccaccgtg   1800

gactcaggaa caggcaggga agctgctgcc tcaccaggcg aag                     1843
```

<210> SEQ ID NO 63
<211> LENGTH: 1160
<212> TYPE: DNA
<213> ORGANISM: Homo sapiens

<400> SEQUENCE: 63

```
gagcactgtc tggagctctc ctgaggagcc cacagatcca actccctagg ccaaggctgc     60
```

agcctggggc agagatgcag aggcctggag gagcctaggg cacgcggcct gcgggctggc 120
tggggttcag agttcgtatg tgtgtggagt gactgggcag gtgttcagaa atgaaggctg 180
gcactgccag gtaaggccct tccctccctg atgtgagagc cctggagcca ccgcagaggc 240
ccagtcagat ctctgttcta attctggcct ggtgtggagg atgaggagag acggcccaga 300
aaggaaggca gactgtgcag accccatgtc ttctggcccg cgaggccctc ctcctgtgcc 360
tgcttatctt aaagaatccg ggataagagg tgacttgggc cttggccggg aggcccctcc 420
tcagcttcag acaaggaggg agctctgggc atgaggacat tgagcaagag gcgatggcag 480
tgcccacaac ttaccctcag ctcggctctg ttgggtccga gaagttgcat ggaaagggct 540
ccttgggggc cagttgtcag taagctgcag aagcctggag ccggccagga aataaccacg 600
tgtaggagcc ttctcagctg agaggaagga ggactcacgc gcggcgagca catgcttgga 660
gccaggcaca gggcatggac tggaactccc aatacccctg acatgggctg agtcaacgtg 720
gtcatgaaca tgtgacagga ggcagcagaa gttgcagaga agagtgaggc acgtttgaaa 780
aaggctgaaa aatgtttctg tccaggcaag ggtgtgtgct gaatgactca aggatttttt 840
gggcaacaca aaccaacacg agccgtgtga ggatcaggtg acagctgccc aaaagctgac 900
acaaggaaca agcctggagg agtgaggatg ggtgctgtga aggaggttgt gcagctgggc 960
ccgcagtcgg acctggtgag atcagaggag gggggtgccac cagtctgtgg acgaagatga 1020
gaagctggaa tagagcagaa aacaggaggc tgccactctc catctttccc aaagtcactc 1080
caggagcaag ggtgtcattt actgaaatga cagactctcc atttcacatt tttcccccaa 1140
gtgcagagtg cagggaagca 1160

<210> SEQ ID NO 64
<211> LENGTH: 572
<212> TYPE: DNA
<213> ORGANISM: Homo sapiens

<400> SEQUENCE: 64
cgctctgctc tgcagcgcat ccggtgccaa ggaggggagt agcgaacgtt gaccttgtcc 60
ctaaggagct tacacgcagg gagggcatgg actggaactc ccaatacccc tgacatgggc 120
tgagtcaacg tggtcatgaa catgtgacag gaggcagcag aagttgcaga gaagagtgag 180
gcacgtttga aaaaggctga aaaatgtttc tgtccaggca agggtgtgtg ctgaatgact 240
caaggatttt ttgggcaaca caaaccaaca cgagccgtgt gaggatcagg tgacagctgc 300
ccaaaagctg acacaaggaa caagcctgga ggagtgagga tgggtgctgt gaaggaggtt 360
gtgcagctgg gcccgcagtc ggacctggtg agatcagagg agggggtgcc accagtctgt 420
ggacgaagat gagaagctgg aatagagcag aaaacaggag gctgccactc tccatctttc 480
ccaaagtcac tccaggagca agggtgtcat ttactgaaat gacagactct ccatttcaca 540
tttttccccc aagtgcagag tgcagggaag ca 572

<210> SEQ ID NO 65
<211> LENGTH: 4435
<212> TYPE: DNA
<213> ORGANISM: Homo sapiens

<400> SEQUENCE: 65
caaatgcctg gcagcgtcct cggtgcttca cctgccatag ccgacagtgg ctgacctccc 60
atgcctgttg ccttttcttt ctgttggatc agggatacac tgccatgtgt gttaagaaaa 120
gctggcctta cctacagggc tggccagtcc cggtcacgtt tctagtaagc cattgcctta 180

```
cataagggta acggcatggg acgctatctt agccaatgtg ataaaagtgg acatgaggtg    240
agaggcttca gagagaggtt ttaaaaaaga gacaaaagca ggacgttgcc tctcttcctc    300
ctctccacgt gtcctacccg gatgtgaagc caaaacagat gcaggcttag tgcaaccatg    360
gggaacccag cataagcaca gattcaacag cagaagagtg gcagagggag aaggtgaaag    420
gaacctaggt tttcctgtcc ttgttgagtc attcagttaa aaatccctgg aattttcctc    480
tctccggcag tgtgttttgt gggataatga gttgccttat tggggttggc ttgctagtcg    540
ggatgtttcg ctcccatcaa catccatacg cttgctctgt gaaccaatga cctgatgagg    600
tagtattagc accaccatca ttatgctgag gatgagattt atggcacagt ggttcagtag    660
cttgcccaag gccatgcggc tggtaggttc tggaggaggg ctcagggcac cccctgagct    720
acccctgctg gccattgcac caccccataa agctgctggc agtcacttct ctgaggggtt    780
agcatgtaag aaatgtcctc ctgaatgctg gccagacaaa tggaaatctg ccagggttgg    840
gtacccccat gacagcagcc agcctgccct cttagtccct gacagctgca gtgacagcat    900
ctgtgattgc aaagcgtgac aatttatatc tctcatttca tcacaccatc tatcagcaga    960
cagtcaggct ttaaaaatca atcccacact gactcagtcc ccagcagaga tggcctctga   1020
caacagtatc cacactgcag gctggacaag ggccctatta attttgagac tcagccaaat   1080
ttccttctga ccctaagctg gtgaatccct gctcctttgc tttggttggg gttggtgtga   1140
gctaaggctg tgatcccatt tgctcctatg gcctccaggt ggcctgggcc tccatgaatg   1200
ggccacatgg tcatactgaa tgcttgatta cactcagacc tagcagtcgt ctgggcgcag   1260
ctggtttatg gatcactttg tcacaatgtt ccatccttcc aggtccccat ccccgcggtg   1320
ggaaaacatt gctttaggca gtgctagagg acttcagcag gcattggcag cttctggatt   1380
caggattaga acaaagaagg aggagtcaca gcaaagatag gaacagaagg cagagagaac   1440
agacagatgg gggtgtttga gaaggagggc ctttgagacc tcagggagtg ggagacactg   1500
gctcgagaat aataataatg gcaatttctc tcatctgtgt tttcagggca tggactggaa   1560
ctcccaatac ccctgacatg ggctgagtca acgtggtcat gaacatgtga caggaggcag   1620
cagaagttgc agagaagagt gaggcacgtt tgaaaaaggc tgaaaaatgt ttctgtccag   1680
gcaagggtgt gtgctgaatg actcaaggat tttttggtgc attgaatgaa cagcgggaca   1740
ttggacacct gctgatccat caccccgggc ccgggcaggc ccgtggatga agagagatgg   1800
agaagaccag gcatgagact gtggagaagc cacaccacca gaaacccctg ccccatgcgc   1860
cgtccagccc acacctgtgg atgcacgggg gattgcaggc agggctccca ccgtggactc   1920
aggaacaggc agggaagctg ctgcctcacc aggcgaaggg gccaggaggg ggaggcggag   1980
aggcccgtct agcccctgcg gctgtcaccg tggtgcctcc tcactggcca gtgcggtcgc   2040
gcctcagctt cgttaatagg ggagggggcc taagagtttt cacgtccagg ctcgggcagt   2100
ggggaggcag gcaggagtgg ccgctggttt ttcagacctc ccagggaggc cgaggaaatg   2160
gcccgtcctg gagtgggcgt ggttctgtct tcagatggat gctggagggt tgggctgcgt   2220
gggaccctgg gccctgctgc ttcccggagg atgcgctgtc cggggctgca caggttggct   2280
gtgtttttttg gatgcttgat attttgtttt ttcttctctt cactctgtca tgaaactggc   2340
aatagtagtt tgtaaataaa tatgtgttat agatgaatat ttgctatgag taaattaata   2400
aaggagtgaa taaatgagcg attgatgtag ggcctgtcct gtctcaggga gccccacgaa   2460
ggcctgcgcg ccggccagag cctgcctgcc tgccagggta ctgggacgtc actctcaaag   2520
```

```
cggcgggacc cagccgctga tcttgctgag gaggcccggt ctcagaaaac tgagcggctg   2580
cttctgcaga ccctgcatcc tcccctccct ggagaaagaa gctctggctg agtcctggga   2640
ccgaaccctt gggtgccaca gaaacgggct ttgctgcctg tcagtcaagc ggcgggagaa   2700
acagacctgg ggaggaggag gctgggaggg ctgtgttttc tgcacagcga gtagctcctt   2760
agcctggtgc catttctctc caaacaccct gaaggttgag tccagggtga agatgtagag   2820
gcaagttttg gggggatgga gtgggcttgg agggatgctg gcgccttagc aggctgtgct   2880
cctgaggtgc ccagtgtctg cgggcacagg aacatgttgc cgagggcatt tgggtgtggg   2940
tggggtgggg aaagggagac agggctgtct cttttaatgg gtatctgcga gcatgtgatt   3000
gtaagagagg aagaagtagg ggaggaagaa ggcctccttg ggaggtgcgt catcctgagg   3060
aaggctgaac aatgagggtc ttggagagtc aattcagaag cacaaccttg cagagcaggc   3120
aaaaacaata gggcttcttg aggctgcccg ggcactcatg caatcaccat ttcctgctgt   3180
gaatgagcct acattttgtt ggggaagaga cgcaacgacg ccaaacgatg gactctgagt   3240
caacgataag atgaaacaaa attaaaacaa agtaggaaat caagagtggc tgctgtgatg   3300
gcgttgcgga gatgatgttt gctttgagaa ctggacaagt gagcccctga gctgcatctg   3360
cacccagagg ctgagccggt gcacaggact tgcagaggga tggcctgggg cttgtagagc   3420
agcacaacgg ccccaggcct ggaggagcaa gggtgggaag gggggcaggc cagctcctgc   3480
caggctggag aaggactcgg acctcaggcc acctgtgcct gggtgattgt gaacttgtaa   3540
caaatgtgat cttatttatg ttttgaaaaa ggcaacacaa accaacacga gccgtgtgag   3600
gatcaggtga cagctgccca aaagctgaca caaggaacaa gcctggagga gtgaggatgg   3660
gtgctgtgaa ggaggttgtg cagctgggcc cgcagtcgga cctggtgaga tcagaggagg   3720
gggtgccacc agtctgtgga cgaagatgag aagctggaat agagcagaaa acaggaggct   3780
gccactctcc atctttccca aagtcactcc aggagcaagg gtgtcattta ctgaaatgac   3840
agactctcca tttcacattt ttccccaag tgcagagtgc agggaagcag atgggctaaa   3900
tttttagagt cagggttatt aatgtatact ttacatagta aactttcccc ttttaagtgt   3960
gcaggcctga ggtttgccaa atatgtgtag gcatttaatc accaccacga tcaagatgta   4020
gaatattccc actatcaaaa agtttgctgt gtcccttgat ggtcatgccc cattccacag   4080
ccccagcccc agcccctgga gattgctgtc tgctttatgt tccagtggtt ttatcttttc   4140
cagactgtat ggatgtgaat ggaatcagat gtgattccaa ggtgttttat cttttccaga   4200
tgtgaatgga atcagatgta cgaaatccta tggtaggggg tcttctgagt ctagctcctt   4260
ttgtttagcg tgatgcattt gaaattaatc catgtctcag gcatcaggag ttcatttctt   4320
tttctgctga gtagtatttc attgtatgga tgtactgcaa tttgcctatc cattcacctg   4380
ttgatgtaca tttgagattt ttggcaatta tgaataaagc tgctataaac agaca        4435
```

```
<210> SEQ ID NO 66
<211> LENGTH: 374
<212> TYPE: DNA
<213> ORGANISM: Homo sapiens

<400> SEQUENCE: 66
```

```
cttctgtcct ctgggtcccc acaagcctgg atgaactcaa gatctgactc agtggcacag     60
tgaggagacc tttgaggcct cagtgaccat ccttggactt cacctctcac ggctttcagg    120
cagagaggcc ctcccatgcc cacaacaggc tgagcccagc cttcctcggg gtttgcttcc    180
aggcctgact tttactcccc tttctaagtg tgctcccggg aatgctgtct acttgttgcg    240
```

attttactcc cgtggcctgt gctagctgcc tgcttggccg ttgggactga agggatgctc 300
atccacttgg cacactgact gcaagcctgg caccggcctt gcctttgttc tcccatgagt 360
cctcttgaag gcaa 374

<210> SEQ ID NO 67
<211> LENGTH: 1245
<212> TYPE: DNA
<213> ORGANISM: Homo sapiens

<400> SEQUENCE: 67
aaatgtcctc ctgaatgctg gccagacaaa tggaaatctg ccagggttgg gtacccccat 60
gacagcagcc agcctgccct cttagtccct gacagctgca gtgacagcat ctgtgattgc 120
aaagcgtgac aatttatatc tctcatttca tcacaccatc tatcagcaga cagtcaggct 180
ttaaaaatca atcccacact gactcagtcc ccagcagaga tggcctctga caacagtatc 240
cacactgcag gctggacaag ggccctatta attttgagac tcagccaaat ttccttctga 300
ccctaagctg gtgaatccct gctcctttgc tttggttggg gttggtgtga gctaaggctg 360
tgatcccatt tgctcctatg gcctccaggt ggcctgggcc tccatgaatg ggccacatgg 420
tcatactgaa tgcttgatta cactcagacc tagcagtcgt ctgggcgcag ctggtttatg 480
gatcactttg tcacaatgtt ccatccttcc aggtccccat ccccgcggtg ggaaaacatt 540
gctttaggca gtgctagagg acttcagcag gcattggcag cttctggatt caggattaga 600
acaaagaagg aggagtcaca gcaaagatag gaacagaagg cagagagaac agacagatgg 660
gggtgtttga gaaggagggc ctttgagacc tcagggagtg ggagacactg gctcgagaat 720
aataataatg gcaatttctc tcatctgtgt tttcagggca tggactggaa ctcccaatac 780
ccctgacatg ggctgagtca acgtggtcat gaacatgtga caggaggcag cagaagttgc 840
agagaagagt gaggcacgtt tgaaaaaggc tgaaaaatgt ttctgtccag gcaagggtgt 900
gtgctgaatg actcaaggat tttttgggca acacaaacca acacgagccg tgtgaggatc 960
aggtgacagc tgcccaaaag ctgacacaag gaacaagcct ggaggagtga ggatgggtgc 1020
tgtgaaggag gttgtgcagc tgggcccgca gtcggacctg gtgagatcag aggagggggt 1080
gccaccagtc tgtggacgaa gatgagaagc tggaatagag cagaaaacag gaggctgcca 1140
ctctccatct ttcccaaagt cactccagga gcaagggtgt catttactga aatgacagac 1200
tctccatttc acatttttcc cccaagtgca gagtgcaggg aagca 1245

<210> SEQ ID NO 68
<211> LENGTH: 537
<212> TYPE: DNA
<213> ORGANISM: Homo sapiens

<400> SEQUENCE: 68
aatgcttgat tacactcaga cctagcagtc gtctgggcgc agctggttta tggatcactt 60
tgtcacaatg ttccatcctt ccaggtcccc atccccgcgg tgggaaaaca ttgctttagg 120
cagtgctaga ggacttcagc aggcattggc agcttctgga ttcaggatta gaacaaagaa 180
ggaggagtca cagcaaagat aggaacagaa ggcagagaga acagacagat gggggtgttt 240
gagaaggagg gcctttgaga cctcagggag tgggagacac tggctcgaga ataataataa 300
tggcaatttc tctcatctgt gttttcaggg catggactgg aactcccaat acccctgaca 360
tgggctgagt caacgtggtc atgaacatgt gacaggaggc agcagaagtt gcagagaaga 420
gtgaggcacg tttgaaaaag gctgaaaaat gtttctgtcc aggcaagggt gtgtgctgaa 480
tgactcaagg attttttggc ctctgcctgt gtcctggccc tcactgcacc cccaaga 537

<210> SEQ ID NO 69
<211> LENGTH: 1863
<212> TYPE: DNA
<213> ORGANISM: Homo sapiens

<400> SEQUENCE: 69
cttcctcggg gtttgcttcc aggcctgact tttactcccc tttctaagtg tgcagatggg 60
atgtgcttct ccacaggagg ccccacggct tccccacccc tcagaggagc gccgtgcgtg 120
cgtctgtgtg gaggattggc agctcctgca gtcggccctt ggtcctattt ggcgacgcct 180
ctgccttccc cttaattata cagtcatgag ccgccctgga atcacggcag ctccggatgg 240
atcctggatg ccagaatgca gcctcagcac ggggctgcag gacaggagtg agcgaggggc 300
tgcagagccg gcggccgcgg tgggcaccat ggagggggct gccctgggca gcacgggcat 360
gagtctcaag gcccaggttt gagtaacagg tgttgagagc ttacttactt ttcctgagac 420
acagtttcct catctcgaga gcacggaaaa tcattctaac ttcagaggat tgttgtgaaa 480
gttaaatgag attaaagagg taaagcccat gacgtgctta gctcgtgctt ggctcttggt 540
caatgccagt tagcgctgca ttttctcccc tctccctccc tccttctctc tttcttttct 600
tctattctcc attcctgttt tctcccccac cccactcccc aaagctctgc gttgagaacc 660
agatgctgtc tggtgggtta gggccagagg aggaaaagct gcccgccgtg ggctgcaccc 720
ataccctctt cattccaatg acatgagggg aggggaaagg acagaggtag actgtcctcc 780
cctacctcct cctaatacaa atggaattcc tggaactgga aaacaaagaa tacccccata 840
aaaataagac agtacttctg gtgcggtgta ataaagggga aagtaaccct caatgtcagg 900
aaactccgca cctcccagct catatttgtg tggaggaaaa gttaaatatt aatttggact 960
caactgaatg tggacacaaa caatggtcac caagtcccgg aacaggttgt gtgagcctct 1020
tcaggggttc atccagcgct gttttggaga aatctctatt tcaatttatt cctatacgtt 1080
agttactgaa aaacaacaga caatcgcaaa agcaagttgc ccgttttgtg ttccttgagc 1140
ccaatcatga agtgccgtcg tgactgggcc tcatgacaaa caacttgtaa caagtaacaa 1200
cagagctcag gtcccagacc gcactgaagc tctgtgagac ctctcctcat ctgtgcatga 1260
acgagtgtct gactctggag cccagcctgc tgcttcccag tctggtggtg aatcctccgt 1320
agtctgatgg aggtttgctc ttgttgccca ggctggagtg caatggcaca atctcggctc 1380
actgcagccc ctgcctccca ggctcaagca attcttacgc ctcagcctcc tgagtagatg 1440
gaactacagg gcatggactg gaactcccaa taccccctgac atgggctgag tcaacgtggt 1500
catgaacatg tgacaggagg cagcagaagt tgcagagaag agtgaggcac gtttgaaaaa 1560
ggctgaaaaa tgtttctgtc caggcaaggg tgtgtgctga atgactcaag gatttttttgg 1620 gcaacacaaa ccaacacgag ccgtgtgagg atcaggtgac agctgcccaa aagctgacac 1680
aaggaacaag cctggaggag tgaggatggg tgctgtgaag gaggttgtgc agctgggccc 1740
gcagtcggac ctggtgagat cagaggaggg ggtgccacca gtctgtggac gaagatgaga 1800
agctggaata gagcagaaaa caggaggctg ccactctcca tctttcccaa agtcactcca 1860
gga 1863

<210> SEQ ID NO 70
<211> LENGTH: 3679

<212> TYPE: DNA
<213> ORGANISM: Homo sapiens

<400> SEQUENCE: 70

```
gaggcagcca tgactggcca cttcatgtgc tcctggagaa gggcttgcac cagccgtttt     60
caggaaagtc aagcagctgt tgactcctga gtctgggtga atttgtgtga agagcataag    120
gcgctgtttc ttaaccaaaa cgcttcctct tgcagtgcag atgggatgtg cttctccaca    180
ggaggcccca cggcttcccc acccctcaga ggagcgccgt gcgtgcgtct gtgtggagga    240
ttggcagctc ctgcagtcgg cccttggtcc tatttggcga cgcctctgcc ttccccttaa    300
ttatacagtc atgagccgcc ctggaatcac ggcagctccg gatggatcct ggatgccaga    360
atgcagcctc agcacggggc tgcaggacag gagtgagcga ggggctgcag agccggcggc    420
cgcggtgggc accatggagg gggctgccct gggcagcacg ggcatgagtc tcaaggccca    480
ggtttgagta acaggtgttg agagcttact tacttttcct gagacacagt ttcctcatct    540
cgagagcacg gaaaatcatt ctaacttcag aggattgttg tgaaagttaa atgagattaa    600
agaggtaaag cccatgacgt gcttagctcg tgcttggctc ttggtcaatg ccagttagcg    660
ctgcattttc tcccctctcc ctccctcctt ctctctttct tttcttctat tctccattcc    720
tgttttctcc cccaccccac tccccaaagc tctgcgttga gaaccagatg ctgtctggtg    780
ggttagggcc agaggaggaa aagctgcccg ccgtgggctg cacccatacc ctcttcattc    840
caatgacatg aggggagggg aaaggacaga ggtagactgt cctcccctac ctcctcctaa    900
tacaaatgga attcctggaa ctggaaaaca aagaataccc ccataaaaat aagacagtac    960
ttctggtgcg gtgtaataaa ggggaaagta accctcaatg tcaggaaact ccgcacctcc   1020
cagctcatat ttgtgtggag gaaaagttaa atattaattt ggactcaact gaatgtggac   1080
acaaacaatg gtcaccaagt cccggaacag gttgtgtgag cctcttcagg ggttcatcca   1140
gcgctgtttt ggagaaatct ctatttcaat ttattcctat acgttagtta ctgaaaaaca   1200
acagacaatc gcaaaagcaa gttgcccgtt ttgtgttcct tgagcccaat catgaagtgc   1260
cgtcgtgact gggcctcatg acaaacaact tgtaacaagt aacaacagag ctcaggtccc   1320
agaccgcact gaagctctgt gagacctctc ctcatctgtg catgaacgag tgtctgactc   1380
tggagcccag cctgctgctt cccagtctgg tggtgaatcc tccgtagtct gatggaggtt   1440
tgctcttgtt gcccaggctg gagtgcaatg gcacaatctc ggctcactgc agcccctgcc   1500
tcccaggctc aagcaattct tacgcctcag cctcctgagt agatggaact acagggcatg   1560
gactggaact cccaataccc ctgacatggg ctgagtcaac gtggtcatga acatgtgaca   1620
ggaggcagca gaagttgcag agaagagtga ggcacgtttg aaaaaggctg aaaaatgttt   1680
ctgtccaggc aagggtgtgt gctgaatgac tcaaggattt tttggagaga attggagtgt   1740
ctcaccagag gagaccacgt ctgaagggct ttgcatccct ccttggacat gtctaatacc   1800
taacactcag aaagcatcca gtaaatattc gtggaaagaa aggagtggag aaggggagaa   1860
aggggaaagg gagtaggcga gagagaagaa agactctgct tcttgcccag ggcctggcat   1920
ggggcggagg caaagcagtg gggtcctcag ctatgtccca ctgtgagtgc acagcgagtc   1980
ctgaccttca gagggtgcag cccgaggggc cctggcctgt ctgaagggtg cgccagccga   2040
gtggcctgct ctgaccacca ggctcaccca tgactacctg ggtggctaca gccagttcct   2100
gacaatgagt acagcactca gttatcgggg cccttccacc cacacgctgt ccacttcctg   2160
gggtactgct gtgggcatgt gagtgcttgc tccccggggc actgctgtgg gcatgcgagt   2220
```

```
gcttgctccc cggggcactg ctgtccactt cctggggtac tgctgtgggc atgcgagtgc   2280

ttgctccccg gggcactgct gtggacatgt gatagcttgc tccccagctc cactagtgac   2340

actggcggcc cctcgctggg gccttccccg cctgctccgc tccattaccg ctgccgggct   2400

cctcacgtct ctccttgctg cttcctgcac tggggtgagg agagtggggc tggtcccctt   2460

gagaccggag aagctccagg cttttaagga aaactgccag ggacgaagag aagatatcac   2520

ttccccacgt ggttggcttc cagattcaga aggaatgtct gtccttgtgg attccgtacc   2580

agatgacccc agatgctgcc tcagtactag gtccctgtgg ctctggagcc tttgctgggt   2640

ctgggcagtg tctcttcctc tccagttcat ccttgggtct cttcaccctt gccaggggca   2700

ggcttcctgg tgagaggtcg acctcctgca tgaaggctct caagaggcca gttcaaagcc   2760

aagctccggg tctgtgcctg tggggctgct cctcgatcag gagatggtca ctcccctcct   2820

ggtctgtatc tgtgggattc tcctccatca ggagatggtc tctcccctcc tggtctatac   2880

ccgtgggatt ctcctccatc aggagatggt cactccccat cctggtctat acccgtggga   2940

ttctcctcca ttagatggtc actcccctcc tggtctattc ccgtggggct gctcctccat   3000

caggaggtgg tcactccccc tcctggtcta tacccgtggg gctgctcctc catcaggaga   3060

tagtcactcc ccctcctggt ctatacccgt gggattctcc tccatctgga gatggtcact   3120

cccctcctgg tctataccca tgggattctc ctccatctgg agatggtcac tcccctcctg   3180

gtctataccc atgggattct cctccatctg gagatagtca ctcccctcct ggtctatacc   3240

cgtggggttc tcctcaatca ggaggtggtc actcccctcc tggtctatac ccgtgggatt   3300

ctcctccatc aggagatggt cactctccct cctggtctat acccgtgggg ctgctcctcc   3360

atcaggagat ggtcactccc ctcctggtct atacctgtgg gattctcctc cctcagaaga   3420

tggtcactcc ccctcctggt ctatacccat gggattctcc tccctcagaa gatggtcact   3480

ccccctcctg gtctataccc gtggggctgc tcctccatca ggagatggtc actctccctc   3540

tcggttgctc agtccaaaaa caacctctct ggaaaactgc gtggaatttt tttttaaaga   3600

attgaaacta gaactagcat ttgatccagc catctgccta ctgggaatac acccaaagaa   3660

aaataaatca ttatatcag                                                3679
```

<210> SEQ ID NO 71
<211> LENGTH: 3620
<212> TYPE: DNA
<213> ORGANISM: Homo sapiens

<400> SEQUENCE: 71

```
gaggcagcca tgactggcca cttcatgtgc tcctggagaa gggcttgcac cagccgtttt     60

caggaaagtc aagcagctgt tgactcctga gtctgggtga atttgtgtga agagcataag    120

gcgctgtttc ttaaccaaaa cgcttcctct tgcagtgcag atgggatgtg cttctccaca    180

ggaggcccca cggcttcccc acccctcaga ggagcgccgt gcgtgcgtct gtgtggagga    240

ttggcagctc ctgcagtcgg cccttggtcc tatttggcga cgcctctgcc ttccccttaa    300

ttatacagtc atgagccgcc ctggaatcac ggcagctccg gatggatcct ggatgccaga    360

atgcagcctc agcacggggc tgcaggacag gagtgagcga ggggctgcag agccggcggc    420

cgcggtgggc accatggagg gggctgccct gggcagcacg ggcatgagtc tcaaggccca    480

ggtttgagta acaggtgttg agagcttact tacttttcct gagacacagt ttcctcatct    540

cgagagcacg gaaaatcatt ctaacttcag aggattgttg tgaaagttaa atgagattaa    600

agaggtaaag cccatgacgt gcttagctcg tgcttggctc ttggtcaatg ccagttagcg    660
```

```
ctgcattttc tcccctctcc ctccctcctt ctctctttct tttcttctat tctccattcc    720
tgttttctcc cccaccccac tccccaaagc tctgcgttga gaaccagatg ctgtctggtg    780
ggttagggcc agaggaggaa aagctgcccg ccgtgggctg cacccatacc ctcttcattc    840
caatgacatg aggggagggg aaaggacaga ggtagactgt cctcccctac ctcctcctaa    900
tacaaatgga attcctggaa ctggaaaaca aagaataccc ccataaaaat aagacagtac    960
ttctggtgcg gtgtaataaa ggggaaagta accctcaatg tcaggaaact ccgcacctcc   1020
cagctcatat ttgtgtggag gaaaagttaa atattaattt ggactcaact gaatgtggac   1080
acaaacaatg gtcaccaagt cccggaacag gttgtgtgag cctcttcagg ggttcatcca   1140
gcgctgtttt ggagaaatct ctatttcaat ttattcctat acgttagtta ctgaaaaaca   1200
acagacaatc gcaaaagcaa gttgcccgtt ttgtgttcct tgagcccaat catgaagtgc   1260
cgtcgtgact gggcctcatg acaaacaact tgtaacaagt aacaacagag ctcaggtccc   1320
agaccgcact gaagctctgt gagacctctc ctcatctgtg catgaacgag tgtctgactc   1380
tggagcccag cctgctgctt cccagtctgg tggtgaatcc tccgtagtct gatggaggtt   1440
tgctcttgtt gcccaggctg gagtgcaatg gcacaatctc ggctcactgc agcccctgcc   1500
tcccaggctc aagcaattct tacgcctcag cctcctgagt agatggaact acagggcatg   1560
gactggaact cccaataccc ctgacatggg ctgagtcaac gtggtcatga acatgtgaca   1620
ggaggcagca gaagttgcag agaagagtga ggcacgtttg aaaaaggctg aaaaatgttt   1680
ctgtccaggc aagggtgtgt gctgaatgac tcaaggattt tttggagaga attggagtgt   1740
ctcaccagag gagaccacgt ctgaagggct ttgcatccct ccttggacat gtctaatacc   1800
taacactcag aaagcatcca gtaaatattc gtggaaagaa aggagtggag aaggggagaa   1860
aggggaaagg gagtaggcga gagagaagaa agactctgct tcttgcccag ggcctggcat   1920
ggggcggagg caaagcagtg gggtcctcag ctatgtccca ctgtgagtgc acagcgagtc   1980
ctgaccttca gagggtgcag cccgaggggc cctggcctgt ctgaagggtg cgccagccga   2040
gtggcctgct ctgaccacca ggctcaccca tgactacctg ggtggctaca gccagttcct   2100
gacaatgagt acagcactca gttatcgggg cccttccacc cacacgctgt ccacttcctg   2160
gggtactgct gtgggcatgt gagtgcttgc tccccggggc actgctgtgg gcatgcgatg   2220
cttgctcccc ggggcactgc tgtggacatg tgatagcttg ctccccagct ccactagtga   2280
cactggcggc ccctcgctgg ggccttcccc gcctgctccg ctccattacc gctgccgggc   2340
tcctcacgtc tctccttgct gcttcctgca ctggggtgag gagagtgggg ctggtcccct   2400
tgagaccgga gaagctccag gcttttaagg aaaactgcca gggacgaaga gaagatatca   2460
cttccccacg tggttggctt ccagattcag aaggaatgtc tgtccttgtg gattccgtac   2520
cagatgaccc cagatgctgc ctcagtacta ggtccctgtg gctctggagc ctttgctggg   2580
tctgggcagt gtctcttcct ctccagttca tccttgggtc tcttcaccct tgccaggggc   2640
aggcttcctg gtgagaggtc gacctcctgc atgaaggctc tcaagaggcc agttcaaagc   2700
caagctccgg gtctgtgcct gtggggctgc tcctcgatca ggagatggtc actcccctcc   2760
tggtctgtat ctgtgggatt ctcctccatc aggagatggt ctctcccctc ctggtctata   2820
cccgtgggat tctcctccat caggagatgg tcactcccca tcctggtcta tacccgtggg   2880
attctcctcc attagatggt cactcccctc ctggtctatt cccgtggggc tgctcctcca   2940
tcaggaggtg gtcactcccc ctcctggtct atacccgtgg ggctgctcct ccatcaggag   3000
```

```
atagtcactc cccctcctgg tctatacccg tgggattctc ctccatctgg agatggtcac   3060

tccccctcctg gtctataccc atgggattct cctccatctg gagatggtca ctcccctcct   3120

ggtctatacc catgggattc tcctccatct ggagatagtc actcccctcc tggtctatac   3180

ccgtggggtt ctcctcaatc aggaggtggt cactcccctc ctggtctata cccgtgggat   3240

tctcctccat caggagatgg tcactctccc tcctggtcta tacccgtggg gctgctcctc   3300

catcaggaga tggtcactcc cctcctggtc tatacctgtg ggattctcct ccctcagaag   3360

atggtcactc cccctcctgg tctataccca tgggattctc ctccctcaga agatggtcac   3420

tccccctcct ggtctatacc cgtggggctg ctcctccatc aggagatggt cactctccct   3480

ctcggttgct cagtccaaaa acaacctctc tggaaaactg cgtggaattt ttttttaaag   3540

aattgaaact agaactagca tttgatccag ccatctgcct actgggaata cacccaaaga   3600

aaaataaatc attatatcag                                                3620
```

```
<210> SEQ ID NO 72
<211> LENGTH: 720
<212> TYPE: DNA
<213> ORGANISM: Homo sapiens

<400> SEQUENCE: 72

ctggagctct cctgaggagc ccacagatcc aactccctag gccaaggctg cagcctgggg     60

cagagatgca gaggcctgga ggagcctagg gcacgcggcc tgcgggctgg ctggggttca    120

gagttcgtat gtgtgtggag tgactgggca ggtgttcaga aatgaaggct ggcactgcca    180

ggtaaggccc ttccctccct gatgtgagag ccctggagcc accgcagagg cccagtcaga    240

tctctgttct aattctggcc tggtgtggag gatgaggaga gacggcccag aaaggaaggc    300

agactgtgca gaccccatgt cttctggccc gcgaggccct cctcctgtgc ctgcttatct    360

taaagaatcc gggataagag gtgacttggg ccttggccgg gaggcccctc ctcagcttca    420

gacaaggagg gagctctggg catgaggaca ttgagcaaga ggcgatggca gtgcccacaa    480

cttaccctca gctcggctct gttgggtccg agaagttgca tggaaagggc tccttggggg    540

ccagttgtca gtaagctgca gaagcctgga gccggccagg aaataaccac gtgtaggagc    600

cttctcagct gagaggaagg aggactcacg cgcggcgagc acatgcttgg agccaggcac    660

agggcatgga ctggaactcc caatacccct gacatgggct gagtcaacgt ggtcatgaac    720
```

```
<210> SEQ ID NO 73
<211> LENGTH: 4387
<212> TYPE: DNA
<213> ORGANISM: Homo sapiens

<400> SEQUENCE: 73

caaatgcctg gcagcgtcct cggtgcttca cctgccatag ccgacagtgg ctgacctccc     60

atgcctgttg ccttttcttt ctgttggatc agggatacac tgccatgtgt gttaagaaaa    120

gctggcctta cctacagggc tggccagtcc cggtcacgtt tctagtaagc cattgcctta    180

cataagggta acggcatggg acgctatctt agccaatgtg ataaaagtgg acatgaggtg    240

agaggcttca gagagaggtt ttaaaaaaga gacaaaagca ggacgttgcc tctcttcctc    300

ctctccacgt gtcctacccg gatgtgaagc caaaacagat gcaggcttag tgcaaccatg    360

gggaacccag cataagcaca gattcaacag cagaagagtg gcagagggag aaggtgaaag    420

gaacctaggt tttcctgtcc ttgttgagtc attcagttaa aaatccctgg aattttcctc    480

tctccggcag tgtgttttgt gggataatga gttgccttat tggggttggc ttgctagtcg    540
```

```
ggatgtttcg ctcccatcaa catccatacg cttgctctgt gaaccaatga cctgatgagg    600
tagtattagc accaccatca ttatgctgag gatgagattt atggcacagt ggttcagtag    660
cttgcccaag gccatgcggc tggtaggttc tggaggaggg ctcagggcac cccctgagct    720
acccctgctg gccattgcac caccccataa agctgctggc agtcacttct ctgaggggtt    780
agcatgtaag aaatgtcctc ctgaatgctg gccagacaaa tggaaatctg ccagggttgg    840
gtacccccat gacagcagcc agcctgccct cttagtccct gacagctgca gtgacagcat    900
ctgtgattgc aaagcgtgac aatttatatc tctcatttca tcacaccatc tatcagcaga    960
cagtcaggct ttaaaaatca atcccacact gactcagtcc ccagcagaga tggcctctga   1020
caacagtatc cacactgcag gctggacaag ggccctatta attttgagac tcagccaaat   1080
ttccttctga ccctaagctg gtgaatccct gctcctttgc tttggttggg gttggtgtga   1140
gctaaggctg tgatcccatt tgctcctatg gcctccaggt ggcctgggcc tccatgaatg   1200
ggccacatgg tcatactgaa tgcttgatta cactcagacc tagcagtcgt ctgggcgcag   1260
ctggtttatg gatcactttg tcacaatgtt ccatccttcc aggtccccat ccccgcggtg   1320
ggaaaacatt gctttaggca gtgctagagg acttcagcag gcattggcag cttctggatt   1380
caggattaga acaaagaagg aggagtcaca gcaaagatag gaacagaagg cagagagaac   1440
agacagatgg gggtgtttga gaaggagggc ctttgagacc tcagggagtg ggagacactg   1500
gctcgagaat aataataatg gcaatttctc tcatctgtgt tttcagggca tggactggaa   1560
ctcccaatac ccctgacatg ggctgagtca acgtggtcat gaacatgtga caggaggcag   1620
cagaagttgc agagaagagt gaggcacgtt tgaaaaaggc tgaaaaatgt ttctgtccag   1680
gcaagggtgt gtgctgaatg actcaaggat tttttggtgc attgaatgaa cagcgggaca   1740
ttggacacct gctgatccat caccccgggc ccgggcaggc ccgtggatga agagagatgg   1800
agaagaccag gcatgagact gtggagaagc cacaccacca gaaacccctg ccccatgcgc   1860
cgtccagccc acacctgtgg atgcacgggg gattgcaggc agggctccca ccgtggactc   1920
aggaacaggc agggaagctg ctgcctcacc aggcgaaggg gccaggaggg ggaggcggag   1980
aggcccgtct agcccctgcg gctgtcaccg tggtgcctcc tcactggcca gtgcggtcgc   2040
gcctcagctt cgttaatagg ggagggggcc taagagtttt cacgtccagg ctcgggcagt   2100
ggggaggcag gcaggagtgg ccgctggttt ttcagacctc ccagggaggc cgaggaaatg   2160
gcccgtcctg gagtgggcgt ggttctgtct tcagatggat gctggagggt tgggctgcgt   2220
gggaccctgg gccctgctgc ttcccggagg atgcgctgtc cggggctgca caggttggct   2280
gtgtttttg gatgcttgat attttgtttt ttcttctctt cactctgtca tgaaactggc    2340
aatagtagtt tgtaaataaa tatgtgttat agatgaatat ttgctatgag taaattaata   2400
aaggagtgaa taaatgagcg attgatgtag ggcctgtcct gtctcaggga gccccacgaa   2460
ggcctgcgcg ccggccagag cctgcctgcc tgccagggta ctgggacgtc actctcaaag   2520
cggcgggacc cagccgctga tcttgctgag gaggcccggt ctcagaaaac tgagcggctg   2580
cttctgcaga ccctgcatcc tcccctccct ggagaaagaa gctctggctg agtcctggga   2640
ccgaaccctt gggtgccaca gaaacgggct ttgctgcctg tcagtcaagc ggcgggagaa   2700
acagacctgg ggaggaggag gctgggaggg ctgtgttttc tgcacagcga gtagctcctt   2760
agcctggtgc catttctctc caaacaccct gaaggttgag tccagggtga agatgtagag   2820
gcaagttttg gggggatgga gtgggcttgg agggatgctg gcgccttagc aggctgtgct   2880
```

```
cctgaggtgc ccagtgtctg cgggcacagg aacatgttgc cgagggcatt tgggtgtggg   2940

tggggtgggg aaagggagac agggctgtct cttttaatgg gtatctgcga gcatgtgatt   3000

gtaagagagg aagaagtagg ggaggaagaa ggcctccttg ggaggtgcgt catcctgagg   3060

aaggctgaac aatgagggtc ttggagagtc aattcagaag cacaaccttg cagagcaggc   3120

aaaaacaata gggcttcttg aggctgcccg ggcactcatg caatcaccat ttcctgctgt   3180

gaatgagcct acattttgtt ggggaagaga cgcaacgacg ccaaacgatg gactctgagt   3240

caacgataag atgaaacaaa attaaaacaa agtaggaaat caagagtggc tgctgtgatg   3300

gcgttgcgga gatgatgttt gctttgagaa ctggacaagt gagcccctga gctgcatctg   3360

cacccagagg ctgagccggt gcacaggact tgcagaggga tgggcctggg cttgtagagc   3420

agcacaacgg ccccaggcct ggaggagcaa gggtgggaag gggggcaggc cagctcctgc   3480

caggctggag aaggactcgg acctcaggcc acctgtgcct gggtgattgt gaacttgtaa   3540

caaatgtgat cttatttatg ttttgaaaaa ggcaacacaa accaacacga gccgtgtgag   3600

gatcaggtga cagctgccca aaagctgaca caaggaacaa gcctggagga gtgaggatgg   3660

gtgctgtgaa ggaggttgtg cagctgggcc cgcagtcgga cctggtgaga tcagaggagg   3720

gggtgccacc agtctgtgga cgaagatgag aagctggaat agagcagaaa acaggaggct   3780

gccactctcc atctttccca aagtcactcc aggagcaagg gtgtcattta ctgaaatgac   3840

agactctcca tttcacattt ttcccccaag tgcagagtgc agggaagcag atgggctaaa   3900

tttttagagt cagggttatt aatgtatact ttacatagta aactttcccc ttttaagtgt   3960

gcaggcctga ggtttgccaa atatgtgtag gcatttaatc accaccacga tcaagatgta   4020

gaatattccc actatcaaaa agtttgctgt gtcccttgat ggtcatgccc cattccacag   4080

ccccagcccc agcccctgga gattgctgtc tgctttatgt tccagtggtt ttatcttttc   4140

cagactgtat ggatgtgaat ggaatcagat gtgattccaa ggtgttttat cttttccaga   4200

tgtgaatgga atcagatgta cgaaatccta tggtaggggg tcttctgagt ctagctcctt   4260

ttgtttagcg tgatgcattt gaaattaatc catgtctcag gcatcaggag ttcatttctt   4320

tttctgctga gtagtatttc attgtatgga tgtactgcaa tttgcctatc cattcacctg   4380

ttgatgt                                                             4387
```

<210> SEQ ID NO 74
<211> LENGTH: 1398
<212> TYPE: DNA
<213> ORGANISM: Homo sapiens

<400> SEQUENCE: 74

```
cgggatgttt cgctcccatc aacatccata cgcttgctct gtgaaccaat gacctgatga     60

ggtagtatta gcaccaccat cattatgctg aggatgagat ttatggcaca gtggttcagt    120

agcttgccca aggccatgcg gctggtaggt tctggaggag ggctcagggc acccccctgag    180

ctacccctgc tggccattgc accaccccat aaagctgctg gcagtcactt ctctgagggg    240

ttagcatgta agaaatgtcc tcctgaatgc tggccagaca aatggaaatc tgccagggtt    300

gggtaccccc atgacagcag ccagcctgcc ctcttagtcc ctgacagctg cagtgacagc    360

atctgtgatt gcaaagcgtg acaatttata tctctcattt catcacacca tctatcagca    420

gacagtcagg ctttaaaaat caatcccaca ctgactcagt ccccagcaga gatggcctct    480

gacaacagta tccacactgc aggctggaca agggccctat taattttgag actcagccaa    540

atttccttct gaccctaagc tggtgaatcc ctgctccttt gctttggttg gggttggtgt    600
```

gagctaaggc tgtgatccca tttgctccta tggcctccag gtggcctggg cctccatgaa 660
tgggccacat ggtcatactg aatgcttgat tacactcaga cctagcagtc gtctgggcgc 720
agctggttta tggatcactt tgtcacaatg ttccatcctt ccaggtcccc atccccgcgg 780
tgggaaaaca ttgctttagg cagtgctaga ggacttcagc aggcattggc agcttctgga 840
ttcaggatta gaacaaagaa ggaggagtca cagcaaagat aggaacagaa ggcagagaga 900
acagacagat gggggtgttt gagaaggagg gcctttgaga cctcagggag tgggagacac 960
tggctcgaga ataataataa tggcaatttc tctcatctgt gttttcaggg catggactgg 1020
aactcccaat accccctgaca tgggctgagt caacgtggtc atgaacatgt gacaggaggc 1080
agcagaagtt gcagagaaga gtgaggcacg tttgaaaaag gctgaaaaat gtttctgtcc 1140
aggcaagggt gtgtgctgaa tgactcaagg atttttgggg tatgtcattt cccatttctc 1200
accctcaaat aggactccgc ttcccatcta agcatttgta taaatattga ttattggtta 1260
gtgtgtatca gagagctatt gagtaaaaat tatatcagaa aaattaagaa tctctagaga 1320
tggcaaggtg tgaaacaaaa aacgccagga aggtaaatgc tcaaagttca ccacacacca 1380
cagtgagaag tgttgggg 1398

<210> SEQ ID NO 75
<211> LENGTH: 939
<212> TYPE: DNA
<213> ORGANISM: Homo sapiens

<400> SEQUENCE: 75
acagcatctg tgattgcaaa gcgtgacaat ttatatctct catttcatca caccatctat 60
cagcagacag tcaggcttta aaaatcaatc ccacactgac tcagtcccca gcagagatgg 120
cctctgacaa cagtatccac actgcaggct ggacaagggc cctattaatt ttgagactca 180
gccaaatttc cttctgaccc taagctggtg aatccctgct cctttgcttt ggttggggtt 240
ggtgtgagct aaggctgtga tcccatttgc tcctatggcc tccaggtggc ctgggcctcc 300
atgaatgggc cacatggtca tactgaatgc ttgattacac tcagacctag cagtcgtctg 360
ggcgcagctg gtttatggat cactttgtca caatgttcca tccttccagg tccccatccc 420
cgcggtggga aaacattgct ttaggcagtg ctagaggact tcagcaggca ttggcagctt 480
ctggattcag gattagaaca aagaaggagg agtcacagca aagataggaa cagaaggcag 540
agagaacaga cagatggggg tgtttgagaa ggagggcctt tgagacctca gggagtggga 600
gacactggct cgagaataat aataatggca atttctctca tctgtgtttt cagggcatgg 660
actggaactc ccaatacccc tgacatgggc tgagtcaacg tggtcatgaa catgtgacag 720
gaggcagcag aagttgcaga gaagagtgag gcacgtttga aaaaggctga aaaatgtttc 780
tgtccaggca agggtgtgtg ctgaatgact caaggatttt ttggctgatt tagtaaacaa 840
acaagaatga agaaggaaac catagctgag tggcagagcg tgcctggctg tttacacagg 900
actccagggc agggctcctg gagagggacg tgccagagg 939

<210> SEQ ID NO 76
<211> LENGTH: 138
<212> TYPE: DNA
<213> ORGANISM: Artificial Sequence
<220> FEATURE:
<223> OTHER INFORMATION: primer

<400> SEQUENCE: 76

```
ctggaaagga ggagaacatg aaacattgct tgaagacaat ggccgagaca gcaggtccca     60

ccctgcacag ccaccagcat ctctcccctc agccctgtct cctcttctgc agttgggatc    120

tgcacattta agcctgaa                                                  138


<210> SEQ ID NO 77
<211> LENGTH: 147
<212> TYPE: DNA
<213> ORGANISM: Artificial Sequence
<220> FEATURE:
<223> OTHER INFORMATION: primer

<400> SEQUENCE: 77

attgtcctgt gaagtgaagt atgatcggac agcctctttt cagcttttat gacaatggag     60

acagaggaat tgtggctctt gccaaggtca caggattgga atacagagcc aagccacccc    120

aggacatgca agagcctcag aagggaa                                        147


<210> SEQ ID NO 78
<211> LENGTH: 19
<212> TYPE: DNA
<213> ORGANISM: Artificial Sequence
<220> FEATURE:
<223> OTHER INFORMATION: primer

<400> SEQUENCE: 78

acagccacca gcatctctc                                                  19


<210> SEQ ID NO 79
<211> LENGTH: 27
<212> TYPE: DNA
<213> ORGANISM: Artificial Sequence
<220> FEATURE:
<223> OTHER INFORMATION: primer

<400> SEQUENCE: 79

tgaagtgaag tatgatcgga cagcctc                                         27


<210> SEQ ID NO 80
<211> LENGTH: 22
<212> TYPE: DNA
<213> ORGANISM: Artificial Sequence
<220> FEATURE:
<223> OTHER INFORMATION: primer

<400> SEQUENCE: 80

ccacaattcc tctgtctcca tt                                              22


<210> SEQ ID NO 81
<211> LENGTH: 90
<212> TYPE: DNA
<213> ORGANISM: Artificial Sequence
<220> FEATURE:
<223> OTHER INFORMATION: primer

<400> SEQUENCE: 81

tctctcatct gtgttttcag ggcatggact ggaactccca atacccctga catgggctga     60

gtcaacgtgg tcatgaacat gtgacaggag                                      90


<210> SEQ ID NO 82
<211> LENGTH: 101
<212> TYPE: DNA
<213> ORGANISM: Artificial Sequence
<220> FEATURE:
<223> OTHER INFORMATION: primer
```

<400> SEQUENCE: 82
gcagcagaag ttgcagagaa gagtgaggca cgtttgaaaa aggctgaaaa atgtttctgt 60
ccaggcaagg gtgtgtgctg aatgactcaa ggatttttttg g 101

<210> SEQ ID NO 83
<211> LENGTH: 21
<212> TYPE: DNA
<213> ORGANISM: Artificial Sequence
<220> FEATURE:
<223> OTHER INFORMATION: primer

<400> SEQUENCE: 83
catggactgg aactcccaat a 21

<210> SEQ ID NO 84
<211> LENGTH: 25
<212> TYPE: DNA
<213> ORGANISM: Homo sapiens

<400> SEQUENCE: 84
tgcagagaag agtgaggcac gtttg 25

<210> SEQ ID NO 85
<211> LENGTH: 21
<212> TYPE: DNA
<213> ORGANISM: Artificial Sequence
<220> FEATURE:
<223> OTHER INFORMATION: primer

<400> SEQUENCE: 85
ccttgcctgg acagaaacat t 21

<210> SEQ ID NO 86
<211> LENGTH: 1434
<212> TYPE: DNA
<213> ORGANISM: Homo sapiens

<400> SEQUENCE: 86
gttcgttgca acaaattgat gagcaatgct tttttataat gccaactttg tacaaaaaag 60
ttggcatgag ccggtcaagg cacctgggca aaatccggaa gcgtctggaa gatgtcaaga 120
gccagtgggt ccggccagcc agggctgact ttagtgacaa cgagagtgcc cggctggcca 180
cggacgccct cttggatggg ggttctgaag cctactggcg ggtgctcagc caggaaggcg 240
aggtggactt cttgtcctcg gtggaggccc agtacatcca ggcccaggcc agggagcccc 300
cgtgtccccc agacaccctg ggaggggcgg aagcaggccc taagggactg gactccagct 360
ccctacagtc cggcacctac ttccctgtgg cctcagaggg cagcgagccg gccctactgc 420
acagctgggc ctcagctgag aagccctacc tgaaggaaaa atccagcgcc actgtgtact 480
tccagaccgt caagcacaac aacatcagag acctcgtccg ccgctgcatc acccggacta 540
gccaggtcct ggtcatcctg atggatgtgt tcacggatgt ggagatcttc tgtgacattc 600
tagaggcagc caacaagcgt ggggtgttcg tttgtgtgct cctggaccag ggaggtgtga 660
agctcttcca ggagatgtgt gacaaagtcc agatctctga cagtcacctc aagaacattt 720
ccatccggag tgtggaagga gagatatact gtgccaagtc aggcaggaaa ttcgctggcc 780
aaatccggga gaagttcatc atctcggact ggagatttgt cctgtctgga tcttacagct 840
tcacctggct ctgcggacac gtgcaccgga acatcctctc caagttcaca ggccaggcgg 900

```
tggagctgtt tgacgaggag ttccgccacc tctacgcctc ctccaagcct gtgatgggcc     960
tgaagtcccc gcggctggtc gcccccgtcc cgcccggagc agccccggcc aatggccgcc    1020
ttagcagcag cagtggctcc gccagtgacc gcacgtcctc caaccccttc agcggccgct    1080
cggcaggcag ccaccccggt acccgaagtg tgtccgcgtc ttcagggccc tgtagccccg    1140
cggccccaca cccgcctcca ccgccccggt tccagcccca ccaaggccct tggggagccc    1200
cgagtcccca ggcccacctc tccccgcggc cccacgacgg cccgcccgcc gctgtctaca    1260
gcaacctggg ggcctacagg cccacgcggc tgcagctgga gcagctgggc ctggtgccga    1320
ggctgactcc aacctggagg cccttcctgc aggcctcccc tcacttctgc ccaactttct    1380
tgtacaaagt tggcattata agaaagcatt gcttatcaat ttgttgcaac gaac          1434
```

<210> SEQ ID NO 87
<211> LENGTH: 3535
<212> TYPE: DNA
<213> ORGANISM: Homo sapiens

<400> SEQUENCE: 87

```
gcggccgcgg cgccgatccc ggctgaggcg cagcggcgag aggtcgcggg cagggccatg      60
gccccggggg gccgctagcg cggaccggcc caacgggagc cgctccgtgc cgccgccgcc     120
gcccgggcgc ccaggccccg ccgctgcgga agaggtttct agagagtgga gcctgcttcc     180
tgggccctag gcccctccca caatgcttgt cgccggtctt cttctctggg cttccctact     240
gaccggggcc tggccatcct tccccaccca ggaccacctc ccggccacgc cccgggtccg     300
gctctcattc aaagagctga aggccacagg caccgcccac ttcttcaact tcctgctcaa     360
cacaaccgac taccgaatct tgctcaagga cgaggaccac gaccgcatgt acgtgggcag     420
caaggactac gtgctgtccc tggacctgca cgacatcaac cgcgagcccc tcattataca     480
ctgggcagcc tccccacagc gcatcgagga atgcgtgctc tcaggcaagg atgtcaacgg     540
cgagtgtggg aacttcgtca ggctcatcca gccctggaac cgaacacacc tgtatgtgtg     600
cgggacaggt gcctacaacc ccatgtgcac ctatgtgaac cgcggacgcc gcgcccaggc     660
cacaccatgg acccagactc aggcggtcag aggccgcggc agcagagcca cggatggtgc     720
cctccgcccg atgcccacag ccccacgcca ggattacatc ttctacctgg agcctgagcg     780
actcgagtca gggaagggca agtgtccgta cgatcccaag ctggacacag catcggccct     840
catcaatgag gagctctatg ctggtgtgta catcgatttt atgggcactg atgcagccat     900
cttccgcaca cttggaaagc agacagccat gcgcacggat cagtacaact cccggtggct     960
gaacgacccg tcgttcatcc atgctgagct cattcctgac agtgcggagc gcaatgatga    1020
taagctttac ttcttcttcc gtgagcggtc ggcagaggcg ccgcagagcc ccgcggtgta    1080
cgcccgcatc gggcgcattt gcctgaacga tgacggtggt cactgttgcc tggtcaacaa    1140
gtggagcaca ttcctgaagg cgcggctcgt ctgctctgtc ccgggcgagg atggcattga    1200
gactcacttt gatgagctcc aggacgtgtt tgtccagcag acccaggacg tgaggaaccc    1260
tgtcatttac gctgtcttta cctcctctgg ctccgtgttc cgaggctctg ccgtgtgtgt    1320
ctactccatg gctgatattc gcatggtctt caacgggccc tttgcccaca aagaggggcc    1380
caactaccag tggatgccct tctcagggaa gatgccctac ccacggccgg gcacgtgccc    1440
tggtggaacc ttcacgccat ctatgaagtc caccaaggat tatcctgatg aggtgatcaa    1500
cttcatgcgc agccacccac tcatgtacca ggccgtgtac cctctgcagc ggcggcccct    1560
ggtagtccgc acaggtgctc cctaccgcct taccactatt gccgtggacc aggtggatgc    1620
```

```
agccgacggg cgctatgagg tgcttttcct gggcacagac cgcgggacag tgcagaaggt   1680

cattgtgctg cccaaggatg accaggagtt ggaggagctc atgctggagg aggtggaggt   1740

cttcaaggat ccagcacccg tcaagaccat gaccatctct tctaagaggc aacaactcta   1800

cgtggcgtca gccgtgggtg tcacacacct gagcctgcac cgctgccagg cgtatggggc   1860

tgcctgtgct gactgctgcc ttgcccggga cccttactgt gcctgggatg gccaggcctg   1920

ctcccgctat acagcatcct ccaagaggcg gagccgccgg caggacgtcc ggcacggaaa   1980

ccccatcagg cagtgccgtg ggttcaactc caatgccaac aagaatgccg tggagtctgt   2040

gcagtatggc gtggccggca gcgcagcctt ccttgagtgc cagccccgct cgccccaagc   2100

cactgttaag tggctgttcc agcgagatcc tggtgaccgg cgccgagaga ttcgtgcaga   2160

ggaccgcttc ctgcgcacag agcagggctt gttgctccgt gcactgcagc tcagcgatcg   2220

tggcctctac tcctgcacag ccactgagaa caactttaag cacgtcgtca cacgagtgca   2280

gctgcatgta ctgggccggg acgccgtcca tgctgccctc ttcccaccac tgtccatgag   2340

cgccccgcca cccccaggcg caggcccccc aacgcctcct taccaggagt tagcccagct   2400

gctggcccag ccagaagtgg gcctcatcca ccagtactgc cagggttact ggcgccatgt   2460

gcccccccagc cccagggagg ctccaggggc accccggtct cctgagcccc aggaccagaa   2520

aaagccccgg aaccgccggc accaccctcc ggacacatga ggccagctgc ctgtgcctgc   2580

catgggccag cctagccctt gtccctttta atataaaaga tatatatata tatatatata   2640

tataaaatat ctatattcta tacacaccct gcccctgcaa agacagtatt tattggtggg   2700

ttgaatatag cctgcctcag tggcagcatc ctccaaaact tagacccatg ctggtcagag   2760

acggcagaaa acagagcctg cctaaccagg cccagccagt tggtggggcc aggccaggac   2820

cacacagtcc ccagactcag ctggaagtct acctgctgga cagcctccgc caagatctac   2880

aggacaaagg gagggagcaa gccctactcg gatggggcac ggactgtcca ccttttctga   2940

tgtgtgttgt cagcctgtgc tgtggcatag acatggatgc gaggaccact ttggagactg   3000

gggtggcctc aagagcacac agagaaggga agaaggggcc atcacaggat gccagcccct   3060

gcctgggttg gggcactca gccacgacca gccccttcct gggtatttat tctctattta   3120

ttggggatag gagaagaggc atcctgcctg ggtgggacag cctcttcagc cccttctccc   3180

ctccccgcct ggccagggca gggccacccc actctacctc cttagctttc cctgtgccac   3240

tttgactcag aggctgggag catagcagag gggccaggcc caggcagagc tgacgggagg   3300

ccccagctct gaggggaggg ggtccgtggt agaggcctgg ggccggtaga ggctccccag   3360

ggctccctta tgtccaccac ttcaggggat gggtgtggat gtaattagct ctgggggggca   3420

gttgggtaga tgggtggggg ctcctggtgg ccttctgctg cccaggccac agccgccttt   3480

gggttccatc ttgctaataa acactggctc tgggactaga aaaaaaaaaa aaaaa        3535
```

```
<210> SEQ ID NO 88
<211> LENGTH: 3558
<212> TYPE: DNA
<213> ORGANISM: Homo sapiens

<400> SEQUENCE: 88

ctgactggtg ctccctctct tccatcttgg gctgtctgca tgtgtctcat tcccccactc     60

tctcctgtgc ctcccctcta ccgtaataat caggtccagg tttctctgta ctgggagaag    120

acctgtggct ggagcaggca gggatgcacc ctatctgttc cccattcctc caggtgggag    180
```

```
ggagaaggag taacccactt tattggccac agatgcaggg gagaaaggag aaagcatgct    240
gggagctgga aagagcccta agatcacctg gtttctagag agtggagcct gcttcctggg    300
ccctaggccc ctcccacaat gcttgtcgcc ggtcttcttc tctgggcttc cctactgacc    360
ggggcctggc catccttccc cacccaggac cacctcccgg ccacgccccg ggtccggctc    420
tcattcaaag agctgaaggc cacaggcacc gcccacttct tcaacttcct gctcaacaca    480
accgactacc gaatcttgct caaggacgag gaccacgacc gcatgtacgt gggcagcaag    540
gactacgtgc tgtccctgga cctgcacgac atcaaccgcg agcccctcat tatacactgg    600
gcagcctccc cacagcgcat cgaggaatgc gtgctctcag gcaaggatgt caacggcgag    660
tgtgggaact tcgtcaggct catccagccc tggaaccgaa cacacctgta tgtgtgcggg    720
acaggtgcct acaaccccat gtgcacctat gtgaaccgcg gacgccgcgc ccaggattac    780
atcttctacc tggagcctga gcgactcgag tcagggaagg gcaagtgtcc gtacgatccc    840
aagctggaca cagcatcggc cctcatcaat gaggagctct atgctggtgt gtacatcgat    900
tttatgggca ctgatgcagc catcttccgc acacttggaa agcagacagc catgcgcacg    960
gatcagtaca actcccggtg gctgaacgac ccgtcgttca tccatgctga gctcattcct   1020
gacagtgcgg agcgcaatga tgataagctt tacttcttct tccgtgagcg gtcggcagag   1080
gcgccgcaga gccccgcggt gtacgcccgc atcgggcgca tttgcctgaa cgatgacggt   1140
ggtcactgtt gcctggtcaa caagtggagc acattcctga aggcgcggct cgtctgctct   1200
gtcccgggcg aggatggcat tgagactcac tttgatgagc tccaggacgt gtttgtccag   1260
cagacccagg acgtgaggaa ccctgtcatt tacgctgtct ttacctcctc tggctccgtg   1320
ttccgaggct ctgccgtgtg tgtctactcc atggctgata ttcgcatggt cttcaacggg   1380
ccctttgccc acaaagaggg gcccaactac cagtggatgc ccttctcagg gaagatgccc   1440
tacccacggc cgggcacgtg ccctggtgga accttcacgc catctatgaa gtccaccaag   1500
gattatcctg atgaggtgat caacttcatg cgcagccacc cactcatgta ccaggccgtg   1560
taccctctgc agcggcggcc cctggtagtc cgcacaggtg ctccctaccg ccttaccact   1620
attgccgtgg accaggtgga tgcagccgac gggcgctatg aggtgctttt cctgggcaca   1680
gaccgcggga cagtgcagaa ggtcattgtg ctgcccaagg atgaccagga gttggaggag   1740
ctcatgctgg aggaggtgga ggtcttcaag gatccagcac ccgtcaagac catgaccatc   1800
tcttctaaga ggcaacaact ctacgtggcg tcagccgtgg gtgtcacaca cctgagcctg   1860
caccgctgcc aggcgtatgg ggctgcctgt gctgactgct gccttgcccg ggacccttac   1920
tgtgcctggg atggccaggc ctgctcccgc tatacagcat cctccaagag gcggagccgc   1980
cggcaggacg tccggcacgg aaaccccatc aggcagtgcc gtgggttcaa ctccaatgcc   2040
aacaagaatg ccgtggagtc tgtgcagtat ggcgtggccg gcagcgcagc cttccttgag   2100
tgccagcccc gctcgcccca agccactgtt aagtggctgt tccagcgaga tcctggtgac   2160
cggcgccgag agattcgtgc agaggaccgc ttcctgcgca cagagcaggg cttgttgctc   2220
cgtgcactgc agctcagcga tcgtggcctc tactcctgca cagccactga gaacaacttt   2280
aagcacgtcg tcacacgagt gcagctgcat gtactgggcc gggacgccgt ccatgctgcc   2340
ctcttcccac cactgtccat gagcgccccg ccaccccag gcgcaggccc cccaacgcct   2400
ccttaccagg agttagccca gctgctggcc cagccagaag tgggcctcat ccaccagtac   2460
tgccagggtt actggcgcca tgtgcccccc agccccaggg aggctccagg ggcaccccgg   2520
tctcctgagc cccaggacca gaaaaagccc cggaaccgcc ggcaccaccc tccggacaca   2580
```

```
tgaggccagc tgcctgtgcc tgccatgggc cagcctagcc cttgtccctt ttaatataaa   2640

agatatatat atatatatat atatataaaa tatctatatt ctatacacac cctgcccctg   2700

caaagacagt atttattggt gggttgaata tagcctgcct cagtggcagc atcctccaaa   2760

acttagaccc atgctggtca gagacggcag aaaacagagc ctgcctaacc aggcccagcc   2820

agttggtggg gccaggccag gaccacacag tccccagact cagctggaag tctacctgct   2880

ggacagcctc cgccaagatc tacaggacaa agggagggag caagccctac tcggatgggg   2940

cacggactgt ccaccttttc tgatgtgtgt tgtcagcctg tgctgtggca tagacatgga   3000

tgcgaggacc actttggaga ctggggtggc ctcaagagca cacagagaag ggaagaaggg   3060

gccatcacag gatgccagcc cctgcctggg ttgggggcac tcagccacga ccagcccctt   3120

cctgggtatt tattctctat ttattgggga taggagaaga ggcatcctgc ctgggtggga   3180

cagcctcttc agccccttct cccctccccg cctggccagg gcagggccac cccactctac   3240

ctccttagct ttccctgtgc cactttgact cagaggctgg gagcatagca gaggggccag   3300

gcccaggcag agctgacggg aggccccagc tctgagggga gggggtccgt ggtagaggcc   3360

tggggccggt agaggctccc cagggctccc ttatgtccac cacttcaggg gatgggtgtg   3420

gatgtaatta gctctggggg gcagttgggt agatgggtgg gggctcctgg tggccttctg   3480

ctgcccaggc cacagccgcc tttgggttcc atcttgctaa taaacactgg ctctgggact   3540

agaaaaaaaa aaaaaaaa                                                  3558
```

<210> SEQ ID NO 89
<211> LENGTH: 3274
<212> TYPE: DNA
<213> ORGANISM: Homo sapiens

<400> SEQUENCE: 89

```
cccgcgcggc tctgagcgcc ccgtcccgcc ggcggccgcg agaccagagc gagcgaacga     60

accgcggcgg tccggagagc cccgagcgca gcgcaggacc tgggaccacc tcccggccac    120

gccccgggtc cggctctcat tcaaagagct gaaggccaca ggcaccgccc acttcttcaa    180

cttcctgctc aacacaaccg actaccgaat cttgctcaag gacgaggacc acgaccgcat    240

gtacgtgggc agcaaggact acgtgctgtc cctggacctg cacgacatca accgcgagcc    300

cctcattata cactgggcag cctccccaca gcgcatcgag gaatgcgtgc tctcaggcaa    360

ggatgtcaac ggcgagtgtg ggaacttcgt caggctcatc cagccctgga accgaacaca    420

cctgtatgtg tgcgggacag gtgcctacaa ccccatgtgc acctatgtga accgcggacg    480

ccgcgcccag gattacatct tctacctgga gcctgagcga ctcgagtcag ggaagggcaa    540

gtgtccgtac gatcccaagc tggacacagc atcggccctc atcaatgagg agctctatgc    600

tggtgtgtac atcgatttta tgggcactga tgcagccatc ttccgcacac ttggaaagca    660

gacagccatg cgcacggatc agtacaactc ccggtggctg aacgacccgt cgttcatcca    720

tgctgagctc attcctgaca gtgcggagcg caatgatgat aagctttact tcttcttccg    780

tgagcggtcg gcagaggcgc cgcagagccc cgcggtgtac gcccgcatcg ggcgcatttg    840

cctgaacgat gacggtggtc actgttgcct ggtcaacaag tggagcacat tcctgaaggc    900

gcggctcgtc tgctctgtcc cgggcgagga tggcattgag actcactttg atgagctcca    960

ggacgtgttt gtccagcaga cccaggacgt gaggaaccct gtcatttacg ctgtctttac   1020

ctcctctggc tccgtgttcc gaggctctgc cgtgtgtgtc tactccatgg ctgatattcg   1080
```

```
catggtcttc aacgggccct ttgcccacaa agaggggccc aactaccagt ggatgccctt   1140

ctcagggaag atgccctacc cacggccggg cacgtgccct ggtggaacct tcacgccatc   1200

tatgaagtcc accaaggatt atcctgatga ggtgatcaac ttcatgcgca gccacccact   1260

catgtaccag gccgtgtacc ctctgcagcg gcggcccctg gtagtccgca caggtgctcc   1320

ctaccgcctt accactattg ccgtggacca ggtggatgca gccgacgggc gctatgaggt   1380

gcttttcctg ggcacagacc gcgggacagt gcagaaggtc attgtgctgc ccaaggatga   1440

ccaggagttg gaggagctca tgctggagga ggtggaggtc ttcaaggatc cagcacccgt   1500

caagaccatg accatctctt ctaagaggca acaactctac gtggcgtcag ccgtgggtgt   1560

cacacacctg agcctgcacc gctgccaggc gtatggggct gcctgtgctg actgctgcct   1620

tgcccgggac ccttactgtg cctgggatgg ccaggcctgc tcccgctata cagcatcctc   1680

caagaggcgg agccgccggc aggacgtccg gcacggaaac cccatcaggc agtgccgtgg   1740

gttcaactcc aatgccaaca agaatgccgt ggagtctgtg cagtatggcg tggccggcag   1800

cgcagccttc cttgagtgcc agccccgctc gccccaagcc actgttaagt ggctgttcca   1860

gcgagatcct ggtgaccggc gccgagagat tcgtgcagag gaccgcttcc tgcgcacaga   1920

gcagggcttg ttgctccgtg cactgcagct cagcgatcgt ggcctctact cctgcacagc   1980

cactgagaac aactttaagc acgtcgtcac acgagtgcag ctgcatgtac tgggccggga   2040

cgccgtccat gctgccctct tcccaccact gtccatgagc gccccgccac ccccaggcgc   2100

aggcccccca acgcctcctt accaggagtt agcccagctg ctggcccagc cagaagtggg   2160

cctcatccac cagtactgcc agggttactg gcgccatgtg ccccccagcc ccagggaggc   2220

tccaggggca ccccggtctc ctgagcccca ggaccagaaa aagccccgga accgccggca   2280

ccaccctccg gacacatgag gccagctgcc tgtgcctgcc atgggccagc ctagcccttg   2340

tcccttttaa tataaaagat atatatatat atatatatat ataaaatatc tatattctat   2400

acacaccctg cccctgcaaa gacagtattt attggtgggt tgaatatagc ctgcctcagt   2460

ggcagcatcc tccaaaactt agacccatgc tggtcagaga cggcagaaaa cagagcctgc   2520

ctaaccaggc ccagccagtt ggtggggcca ggccaggacc acacagtccc cagactcagc   2580

tggaagtcta cctgctggac agcctccgcc aagatctaca ggacaaaggg agggagcaag   2640

ccctactcgg atggggcacg gactgtccac cttttctgat gtgtgttgtc agcctgtgct   2700

gtggcataga catggatgcg aggaccactt tggagactgg ggtggcctca agagcacaca   2760

gagaagggaa gaaggggcca tcacaggatg ccagcccctg cctgggttgg gggcactcag   2820

ccacgaccag ccccttcctg ggtatttatt ctctatttat tggggatagg agaagaggca   2880

tcctgcctgg gtgggacagc ctcttcagcc ccttctcccc tccccgcctg gccagggcag   2940

ggccacccca ctctacctcc ttagctttcc ctgtgccact ttgactcaga ggctgggagc   3000

atagcagagg ggccaggccc aggcagagct gacgggaggc cccagctctg aggggagggg   3060

gtccgtggta gaggcctggg gccggtagag gctccccagg gctcccttat gtccaccact   3120

tcaggggatg ggtgtggatg taattagctc tggggggcag ttgggtagat gggtgggggc   3180

tcctggtggc cttctgctgc ccaggccaca gccgcctttg ggttccatct tgctaataaa   3240

cactggctct gggactagaa aaaaaaaaaa aaaa                              3274
```

<210> SEQ ID NO 90
<211> LENGTH: 2658
<212> TYPE: DNA
<213> ORGANISM: Homo sapiens

<400> SEQUENCE: 90

```
aataaatatc cgtgtagaaa atcagaacga ctctttcagg ccatctttaa aatgtcattg     60
gtaaaccata cttgatccta aattcctgta cttcctcagg ccatccgagc atgaaacgct    120
gtcacctacc cacatccgct ggctgtgacg cttgtcaaag tgttctctat cggctgcatg    180
cctagaccac caaagcgttc tgaccggaca gtgtcactgg agaaggcggc gcgacatgtc    240
cagggcgcag atctgggctc tggtgtctgg tgtcggaggg tttggagctc tcgttgctgc    300
taccacgtcc aatgagtgga aagtgaccac gcgagcctcc tcggtgataa cagccacttg    360
ggtttaccag ggtctgtgga tgaactgcgc aggtaacgcg ttgggttctt tccattgccg    420
accgcatttt actatcttca aagtagcagg ttatatacag gcatgtagag gacttatgat    480
cgctgctgtc agcctgggct tctttggttc catatttgcg ctctttggaa tgaagtgtac    540
caaagtcgga ggctccgata aagccaaagc taaaattgct tgtttggctg ggattgtatt    600
catactgtca gggctgtgct caatgactgg atgttcccta tatgcaaaca aaatcacaac    660
ggaattcttt gatcctctct ttgttgagca aaagtatgaa ttaggagccg ctctgtttat    720
tggatgggca ggagcctcac tgtgcataat tggtggtgtc atattttgct tttcaatatc    780
tgacaacaac aaaacaccca gatacacata caacggggcc acatctgtca tgtcttctcg    840
gacaaagtat catggtggag aagattttaa aacaacaaac ccttcaaaac agtttgataa    900
aaatgcttat gtctaaaaga gctcgctggc aagctgcctc ttgagtttgt tataaaagcg    960
aactgttcac aaaatgatcc catcaaggcc ctcccataat taacactcaa aactattttt   1020
aaaatatgca tttgaagcat ctgttgattg tatggatgta agtgttctta catagttagt   1080
tatatactaa tcattttctg ttgtggcttt ctataaaaaa taaacagttt atttacagga   1140
tttgtaaaat gttttctaca tttatataga acatgaaaag catttagtac caaaggttca   1200
agaagtattc gtactctagc ctttttaatc attcatagat agaagtcttt gtacccactc   1260
cttatgtttc ttttcattca taaacaggtg tataaggaac aatgtcttat aaacagcatg   1320
ggggcaatct gagaatattc ctcaaaaggt gtccaggtta aatagacatg ttactggctg   1380
cacacaggca aattctagtt tgtttttttt aagtattcta caacatttat ttaaaaaggt   1440
aaatcttttt gttgaagcag caagttatct ggtagaactt aacttctaca ggatcagaga   1500
ggatcttgct cattcatggc catatccaca tgcccatggc cactcagtag attgttgaaa   1560
aagcaaagcc acaccattct ctttgatgta tgcagagagt tacgtagcag ggatgttct    1620
ctgatttatt ccactggcac cattagtgaa tatttagttg ttttcataaa cgatgctgtg   1680
atgaagactc atgtacatat ttagcaaatt ttggtttctt acatgtgcct gtcatgactg   1740
taattcatta tgactgctcc aggaagggct aatggggcca atatattatt gcctgtcatg   1800
tggcacatcc atgttaaggg gctgaggcgt ccctggcacg gaatgcagag ccctgagcta   1860
gggcatcagc agaagctgag atagagatat tggtcatggt tgactgagga gccaattaaa   1920
acctgtttat gcctagtgtt ccattattgg aacactaagc atgtgggagt tatttatatc   1980
ctactgctca aggtcatcgc caaggtgtga ttggaaaaat tcaaaaaatt gcaacctcag   2040
gcataaatgg gttaaggaca tcccaagccc aagtggtacg tgcctcactc agaactgacg   2100
ggccgagttc tatctaggtg tgtcttccag aacctgttta cggctaactg gataactgag   2160
agacttgtca tttctaaaga catttaagtt gctccaggga tttctgaaaa aagacacagg   2220
cttcttccta gagccagccc tatataacat gcccacaagg gcaacagtta tcacagttca   2280
```

```
tacacacctt tcatgtcctg tctcactcac tcctcacagc catcctagga gatacatatt   2340

gttttcatcc tgcatttaca gaaaaagaaa tgaaaacaga gagcttaaat aatttgccac   2400

agtaatgtcg aaactaggcc tttgaaccaa ggcagtctag ggtaaaatat agtttcaaag   2460

tatgaataag aattggtatt tgtgttatct ttgagtaaga aactgtccga tatgaatcac   2520

aacgtgggtg aatgtagtat tttcctgaag tgtgaaagac ttaaaaaaaa gaatcacatt   2580

gttcagaggt gctcaatgga aagaaaagga aatgaacaag tttgttaaaa gataaaaaat   2640

aaaaaaaatt ccatacct                                                 2658
```

<210> SEQ ID NO 91
<211> LENGTH: 2490
<212> TYPE: DNA
<213> ORGANISM: Homo sapiens

<400> SEQUENCE: 91

```
gagtgcgggg gtcgcggcgc agagtgggag ccggagagcg agcgcggctg cagccggcgg     60

catggctagc acggcttcgg agatcatcgc cttcatggtc tccatctcag gctgggtact    120

ggtgtcctcc acgctgccca ccgactactg gaaggtgtct accatcgacg gcacggtcat    180

cacaaccgcc acctattggg ccaacctgtg gaaggcgtgc gttaccgact ccacgggcgt    240

ctccaactgc aaggacttcc cctccatgct ggcgctggac ggttatatac aggcatgtag    300

aggacttatg atcgctgctg tcagcctggg cttctttggt tccatatttg cgctctttgg    360

aatgaagtgt accaaagtcg gaggctccga taaagccaaa gctaaaattg cttgtttggc    420

tgggattgta ttcatactgt cagggctgtg ctcaatgact ggatgttccc tatatgcaaa    480

caaaatcaca acggaattct ttgatcctct ctttgttgag caaaagtatg aattaggagc    540

cgctctgttt attggatggg caggagcctc actgtgcata attggtggtg tcatattttg    600

cttttcaata tctgacaaca acaaaacacc cagatacaca tacaacgggg ccacatctgt    660

catgtcttct cggacaaagt atcatggtgg agaagatttt aaaacaacaa acccttcaaa    720

acagtttgat aaaaatgctt atgtctaaaa gagctcgctg gcaagctgcc tcttgagttt    780

gttataaaag cgaactgttc acaaaatgat cccatcaagg ccctcccata attaacactc    840

aaaactattt ttaaaatatg catttgaagc atctgttgat tgtatggatg taagtgttct    900

tacatagtta gttatatact aatcattttc tgttgtggct ttctataaaa aataaacagt    960

ttatttacag gatttgtaaa atgttttcta catttatata gaacatgaaa agcatttagt   1020

accaaaggtt caagaagtat tcgtactcta gcctttttaa tcattcatag atagaagtct   1080

ttgtacccac tccttatgtt tcttttcatt cataaacagg tgtataagga acaatgtctt   1140

ataaacagca tgggggcaat ctgagaatat tcctcaaaag gtgtccaggt taaatagaca   1200

tgttactggc tgcacacagg caaattctag tttgtttttt ttaagtattc tacaacattt   1260

atttaaaaag gtaaatcttt ttgttgaagc agcaagttat ctggtagaac ttaacttcta   1320

caggatcaga gaggatcttg ctcattcatg gccatatcca catgcccatg gccactcagt   1380

agattgttga aaaagcaaag ccacaccatt ctctttgatg tatgcagaga gttacgtagc   1440

aggggatgtt ctctgattta ttccactggc accattagtg aatatttagt tgttttcata   1500

aacgatgctg tgatgaagac tcatgtacat atttagcaaa ttttggtttc ttacatgtgc   1560

ctgtcatgac tgtaattcat tatgactgct ccaggaaggg ctaatggggc caatatatta   1620

ttgcctgtca tgtggcacat ccatgttaag ggctgaggc gtccctggca cggaatgcag    1680

agccctgagc tagggcatca gcagaagctg agatagagat attggtcatg gttgactgag   1740
```

```
gagccaatta aaacctgttt atgcctagtg ttccattatt ggaacactaa gcatgtggga   1800

gttatttata tcctactgct caaggtcatc gccaaggtgt gattggaaaa attcaaaaaa   1860

ttgcaacctc aggcataaat gggttaagga catcccaagc ccaagtggta cgtgcctcac   1920

tcagaactga cgggccgagt tctatctagg tgtgtcttcc agaacctgtt tacggctaac   1980

tggataactg agagacttgt catttctaaa gacatttaag ttgctccagg gatttctgaa   2040

aaaagacaca ggcttcttcc tagagccagc cctatataac atgcccacaa gggcaacagt   2100

tatcacagtt catacacacc tttcatgtcc tgtctcactc actcctcaca gccatcctag   2160

gagatacata ttgttttcat cctgcattta cagaaaaaga aatgaaaaca gagagcttaa   2220

ataatttgcc acagtaatgt cgaaactagg cctttgaacc aaggcagtct agggtaaaat   2280

atagtttcaa agtatgaata agaattggta tttgtgttat ctttgagtaa gaaactgtcc   2340

gatatgaatc acaacgtggg tgaatgtagt attttcctga agtgtgaaag acttaaaaaa   2400

aagaatcaca ttgttcagag gtgctcaatg gaaagaaaag gaaatgaaca agtttgttaa   2460

aagataaaaa ataaaaaaaa ttccatacct                                    2490
```

<210> SEQ ID NO 92
<211> LENGTH: 2424
<212> TYPE: DNA
<213> ORGANISM: Homo sapiens

<400> SEQUENCE: 92

```
gttccccgcg tgccaccagg aagctcgggc cggccaagag cgtagactct tgagaggagt     60

gagacaggtg cgcgccagcc ggccttcggg gctttatggg aactgggccg tgcggcggtc    120

ccgccctcgt gcgcaggcgc agaaccgttg tgaccagagc ggttgcgggc tgagcggttt    180

cgagccggcg tcggggagcg gcggtaccgg gcggctgcgg ggctggctcg acccagcttg    240

aggtctcggc gtccgcgtcc tgcggtgccc tggggtctcc cgaggacctt gtacccgcgc    300

ggcttccttg ggctggcttt ggacgacgct ttcgccttcc tgctgcctag gatccgccga    360

catgaatccc atcgtagtgg tccacggcgg cggagccggt cccatctcca aggatcggaa    420

ggagcgagtg caccagggca tggtcagagc cgccaccgtg ggctacggca tcctccggga    480

gggcgggagc gccgtggatg ccgtagaggg agctgtcgtc gccctggaag acgatcccga    540

gttcaacgca ggttgtgggt ctgtcttgaa cacaaatggt gaggttgaaa tggatgctag    600

tatcatggat ggaaaagacc tgtctgcagg agcagtgtcc gcagtccagt gtatagcaaa    660

tcccattaaa cttgctcggc ttgtcatgga aaagacacct cattgctttc tgactgacca    720

aggcgcagcg cagtttgcag cagctatggg ggttccagag attcctggag aaaaactggt    780

gacagagaga aacaaaaagc gcctggaaaa agagaagcat gaaaaaggtg ctcagaaaac    840

agattgtcaa aaaaacttgg gaaccgtggg tgctgttgcc ttggactgca aagggaatgt    900

agcctacgca acctccacag gcggtatcgt taataaaatg gtcggccgcg ttggggactc    960

accgtgtcta ggagctggag gttatgccga caatgacatc ggagccgtct caaccacagg   1020

gcatggggaa agcatcctga aggtgaacct ggctagactc accctgttcc acatagaaca   1080

aggaaagacg gtagaagagg ctgcggacct atcgttgggt tatatgaagt caagggttaa   1140

aggtttaggt ggcctcatcg tggttagcaa aacaggagac tgggtggcaa agtggacctc   1200

cacctccatg ccctgggcag ccgccaagga cggcaagctg cacttcggaa ttgatcctga   1260

cgatactact atcaccgacc ttccctaagc cgctggaaga ttgtattcca gatgctagct   1320
```

tagaggtcaa gtacagtctc ctcatgagac atagcctaat caattagatc tagaattgga 1380
aaaattgtcc cgtctgtcac ttgttttgtt gccttaataa gcatctgaat gtttggttgt 1440
ggggcgggtt ctgaagcgat gagagaaatg cccgtattag gaggattact tgagcccagg 1500
aggtcaaagc tgaggtgagc catgattact ccactgcact ccagcctggg caacagagcc 1560
aggccctgta tcaaaaaaaa aaaaaaaaag aaaagggaaa aaagaaagaa agcagcagca 1620
tgatcctgac atgacagatg tgggagaccc acagcctgca gacactgtgg gctggaaggt 1680
gggaagggag gggccggtgg aggtggagct gtttgaaagt gacacagcag cagtagaagc 1740
agtggtgggc gaagcccagg tgaccctcag aacgttgcac aagaacatca gggaaaagaa 1800
ccagaatcct ttaaggaaaa tgttcttcat gtatgagaga ctaaagtgat tttctaaga 1860 aagttcagcc cttctctgac ttacctggac atttctagat acttccaaag gaccctctgg 1920
gaatccatag cttcctaatc tggagatggg aggtcataag ggagacgctg tggggttcct 1980
tgaagtttct tgggttcaca gaggagcccc ctcacttggt gttctcccgt gagccagcct 2040
ccacctgcca aagacactct ggtcctcgta tagtgagtaa tggggctcag ggcctctcca 2100
acaacagaga ggagctgatg ctgtagggct gaccccgtga cttcctgagt cctcaccctg 2160
tccagtgctt tgagattctt cccacctccc catcctcacc agccggatcg ggcgctgtgc 2220
agtgtggtca gcatggtgaa gaaagtcatt tcctcggtgg gcagtattcc tctttatctc 2280
tcattacact ggaaatgtta tttctgctgt atcatccgtg ctcaacgttt tagtctgtca 2340
ggctcacctt ctctctggaa agaatttgct taacttgaca ttccatgtgc cgctaataaa 2400
atatattttg aaagaataaa aaaa 2424

<210> SEQ ID NO 93
<211> LENGTH: 2347
<212> TYPE: DNA
<213> ORGANISM: Homo sapiens

<400> SEQUENCE: 93
gttccccgcg tgccaccagg aagctcgggc cggccaagag cgtagactct tgagaggagt 60
gagacaggtg cgcgccagcc ggccttcggg gctttatggg aactgggccg tgcggcggtc 120
ccgccctcgt gcgcaggcgc agaaccgttg tgaccagagc ggttgcgggc tgagcggttt 180
cgagccggcg tcggggagcg gcggtaccgg gcggctgcgg ggctggctcg acccagcttg 240
aggtctcggc gtccgcgtcc tgcggtgccc tgggatccgc cgacatgaat cccatcgtag 300
tggtccacgg cggcggagcc ggtcccatct ccaaggatcg gaaggagcga gtgcaccagg 360
gcatggtcag agccgccacc gtgggctacg gcatcctccg ggagggcggg agcgccgtgg 420
atgccgtaga gggagctgtc gtcgccctgg aagacgatcc cgagttcaac gcaggttgtg 480
ggtctgtctt gaacacaaat ggtgaggttg aaatggatgc tagtatcatg gatggaaaag 540
acctgtctgc aggagcagtg tccgcagtcc agtgtatagc aaatcccatt aaacttgctc 600
ggcttgtcat ggaaaagaca cctcattgct ttctgactga ccaaggcgca gcgcagtttg 660
cagcagctat gggggttcca gagattcctg gagaaaaact ggtgacagag agaaacaaaa 720
agcgcctgga aaaagagaag catgaaaaag gtgctcagaa aacagattgt caaaaaaact 780
tgggaaccgt gggtgctgtt gccttggact gcaaagggaa tgtagcctac gcaacctcca 840
caggcggtat cgttaataaa atggtcggcc gcgttgggga ctcaccgtgt ctaggagctg 900
gaggttatgc cgacaatgac atcggagccg tctcaaccac agggcatggg gaaagcatcc 960
tgaaggtgaa cctggctaga ctcaccctgt tccacataga acaaggaaag acggtagaag 1020

```
aggctgcgga cctatcgttg ggttatatga agtcaagggt taaaggttta ggtggcctca   1080

tcgtggttag caaaacagga gactgggtgg caaagtggac ctccacctcc atgccctggg   1140

cagccgccaa ggacggcaag ctgcacttcg gaattgatcc tgacgatact actatcaccg   1200

accttcccta agccgctgga agattgtatt ccagatgcta gcttagaggt caagtacagt   1260

ctcctcatga gacatagcct aatcaattag atctagaatt ggaaaaattg tcccgtctgt   1320

cacttgtttt gttgccttaa taagcatctg aatgtttggt tgtggggcgg gttctgaagc   1380

gatgagagaa atgcccgtat taggaggatt acttgagccc aggaggtcaa agctgaggtg   1440

agccatgatt actccactgc actccagcct gggcaacaga gccaggccct gtatcaaaaa   1500

aaaaaaaaaa aagaaaaggg aaaaaagaaa gaaagcagca gcatgatcct gacatgacag   1560

atgtgggaga cccacagcct gcagacactg tgggctggaa ggtgggaagg gaggggccgg   1620

tggaggtgga gctgtttgaa agtgacacag cagcagtaga agcagtggtg ggcgaagccc   1680

aggtgaccct cagaacgttg cacaagaaca tcagggaaaa gaaccagaat cctttaagga   1740

aaatgttctt catgtatgag agactaaagt gatttttcta agaaagttca gcccttctct   1800

gacttacctg gacatttcta gatacttcca aaggaccctc tgggaatcca tagcttccta   1860

atctggagat gggaggtcat aagggagacg ctgtggggtt ccttgaagtt tcttgggttc   1920

acagaggagc cccctcactt ggtgttctcc cgtgagccag cctccacctg ccaaagacac   1980

tctggtcctc gtatagtgag taatggggct cagggcctct ccaacaacag agaggagctg   2040

atgctgtagg gctgaccccg tgacttcctg agtcctcacc ctgtccagtg ctttgagatt   2100

cttcccacct ccccatcctc accagccgga tcgggcgctg tgcagtgtgg tcagcatggt   2160

gaagaaagtc atttcctcgg tgggcagtat tcctctttat ctctcattac actggaaatg   2220

ttatttctgc tgtatcatcc gtgctcaacg ttttagtctg tcaggctcac cttctctctg   2280

gaaagaattt gcttaacttg acattccatg tgccgctaat aaaatatatt ttgaaagaat   2340

aaaaaaa                                                             2347
```

<210> SEQ ID NO 94
<211> LENGTH: 2205
<212> TYPE: DNA
<213> ORGANISM: Homo sapiens

<400> SEQUENCE: 94

```
tcccctggac ccgcccccat ctgcccaaga taattttagt ttccttgggc ctggaatctg     60

gacacacagg gctccccccc gcctctgact tctctgtccg aagtcgggac accctcctac    120

cacctgtaga gaagcgggag tggatctgaa ataaaatcca ggaatctggg ggttcctaga    180

cggagccaga cttcggaacg ggtgtcctgc tactcctgct ggggctcctc caggacaagg    240

gcacacaact ggttccgtta agcccctctc ttgctcagac gccatggagc tggatctgtc    300

tccacctcat cttagcagct ctccggaaga cctttgccca gcccctggga cccctcctgg    360

gactccccgg ccccctgata cccctctgcc tgaggaggta aagaggtccc agcctctcct    420

catcccaacc accggcagga aacttcgaga ggaggagagg cgtgccacct ccctcccctc    480

tatccccaac cccttccctg agctctgcag tcctccctca cagagcccaa ttctcggggg    540

cccctccagt gcaagggggc tgctcccccg cgatgccagc cgcccccatg tagtaaaggt    600

gtacagtgag gatggggcct gcaggtctgt ggaggtggca gcaggtgcca cagctcgcca    660

cgtgtgtgaa atgctggtgc agcgagctca cgccttgagc gacgagacct gggggctggt    720
```

```
ggagtgccac ccccacctag cactggagcg gggtttggag gaccacgagt ccgtggtgga    780

agtgcaggct gcctggcccg tgggcggaga tagccgcttc gtcttccgga aaaacttcgc    840

caagtacgaa ctgttcaaga gctccccaca ctccctgttc ccagaaaaaa tggtctccag    900

ctgtctcgat gcacacactg gtatatccca tgaagacctc atccagaact tcctgaatgc    960

tggcagcttt cctgagatcc agggctttct gcagctgcgg ggttcaggac ggaagctttg   1020

gaaacgcttt ttctgcttct tgcgccgatc tggcctctat tactccacca agggcacctc   1080

taaggatccg aggcacctgc agtacgtggc agatgtgaac gagtccaacg tgtacgtggt   1140

gacgcagggc cgcaagctct acgggatgcc cactgacttc ggtttctgtg tcaagcccaa   1200

caagcttcga aatggccaca aggggcttcg gatcttctgc agtgaagatg agcagagccg   1260

cacctgctgg ctggctgcct tccgcctctt caagtacggg gtgcagctgt acaagaatta   1320

ccagcaggca cagtctcgcc atctgcatcc atcttgtttg ggctccccac ccttgagaag   1380

tgcctcagat aataccctgg tggccatgga cttctctggc catgctgggc gtgtcattga   1440

gaacccccgg gaggctctga gtgtggccct ggaggaggcc caggcctgga ggaagaagac   1500

aaaccaccgc ctcagcctgc ccatgccagc ctccggcacg agcctcagtg cagcctgttc   1560

ctggtccggg agagtcagcg gaacccccag ggctttgtcc tctctttgtg ccacctgcag   1620

aaagtgaagc attatctcat cctgccgagc gaggaggagg gccgcctgta cttcagcatg   1680

gatgatggcc agacccgctt cactgacctg ctgcagctcg tggagttcca ccagctgaac   1740

cgcggcatcc tgccgtgctt gctgcgccat tgctgcacgc gggtggccct ctgaccaggc   1800

cgtggactgg ctcatgcctc agcccgcctt caggctgccc gccgcccctc cacccatcca   1860

gtggactctg gggcgcggcc acaggggacg ggatgaggag cgggagggtt ccgccactcc   1920

agttttctcc tctgcttctt tgcctccctc agatagaaaa cagcccccac tccagtccac   1980

tcctgacccc tctcctcaag ggaaggcctt gggtggcccc ctctccttct cctagctctg   2040

gaggtgctgc tctagggcag ggaattatgg gagaagtggg ggcagcccag gcggtttcac   2100

gccccacact ttgtacagac cgagaggcca gttgatctgc tctgttttat actagtgaca   2160

ataaagatta ttttttgata caaaaaaaaa aaaaaaaaaa aaaaa                   2205
```

<210> SEQ ID NO 95
<211> LENGTH: 1210
<212> TYPE: DNA
<213> ORGANISM: Homo sapiens

<400> SEQUENCE: 95

```
ctctcccttc tccactctct ccccctgtct cctttcttct tcttctttca ccctccgtct     60

ctcacacccc ctccattccc ctgtctcctt tctgacactg cactgcagct gctcctcagc    120

cctgccccct ccccagtgag aacaaaccag caacattgct ttttttccta aagagattta    180

tattgatccg attaaaaaaa aaaaacctta agaaacccca aacgcaaaaa aaaaaaaaaa    240

aaaaaaagaa aaaagaaaag aaaaagccaa aacaaaaggg agaaccttct cccggtagca    300

gcggcaggaa ctgcaaacat gatggcggca gctcccatcc agcagaacgg gacccacact    360

ggggttccca tagacctgga cccgccggac tcgcggaaaa ggccgctgga agcccccccct    420

gaagccggca gcaccaagag gaccaatacg ggcgaagacg gccagtattt tctaaaggtt    480

ctcataccta gttatgctgc tggatctata attgggaagg gaggacagac aattgttcag    540

ttgcaaaaag aaactggagc caccatcaag ctgtctaagt ccaaagattt ttacccaggt    600

actactgagc gagtgtgctt gatccaggga acggttgaag cactgaatgc agttcatgga    660
```

-continued

```
ttcattgcag aaaaaattcg agaaatgccc caaaatgtgg ccaagacaga accagtcagc     720

attctacaac cccagaccac cgttaatcca gatcgcatca aacaaacatt gccatcttcc     780

ccaactacca ccaagtcctc tccatctgat cccatgacca cctccagagc taatcagaag     840

cataatatct cctggatatc atgaagcaag atataagaga agaacaaaac aaaatccgta     900

attcattgaa agaattgtaa tcatcaatct ttcatattat taatactttg taattatttt     960

ctccccaaca gtattttcca gtagattcta atcatgtggt agggcagaag gaaatgtgtt    1020

ttttgttgtt catttgtttc ttgtcaatag tcctgattaa tttagctttg ctatactgac    1080

ttatatctgg aagtatataa ccaagataag aaaataggtt ttaatatgat catcttaagc    1140

taattgtaat gaaaagaact aatggactgt caatattcag aaaaccaaaa ataaaaaata    1200

cagaaaacta                                                           1210
```

METHODS FOR DETECTING EXPRESSION OF LNC-FANCI-2 IN CERVICAL CELLS

STATEMENT REGARDING FEDERALLY SPONSORED RESEARCH & DEVELOPMENT

This invention was made in part with government support from the National Institutes of Health. The government has certain rights in this invention.

FIELD OF THE DISCLOSURE

The present disclosure is related to novel polynucleotide biomarkers which can be detected and can be used for the diagnosis of HPV-associated pre-cancers and HPV-associated cancers such as cervical cancer and cervical intraepithelial neoplasia as well as methods of treatment of HPV-associated pre-cancers and HPV-associated cancers.

BACKGROUND

High-risk HPV persistent infection leads to the development of certain types of cancers in the cervix, anus, and oropharynx, for example. Fifteen mucosal HPV types are identified as oncogenic or high-risk (HR) HPVs, with HPV16 and HPV18 being particularly associated with invasive cervical cancer. Cervical cancer is the second most common cancer among women worldwide. Approximately 500,000 incident cases of cervical cancer and approximately 320,000 cervical cancer deaths are estimated each year and more than 80% of the cases arise in developing countries.

There is a need for diagnostic markers that can be detected and used for early diagnosis of high-risk HPV infection, HPV-associated pre-cancer and HPV-associated cancer and for the development of intervention strategies for treatment of HPV-induced cancers.

SUMMARY

In one aspect, a method of determining if a test patient has stage 1, stage 2, or stage 3 cervical intraepithelial neoplasia or cervical cancer comprises determining an expression level of a first polynucleotide biomarker in a sample containing cells from the test patient's cervix with one or more first polynucleotides that hybridizes to the first polynucleotide biomarker, wherein the first polynucleotide biomarker is lnc-FANCI-2, lnc-GLB1L2-1, GRB7 (SEQ ID NOs: 8-11 and 94), NOVA1 (SEQ ID NOs: 14, 15 and 95), RNASEH2A (SEQ ID NO: 19), CDKN2A (SEQ ID NOs: 1-4), ELAVL2 (SEQ ID NOs: 5-7), HSPB1 (SEQ ID NO: 12), KHSRP (SEQ ID NO: 13), PTBP1 (SEQ ID NOs: 16-18), or a combination thereof, correlating the expression level of the first polynucleotide biomarker in the sample containing cells from the test patient's cervix to a reference expression level of the first polynucleotide biomarker in a reference sample, wherein the reference sample is

- a control sample from a patient or patients with no evidence of cervical cancer,
- a control sample from a cervical cancer patient or patients, or
- a control sample from a patient or patients with stage 1, stage 2, or stage 3 cervical intraepithelial neoplasia, and determining, based on said correlation, if the test patient has cervical cancer, or stage 1, stage 2, or stage 3 cervical intraepithelial neoplasia.

In another aspect, the method of determining if a test patient has stage 1, stage 2, or stage 3 cervical intraepithelial neoplasia or cervical cancer comprises determining an expression level of a first polynucleotide biomarker in a sample containing cells from the test patient's cervix with one or more first polynucleotides that hybridizes to the first polynucleotide biomarker, wherein the first polynucleotide biomarker is GRB7 (SEQ ID NOs: 8-11 and 84), NOVA1 (SEQ ID NOs: 14, 15 and 95), RNASEH2A (SEQ ID NO: 19), or a combination thereof, and/or determining an expression level of a second polynucleotide biomarker in the sample containing cells from the test patient's cervix with one or more second polynucleotides that hybridizes to the second polynucleotide biomarker, wherein the second polynucleotide biomarker is lnc-FANCI-2, lnc-GLB1L2-1, or a combination thereof.

In a further aspect, a method of quantitating an expression level of a first polynucleotide biomarker in a sample containing cells from a test patient's cervix with one or more first polynucleotides that hybridizes to the first polynucleotide biomarker comprises contacting the sample containing cells from test patient's cervix with the one or more first polynucleotides, and detecting the level of hybridization of the one or more first polynucleotides to the first polynucleotide biomarker, wherein the first polynucleotide biomarker is lnc-FANCI-2, lnc-GLB1L2-1, GRB7 (SEQ ID NOs: 8-11 and 94), NOVA1 (SEQ ID NOs: 14, 15 and 95), RNASEH2A (SEQ ID NO: 19), CDKN2A (SEQ ID NOs: 1-4), ELAVL2 (SEQ ID NOs: 5-7), HSPB1 (SEQ ID NO: 12), KHSRP (SEQ ID NO: 13), PTBP1 (SEQ ID NOs: 16-18), or a combination thereof.

In a yet further aspect, a method of treating a test patient in need of treatment for stage 1, stage 2, or stage 3 cervical intraepithelial neoplasia or cervical cancer comprises determining an expression level of a first polynucleotide biomarker in a sample containing cells from the test patient's cervix with one or more first polynucleotides that hybridizes to the first polynucleotide biomarker, wherein the first polynucleotide biomarker is lnc-FANCI-2, lnc-GLB1L2-1, GRB7 (SEQ ID NOs: 8-11 and 94), NOVA1 (SEQ ID NOs: 14, 15 and 95), RNASEH2A (SEQ ID NO: 19), CDKN2A (SEQ ID NOs: 1-4), ELAVL2 (SEQ ID NOs: 5-7), HSPB1 (SEQ ID NO: 12), KHSRP (SEQ ID NO: 13), PTBP1 (SEQ ID NOs: 16-18), or a combination thereof, correlating the expression level of the first polynucleotide biomarker in the sample containing cells from the test patient's cervix to a reference expression level of the first polynucleotide biomarker in a reference sample, wherein the reference sample is

- a control sample from a patient or patients with no evidence of cervical cancer,
- a control sample from a cervical cancer patient or patients, or
- a control sample from a patient or patients with stage 1, stage 2, or stage 3 cervical intraepithelial neoplasia, and administering a therapeutic intervention for the treatment of stage 1, stage 2, or stage 3 cervical intraepithelial neoplasia, or cervical cancer when it is determined, based on said expression levels, that the test patient has stage 1, stage 2, or stage 3 cervical intraepithelial neoplasia.

In a still further aspect, a method of determining if a test patient has an HPV-associated pre-cancer or an HPV-associated cancer comprises determining an expression level of a first polynucleotide biomarker in a sample containing cells from a tissue of the test patient with one or more first polynucleotides that hybridizes to the first polynucleotide biomarker, correlating the expression level of the first polynucleotide biomarker in the sample containing cells from the tissue of the test patient to a reference expression level of the first polynucleotide biomarker in a reference sample, wherein the reference sample is

- a control sample from a patient or patients with no evidence of HPV-associated pre-cancer or HPV-associated cancer,
- a control sample from a patient or patients with HPV-associated pre-cancer, or
- a control sample from a patient or patients with HPV-associated cancer, and determining, based on said correlation, if the test patient has HPV-associated pre-cancer or HPV-associated cancer, wherein the first polynucleotide biomarker is lnc-FANCI-2, lnc-GLB1L2-1, GRB7 (SEQ ID NOs: 8-11 and 94), NOVA1 (SEQ ID NOs: 14, 15 and 95), RNASEH2A (SEQ ID NO: 19), CDKN2A (SEQ ID NOs: 1-4), ELAVL2 (SEQ ID NOs: 5-7), HSPB1 (SEQ ID NO: 12), KHSRP (SEQ ID NO: 13), PTBP1 (SEQ ID NOs: 16-18), or a combination thereof.

In another aspect, a method of quantitating an expression level of a first polynucleotide biomarker in a sample containing cells from a tissue of the test patient with one or more first polynucleotides that hybridizes to the first polynucleotide biomarker comprises contacting the sample containing cells from a tissue of the test patient with the one or more first polynucleotides, and detecting the level of hybridization of the one or more first polynucleotides to the first polynucleotide biomarker, wherein the first polynucleotide biomarker lnc-FANCI-2, lnc-GLB1L2-1, is GRB7 (SEQ ID NOs: 8-11 and 94), NOVA1 (SEQ ID NOs: 14, 15 and 95), RNASEH2A (SEQ ID NO: 19), CDKN2A (SEQ ID NOs: 1-4), ELAVL2 (SEQ ID NOs: 5-7), HSPB1 (SEQ ID NO: 12), KHSRP (SEQ ID NO: 13), PTBP1 (SEQ ID NOs: 16-18), or a combination thereof.

In a yet further aspect, a method of treating a test patient in need of treatment for an HPV-associated pre-cancer or an HPV-associated cancer comprises determining an expression level of a first polynucleotide biomarker in a sample containing cells from a tissue of the test patient with one or more first polynucleotides that hybridizes to the first polynucleotide biomarker, correlating the expression level of the first polynucleotide biomarker in the sample containing cells from the tissue of the test patient to a reference expression level of the first polynucleotide biomarker in a reference sample, wherein the reference sample is

- a control sample from a patient or patients with no evidence of HPV-associated pre-cancer or HPV-associated cancer,
- a control sample from a patient or patients with HPV-associated pre-cancer, or
- a control sample from a patient or patients with HPV-associated cancer, and administering a therapeutic intervention for the treatment of HPV-associated pre-cancer or HPV-associated cancer when it is determined, based on said expression levels, that the test patient has HPV-associated pre-cancer or an HPV-associated cancer, wherein the first polynucleotide biomarker is lnc-FANCI-2, lnc-GLB1L2-1, GRB7 (SEQ ID NOs: 8-11 and 94), NOVA1 (SEQ ID NOs: 14, 15 and 95), RNASEH2A (SEQ ID NO: 19), CDKN2A (SEQ ID NOs: 1-4), ELAVL2 (SEQ ID NOs: 5-7), HSPB1 (SEQ ID NO: 12), KHSRP (SEQ ID NO: 13), PTBP1 (SEQ ID NOs: 16-18), or a combination thereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Figure 1:
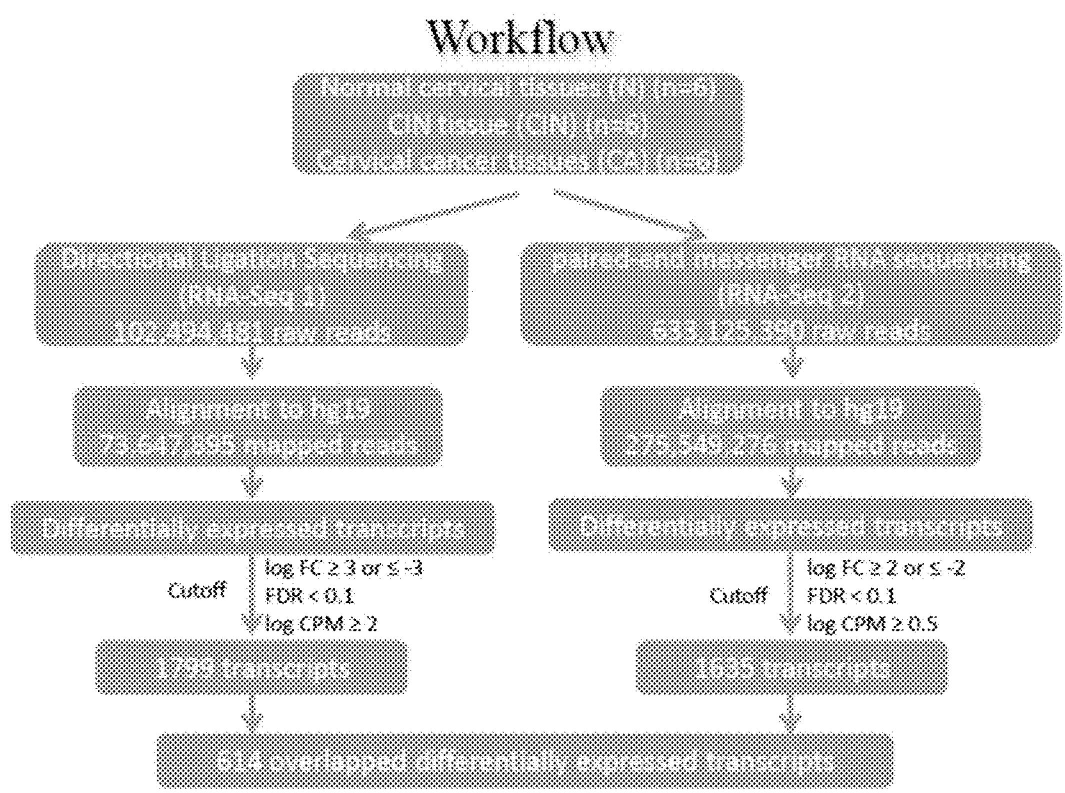
FIG. 1 is a flowchart of the RNA-sequencing (RNA-Seq) analyses for RNA-binding proteins (RBPs).

The above-described and other features will be appreciated and understood by those skilled in the art from the following detailed description, drawings, and appended claims.

DETAILED DESCRIPTION

Using an RNA-sequencing (RNA-Seq) approach, the inventors of the present application examined seven normal cervical tissues and seven cervical cancer tissues for their expression landscapes of approximately 19,000 coding and 113,513 noncoding RNAs. 614 differentially expressed coding transcripts enriched in cancer related pathways were identified, with 95 of them encoding RNA-binding proteins (RBPs) from the analyzed 1502 human RBPs. Moreover, 209 differentially, abundantly expressed long-noncoding RNAs (lnc-RNAs) from normal cervix to cervical cancer were identified. Validation of the altered expression of 26 candidates, including 8 RBP genes by using TaqMan® real-time PCR in a cohort of 47 human cervical tissue samples, including 24 normal cervical tissues and 23 cervical cancer tissues, showed that they are broadly involved in cervical carcinogenesis. Many of the identified RBP candidates had not been previously reported. Using human vaginal keratinocyte-derived raft culture tissues with or without HPV16 and HPV18 infection, it was further corroborated that these RBP candidates, including CDKN2A, ELAVL2, GRB7, HSPB1, KHSRP, PTBP1, RNASEH2A, and NOVA1, are regulated by HPV infection. Further, the inventors found that lnc-FANCI-2 was increasingly expressed along with cervical lesion progression from cervical intraepithelial neoplasia (CIN) to cervical cancer, when compared to the normal tissues. In contrast, lncGLB1L2-1 was gradually decreased along with the lesion progression, when compared to the normal tissues. In addition, FAM83A, SEMA3F, CLDN10, ASRGL1, which are not RBPs, were also found to have altered expression in cervical cancer compared to normal tissue, with FAM83A and SEMA3F being increased in cervical cancer and CLDN10 and ASRGL1 being decreased in cervical cancer. The results presented herein provide the first comprehensive expression atlas of RBPs and lnc-RNAs in normal cervix and cervical cancer, which can be detected to provide better diagnosis and treatment of patients with cervical cancer.

More specifically, an increase of lnc-FANCI-2 RNA, including all of its 35 isoforms, and a decrease of lnc-GLB1L2-1, including its 21 isoforms, were identified in cervical cancer. Fanconi anemia (FA) frequently develops squamous cell carcinoma at sites that are associated with HPV-driven cancer including the female reproductive tract, and is caused by mutations in one of 15 genes in the FA pathway (including FANCA, FANCD2, and FANCI). Loss of FA pathway components FANCA and FANCD2 stimulates E7 protein accumulation in human keratinocytes, and loss of FANCD2 stimulates HPV DNA replication. Both FANCI and lnc-FANCI-2 are expressed from the same location at chromosome 15q26.1. Further, both GLB1L2 (galactosidase, beta 1-like 2) and lnc-GLB1L2-1 are expressed from Chromosome 11q25, with unknown function in cancer development. By using TaqMan® qRT-PCR validation of lnc-FANCI-2 and lnc-GLB1L2-1 in 24 normal, 25 CIN 2-3, and 23 cervical cancer tissues, it was confirmed that altered expression of these lnc-RNAs is remarkably related to cervical lesion progression from CIN to cancer. Moreover, the altered changes of lnc-FANCI-2 could be attributed to HPV16 and HPV18 infection in raft cultures and viral E7 expression. These lnc-RNAs are biomarkers for early diagnosis of high-risk HPV infection with high risk of progression and for development of intervention strategies to treat HPV-induced cancers.

As used herein, a non-coding RNA (ncRNA) is an RNA transcript that does not encode a protein. ncRNAs include short ncRNAs and long ncRNAs (lnc-RNAs). Short ncRNAs are ncRNAs that are generally 18-200 nucleotides (nt) in length. Examples of short ncRNAs include, but are not limited to, microRNAs (miRNAs), piwi-associated RNAs (piRNAs), short interfering RNAs (siRNAs), promoter-associated short RNAs (PASRs), transcription initiation RNAs (tiRNAs), termini-associated short RNAs (TASRs), antisense termini associated short RNAs (aTASRs), small nucleolar RNAs (snoRNAs), transcription start site antisense RNAs (TSSa-RNAs), small nuclear RNAs (snRNAs), retroposon-derived RNAs (RE-RNAs), 3'UTR-derived RNAs (uaRNAs), x-ncRNA, human Y RNA (hY RNA), unusually small RNAs (usRNAs), small NF90-associated RNAs (snaRs), vault RNAs (vtRNAs), small Cajal body-specific RNAs (scaRNAs), and telomere specific small RNAs (tel-sRNAs). lnc-RNAs are cellular RNAs, exclusive of rRNAs, greater than 200 nucleotides in length and having no obvious protein-coding capacity. Lnc-RNAs include, but are not limited to, large or long intergenic ncRNAs (lincRNAs), transcribed ultraconserved regions (T-UCRs), pseudogenes, GAA-repeat containing RNAs (GRC-RNAs), long intronic ncRNAs, antisense RNAs (aRNAs), promoter-associated long RNAs (PALRs), promoter upstream transcripts (PROMPTs), and long stress-induced non-coding transcripts (LSINCTs).

An RNA-binding protein is a protein that binds single or double stranded RNA to form ribonucleoprotein complexes. RBPs contain conserved structural motifs such as the RNA recognition motif (RRM), dsRNA binding domain, zinc finger domain, and others.

The biomarkers for detection and diagnosis of CIN and cervical cancer include the RBP and lnc-RNA biomarkers of Tables 1-3:

TABLE 1

| RBP biomarkers | | | | | | |
|---|---|---|---|---|---|---|
| SEQ ID NO: | chr | start | end | refseqID | Symbol | description |
| 1 | chr9 | 21967750 | 21975132 | NM_000077 | CDKN2A | cyclin-dependent kinase inhibitor 2A (CDKN2A), transcript variant 1, mRNA. |

TABLE 1-continued

| RBP biomarkers | | | | | | |
|---|---|---|---|---|---|---|
| SEQ ID NO: | chr | start | end | refseqID | Symbol | description |
| 2 | chr9 | 21967750 | 21975132 | NM_001195132 | CDKN2A | *Homo sapiens* cyclin-dependent kinase inhibitor 2A (CDKN2A), transcript variant 5, mRNA. |
| 3 | chr9 | 21967750 | 21994490 | NM_058195 | CDKN2A | cyclin-dependent kinase inhibitor 2A (CDKN2A), transcript variant 4, mRNA. |
| 4 | chr9 | 21967750 | 21974826 | NM_058197 | CDKN2A | cyclin-dependent kinase inhibitor 2A (CDKN2A), transcript variant 3, mRNA. |
| 5 | chr9 | 23690102 | 23821843 | NM_001171195 | ELAVL2 | *Homo sapiens* ELAV (embryonic lethal, abnormal vision, *Drosophila*)-like 2 (Hu antigen B) (ELAVL2), transcript variant 2, mRNA. |
| 6 | chr9 | 23690102 | 23821478 | NM_001171197 | ELAVL2 | *Homo sapiens* ELAV (embryonic lethal, abnormal vision, *Drosophila*)-like 2 (Hu antigen B) (ELAVL2), transcript variant 3, mRNA. |
| 7 | chr9 | 23690102 | 23826063 | NM_004432 | ELAVL2 | ELAV (embryonic lethal, abnormal vision, *Drosophila*)-like 2 (Hu antigen B) (ELAVL2), transcript variant 1, mRNA. |
| 8 | chr17 | 37894575 | 37903538 | NM_001030002 | GRB7 | growth factor receptor-bound protein 7 (GRB7), transcript variant 2, mRNA. |
| 9 | chr17 | 37895023 | 37903538 | NM_001242442 | GRB7 | *Homo sapiens* growth factor receptor-bound protein 7 (GRB7), transcript variant 4, mRNA. |
| 10 | chr17 | 37896219 | 37903538 | NM_001242443 | GRB7 | *Homo sapiens* growth factor receptor-bound protein 7 (GRB7), transcript variant 3, mRNA. |
| 11 | chr17 | 37894161 | 37903538 | NM_005310 | GRB7 | growth factor receptor-bound protein 7 (GRB7), transcript variant 1, mRNA. |
| 94 | chr17 | | | NM_001330207.1 | GRB7 | growth factor receptor-bound protein 7 (GRB7), transcript variant 5, mRNA. |
| 12 | chr7 | 75931874 | 75933614 | NM_001540 | HSPB1 | heat shock 27 kDa protein 1 (HSPB1), mRNA. |
| 13 | chr19 | 6413118 | 6424822 | NM_003685 | KHSRP | KH-type splicing regulatory protein (KHSRP), mRNA. |
| 14 | chr14 | 26915088 | 27066960 | NM_002515 | NOVA1 | neuro-oncological ventral antigen 1 (NOVA1), transcript variant 1, mRNA. |
| 15 | chr14 | 26915088 | 27066960 | NM_006489 | NOVA1 | neuro-oncological ventral antigen 1 (NOVA1), transcript variant 2, mRNA. |
| 95 | chr14 | | | NM_006491.2 | NOVA1 | neuro-oncological ventral antigen 1 (NOVA1), transcript variant 3, mRNA. |
| 16 | chr19 | 797391 | 812327 | NM_002819 | PTBP1 | polypyrimidine tract binding protein 1 (PTBP1), transcript variant 1, mRNA. |
| 17 | chr19 | 797391 | 812327 | NM_031990 | PTBP1 | polypyrimidine tract binding protein 1 (PTBP1), transcript variant 2, mRNA. |
| 18 | chr19 | 797391 | 812327 | NM_031991 | PTBP1 | polypyrimidine tract binding protein 1 (PTBP1), transcript variant 3, mRNA. |
| 19 | chr19 | 12917427 | 12924462 | NM_006397 | RNASEH2A | ribonuclease H2, subunit A (RNASEH2A), mRNA. |

TABLE 2

| lnc-FANCI-2 isoforms | | | |
|---|---|---|---|
| Transcript ID | SEQ ID NO: | Location (hg19) | Length |
| lnc-FANCI-2: 1 | 20 | chr15: 89904810-89938553 | 1613 |
| lnc-FANCI-2: 10 | 21 | chr15: 89921280-89938544 | 606 |
| lnc-FANCI-2: 11 | 22 | chr15: 89921331-89938354 | 551 |
| lnc-FANCI-2: 12 | 23 | chr15: 89921347-89939471 | 1877 |

TABLE 2-continued

| lnc-FANCI-2 isoforms | | | |
|---|---|---|---|
| Transcript ID | SEQ ID NO: | Location (hg19) | Length |
| lnc-FANCI-2: 13 | 24 | chr15: 89921362-89938500 | 561 |
| lnc-FANCI-2: 14 | 25 | chr15: 89921794-89931745 | 786 |
| lnc-FANCI-2: 15 | 26 | chr15: 89922355-89938350 | 569 |
| lnc-FANCI-2: 16 | 27 | chr15: 89922468-89941720 | 3779 |

TABLE 2-continued

| lnc-FANCI-2 isoforms | | | |
|---|---|---|---|
| Transcript ID | SEQ ID NO: | Location (hg19) | Length |
| lnc-FANCI-2: 17 | 28 | chr15: 89922495-89941719 | 3670 |
| lnc-FANCI-2: 18 | 29 | chr15: 89923111-89941720 | 3784 |
| lnc-FANCI-2: 19 | 30 | chr15: 89925731-89938271 | 779 |
| lnc-FANCI-2: 2 | 31 | chr15: 89904810-89938551 | 1611 |
| lnc-FANCI-2: 20 | 32 | chr15: 89929827-89939471 | 2718 |
| lnc-FANCI-2: 21 | 33 | chr15: 89930671-89941720 | 3723 |
| lnc-FANCI-2: 22 | 34 | chr15: 89904810-89941718 | 4778 |
| lnc-FANCI-2: 23 | 35 | chr15: 89911330-89941718 | 4113 |
| lnc-FANCI-2: 24 | 36 | chr15: 89911399-89941721 | 3936 |
| lnc-FANCI-2: 25 | 37 | chr15: 89912393-89941683 | 4026 |
| lnc-FANCI-2: 26 | 38 | chr15: 89921102-89941708 | 4334 |
| lnc-FANCI-2: 27 | 39 | chr15: 89921273-89941718 | 3868 |
| lnc-FANCI-2: 28 | 40 | chr15: 89922232-89941683 | 3978 |
| lnc-FANCI-2: 29 | 41 | chr15: 89923021-89941683 | 3837 |
| lnc-FANCI-2: 3 | 42 | chr15: 89905705-89922463 | 571 |
| lnc-FANCI-2: 30 | 43 | chr15: 89929880-89941721 | 4915 |
| lnc-FANCI-2: 31 | 44 | chr15: 89930027-89941721 | 4687 |
| lnc-FANCI-2: 32 | 45 | chr15: 89930389-89931372 | 706 |
| lnc-FANCI-2: 33 | 46 | chr15: 89930557-89941683 | 3922 |
| lnc-FANCI-2: 34 | 47 | chr15: 89931724-89941721 | 3690 |
| lnc-FANCI-2: 35 | 48 | chr15: 89932071-89941708 | 4093 |
| lnc-FANCI-2: 4 | 49 | chr15: 89905718-89938562 | 957 |
| lnc-FANCI-2: 5 | 50 | chr15: 89911330-89941718 | 2124 |
| lnc-FANCI-2: 6 | 51 | chr15: 89912386-89931074 | 576 |
| lnc-FANCI-2: 7 | 52 | chr15: 89918593-89941720 | 6547 |
| lnc-FANCI-2: 8 | 53 | chr15: 89921220-89941692 | 3814 |
| lnc-FANCI-2: 9 | 54 | chr15: 89921273-89941718 | 4198 |

TABLE 3

| lnc-GLB1L2-1 isoforms | | | |
|---|---|---|---|
| Transcript ID | SEQ ID NO: | Location (hg19) | Length |
| lnc-GLB1L2-1: 1 | 55 | chr11: 134306367-134337169 | 1402 bp |
| lnc-GLB1L2-1: 10 | 56 | chr11: 134350719-134372941 | 295 bp |
| lnc-GLB1L2-1: 11 | 57 | chr11: 134352524-134373110 | 374 bp |
| lnc-GLB1L2-1: 12 | 58 | chr11: 134306376-134375555 | 2737 bp |
| lnc-GLB1L2-1: 13 | 59 | chr11: 134339378-134360125 | 15706 bp |
| lnc-GLB1L2-1: 14 | 60 | chr11: 134339400-134373384 | 744 bp |
| lnc-GLB1L2-1: 15 | 61 | chr11: 134339400-134375553 | 1129 bp |
| lnc-GLB1L2-1: 16 | 62 | chr11: 134343291-134373078 | 1843 bp |
| lnc-GLB1L2-1: 17 | 63 | chr11: 134344051-134375009 | 1160 bp |
| lnc-GLB1L2-1: 18 | 64 | chr11: 134346572-134375009 | 572 bp |
| lnc-GLB1L2-1: 19 | 65 | chr11: 134349193-134375555 | 4435 bp |
| lnc-GLB1L2-1: 2 | 66 | chr11: 134306469-134308558 | 374 bp |
| lnc-GLB1L2-1: 20 | 67 | chr11: 134349983-134375009 | 1245 bp |
| lnc-GLB1L2-1: 21 | 68 | chr11: 134350411-134401542 | 537 bp |
| lnc-GLB1L2-1: 3 | 69 | chr11: 134306629-134374934 | 1863 bp |
| lnc-GLB1L2-1: 4 | 70 | chr11: 134336079-134357809 | 3679 bp |
| lnc-GLB1L2-1: 5 | 71 | chr11: 134336079-134357809 | 3620 bp |
| lnc-GLB1L2-1: 6 | 72 | chr11: 134344060-134350796 | 720 bp |
| lnc-GLB1L2-1: 7 | 73 | chr11: 134349193-134375507 | 4387 bp |
| lnc-GLB1L2-1: 8 | 74 | chr11: 134349731-134352843 | 1398 bp |
| lnc-GLB1L2-1: 9 | 75 | chr11: 134350086-134367700 | 939 bp |

In additional aspects, the biomarker includes FAM83A (SEQ ID NO: 86; KJ895067.1), SEMA3F (SEQ ID NOs: 87-89; NM_004186.4; NM_001318800.1; NM_001318798.1), CLDN10 (SEQ ID NO: 90-91; NM_182848.3; NM_006984.4), ASRGL1 (SEQ ID NO: 92, 93; NM_001083926.1; NM_025080.3), or a combination thereof.

An RBP, lnc-RNA, or additional RNA biomarker is differentially expressed between two samples if the amount of the RBP, lnc-RNA, or additional RNA biomarker in one sample is statistically significantly different from the amount of the RBP, lnc-RNA, or additional RNA biomarker in the other sample. The expression level of an RBP, lnc-RNA, or additional RNA biomarker can be increased or decreased in a test sample relative to a reference sample. For example, an RBP gene, lnc-RNA, or additional RNA biomarker is differentially expressed in two samples if it is present at least about 120%, at least about 130%, at least about 150%, at least about 180%, at least about 200%, at least about 300%, at least about 500%, at least about 700%, at least about 900%, or at least about 1000% greater than it is present in the other sample, or if it is detectable in one sample and not detectable in the other.

Alternatively or additionally, an RBP gene, lnc-RNA, or additional RNA biomarker is differentially expressed in two sets of samples if the frequency of detecting the RBP gene, lnc-RNA, or additional RNA biomarker in samples is statistically significantly higher or lower than in the control samples. For example, an RBP gene, lnc-RNA, or additional RNA biomarker is differentially expressed in two sets of samples if it is detected at least about 120%, at least about 130%, at least about 150%, at least about 180%, at least about 200%, at least about 300%, at least about 500%, at least about 700%, at least about 900%, or at least about 1000% more frequently or less frequently observed in one set of samples than the other set of samples.

A test amount and a control amount of a biomarker can be either an absolute amount (e.g., number of copies/ml, nanogram/ml or microgram/ml) or a relative amount (e.g., relative intensity of signals).

Diagnostic samples for use in the methods described herein comprise nucleic acids suitable for providing polynucleotide, e.g., RNA, expression information. The sample contains cells from a tissue of the test patient. For example, when the HPV-associated pre-cancer or HPV-associated cancer is anal cancer, the tissue of the test patient contains anal cells; when the HPV-associated pre-cancer or HPV-associated cancer is vulvovaginal cancer, the tissue of the test patient contains vulvovaginal cells; when the HPV-associated pre-cancer or HPV-associated cancer is penile cancer, the tissue of the test patient contains penal cells; or when the HPV-associated pre-cancer or HPV-associated cancer is oropharyngeal cancer, the tissue of the test patient contains oropharyngeal cells.

In one aspect, samples for the methods disclosed herein contain cells from a patient's cervix. Exemplary test samples include a PAP smear, a vaginal wash, or a cervical biopsy sample. In certain aspects, the methods described herein include obtaining from the test patient the sample containing cells from the test patient's cervix.

In certain aspects, the test patient is a patient at risk for an HPV-associated pre-cancer or an HPV-associated cancer, such as a patient diagnosed with HPV infection or a patient at high risk for HPV infection.

In certain aspects, the test patient is a patient at high risk for cervical cancer such as a woman at high risk for HPV infection, a woman with a diagnosed HPV infection, a woman with a history of DES exposure, a woman with a previous history of gynecological cancer, a woman with an abnormal PAP test, a woman immunosuppressed due to AIDS or therapy following organ transplantation, or a woman with abnormal endometrial cells.

In certain aspects, the methods disclosed herein comprise detecting the expression level of one or more biomarkers as disclosed herein.

In addition, the methods disclosed herein include the comparison/correlation of the expression levels of biomarkers in the diagnostic sample from the test patient to a reference sample. Exemplary reference samples include a control sample from a patient or patients with no evidence of HPV-associated pre-cancer or HPV-associated cancer, a control sample from a patient or patients with HPV-associated pre-cancer, and a control sample from a patient or patients with HPV-associated cancer. Additional exemplary reference samples include a control sample from a patient or patients with no evidence of cervical cancer, a control sample from a cervical cancer patient or patients, or a control sample from a patient or patients with stage 1, stage 2, or stage 3 cervical intraepithelial neoplasia. The reference sample can be a single sample from a control patient with a known disease state, or preferably samples from a plurality of subjects such that the reference expression level is averaged over the expression levels for a population of known disease state. Useful population sizes for a reference population are greater than 100 subjects, specifically about 500 subjects for each reference group (CIN 1, 2, 3 and cervical cancer), for example.

RNA can be extracted and purified from biological samples using suitable techniques that are known in the art, and several are commercially available (e.g., FormaPure® nucleic acid extraction kit, Agencourt® Biosciences, Beverly Mass., High Pure FFPE RNA Micro Kit, Roche Applied Science, Indianapolis, Ind.). RNA can be extracted from frozen tissue sections using TRIzol® (Invitrogen, Carlsbad, Calif.) and purified using RNeasy® Protect kit (Qiagen, Valencia, Calif.). RNA can be further purified using DNase I treatment (Ambion, Austin, Tex.) to eliminate any contaminating DNA. RNA concentrations can be made using a NanoDrop ND-1000 spectrophotometer (NanoDdrop Technologies, Rockland, Del.). RNA can be further purified to eliminate contaminants that interfere with cDNA synthesis by cold sodium acetate precipitation. RNA integrity can be evaluated by running electropherograms, and RNA integrity number (RIN, a correlative measure that indicates intactness of mRNA) can be determined using the RNA 6000 PicoAssay for the Bioanalyzer 2100 (Agilent Technologies, Santa Clara, Calif.).

Following sample collection and nucleic acid extraction, the nucleic acid portion of the sample comprising RNA that is or can be used to prepare the target polynucleotide(s) of interest can be subjected to one or more preparative reactions. These preparative reactions can include in vitro transcription (IVT), labeling, fragmentation, amplification, and other reactions. mRNA can first be treated with reverse transcriptase and a primer to create cDNA prior to detection, quantitation, or amplification; this can be done in vitro with purified mRNA or in situ, e.g., in cells or tissues affixed to a slide.

By "amplification" is meant a process of producing at least one copy of a nucleic acid, in this case an expressed RNA, and in many cases produces multiple copies. An amplification product can be RNA or DNA, and may include a complementary strand to the expressed target sequence. DNA amplification products can be produced initially through reverse transcription and then optionally from further amplification reactions. The amplification product may include all or a portion of a target sequence, and may optionally be labeled. A variety of amplification methods are suitable for use, including polymerase-based methods and ligation-based methods.

The expression level of a polynucleotide biomarker can be determined by reverse transcriptase-polymerase chain reaction (RT-PCR) methods, quantitative real-time RT-PCR (RT-qPCR), microarray, serial analysis of gene expression (SAGE), next-generation RNA sequencing (deep sequencing), gene expression analysis by massively parallel signature sequencing (MPSS), immunoassays such as ELISA, in situ hybridization (ISH) formulations that allow histopathological analysis, mass spectrometry (MS) methods, transcriptomics, RNA pull-down and chromatin isolation by RNA purification (ChiRP), proteomics-based identification of lncRNA, detection of single nucleotide polymorphisms (SNPs), measurement of DNA methylation or unmethylation, measurement of siRNA silencing or miRNA silencing, or measurement of downstream targets.

As used herein, the terms "quantitative real time polymerase chain reaction," "real-time polymerase chain reaction," and "qPCR" are synonymous and refer to a laboratory technique based on a polymerase chain reaction used to amplify and simultaneously quantify a targeted DNA molecule. Frequently, real-time PCR is combined with reverse transcription to quantify messenger RNA and non-coding RNA in cells or tissues, e.g., RT-qPCR.

Additional methods for detecting and/or quantifying a polynucleotide biomarker can comprise single-molecule sequencing (e.g., Illumina®, PacBio, ABI SOLID™), in situ hybridization, bead-array technologies (e.g., Luminex xMAP®, Illumina® BeadChips), branched DNA technology (e.g., Affymetrix®, Genisphere®), and Ion Torrent™. In some instances, methods for detecting and/or quantifying a target sequence comprise transcriptome sequencing techniques. Transcription sequencing (e.g., RNA-seq, "Whole Transcriptome Shotgun Sequencing" (WTSS)) may comprise the use of high-throughput sequencing technologies to sequence cDNA in order to get information about a sample's RNA content. Transcriptome sequencing can provide information on differential expression of genes, including gene alleles and differently spliced transcripts, non-coding RNAs, post-transcriptional mutations or editing, and gene fusions.

Included herein is a method for measuring the expression levels of biomarkers for HPV-associated pre-cancers and cancers as described herein. The methods optionally include identifying HPV-associated pre-cancer or cancer status of a test subject (e.g., cervical cancer). The data obtained from the expression profiles of a population (e.g., normal, CIN1-3, or cervical cancer) can be evaluated using one or more pattern recognition algorithms. In addition, the results of imaging tests or histological evaluation may optionally be combined with expression profiles generated using the genes disclosed herein.

In one aspect, the methods include comparing (correlating) the expression level of the first polynucleotide biomarker in the sample containing cells from a tissue of the test patient to a reference expression level of the first polynucleotide biomarker in a reference sample, wherein the reference sample is a control sample from a patient or patients with no evidence of HPV-associated pre-cancer or HPV-associated cancer, a control sample from a patient or patients with HPV-associated pre-cancer, or a control sample from a patient or patients with HPV-associated cancer, and determining, based on said correlation, if the test patient has HPV-associated pre-cancer or HPV-associated cancer In another aspect, the methods comprise predicting (or determining), based on the expression level of one or more polynucleotide biomarkers in the containing cells from a tissue of the test patient and a reference expression level of the one or more polynucleotide biomarkers in a reference sample that the patient has no HPV-associated pre-cancer or cancer, that the test patient has HPV-associated pre-cancer, or that the patient has HPV-associated cancer, wherein the reference sample is a control sample from a patient or patients with no evidence of HPV-associated pre-cancer or HPV-associated cancer, a control sample from a patient or patients with HPV-associated pre-cancer, or a control sample from a patient or patients with HPV-associated cancer.

In a further aspect, the methods include classifying the patient as having no cervical cancer or cervical intraepithelial neoplasia, or as having HPV-associated pre-cancer or cancer based on the expression level of one or more polynucleotide biomarkers in the sample containing cells from a tissue of the test patient and a reference expression level of the one or more polynucleotide biomarkers in a reference sample, wherein the reference sample is a control sample from a patient or patients with no evidence of HPV-associated pre-cancer or HPV-associated cancer, a control sample from a patient or patients with HPV-associated pre-cancer, or a control sample from a patient or patients with HPV-associated cancer.

In one aspect, the methods include comparing (or correlating) the expression level of one or more polynucleotide biomarkers in the sample containing cells from the test patient's cervix to a reference expression level of the one or more polynucleotide biomarkers in a reference sample, wherein the reference sample is a control sample from a patient or patients with no evidence of cervical cancer, a control sample from a cervical cancer patient or patients, or a control sample from a patient or patients with stage 1, stage 2, or stage 3 cervical intraepithelial neoplasia, and determining, based on said comparison, if the test patient has cervical cancer, or stage 1, stage 2, or stage 3 cervical intraepithelial neoplasia.

In another aspect, the methods comprise predicting (or determining), based on the expression level of one or more polynucleotide biomarkers in the sample containing cells from the test patient's cervix and a reference expression level of the one or more polynucleotide biomarkers in a reference sample that the patient has no cervical cancer or cervical intraepithelial neoplasia, that the test patient has cervical cancer, or that the patient has stage 1, stage 2, or stage 3 cervical intraepithelial neoplasia, wherein the reference sample is a control sample from a patient or patients with no evidence of cervical cancer, a control sample from a cervical cancer patient or patients, or a control sample from a patient or patients with stage 1, stage 2, or stage 3 cervical intraepithelial neoplasia.

In a further aspect, the methods include classifying the patient as having no cervical cancer or cervical intraepithelial neoplasia, as having cervical cancer, or as having stage 1, stage 2, or stage 3 cervical intraepithelial neoplasia based on the expression level of one or more polynucleotide biomarkers in the sample containing cells from the test patient's cervix and a reference expression level of the one or more polynucleotide biomarkers in a reference sample, wherein the reference sample is a control sample from a patient or patients with no evidence of cervical cancer, a control sample from a cervical cancer patient or patients, or a control sample from a patient or patients with stage 1, stage 2, or stage 3 cervical intraepithelial neoplasia.

Analysis methods may be used to form a predictive model, and then the predictive model may be used to classify test data. For example, one convenient and particularly effective method of classification employs multivariate statistical analysis modeling, first to form a model (a "predictive mathematical model") using data ("modeling data") from samples of known class (e.g., from subjects known to have, or not have, a particular grade of CIN or cervical cancer), and second to classify an unknown sample (e.g., "test data"), according to HPV-associated (e.g., cervical) cancer status.

Pattern recognition (PR) is the use of multivariate statistics, both parametric and non-parametric, to analyze spectroscopic data, and hence to classify samples and to predict the value of some dependent variable based on a range of observed measurements. There are two main approaches. One set of methods is termed "unsupervised" and these simply reduce data complexity in a rational way and also produce display plots which can be interpreted by the human eye. The other approach is termed "supervised" whereby a training set of samples with known class or outcome is used to produce a mathematical model and is then evaluated with independent validation data sets.

Unsupervised PR methods are used to analyze data without reference to any other independent knowledge. Examples of unsupervised pattern recognition methods include principal component analysis (PCA), hierarchical cluster analysis (HCA), and non-linear mapping (NLM).

Alternatively, and in order to develop automatic classification methods, it has proved efficient to use a "supervised" approach to data analysis. Here, a "training set" of biomarker expression data is used to construct a statistical model that predicts correctly the "class" of each sample. This training set is then tested with independent data (referred to as a test or validation set) to determine the robustness of the computer-based model. These models are sometimes termed "expert systems," but may be based on a range of different mathematical procedures. Supervised methods can use a data set with reduced dimensionality (for example, the first few principal components), but typically use unreduced data, with all dimensionality. In all cases the methods allow the quantitative description of the multivariate boundaries that characterize and separate each class, for example, each class of cervical cancer in terms of its biomarker expression profile. It is also possible to obtain confidence limits on any predictions, for example, a level of probability to be placed on the goodness of fit. The robustness of the predictive models can also be checked using cross-validation, by leaving out selected samples from the analysis.

It is often useful to pre-process data, for example, by addressing missing data, translation, scaling, weighting, etc. Multivariate projection methods, such as principal component analysis (PCA) and partial least squares analysis (PLS), are so-called scaling sensitive methods. By using prior knowledge and experience about the type of data studied, the quality of the data prior to multivariate modeling can be enhanced by scaling and/or weighting. Adequate scaling and/or weighting can reveal important and interesting variation hidden within the data, and therefore make subsequent multivariate modeling more efficient. Scaling and weighting may be used to place the data in the correct metric, based on knowledge and experience of the studied system, and therefore reveal patterns already inherently present in the data.

The methods described herein may be implemented and/or the results recorded using a device capable of implementing the methods and/or recording the results. Examples of devices that may be used include but are not limited to electronic computational devices, including computers of all types. When the methods described herein are implemented and/or recorded in a computer, the computer program that may be used to configure the computer to carry out the steps of the methods may be contained in any computer readable medium capable of containing the computer program. Examples of computer readable medium that may be used include but are not limited to diskettes, CD-ROMs, DVDs, ROM, RAM, and other memory and computer storage devices. The computer program that may be used to configure the computer to carry out the steps of the methods and/or record the results may also be provided over an electronic network, for example, over the internet, an intranet, or other network.

The process of comparing a measured value and a reference value can be carried out in a convenient manner appropriate to the type of measured value and reference value for the discriminative gene at issue. "Measuring" can be performed using quantitative or qualitative measurement techniques, and the mode of comparing a measured value and a reference value can vary depending on the measurement technology employed. For example, when a qualitative colorimetric assay is used to measure expression levels, the levels may be compared by visually comparing the intensity of the colored reaction product, or by comparing data from densitometric or spectrometric measurements of the colored reaction product (e.g., comparing numerical data or graphical data, such as bar charts, derived from the measuring device). However, it is expected that the measured values used in the methods will most commonly be quantitative values. In other examples, measured values are qualitative. As with qualitative measurements, the comparison can be made by inspecting the numerical data, or by inspecting representations of the data (e.g., inspecting graphical representations such as bar or line graphs).

The process of comparing may be manual (such as visual inspection by the practitioner of the method) or it may be automated. For example, an assay device (such as a luminometer for measuring chemiluminescent signals) may include circuitry and software enabling it to compare a measured value with a reference value for a biomarker. Alternately, a separate device (e.g., a digital computer) may be used to compare the measured value(s) and the reference value(s). Automated devices for comparison may include stored reference values for the biomarker(s) being measured, or they may compare the measured value(s) with reference values that are derived from contemporaneously measured reference samples (e.g., samples from control subjects).

As will be apparent to those of skill in the art, when replicate measurements are taken, the measured value that is compared with the reference value is a value that takes into account the replicate measurements. The replicate measurements may be taken into account by using either the mean or median of the measured values as the "measured value."

When it has been determined that the test patient has HPV-pre-cancer or cancer, the methods optionally include HPV detection and or typing.

When it has been determined that the test patient has CIN 1, 2, or 3 cervical cancer, the methods optionally include HPV detection and or typing, for example, using the Cobas® HPV test marketed by Roche Diagnostics.

Also included herein are methods of treating the test patient with an interventional strategy for HPV-associated pre-cancer or cancer.

Interventional therapies for anal, vulvovaginal, penile, and oropharyngeal cancer include radiation therapy, surgery, and chemotherapy.

Further included herein are methods of treating the test patient with an interventional strategy for CIN or cervical cancer. When the patient is determined to have stage 1 CIN, the interventional strategy may include screening for further cervical changes, screening the patient for HPV infection, HPV typing, or a combination thereof. Exemplary tests for the detection of HPV infection include detection of HPV infection via DNA/RNA amplification with PCR using, for example, the Cobas® HPV test marketed by Roche Diagnostics. Advantageously, early identification of CIN 1 optionally coupled with determining the HPV infection type will provide critical information regarding the type of intervention required to treat the patient. Early diagnosis and treatment at stage CIN 1 could prevent or slow progression to later disease stages.

When the patient is determined to have stage 2 or stage 3 CIN, interventional strategies may include, in addition to monitoring, cryosurgery to freeze abnormal cells, laser therapy to remove abnormal tissue, loop electrosurgical procedure excision, surgery to remove abnormal tissue, or hysterectomy. At early stages, for example, low cost outpatient procedures such as loop electrosurgical excision are 90-95% effective. Thus, a benefit to the methods disclosed herein is the ability to use minor surgical intervention before CIN progresses to cervical cancer.

Interventional strategies for the treatment of cervical cancer include surgery, radiation therapy, chemotherapy, targeted therapy, or a combination thereof. Surgery involves removal of the cancer and may include conization to remove tissue from the cervix and/or cervical canal or hysterectomy such as total, radical, modified radical hysterectomy. Radiation therapy includes internal and external radiation therapy in addition to intensity-modulated radiation therapy. Chemotherapy involves the use of drugs to inhibit the growth of cancer calls and can involve systemic or regional chemotherapy. Drugs approved for the treatment of cervical cancer include bleomycin, cisplatin, topotecan hydrochloride, and gemcitabine-cisplatin. Targeted therapy involves the use of drugs that identify and attack specific cancer cells without harming normal cells. Targeted therapy includes antibody therapy such as bevacizumab therapy.

Further disclosed herein, is a probe set for diagnosing, predicting, and/or monitoring cervical cancer in a subject. The probe set comprises a plurality of polynucleotide probes capable of detecting an expression level of at least one biomarker for CIN or cervical cancer, wherein the expression level determines the CIN or cervical cancer status of the subject.

In one aspect, a probe set comprises one or more polynucleotides that hybridizes to a first polynucleotide biomarker, wherein the first polynucleotide biomarker is GRB7 (SEQ ID NOs: 8-11), NOVA1 (SEQ ID Nos: 14 and 15), RNASEH2A (SEQ ID NO: 19), or a combination thereof, and one or more polynucleotides that hybridizes to a second polynucleotide biomarker, wherein the second polynucleotide biomarker is lnc-FANCI-2, lnc-GLB1L2-1, or a combination thereof.

In certain aspects, the probe set is attached to a solid support, and/or each member of the probe set comprises a detectable moiety.

One skilled in the art understands that the nucleotide sequence of the polynucleotide probe need not be identical to its target sequence in order to specifically hybridize thereto. The polynucleotide probes, therefore, comprise a nucleotide sequence that is at least about 65%, 70%, 75%, 80%, 85%, 90%, 95%, or more identical to a region of the coding target or non-coding target. Methods of determining sequence identity are known in the art and can be determined, for example, by using the BLASTN program of the University of Wisconsin Computer Group (GCG) software or provided on the NCBI website. The nucleotide sequence of the polynucleotide probes may exhibit variability by differing (e.g. by nucleotide substitution, including transition or transversion) at one, two, three, four or more nucleotides from the sequence of the coding target or non-coding target.

Primers/probes based on the nucleotide sequences of target sequences can be used in amplification of the target sequences. For use in amplification reactions such as PCR, a pair of primers can be used. The exact composition of the primer sequences is selected so that the primers hybridize to specific sequences of the probe set under stringent conditions, particularly under conditions of high stringency. The pairs of primers are usually chosen so as to generate an amplification product of at least about 50 nucleotides, more usually at least about 100 nucleotides. Algorithms for the selection of primer sequences are generally known, and are available in commercial software packages. These primers may be used in standard quantitative or qualitative PCR-based assays to assess transcript expression levels of RNAs defined by the probe set. Alternatively, these primers may be used in combination with probes, such as molecular beacons in amplifications using real-time PCR.

The polynucleotide probes or primers can incorporate moieties useful in detection, isolation, purification, or immobilization, if desired. Such moieties are detectable labels, such as radioisotopes, fluorophores, chemiluminophores, enzymes, colloidal particles, and fluorescent microparticles, as well as antigens, antibodies, haptens, avidin/streptavidin, biotin, haptens, enzyme cofactors/substrates, enzymes, and the like. A label can optionally be attached to or incorporated into a probe or primer polynucleotide to allow detection and/or quantitation of a target polynucleotide representing the target sequence of interest.

In some embodiments, one or more polynucleotide probes/primers provided herein can be provided on a substrate. The substrate can comprise a wide range of material, either biological, nonbiological, organic, inorganic, or a combination of any of these. For example, the substrate may be a polymerized Langmuir Blodgett film, functionalized glass, Si, Ge, GaAs, GaP, $SiO_2$, $SiN_4$, modified silicon, or any one of a wide variety of gels or polymers such as (poly)tetrafluoroethylene, (poly)vinylidenedifluoride, polystyrene, cross-linked polystyrene, polyacrylic, polylactic acid, polyglycolic acid, poly(lactide coglycolide), polyanhydrides, poly(methyl methacrylate), poly(ethylene-co-vinyl acetate), polysiloxanes, polymeric silica, latexes, dextran polymers, epoxies, polycarbonates, or combinations thereof. Conducting polymers and photoconductive materials can be used.

Substrates can be planar crystalline substrates such as silica based substrates (e.g., glass, quartz, or the like), or crystalline substrates used in, e.g., the semiconductor and microprocessor industries, such as silicon, gallium arsenide, indium doped GaN and the like, and include semiconductor nanocrystals.

The substrate can take the form of an array, a photodiode, an optoelectronic sensor such as an optoelectronic semiconductor chip or optoelectronic thin-film semiconductor, or a biochip. The location(s) of probe(s) on the substrate can be addressable; this can be done in highly dense formats, and the location(s) can be microaddressable or nanoaddressable.

The substrate can be a plate, slide, bead, pellet, disk, particle, microparticle, nanoparticle, strand, precipitate, optionally porous gel, sheets, tube, sphere, capillary, film, chip, multiwell plate or dish, optical fiber, etc. The substrate can be a form that is rigid or semi-rigid. The substrate may contain raised or depressed regions on which an assay component is located. The surface of the substrate can be etched using known techniques to provide for desired surface features, for example trenches, v-grooves, mesa structures, or the like.

Surfaces on the substrate can be composed of the same material as the substrate or can be made from a different material, and can be coupled to the substrate by chemical or physical means. Such coupled surfaces may be composed of any of a wide variety of materials, for example, polymers, plastics, resins, polysaccharides, silica or silica-based materials, carbon, metals, inorganic glasses, membranes, or any of the above-listed substrate materials. The surface can be optically transparent and can have surface Si—OH functionalities, such as those found on silica surfaces.

The substrate and/or its optional surface can be chosen to provide appropriate characteristics for the synthetic and/or detection methods used. The substrate and/or surface can be transparent to allow the exposure of the substrate by light applied from multiple directions. The substrate and/or its surface is generally resistant to, or is treated to resist, the conditions to which it is to be exposed in use, and can be optionally treated to remove any resistant material after exposure to such conditions.

The substrate or a region thereof may be encoded so that the identity of the sensor located in the substrate or region being queried may be determined. A suitable coding scheme can be used, for example optical codes, RFID tags, magnetic codes, physical codes, fluorescent codes, and combinations of codes.

The invention is further illustrated by the following non-limiting examples.

EXAMPLES

Materials and Methods

Human patient samples: Samples for RNA sequencing, containing 7 normal cervical tissues, 7 pre-cancer tissues and 7 cervical cancer tissues, and samples for validation, including 24 normal cervical tissues, 25 CIN 2-3 tissues, and 23 cervical cancer tissues, were all collected from the Women's Hospital, School of Medicine, Zhejiang University. All the human samples were used in accordance with the Institutional Review Board procedures of the hospital. Informed consent was obtained from each participant prior to the study. Samples were snap-frozen and stored at −80° C. until use.

RNA isolation: RNA was isolated from each human tissue sample by TRIzol® (Invitrogen, CA, USA) according to the instructions provided by the manufacturer. Total RNA quality and quantity were verified spectrophotometrically (NanoDrop ND-1000 spectrometer; Thermo Scientific, DE, USA) and electrophoretically (Bioanalyzer 2100; Agilent Technologies, CA, USA).

RNA sequencing and mapping: RNA-seq libraries were prepared using TruSeq® Stranded Total RNA Sample Preparation Kit with Ribo-Zero™ depletion and sequenced on an Illumina® HiSeq™-2500 platform as paired-end reads. In brief, high-quality of human total RNA (1 μg) was Ribo-Zero™ depleted, fragmented, and then reverse transcribed. The double-stranded cDNA were A-tailed and ligated with Illumia® sequencing adapters. Subsequently, the ligated products were enriched by PCR and size-selected by agarose gel electrophoresis. The products of approximately 200-400-bp in size were sequenced by the Illumina® HiSeq™-2500 platform. The raw data in fastq format were mapped to the human reference genome (hg19, GRCh37) by Tophat v2.0.11(-g 1), which had the aligner Bowtie (v2.2.1.0) with the parameter settings (-N 0, -L 20, -i S,1,1.25, -n-ceil L,0,0.15 and -gbar 4). The mapping results were further sorted in coordination position by samtools (v0.1.19.0) (Robinson M D, Oshlack A., "A scaling normalization method for differential expression analysis of RNA-seq data," *Genome Biology,* 11:R25 (2010); Robinson M D, McCarthy D J and Smyth G K., "edgeR: a Bioconductor package for differential expression analysis of digital gene expression data," *Bioinformatics,* 26, pp. 139-140 (2010)). The latest annotation of LncRNA was downloaded from the publicly available Incipedia database version 3.0. The mapped reads in individual lncRNA region of each sample were counted by bedtools (v2.19.0). The R Bioconductor edgeR package was used to normalize raw reads by the scaling method. Differentially expressed lncRNAs were identified by one-way ANOVA method with 10% false discovery rate (FDR) and four-fold changes between the conditions. The FDR was controlled by the Benjamini-Hochberg (BH) procedure. RNA-binding protein genes were compiled from the literature (Alfredo Castello, et al., "Insights into RNA Biology from an Atlas of Mammalian mRNA-Binding Proteins," *Cell,* 149, pp. 1393-1406 (2012); Alfredo Castello, et al., "RNA-binding proteins in Mendelian disease," *Trends in Genetics,* 29, pp. 318-327 (2013)). The normalized reads from the multiple transcripts of each gene were averaged to represent composite gene expression. The expression results were clustered using unsupervised hierarchical clustering analysis, in which the Euclidean Distance is used as the similarity measure.

Human primary keratinocytes and organotypic (raft) epithelial cultures: Total RNA extracted from various raft tissues were leftovers from previous studies (Wang, X. et al., "Oncogenic HPV infection interrupts the expression of tumor-suppressive miR-34a through viral oncoprotein E6," *RNA,* 15, pp. 637-647 (2009); Wang, X., et al., "microRNAs are biomarkers of oncogenic human papillomavirus infections," *Proc. Natl. Acad. Sci. USA,* 111, pp. 4262-4267 (2014)). Briefly, primary human foreskin keratinocytes (HFK) and primary human vaginal keratinocytes (HVK) were isolated from newborn circumcision and adult vaginectomy tissue specimens, respectively, as previously described (Meyers, C., Mayer, T. J., and Ozbun, M. A., "Synthesis of infectious human papillomavirus type 18 in differentiating epithelium transfected with viral DNA," *J. Virol.,* 71, pp, 7381-7386 (1997)). Keratinocytes were grown in monolayer culture by using epithelial (E) medium plus epidermal growth factor (5 ng/ml) in the presence of mitomycin C (4 μg/ml)-treated J2 3T3 feeder cells. Keratinocyte lines stably maintaining HPV16 and HPV18 DNA following electroporation were subcloned by limiting dilutions of cells. Organotypic (raft) epithelial culture tissues derived from HPV16 and HPV18-immortalized HFK or HVK were prepared as described previously (McLaughlin-Drubin, M. E. and Meyers, C., "Propagation of infectious, high-risk HPV in organotypic "raft" culture," *Methods Mol. Med.,* 119, pp. 171-186 (2005)). The stratified and differentiated raft culture epidermal tissues were collected free from collagen (no fibroblasts) on day 10 and frozen on dry ice for total cell RNA preparation. Additional productive HPV18 raft cultures of HFKs were obtained by Cre-loxP-mediated recombination as described (Wang, H. K., Duffy, A. A., Broker, T. R., and Chow, L. T., "Robust production and passaging of infectious HPV in squamous epithelium of primary human keratinocytes", *Genes Dev.,* 23, pp. 181-194 (2009)), and the derived raft cultures were collected on day 8, day 12, and day 16.

Plasmid pLJd-HPV-18URR-E6, pLC-HPV-18URR-E7, and pLJd-HPV-18URR-E6E7 have been described (Cheng, S., Schmidt-Grimminger, D. C., Murant, T., Broker, T. R., and Chow, L. T., "Differentiation-dependent up-regulation of the human papillomavirus E7 gene reactivates cellular DNA replication in suprabasal differentiated keratinocytes.," *Genes Dev.,* 9, pp. 2335-2349 (1995); Genovese, N. J., Banerjee, N. S., Broker, T. R., and Chow, L. T., "Casein kinase II motif-dependent phosphorylation of human papillomavirus E7 protein promotes p130 degradation and S-phase induction in differentiated human keratinocytes," *J. Virol.,* 82, pp. 4862-4873 (2008)). Retroviruses derived from the above vectors were prepared as described (Banerjee, N. S., Chow, L. T., and Broker, T. R., "Retrovirus-mediated gene transfer to analyze HPV gene regulation and protein functions in organotypic "raft" cultures," *Methods Mol. Med.,* 119, pp. 187-202 (2005)). Primary HFKs were acutely infected with the retroviruses and selected with G-418 (300 μg/mL). The selected HFKs were used to establish epithelial raft cultures and harvested on day 11.

TaqMan® real-time quantitative PCR assays: Quantitative validation of genes in clinical samples and raft tissues was analyzed by real-time PCR TaqMan® gene expression assays (Applied Biosystems). In brief, 2 μg of total RNA from each sample was reversely transcribed using Superscript® First-stand Synthesis kit (Invitrogen) according to the manufacturer's instructions. TaqMan® gene expression assays for RNA-binding protein gene expression were obtained from life technologies and lncRNA primers for RT-qPCR were designed as given in Example 2.

The TaqMan® assay probes that span over exon-exon junctions were designed to amplify spliced RNA products to avoid detection of any contaminated residual genomic DNA in our RNA samples. After reverse transcription, PCR products were amplified from the cDNA samples using TaqMan® gene expression Master Mix (Applied Biosystems) together with TaqMan® gene expression assays on a StepOne Plus™ Real-Time PCR system (Applied Biosystems). Gene enrichment was calculated using the $2^{-\Delta\Delta C_t}$ method in relation to the housekeeping gene GAPDH. The mean Ct value of a given gene from 24 normal cervical tissues after normalization was served as a basal level to calculate a relative level of the gene detected in each clinical sample. Data are presented as a bar graph with mean±SE for each group. Significance of mRNA levels among clinical tissue groups was analyzed using the nonparametric Mann-Whitney U-test, while significance of the mRNA levels between raft culture tissue groups was analyzed by Student t-test.

Example 1: Identification of Altered Expression of RNA-Binding Protein Genes in Cervical Cancer Using RNA-sequencing (RNA-Seq) approach, seven normal cervical tissues and seven cervical cancer tissues were examined for their expression landscapes of approximately 19,000 coding and 113,513 noncoding RNAs. We identified 614 differentially expressed coding transcripts enriched in cancer related pathways and 95 of them encoding RNA-binding proteins (RBPs) from the analyzed 1502 human RBPs. Moreover, we identified 34 differentially, abundantly expressed lnc-RNAs from normal cervix to cervical cancer. Table 4 shows the two RNA-Seq analyses of 14 different clinical cervical tissues with two different RNA-seq platforms, each containing normal cervical tissues without HPV infection and cervical cancer tissues with HPV infection. The right column of the table shows the raw reads of individual samples from each RNA-Seq platform.

TABLE 4

RNA-Seq detection from 14 cervical tissue samples

| Sample No. | Age (yr) | Pathology | HPV infection | Total reads |
|---|---|---|---|---|
| RNA-Seq-1 | | | | |
| 1 | 27 | N | No | 13,171,863 |
| 2 | 38 | N | No | 12,028,762 |
| 3 | 42 | N | No | 31,143,321 |
| 4 | 40 | SCC | Yes | 12,422,476 |
| 5 | 42 | SCC | Yes | 11,425,454 |
| 6 | 24 | SCC | Yes | 22,302,605 |
| RNA-Seq-2 | | | | |
| 7 | 42 | N | No | 85,255,279 |
| 8 | 37 | N | No | 83,376,820 |
| 9 | 52 | N | No | 80,265,055 |
| 10 | 44 | N | No | 81,954,460 |
| 11 | 48 | SCC | Yes | 66,982,821 |
| 12 | 45 | SCC | Yes | 74,819,347 |
| 13 | 47 | SCC | Yes | 93,579,886 |
| 14 | 49 | SCC | Yes | 66,891,722 |

Figure 2:
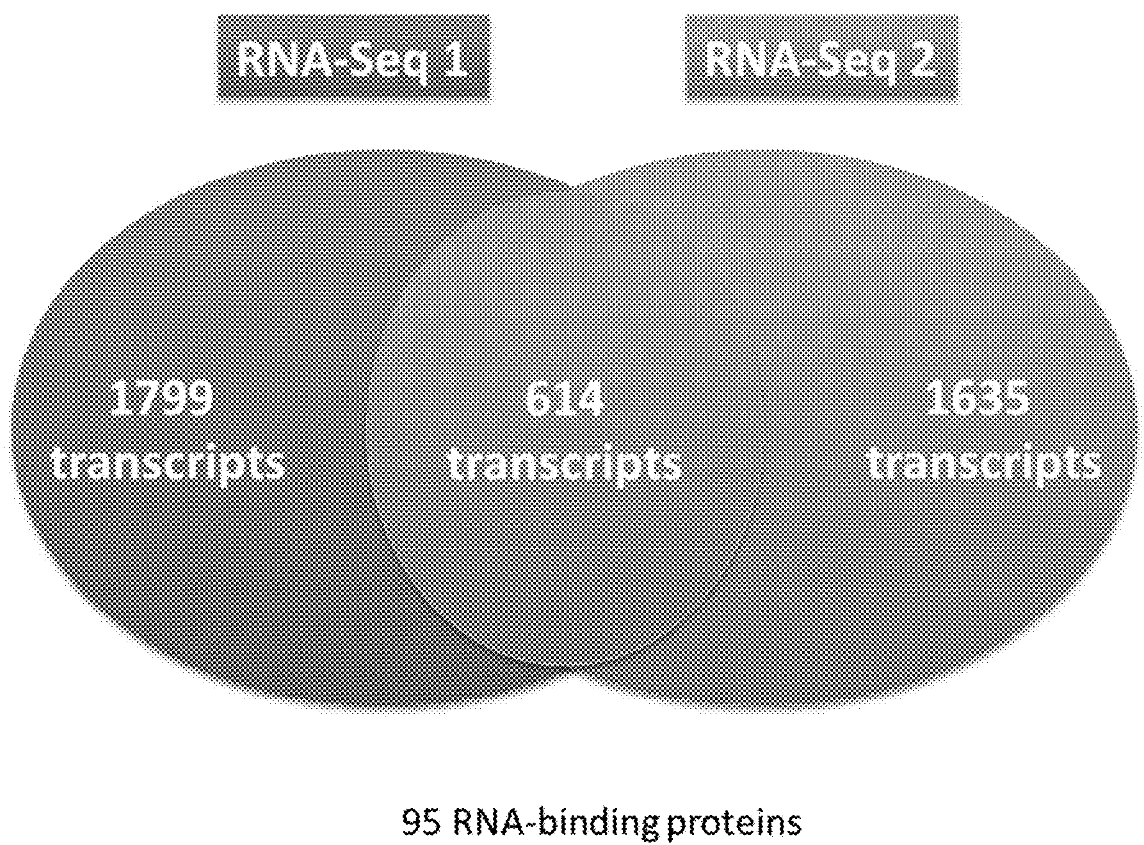
FIG. 2 shows Venn diagrams showing 95 differentially expressed RBP genes being identified from two separate RNA-seq analyses of cervical cancer, pre-cancer to normal cervical tissues.
Figure 3:
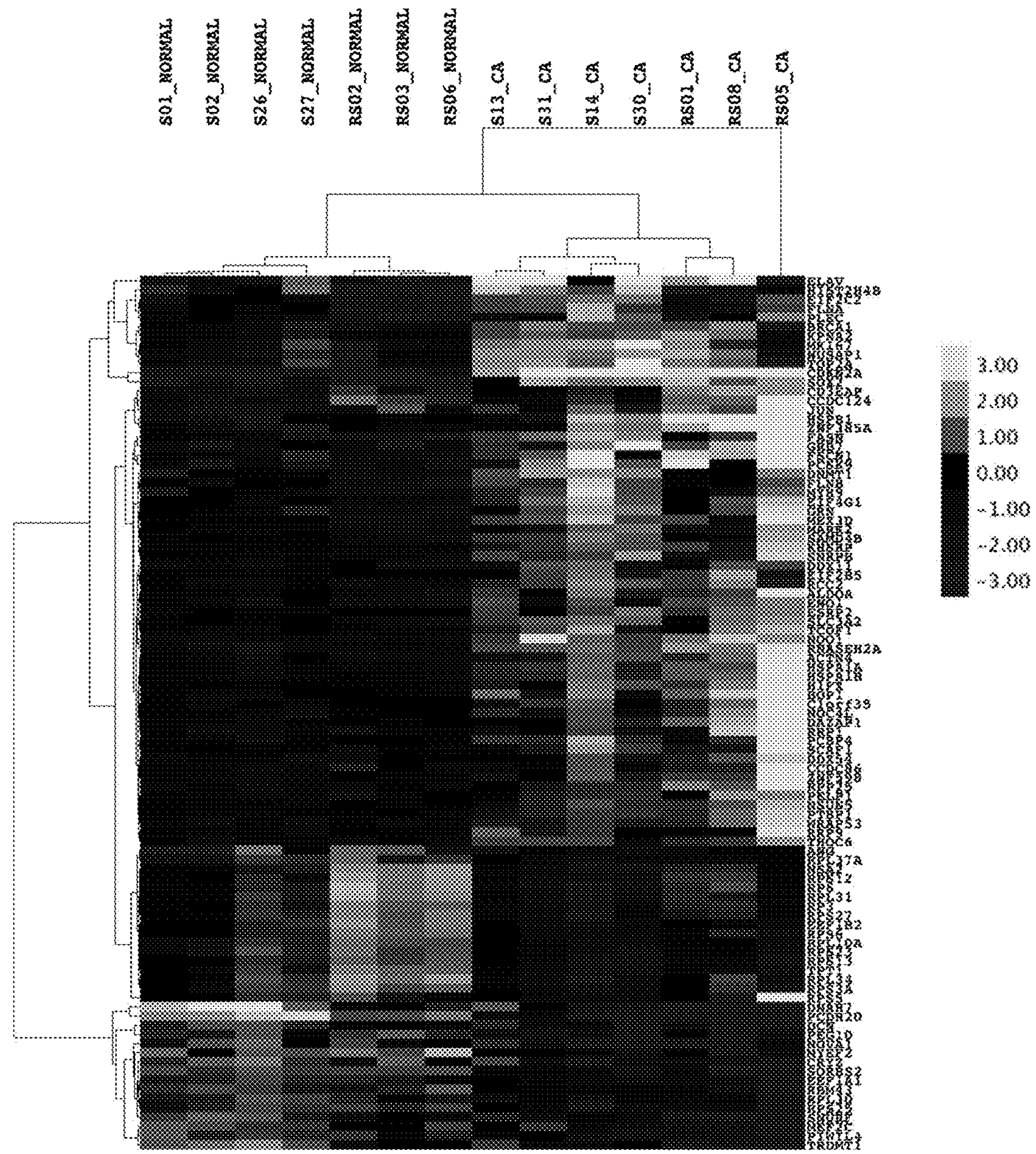
FIG. 3 shows a heat map comparing 95 differentially expressed RBP genes in cervical cancer to normal cervical tissues.

FIG. 1 is a flowchart of the RNA-Seq analyses. FIG. 2 shows Venn diagrams and FIG. 3 shows a heat map showing 95 differentially expressed RNA-binding protein genes in cervical cancer (n=7) compared to normal cervical tissues (n=7). Table 5 summarizes the 8 RBPs with expression changes between normal and cancer tissues by RNA-Seq. (CPM: Counts per Million)

TABLE 5

RNA-Seq data of the 8 RBP genes between normal and cancer tissues

| RNA-binding protein genes | Description | Normal ($log_2$ CPM, mean ± SD) | Cancer ($log_2$ CPM, mean ± SD) |
|---|---|---|---|
| CDKN2A | Cyclin-dependent kinase inhibitor 2A | −0.24 ± 0.88 | 6.3 ± 1.12 |
| ELAVL2 | ELAV like neuron-specific RNA binding protein 2 | −3.38 ± 1.89 | 0.17 ± 3.54 |
| GRB7 | Growth factor receptor-bound protein 7 | 0.9 ± 0.96 | 4.07 ± 1.22 |
| HSPB1 | Heat shock 27 kDa protein 1 | 5.74 ± 1.09 | 8.84 ± 2.49 |
| KHSRP | KH-type splicing regulatory protein | 4.35 ± 0.18 | 5.85 ± 0.78 |
| NOVA1 | Neuro-oncological ventral antigen 1 | 2.82 ± 0.55 | 0.1 ± 1.55 |
| PTBP1 | Polypyrimidine tract binding protein 1 | 5.74 ± 0.21 | 7.18 ± 0.83 |
| RNASEH2A | Ribonuclease H2, subunit A | 2.32 ± 0.47 | 5.01 ± 0.72 |

Table 6 provides the TaqMan® probe information of each RBP.

TABLE 6

TaqMan ® probe information of each RBP

| Company | Order name | Cat No | ID No |
|---|---|---|---|
| Applied Biosystems ® | Single Tube TaqMan ® Assay for GRB7 | Cat. # 4331182 | Hs00918009_g1 |
| Applied Biosystems ® | Single Tube TaqMan ® Assay for ELAVL2 | Cat. # 4331182 | Hs00270011_m1 |
| Applied Biosystems ® | Single Tube TaqMan ® Assay for RNASEH2A | Cat. # 4331182 | Hs00958451_g1 |
| Applied Biosystems ® | Single Tube TaqMan ® Assay for KHSRP | Cat. # 4351372 | Hs01100863_g1 |
| Applied Biosystems ® | Single Tube TaqMan ® Assay for NOVA1 | Cat. # 4351372 | Hs01103130_m1 |
| Applied Biosystems ® | Single Tube TaqMan ® Assay for PTBP1 | Cat. # 4351372 | Hs00914687_g1 |
| Applied Biosystems ® | Single Tube TaqMan ® Assay for CDKN2A | Cat. # 4331182 | Hs00923894_m1 |
| Applied Biosystems ® | Single Tube TaqMan ® Assay for HSPB1 | Cat. # 4331182 | Hs03044127_g1 |

Figure 4:
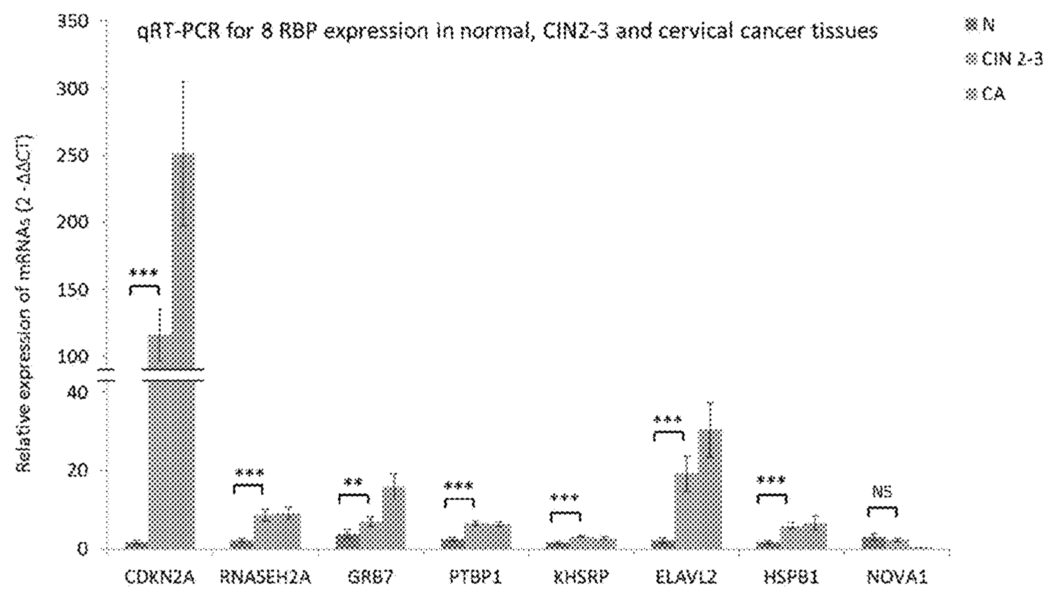
FIG. 4 shows the TaqMan® RT-qPCR validation of the 8 selected RBPs.

FIG. 4 shows the TaqMan® RT-qPCR validation confirming that all 8 RBPs significantly increased (7 RBPs) or decreased (1 RBP) in cervical cancer tissues (n=23), compared to normal cervical tissues (n=24). 7 increased RBP genes in cervical cancer were also shown higher expression in pre-cancerous lesions (CIN 2-3, n=25) when compared to the normal tissues, indicating these changes appear even at the early stage of cervical carcinogenesis. , P<0.01; *, P<0.001; NS, no statistics significance.

Figure 5:
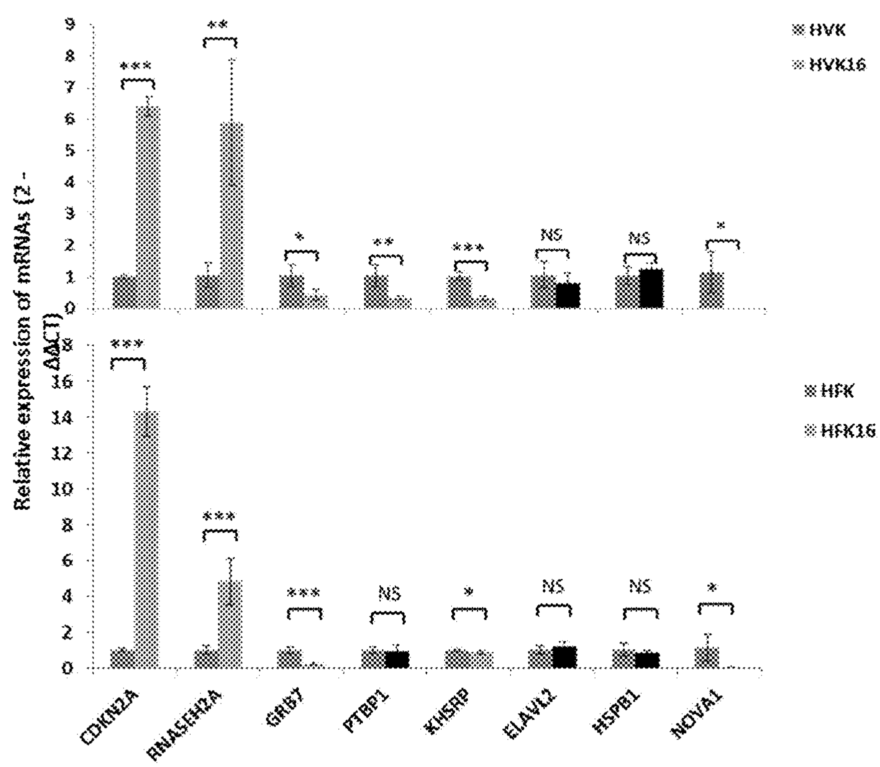
FIG. 5 shows that high-risk HPV16 infection affects the expression of RBPs. Total RNA extracted from human vaginal keratinocyte (HVK)-derived raft cultures with (HVK16) or without (HVK) productive HPV16 infection and human foreskin keratinocyte (HFK) derived raft cultures with (HFK16) or without (HFK) productive HPV16 infection were examined by TaqMan® RT-qPCR for the expression of 8 RBPs.
Figure 6:
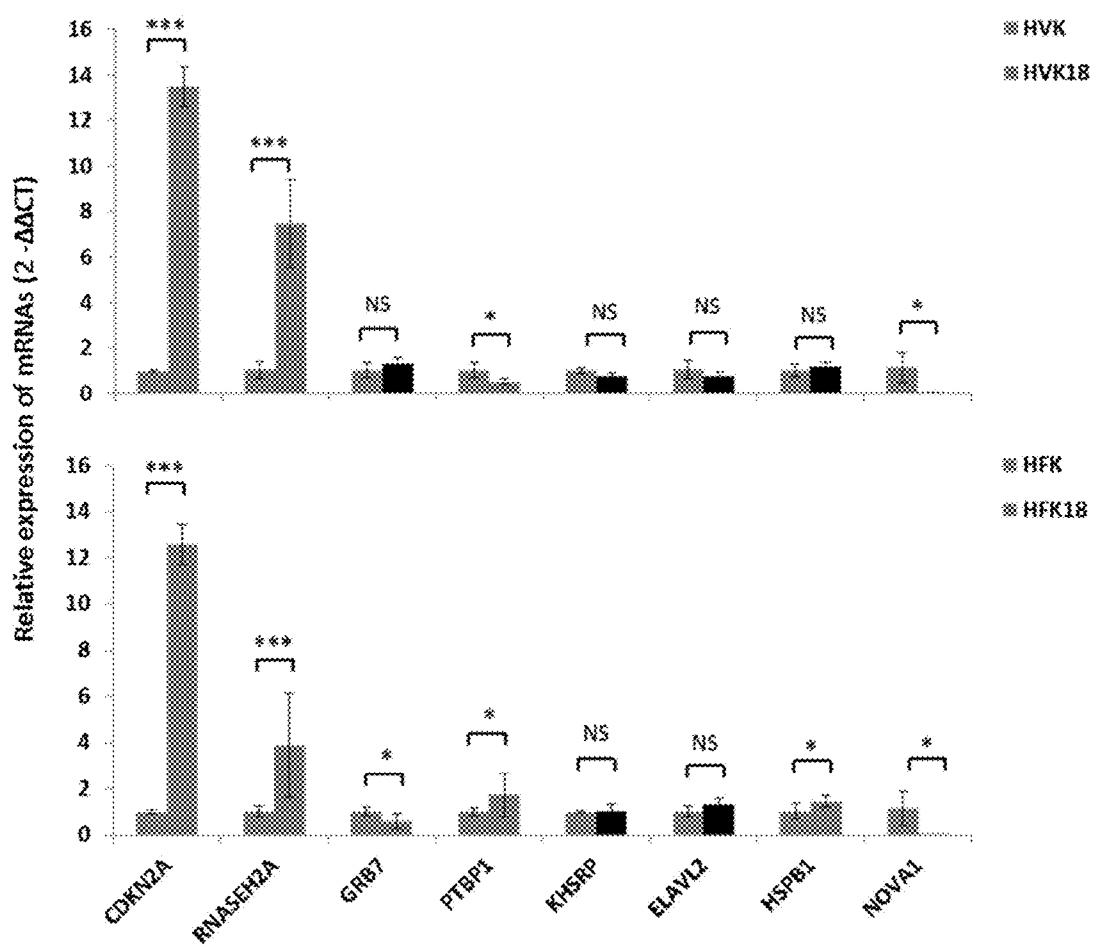
FIG. 6 shows that high-risk HPV18 infection affects the expression of RBPs. Total RNA extracted from human vaginal keratinocyte (HVK)-derived raft cultures with (HVK18) or without (HVK) productive HPV18 infection and human foreskin keratinocyte (HFK) derived raft cultures with (HFK18) or without (HFK) productive HPV18 infection were examined by TaqMan® RT-qPCR for the expression of 8 RBPs.
Figure 7:
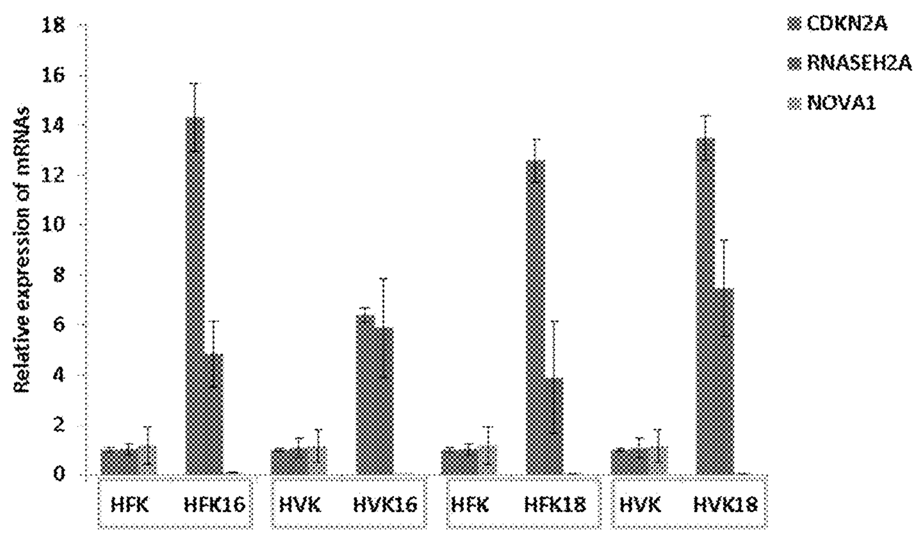
FIG. 7 shows that both HPV16 and HPV18 increase the expression of CDKN2A and RNASEH2A, but decrease the expression of NOVA1 in HFK- and HVK-derived rafts.
Figure 8:
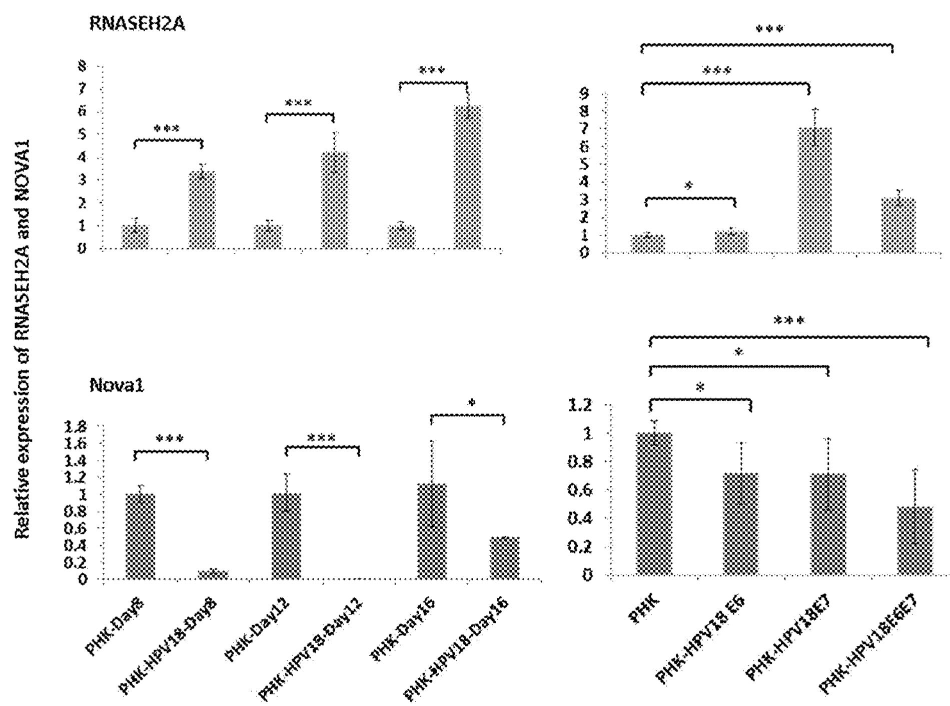
FIG. 8 shows that HPV18 infection and viral E6 and/or E7 affect the expression of RNASEH2A and Nova1. The expression of RNASEH2A and NOVA1 in primary human keratinocytes (PHK)-derived raft tissues with or without HPV18 infection on day 8, day 12, and day 16 or PHK rafts transduced with a retrovirus expression HPV18 E6, E7 or E6E7 or with an empty control retrovirus were further validated by TaqMan® RT-qPCR.

FIGS. 5 and 6 show that high-risk HPV16 and HPV18 infection affects the expression of RBPs. FIG. 5 shows Total RNA extracted from human vaginal keratinocyte (HVK)-derived raft cultures with (HVK16) or without (HVK) productive HPV16 infection and human foreskin keratinocyte (HFK) derived raft cultures with (HFK16) or without (HFK) productive HPV16 infection were examined by TaqMan® RT-qPCR for the expression of 8 RBPs. *, P<0.05; , P<0.01; *, P<0.001; NS, no statistics significance. FIG. 6 shows Total RNA extracted from human vaginal keratinocyte (HVK)-derived raft cultures with (HVK18) or without (HVK) productive HPV18 infection and human foreskin keratinocyte (HFK) derived raft cultures with (HFK18) or without (HFK) productive HPV18 infection were examined by TaqMan® RT-qPCR for the expression of 8 RBPs. *, P<0.05; *, P<0.001; NS, no statistics significance. FIG. 7 shows that both HPV16 and HPV18 increase the expression of CDKN2A and RNASEH2A, but decrease the expression of NOVA1 in HFK- and HVK-derived rafts. In this experiment, total RNA was used to determine the relative levels of individual proteins by TaqMan® RT-qPCR. FIG. 8** shows that HPV18 infection and viral E6 and/or E7 affect the expression of RNASEH2A and Nova1. The expression of RNASEH2A and NOVA1 in primary human keratinocytes (PHK)-derived raft tissues with or without HPV18 infection on day 8, day 12, and day 16 or PHK rafts transduced with a retrovirus expression HPV18 E6, E7 or E6E7 or with an empty control retrovirus were further validated by TaqMan® RT-qPCR. These results demonstrate that RNASEH2A and NOVA1 respond to HPV18 infection and their altered expression in cervical cancer could be attributed to viral oncoprotein E6 and/or E7. *, P<0.05; ***, P<0.001; NS, no statistics significance.

Figure 9:
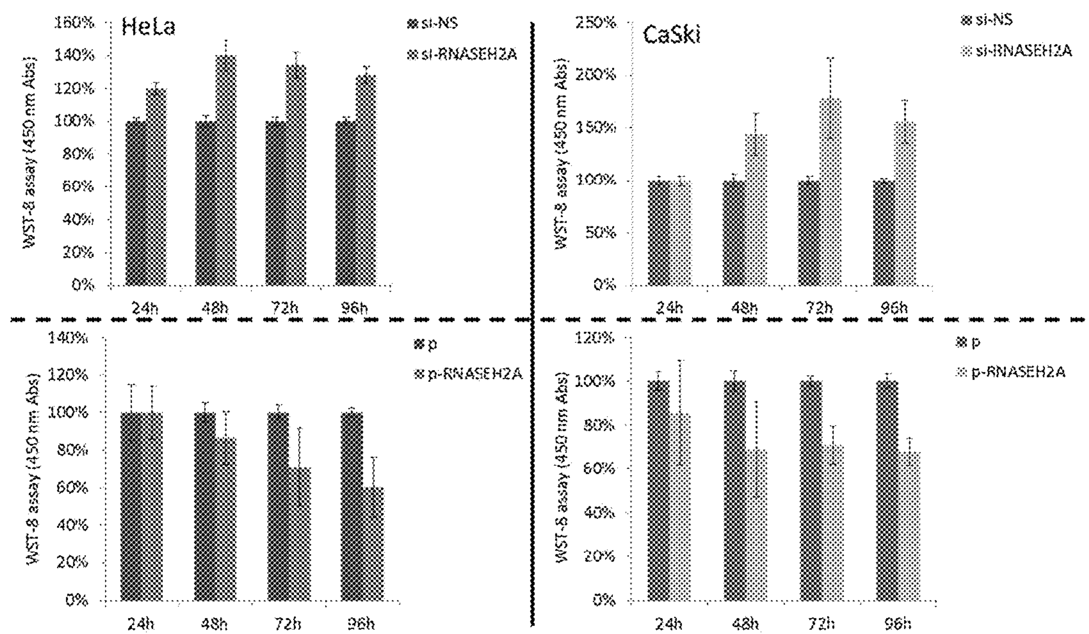
FIG. 9 shows that knockdown or overexpression of RNASEH2A in HeLa or CaSki cells affects cell proliferation. Specific-siRNA knockdown or ectopic expression of RNASEH2A from a mammalian expression vector in HeLa or CaSki cells on cell proliferation was evaluated by Cell Counting Kit-8 (CCK-8) assay
Figure 10:
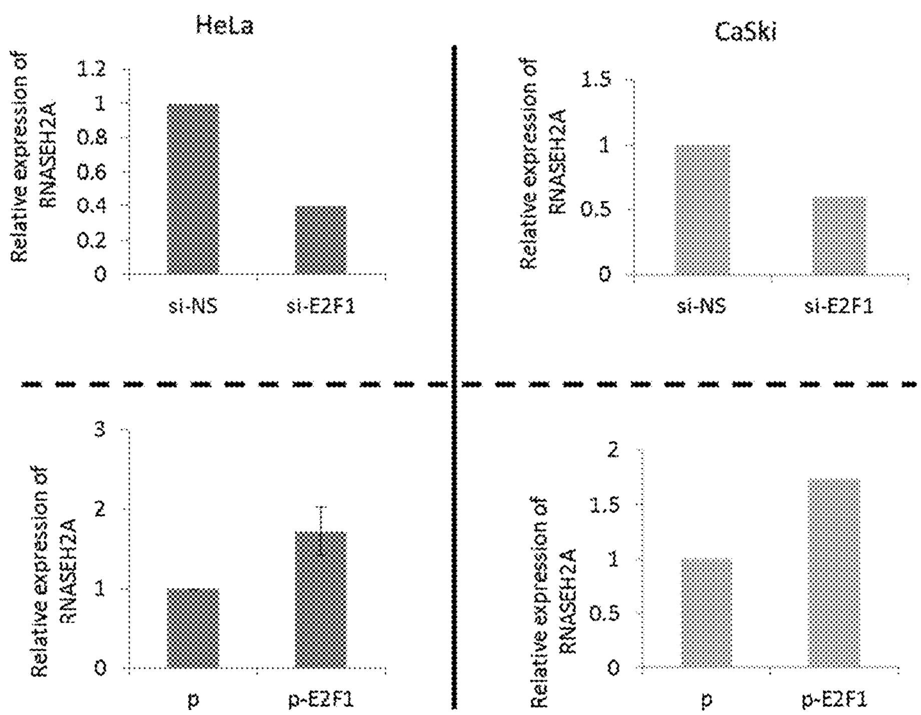
FIG. 10 shows HPV oncoprotein E7 regulates the expression of RNASEH2A via E2F1. Specific-siRNA knockdown or ectopic expression of E2F1 from a mammalian expression vector in HeLa or CaSki cells on RNASEH2A was evaluated by Western blot.

FIG. 9 shows that knockdown or overexpression of RNASEH2A in HeLa or CaSki cells affects cell proliferation. Specific-siRNA knockdown or ectopic expression of RNASEH2A from a mammalian expression vector in HeLa or CaSki cells on cell proliferation was evaluated by Cell Counting Kit-8 (CCK-8) assay at time indicated. si-NS, non-specific siRNA; siRNASEH2A, RNASEH2A-specific siRNA; P, control vector; p-RNASEH2A, RNASEH2A-expression vector. FIG. 10 shows HPV oncoprotein E7 regulates the expression of RNASEH2A via E2F1. Specific-siRNA knockdown or ectopic expression of E2F1 from a mammalian expression vector in HeLa or CaSki cells on RNASEH2A was evaluated by Western blot using anti-RNASEH2A antibody. si-NS, non-specific siRNA; si-E2F1, E2F1-specific siRNA; P, control vector; p-E2F1, E2F1-expression vector.

Figure 11:
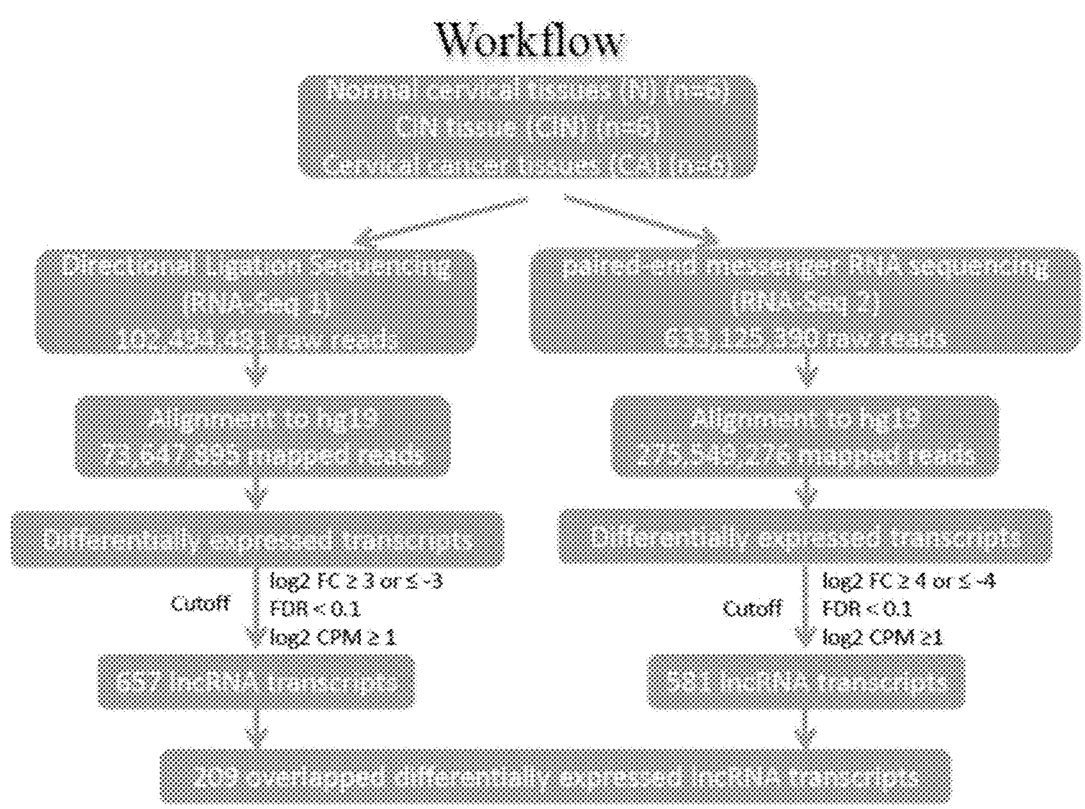
FIG. 11 is a flowchart of the RNA-Seq analyses for long-noncoding RNAs (lnc-RNAs).
Figure 12:
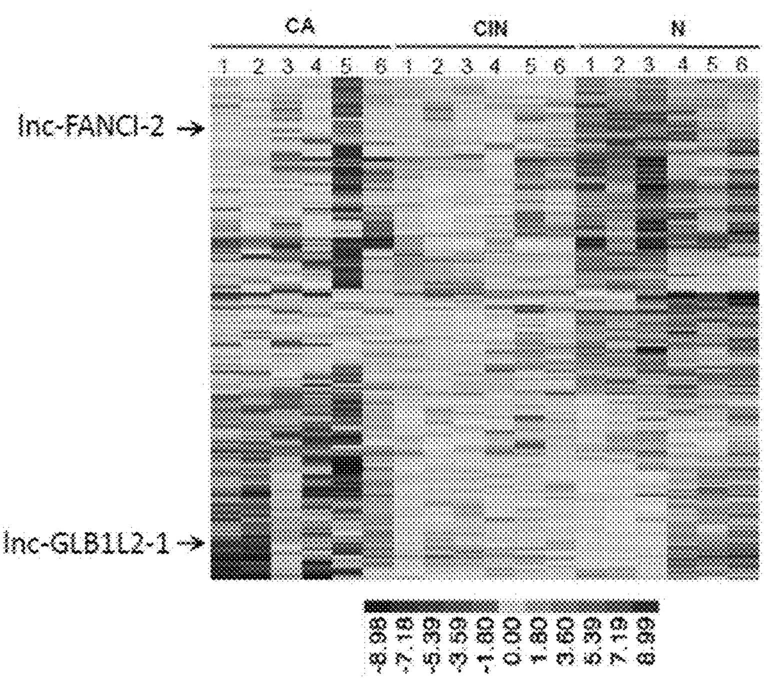
FIG. 12 is a heat map showing 209 overlapped, differentially expressed lnc-RNAs from cervical cancer, pre-cancer to normal cervical tissues.

Example 2: The Expression Profile of Long Noncoding RNAs Distinguishes Normal Cervix from and Cancerous Cervix RNA was extracted from each sample using Trizol® reagent (Life technologies). RNAseq libraries were prepared using TruSeq® Stranded Total RNA Kit with Ribo-Zero depletion and sequenced on an Illumina HiSeq™ 2000 platform as paired-end reads. The fastq data were mapped to human reference genome (hg19, GRCh37) by Bowtie (v2.2.1.0), and the mapping results were further filtered by samtools (v0.1.19.0). The latest annotation of LncRNA was downloaded from Incipedia database version 3.0. We counted the mapped reads in individual lncRNA region of each sample by bedtools (v2.19.0). The R Bioconductor edgeR package was used to normalize raw reads by the scaling method. The differentially expressed lncRNAs were detected by one-way ANOVA method with 10% false discovery rate (FDR) and four fold changes between the conditions. FIG. 11 is a flow chart of the RNA-Seq analysis. FIG. 12 is a heat map showing 34 overlapped, differentially expressed lnc-RNAs in cervical cancer compared to normal cervical tissues. lnc-FANCI-2 and lnc-GLB1L2-1 were specifically identified as associated with cervical cancer. Tables 2 and 3 list all of the isoforms of these two lnc-RNAs.

Taqman ® primer design for lnc-FANCI-2
Exon 6:

(SEQ ID NO: 76)
CTGGAAAGGAGGAGAACATGAAACATTGCTTGAAGACAATGGCCGAGACA

GCAGGTCCCACCCTGCACAGCCACCAGCATCTCTCCCCTCAGCCCTGTCT

CCTCTTCTGCAGTTGGGATCTGCACATTTAAGCCTGAA

Exon 7:

(SEQ ID NO: 77)
ATTGTCCTGTGAAGTGAAGTATGATCGGACAGCCTCTTTTCAGCTTTTAT

GACAATGGAGACAGAGGAATTGTGGCTCTTGCCAAGGTCACAGGATTGGA

ATACAGAGCCAAGCCACCCCAGGACATGCAAGAGCCTCAGAAGGGAA

Primers for RT-qPCR
Forward:

(SEQ ID NO: 78)
5'- ACAGCCACCAGCATCTCTC -3'

Probe:

(SEQ ID NO: 79)
5'- TGAAGTGAAGTATGATCGGACAGCCTC -3'

-continued

Reverse:

(SEQ ID NO: 80)
5'- CCACAATTCCTCTGTCTCCATT -3'

TaqMan ® primer design for lnc-GLB1L2-1:
Last Exon 3:

(SEQ ID NO: 81)
TCTCTCATCTGTGTTTTCAGGGCATGGACTGGAACTCCCAATACCCCTGA

CATGGGCTGAGTCAACGTGGTCATGAACATGTGACAGGAG

Last Exon 2:

(SEQ ID NO: 82)
GCAGCAGAAGTTGCAGAGAAGAGTGAGGCACGTTTGAAAAAGGCTGAAAA

ATGTTTCTGTCCAGGCAAGGGTGTGTGCTGAATGACTCAAGGATTTTTTG

G

Primers for RT-qPCR
Forward:

(SEQ ID NO: 83)
5'- CATGGACTGGAACTCCCAATA -3'

Probe:

(SEQ ID NO: 84)
5'- TGCAGAGAAGAGTGAGGCACGTTTG -3'

Reverse:

(SEQ ID NO: 85)
5'- CCTTGCCTGGACAGAAACATT -3'

Figure 13:
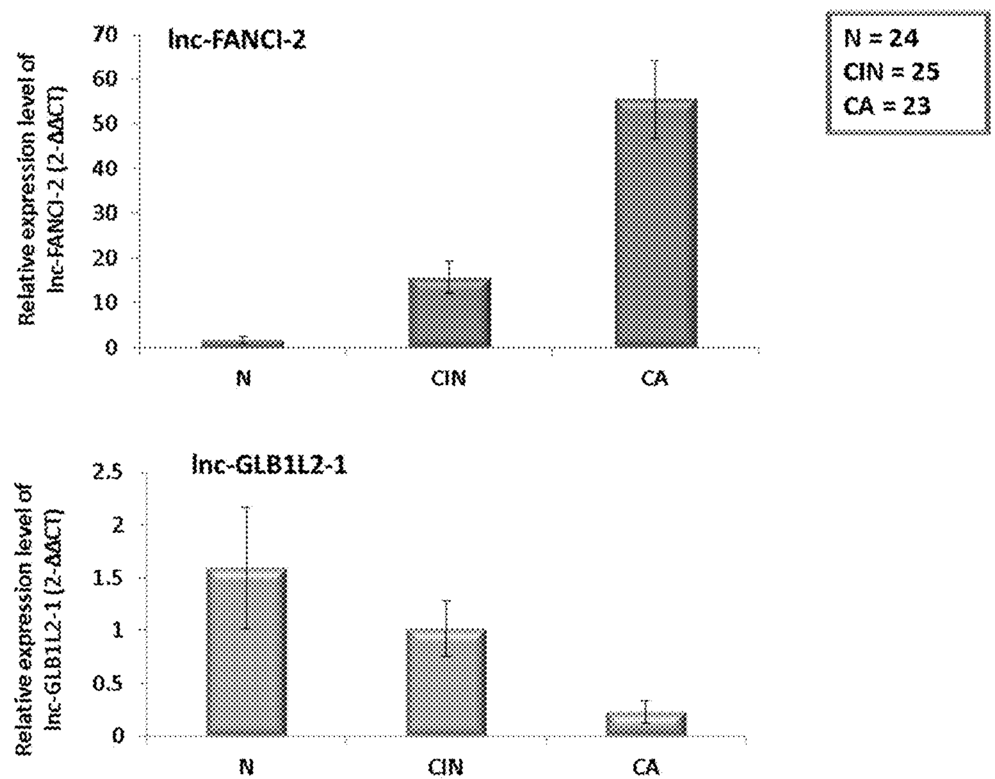
FIG. 13 shows an increase of lnc-FANCI-2, and decrease of lnc-GLB1L2-1 expression along with the cervical lesion progression from normal cervix. Lnc-FANCI-2 and lnc- GLB1L2-1 RNA expression was examined by RT-qPCR in 24 normal, 25 CIN 2-3, and 23 cancer tissues.
Figure 14:
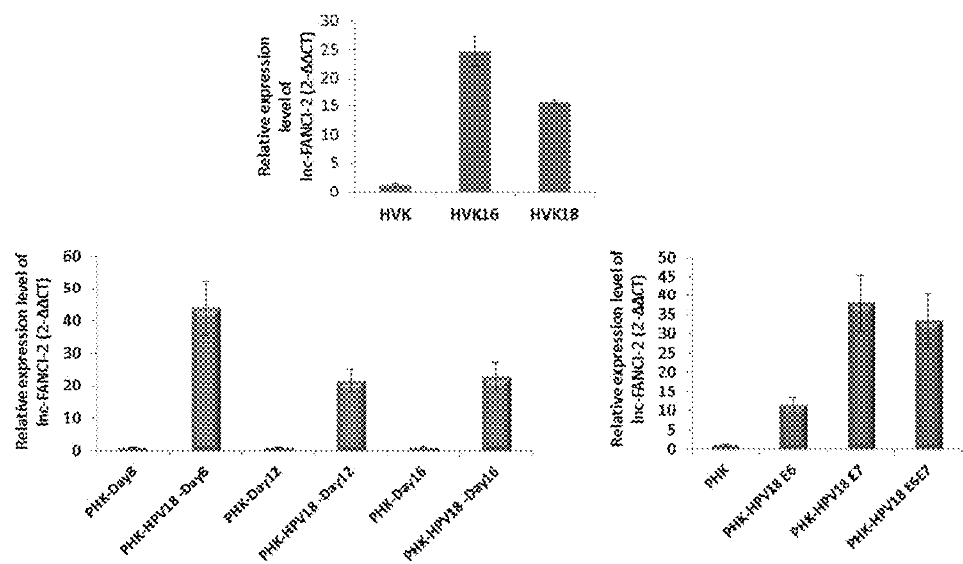
FIG. 14 shows that HPV infection increases lnc-FANCI-2 expression in HVK- and PHK-derived rafts and viral E7 or E6 is responsible for the increase. The expression of lnc-FANCI-2 in human vaginal keratinocytes (HVK)-derived raft tissues without (HVK) or with HPV16 (HVK16) or HPV18 (HVK18) infection or primary human keratinocytes (PHK)-derived raft tissues without or with HPV18 infection.

FIG. 13 shows an increase of lnc-FANCI-2, and decrease of lnc-GLB1L2-1 expression along with the cervical lesion progression from normal cervix. Lnc-FANCI-2 and lnc-GLB1L2-1 RNA expression was examined by RT-qPCR in 24 normal, 25 CIN 2-3, and 23 cancer tissues. FIG. 14 shows that HPV infection increases lnc-FANCI-2 expression in HVK- and PHK-derived rafts and viral E7 or E6 is responsible for the increase. The expression of lnc-FANCI-2 in human vaginal keratinocytes (HVK)-derived raft tissues without (HVK) or with HPV16 (HVK16) or HPV18 (HVK18) infection or primary human keratinocytes (PHK)-derived raft tissues without or with HPV18 infection on day 8, day 12, and day 16 or PHK rafts transduced with a retrovirus expressing HPV18 E6, E7 or E6E7 or with an empty control retrovirus were further validated by RT-qPCR. These results demonstrate that lnc-FANCI-2 expression responds to HPV18 infection and viral oncoprotein E6 and/or E7.

In data not shown, lnc-FANCI-2 was upregulated in isolated keratinocyte lines infected by high-risk HPVs, but not low risk HPV11 and epidermodysplasia verruciformis-associated HPV5 and 10.

The term "polynucleotide" as used herein refers to a polymer of greater than one nucleotide in length of ribonucleic acid (RNA), deoxyribonucleic acid (DNA), hybrid RNA/DNA, modified RNA or DNA, or RNA or DNA mimetics, including peptide nucleic acids (PNAs). The polynucleotides may be single- or double-stranded. The term includes polynucleotides composed of naturally-occurring nucleobases, sugars, and covalent internucleoside (backbone) linkages as well as polynucleotides having non-naturally-occurring portions which function similarly. Such modified or substituted polynucleotides are well known in the art and are referred to as "analogues."

"Complementary" or "substantially complementary" refers to the ability to hybridize or base pair between nucleotides or nucleic acids, such as, for instance, between a sensor peptide nucleic acid or polynucleotide and a target polynucleotide. Complementary nucleotides are, generally, A and T (or A and U), or C and G. Two single-stranded polynucleotides or PNAs are said to be substantially complementary when the bases of one strand, optimally aligned and compared and with appropriate insertions or deletions, pair with at least about 80% of the bases of the other strand, usually at least about 90% to 95%, and more preferably from about 98 to 100%.

Alternatively, substantial complementarity exists when a polynucleotide may hybridize under selective hybridization conditions to its complement. Typically, selective hybridization may occur when there is at least about 65% complementarity over a stretch of at least 14 to 25 bases, for example at least about 75%, or at least about 90% complementarity.

The term "homologous region" refers to a region of a nucleic acid with homology to another nucleic acid region. Whether a "homologous region" is present in a nucleic acid molecule is determined with reference to another nucleic acid region in the same or a different molecule.

Hybridization conditions typically include salt concentrations of less than about 1M, more usually less than about 500 mM, for example, less than about 200 mM. In the case of hybridization between a peptide nucleic acid and a polynucleotide, the hybridization can be done in solutions containing little or no salt. Hybridization temperatures can be as low as 5° C., but are typically greater than 22° C., and more typically greater than about 30° C., for example in excess of about 37° C. Longer fragments may require higher hybridization temperatures for specific hybridization as is known in the art. Other factors may affect the stringency of hybridization, including base composition and length of the complementary strands, presence of organic solvents and extent of base mismatching, and the combination of parameters used is more important than the absolute measure of any one alone. Other hybridization conditions which may be controlled include buffer type and concentration, solution pH, presence and concentration of blocking reagents to decrease background binding such as repeat sequences or blocking protein solutions, detergent type(s) and concentrations, molecules such as polymers which increase the relative concentration of the polynucleotides, metal ion(s) and their concentration(s), chelator(s) and their concentrations, and other conditions known in the art.

As used herein, a "probe" is a polynucleotide capable of selectively hybridizing to a target sequence, a complement thereof, a reverse complement thereof, or to an RNA version of the target sequence, the complement thereof, or the reverse complement thereof. A probe may comprise ribonucleotides, deoxyribonucleotides, peptide nucleic acids, and combinations thereof. A probe may optionally comprise one or more labels. In some embodiments, a probe may be used to amplify one or both strands of a target sequence or an RNA form thereof, acting as a sole primer in an amplification reaction or as a member of a set of primers. In one aspect, probes include nucleotide sequences of 10 to 1,000 nucleotides. In other embodiments, the probes are 10-200, 10-30, 10-40, 20-50, 40-80, 50-150, or 80-120 nucleotides in length.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. A method of quantitating an expression level of a lnc-FANCI-2 polynucleotide in a sample containing cells from a test patient's cervix with one or more first polynucleotides that hybridizes to the lnc-FANCI-2 polynucleotide, the method comprising contacting the sample containing cells from the test patient's cervix with the one or more first polynucleotides, and detecting the level of hybridization of the one or more first polynucleotides to the lnc-FANCI-2 polynucleotide, comparing the level of hybridization in the sample containing cells from the test patient's cervix to a control level of hybridization in a control sample of normal cervical tissues, and determining differential expression of the lnc-FANCI-2 polynucleotide in the sample containing cells from the test patient's cervix when the level of hybridization for the sample containing cells from the test patient's cervix is at least about 300% of the control level of hybridization in the control sample, wherein the one or more first polynucleotides are SEQ ID NOs: 78, 79 and 80.

2. The method of claim 1, wherein detecting the level of hybridization of the one or more first polynucleotides to the Inc-FANCI-2 polynucleotide is done with real-time RT-PCR.

3. The method of claim 1, wherein the sample containing cells from the test patient's cervix comprises a PAP smear, a vaginal wash, or a cervical biopsy sample.

* * * * *